(12) United States Patent
Harvey et al.

(10) Patent No.: US 9,493,451 B2
(45) Date of Patent: *Nov. 15, 2016

(54) AMINE DERIVATIVES AS POTASSIUM CHANNEL BLOCKERS

(75) Inventors: Andrew Harvey, Goodwood (AU);
Agnes Bombrun, Chambesy (CH);
Rachel Cooke, Woodville West (AU);
Isabelle Jeanclaude-Etter, Bellevue (CH); Nathan Kuchel, Cumberland Park (AU); Jerome Molette, Versonnex (FR); Jorgen Mould, Semaphore South (AU); Dharam Paul, Flinders Park (AU); Rajinder Singh, Cowandilla (AU); Cristina Donini, Geneva (CH);
Veronique Colovray, Geneva (CH);
Thomas Avery, Rostrevor (AU); Julia Crossman, Thebarton (AU); Justin Ripper, Cumberland Park (AU)

(73) Assignees: Bionomics Limited, Thebarton (AU);
Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/118,170

(22) PCT Filed: May 16, 2012

(86) PCT No.: PCT/AU2012/000538
§ 371 (c)(1),
(2), (4) Date: Jul. 30, 2014

(87) PCT Pub. No.: WO2012/155199
PCT Pub. Date: Nov. 22, 2012

(65) Prior Publication Data
US 2014/0336198 A1    Nov. 13, 2014

Related U.S. Application Data

(60) Provisional application No. 61/486,536, filed on May 16, 2011.

(51) Int. Cl.
*A61K 31/497* (2006.01)
*C07D 451/04* (2006.01)
*C07D 309/14* (2006.01)
*C07D 213/89* (2006.01)
(Continued)

(52) U.S. Cl.
CPC .......... *C07D 451/04* (2013.01); *C07C 217/90* (2013.01); *C07D 209/52* (2013.01);
(Continued)

(58) Field of Classification Search
CPC .................................................. C07D 451/04
USPC ..................................................... 514/252.1
See application file for complete search history.

(56) References Cited

U.S. PATENT DOCUMENTS

| 5,494,895 A | 2/1996 | Garcia et al. |
| 2005/0203143 A1 | 9/2005 | Breslin et al. |
| 2008/0221194 A1 | 9/2008 | Harvey et al. |

FOREIGN PATENT DOCUMENTS

| AU | 491880 B2 | 6/1976 |
| EP | 2 524 912 A1 | 11/2012 |

(Continued)

OTHER PUBLICATIONS

U.S. Appl. No. 61/486,536, filed May 16, 2011.
(Continued)

*Primary Examiner* — Nizal Chandrakumar
(74) *Attorney, Agent, or Firm* — Choate, Hall & Stewart LLP; Charles E. Lyon

(57) ABSTRACT

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

28 Claims, 2 Drawing Sheets

(51) Int. Cl.
| | |
|---|---|
| C07D 231/12 | (2006.01) |
| C07D 233/56 | (2006.01) |
| C07D 401/12 | (2006.01) |
| C07D 237/08 | (2006.01) |
| C07D 239/24 | (2006.01) |
| C07D 405/12 | (2006.01) |
| C07D 411/12 | (2006.01) |
| C07C 217/90 | (2006.01) |
| C07D 413/12 | (2006.01) |
| C07D 241/12 | (2006.01) |
| C07D 209/52 | (2006.01) |
| C07D 211/16 | (2006.01) |
| C07D 211/26 | (2006.01) |
| C07D 211/38 | (2006.01) |
| C07D 213/16 | (2006.01) |
| C07D 213/61 | (2006.01) |
| C07D 213/64 | (2006.01) |
| C07D 213/70 | (2006.01) |
| C07D 213/40 | (2006.01) |
| C07D 241/18 | (2006.01) |

(52) U.S. Cl.
CPC ........... C07D211/16 (2013.01); C07D 211/26 (2013.01); C07D 211/38 (2013.01); C07D 213/16 (2013.01); C07D 213/40 (2013.01); C07D 213/61 (2013.01); C07D 213/64 (2013.01); C07D 213/70 (2013.01); C07D 213/89 (2013.01); C07D 231/12 (2013.01); C07D 233/56 (2013.01); C07D 237/08 (2013.01); C07D 239/24 (2013.01); C07D 241/12 (2013.01); C07D 241/18 (2013.01); C07D 309/14 (2013.01); C07D 401/12 (2013.01); C07D 405/12 (2013.01); C07D 411/12 (2013.01); C07D 413/12 (2013.01)

(56) References Cited

FOREIGN PATENT DOCUMENTS

| | | |
|---|---|---|
| JP | S58-103348 A | 6/1983 |
| JP | 58131977 A | 8/1983 |
| JP | S59-16831 A | 1/1984 |
| JP | 59155304 A | 9/1984 |
| JP | 59155366 A | 9/1984 |
| JP | 6041603 A | 3/1985 |
| JP | 6084204 A | 5/1985 |
| JP | H04-308558 A | 10/1992 |
| WO | WO-9630339 A1 | 10/1996 |
| WO | WO-97/16437 A1 | 5/1997 |
| WO | WO-97/16438 A1 | 5/1997 |
| WO | WO-0020358 A2 | 4/2000 |
| WO | WO-02083143 A1 | 10/2002 |
| WO | WO-03/037865 A1 | 5/2003 |
| WO | WO-03057671 A1 | 7/2003 |
| WO | WO-2006013048 A1 | 2/2006 |
| WO | WO-2007/015775 A2 | 2/2007 |
| WO | WO-2007/041341 A2 | 4/2007 |
| WO | WO-2007/089735 A2 | 8/2007 |
| WO | WO-2009/043117 A1 | 4/2009 |
| WO | WO-2010/015935 A2 | 2/2010 |
| WO | WO-2011020806 A1 | 2/2011 |
| WO | WO-2012/155199 A1 | 11/2012 |

OTHER PUBLICATIONS

Azam, P. et al., Targeting effector memory T cells with the small molecule Kv1.3 blocker PAP-1 suppresses allergic contact dermatitis, J Invest Dermatol, 127(6):1419-29 (2007).

Beeton, C. et al., Kv1.3 channels are a therapeutic target for T cell-mediated autoimmune diseases, Proc Natl Acad Sci U S A, 103(46):17414-9 (2006).

Bradding, P. and Wulff, H., The K+ channels K(Ca)3.1 and K(v)1.3 as novel targets for asthma therapy, Br J Pharmacol, 157(8):1330-9 (2009).

Chandy, K.G. et al., K+ channels as targets for specific immunomodulation, Trends Pharmacol Sci, 25(5):280-9 (2004).

Decoursey, T.E. et al., Voltage-gated K+ channels in human T lymphocytes: a role in mitogenesis?, Nature, 307(5950):465-8 (1984).

Grissmer, S. et al., Expression and chromosomal localization of a lymphocyte K+ channel gene, Proc Natl Acad Sci U S A, 87(23):9411-5 (1990).

Kolb, J. et al., New MCRs: the first 4-component reaction leading to 2,4-disubstituted thiazoles, Mol Divers, 6(3-4):297-313 (2003).

Matheu, M.P. et al., Imaging of effector memory T cells during a delayed-type hypersensitivity reaction and suppression by Kv1.3 channel block, Immunity, 29(4):602-14 (2008).

Panyi, G. et al., Kv1.3 potassium channels are localized in the immunological synapse formed between cytotoxic and target cells, Proc Natl Acad Sci U S A, 101(5):1285-90 (2004).

Panyi, G. et al., Looking through ion channels: recharged concepts in T-cell signaling, Trends Immunol, 25(11):565-9 (2004).

Rus, H. et al., The voltage-gated potassium channel Kv1.3 is highly expressed on inflammatory infiltrates in multiple sclerosis brain, Proc Natl Acad Sci U S A, 102(31):11094-9 (2005).

Sosa-Rivadeneyra, M. et al., N,N'-Bis[(R)-2-hydroxy-2-phenylethyl]-N,N'-bis[(S)-1-phenylethyl] pyridine-2,6-dicarboxamide: stabilization of an asymmetric conformer through the formation of a double intramolecular hydrogen bond, Acta Crystallographica Section E: Structure Reports, E61: 0536-538 (2005).

Szabò, I. et al., A novel potassium channel in lymphocyte mitochondria, J Biol Chem, 280(13):12790-8 (2005).

Szabó, I. et al., Mitochondrial potassium channel Kv1.3 mediates Bax-induced apoptosis in lymphocytes, Proc Natl Acad Sci U S A, 105(39):14861-6 (2008).

Takaba, K. and Kunitomo, J., Asymmetric synthesis of so-called "fumarizine" isomer, English Abstract, Yakugaku Zasshi, 117(8):555-559 (1997).

Takaba, K. et al., Asymmetric synthesis of (R)-1-(2-Methoxy-3,4-methylenedioxybenzyl)-2-methyl-6,7-methylenedioxy-1,2,3,4-tetrahydroisoquinoline (so-called "fumarizine"), Heterocycles, 43(8): 1777-86 (1996).

Tschritter, O. et al., A new variant in the human Kv1.3 gene is associated with low insulin sensitivity and impaired glucose tolerance, J Clin Endocrinol Metab, 91(2):654-8 (2006).

Tucker, K. et al., Kv1.3 gene-targeted deletion alters longevity and reduces adiposity by increasing locomotion and metabolism in melanocortin-4 receptor-null mice, Int J Obes (Lond), 32(8):1222-32 (2008).

Valverde, P. et al., Potassium channel-blockers as therapeutic agents to interfere with bone resorption of periodontal disease, J Dent Res, 84(6):488-99 (2005).

Wulff, H. et al., K+ channel expression during B cell differentiation: implications for immunomodulation and autoimmunity, J Immunol, 173(2):776-86 (2004).

Wulff, H et al., The voltage-gated Kv1.3 K(+) channel in effector memory T cells as new target for MS, J Clin Invest, 111(11):1703-13 (2003).

Xu J, et al., The voltage-gated potassium channel Kv1.3 regulates energy homeostasis and body weight, Hum Mol Genet, 12(5):551-9 (2003).

Xu, J. et al., The voltage-gated potassium channel Kv1.3 regulates peripheral insulin sensitivity, Proc Natl Acad Sci U S A, 101(9):3112-7 (2004).

Extended European Search Report for EP 12785759.7, 5 pages (Nov. 12, 2014).

(56) References Cited

OTHER PUBLICATIONS

International Search Report for PCT/AU2012/000538, 4 pages (Jun. 7, 2012).

STN Accession No. 1277997-05-3, entered STN Apr. 10, 2011, cited in International Search Report for PCT/AU2012/000538 on Jun. 7, 2012.

STN Accession No. 1279264-78-6, entered STN Apr. 13, 2011, cited in International Search Report for PCT/AU2012/000538 on Jun. 7, 2012.

STN Accession No. 1289770-12-2, entered STN May 4, 2011, cited in International Search Report for PCT/AU2012/000538 on Jun. 7, 2012.

STN Accession No. 1290480-74-8, entered STN May 5, 2011, cited in International Search Report for PCT/AU2012/000538 on Jun. 7, 2012.

STN Accession No. 1290492-99-7, entered STN May 5, 2011, cited in International Search Report for PCT/AU2012/000538 on Jun. 7, 2012.

Written Opinion for PCT/AU2012/000538, 7 pages (Jun. 7, 2012).

Venkatesh and Lipper, Role of the Development Scientist in Compound Lead Selection and Optimization., J. Pharm. Sci, 89: 145-154 (2000).

AMINE DERIVATIVES AS POTASSIUM CHANNEL BLOCKERS

CROSS-REFERENCE TO RELATED APPLICATIONS

This application is a national phase application under 35 U.S.C. §371 of International application number PCT/AU2012/000538, filed May 16, 2012, which claims priority to U.S. provisional application Ser. No. 61/486,536, filed on May 16, 2011, the entirety of each of which is hereby incorporated by reference.

FIELD OF INVENTION

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

BACKGROUND

Potassium channels represent a complex class of voltage-gated ion channels from both functional and structural standpoints. Their functions include regulating neurotransmitter release, heart rate, insulin secretion, neuronal excitability, epithelial electrolyte transport, smooth muscle contraction, and cell volume. In general, four sequence-related potassium channel genes—shaker, shaw, shab, and shal—have been identified in *Drosophila*, and each has been shown to have human homolog(s). KCNA3 encodes the voltage-gated $K_V1.3$ potassium channel, which is shaker-related and is expressed in lymphocytes (T and B lymphocytes), the central nervous system, fat and other tissues. The functional channel is composed of four identical $K_V1.3$ α-sub units. The $K_V1.3$ potassium channel regulates membrane potential and thereby indirectly influences calcium signaling in human effector-memory T cells (Grissmer S. et al, Proc. Natl. Acad. Sci. U.S.A. 87(23): 9411-5; DeCoursey T. E. et al, Nature 307 (5950): 465-8; Chandy K. G. et al, Trends Pharmacol. Sci. 25(5): 280-9; Wulff H. et al, J. Clin. Invest. 111 (11): 1703-13). Effector memory T cells are important mediators of multiple sclerosis, Type I diabetes mellitus, psoriasis, and rheumatoid arthritis.

The $K_v1.3$ channel is expressed in T and B lymphocytes in a distinct pattern that depends on the state of lymphocyte activation and differentiation. Upon activation, naive and central memory T cells increase expression of the KCa3.1 channel per cell, while effector-memory T cells increase expression of the $K_V1.3$ channel. Amongst human B cells, naive and early memory B cells express small numbers of $K_V1.3$ and KCa3.1 channels when they are quiescent, and augment KCa3.1 expression after activation. In contrast, class-switched memory B cells express high numbers of $K_V1.3$ channels per cell (about 1500/cell) and this number increases after activation (Chandy K. G. et al, Trends Pharmacol. Sci. 25(5): 280-9; Wulff H. et al, J. Clin. Invest. III (11): 1703-13; Wulff H. et al, J. Immunol. 173(2): 776-86). The $K_v1.3$ channel promotes the calcium homeostasis required for T-cell receptor-mediated cell activation, gene transcription, and proliferation (Panyi, G et al (2004) Trends Immunol 25:565-569). Kv1.3 is physically coupled through a series of adaptor proteins to the T-cell receptor signaling complex and it traffics to the immunological synapse during antigen presentation. However, blockade of the channel does not prevent immune synapse formation (Panyi G. et al, Proc. Natl. Acad. Sci. U.S.A., 101(5):1285-90; Beeton C. et al, Proc. Natl. Acad. Sci. U.S.A., 103(46): 17414-9). $K_V1.3$ and KCa3.1 regulate membrane potential and calcium signaling of T cells. Calcium entry through the CRAC channel is promoted by potassium efflux through the Kv1.3 and KCa3.1 potassium channels. Blockade of $K_V1.3$ channels in effector-memory T cells suppresses activities like calcium signaling, cytokine production (interferon-gamma, interleukin 2) and cell proliferation. Effector-memory T cells (TEM) were originally defined by their expression of cell surface markers, and can enter sites of inflammation in non-lymphoid tissues, while not participating in the process of lymphoid recirculation carried out by most other lymphocytes. TEMs have been shown to uniquely express high numbers of the $K_V1.3$ potassium channel and depend on these channels for their function. In vivo, $K_V1.3$ blockers paralyze effector-memory T cells at the sites of inflammation and prevent their reactivation in inflamed tissues. In contrast, $K_V1.3$ blockers do not affect the homing to and motility within lymph nodes of naive and central memory T cells, most likely because these cells express the KCa3.1 channel and are therefore protected from the effect of $K_V1.3$ blockade. Suppressing the function of these cells by selectively blocking the $K_V1.3$ channel offers the potential for highly effective therapy of autoimmune diseases with minimal effects on either beneficial immune responses or other organs (Chandy K. G. et al, Trends Pharmacol. Sci. 25(5): 280-9; Wulff H. et al, J. Clin. Invest. III (11): 1703-13; Beeton C. et al, Proc. Natl. Acad. Sci. U.S.A., 103(46): 17414-9; Matheu M. P. et al, Immunity 29(4): 602-14). $K_v1.3$ has been reported to be expressed in the inner mitochondrial membrane in lymphocytes. The apoptotic protein Bax has been suggested to insert into the outer membrane of the mitochondria and occlude the pore of $K_V1.3$ via a lysine residue. Thus, $K_V1.3$ blockade may contribute to apoptosis (Szabo I. et al, J. Biol. Chem. 280(13): 12790-8; Szabo I. et al., Proc. Natl. Acad. Sci. U.S.A. 105(39): 14861-6).

Autoimmune Disease is a family of disorders resulting from tissue damage caused by a malfunctioning immune system, affecting tens of millions of people worldwide. Such diseases may be restricted to a single organ, as e.g. in multiple sclerosis and Type I diabetes mellitus, or may involve multiple organs as in the case of rheumatoid arthritis and systemic lupus erythematosus. Treatment is generally palliative and typically includes anti-inflammatory and immunosuppressive drugs. The severe side effects of many of these therapies have fueled a continuing search for more effective and selective immunosuppressive drugs. Among these are those which can selectively inhibit the function of effector-memory T cells, known to be involved in the etiology of many of these autoimmune diseases and thereby ameliorate many autoimmune diseases without compromising the protective immune response. Multiple sclerosis is a disease caused by autoimmune damage to the central nervous system including the brain, which affects roughly two and a half million people worldwide. Symptoms include muscle weakness and paralysis, and the disease can progress rapidly and unpredictably and may eventually lead to death. Treatment usually includes the use of anti-inflammatory and immunosuppressive drugs which have potentially severe side effects. $K_V1.3$ has been shown to be highly expressed in autoreactive effector memory T cells from MS patients (Wulff, H et al (2003) J Clin Invest 111:1703-1713; Rus H et al (2005) PNAS 102:11094-11099). Animal models of multiple sclerosis have been successfully treated using blockers of the $K_V1.3$ potassium channel. In patients with multiple sclerosis, disease-associated myelin-specific T cells from the blood are predominantly co-stimulation independent effector-memory T cells that express high numbers of $K_V1.3$ channels. T cells in MS lesions in postmortem brain lesions are also predominantly effector-memory T cells that express high levels of the $K_V1.3$ channel (Wulff H. et al, J. Clin. Invest. 111(11): 1703-13; Beeton C. et al, Proc. Natl. Acad. Sci. U.S.A. 103(46): 17414-9).

Type 1 diabetes mellitus is a disease caused by autoimmune destruction of insulin-producing cells in the pancreas, resulting in high blood sugar and other metabolic abnormalities. Type 1 diabetes mellitus affects close to four hundred thousand people in the US alone, and is usually diagnosed before age 20. Its long-term consequences may include blindness, nerve damage and kidney failure, and left untreated is rapidly fatal. Treatment involves life-long administration of insulin or pancreas transplantation, both of which may entail serious side effects (Beeton C. et al, Proc. Natl. Acad. Sci. U.S.A. 103(46): 17414-9).

$K_V1.3$ is also considered a therapeutic target for the treatment of obesity, for enhancing peripheral insulin sensitivity in patients with type-2 diabetes mellitus, for preventing bone resorption in periodontal disease, for rheumatoid arthritis, for inflammatory skin conditions, such as psoriasis, and for asthma (Tucker K. et al, Int. J. Obes. (Lond) 32(8): 1222-32; Xu J. et al, Hum. Mol Genet. 12(5): 551-9; Xu J. et al, Proc. Natl. Acad. Sci. U.S.A. 101(9): 3112-7; Valverde P. et al, J. Dent. Res 84(6): 488-99; Tschritter O. et al, J. Clin. Endocrinol. Metab. 91(2): 654-8; Beeton, C. et al, Proc. Natl. Acad. Sci. U.S.A. 103(46): 17414-17419; Azam, P. et al, J. Invest. Derm. 127: 1419-1429; Bradding, P et al, Br. J. Pharmacol. 157: 1330-1339).

Compounds which are selective $K_V1.3$ blockers are thus potential therapeutic agents as immunosuppressants or immune system modulators including for the prevention of graft rejection, and the treatment of autoimmune and inflammatory disorders. $K_V1.3$ modulators may be used alone or in conjunction with other immunosuppressants, such as selective KCa3.1 blockers or cyclosporin, in order to possibly achieve synergism and/or to reduce toxicity, especially of cyclosporin. At present there exist a number of non-selective K channels that will inhibit lymphocyte proliferation, but have adverse side effects. Other K channels exist in a wide range of tissues including the heart and brain, and generally blocking these channels is undesirable. U.S. Pat. No. 5,494,895 discloses the use of a thirty-one amino acid peptide, scorpion peptide margatoxin, as a selective inhibitor and probe of $K_V1.3$ channels present in human lymphocytes, and also as an immunosuppressant. However the use of this compound is limited by its potent toxicity.

International patent Application publications numbers WO 97/16438 and WO 09/716437, and U.S. Pat. No. 6,051,590 describe the use of the triterpene, correolide and related compounds as immunosuppressants in the treatment of conditions in mammals affected or facilitated by $K_V1.3$ inhibition.

There is still a need for improved and specific therapies for immune diseases, including autoimmune diseases, and for immunosuppressive agents which lack problematic side effects and specifically target channels involved in immune cell mediated actions.

SUMMARY OF THE INVENTION

The present invention provides compounds of Formula (I) and related Formulae, and pharmaceutical compositions thereof. In certain embodiments compounds of Formula (I) have potency and selectivity in the prevention and treatment of conditions that have been associated with autoimmune disorders, immune-mediated disorders, inflammatory disorders, or other disorders, or conditions which benefit clinically from immunosuppressants, including multiple sclerosis, type-1 diabetes mellitus, type-2 diabetes mellitus, rheumatoid arthritis, systemic lupus erythematosus, psoriasis, contact dermatitis, obesity, graft-versus host disease, transplant rejection, and delayed type hypersensitivity. In particular, compounds, pharmaceutical compositions and methods provided are useful to treat, prevent or ameliorate a range of conditions in mammals such as, but not limited to, immune disorders and autoimmune diseases of various genesis or etiology, for example rheumatoid arthritis, multiple sclerosis, psoriasis, type 1 diabetes, graft-versus host disease, transplant rejection. In some embodiments, compounds, pharmaceutical compositions and methods provided are useful as antiinflammatory agents for the treatment of arthritis, and as agents to treat Parkinson's Disease, Alzheimer's Disease, asthma, myocardial infarction, neurodegenerative disorders, inflammatory bowel disease and autoimmune disorders, renal disorders, obesity, eating disorders, cancer, schizophrenia, epilepsy, sleeping disorders, cognitive disorders, depression, anxiety, blood pressure, and lipid disorders.

In one aspect the present invention provides compounds of Formula (I):

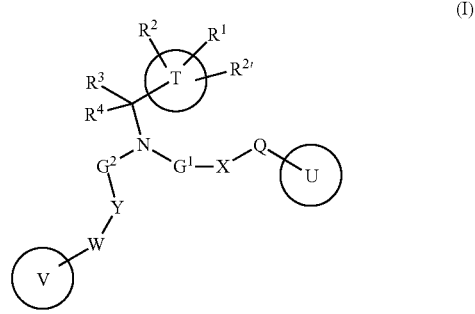

Wherein
G$^1$ denotes a single bond,
G$^2$ denotes a CO group,
X is selected from a single bond, an alkylene group having 1 to 6 carbon atoms optionally substituted with 1 or 2 substituents selected from fluoro or $C_1$-$C_6$-alkyl,
Y is selected from an alkylene group having 1 to 6 carbon atoms optionally substituted one or two times with $C_3$-$C_8$-cycloalkyl or $C_1$-$C_3$-alkyl; or a 3-8-membered cycloalkylene group,
Q is selected from O, NH or a single bond,
W is selected from SO, SO$_2$ or a single bond,
U is cycloalkyl, cycloalkenyl, heterocyclyl or heteroaryl, each of the above groups being optionally substituted with 1 to 3 substitutents selected from Hal, NO$_2$, CN, —SO$_2$—$C_1$-$C_6$-alkyl, —S—$C_1$-$C_6$-alkyl, NMe$_2$, $C_1$-$C_6$-alkyl, —C(O)O—$C_1$-$C_6$-alkyl, O—$C_1$-$C_6$-alkyl, —(CH$_2$)$_m$—O—$C_1$-$C_6$-alkyl, —$C_1$-$C_6$-halo-alkyl, or a 5-6-membered heteroaromatic group being optionally substituted by Hal,
V is an aryl group optionally substituted with 1 to 3 substitutents selected from Hal, NO$_2$, CN, SO$_2$—$C_1$-$C_6$ alkyl, NMe$_2$, $C_1$-$C_6$-alkyl, O—$C_1$-$C_6$-alkyl, —(CH$_2$)$_m$—

O—$C_1$-$C_6$-alkyl, —$C_1$-$C_6$-halo-alkyl, O—$C_1$-$C_6$-halo-alkyl or a 5-6-membered heteroaromatic group, T denotes phenyl, triazolyl, thiazolyl, oxazolyl, oxadiazolyl, or pyrazolyl, $R^1$ is Hal, —$C_1$-$C_6$-alkyl, O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, cyano or —$C_1$-$C_6$-halo-alkyl, $R^2$ and $R^{2'}$ are independently from one another H, Hal, —$C_1$-$C_6$-alkyl, —O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, —$C_1$-$C_6$-halo-alkyl, or $R^1$ and $R^2$ are linked to form with the ring T to which they are attached a 7-12-membered fused heterocyclyl or 7-12-membered fused cycloalkyl, each of which may be optionally substituted with 1 to 3 Hal, —$C_1$-$C_6$-halo-alkyl, $NO_2$, CN, $C_1$-$C_6$-alkyl, —$(CH_2)_m$—O—$C_1$-$C_6$-alkyl, or —O—$C_1$-$C_6$-alkyl, $R^3$ is $C_1$-$C_6$-alkyl, $C_1$-$C_6$-haloalkyl, —$(CH_2)_m$—O—$C_1$-$C_6$-alkyl, or —$(CH_2)_m$—O—$C_1$-$C_6$-haloalkyl; a 3-8-membered cycloalkyl group, optionally substituted with 1 to 3 substitutents independently selected from Hal, —$C_1$-$C_6$-halo-alkyl, or $C_1$-$C_6$-alkyl; or a 3-8-membered heterocyclic group, optionally substituted with 1 to 3 substitutents independently selected from Hal, —$C_1$-$C_6$-halo-alkyl, $NO_2$, CN, $C_1$-$C_6$-alkyl, —$(CH_2)_m$—O—$C_1$-$C_6$-alkyl, —$(CH_2)_m$—$SO_2$—$C_1$-$C_6$-alkyl, —$SO_2$—$C_1$-$C_6$-alkyl, —O—$C_1$-$C_6$-alkyl, —$(CH_2)_m$—O—$C_1$-$C_6$-halo-alkyl, —$(CH_2)_m$—$SO_2$—$C_1$-$C_6$-halo-alkyl, —$SO_2$—$C_1$-$C_6$-halo-alkyl, —O—$C_1$-$C_6$-halo-alkyl, —C(O)—$C_1$-$C_6$-alkyl, or —C(O)O—$C_1$-$C_6$-alkyl, $R^4$ denotes H, $C_1$-$C_6$-alkyl, or forms together with $R^3$ a 3-8-membered cycloalkyl ring, optionally substituted with Hal, —$C_1$-$C_6$-halo-alkyl, $NO_2$, CN, $C_1$-$C_6$-alkyl, —$(CH_2)_m$—O—$C_1$-$C_6$-alkyl, —O—$C_1$-$C_6$-alkyl, —C(O)—$C_1$-$C_6$-alkyl, or —C(O)O—$C_1$-$C_6$-alkyl, m is selected from 1, 2, 3 or 4, preferably 1 or 2, Hal is F, Cl, Br, or I, wherein -$G^2$-Y—W together is at least 3 atoms in length, as well as pharmaceutically acceptable salts thereof, or is an enantiomeric mixture of 2 enantiomers in all ratios, and/or as a mixture of diastereoisomers in all ratios.

In a second aspect, the present invention provides a kit or a set comprising at least one compound of Formula (I) or related Formulae, preferably in combination with immunomodulating agents. Preferably, the kit consists of separate packs of:

(a) an effective amount of a compound of the Formula (I) and/or pharmaceutically usable derivatives, solvates, salts, hydrates and stereoisomers thereof, including mixtures thereof in all ratios, and (b) an effective amount of a further medicament active ingredient.

In another aspect, the present invention relates to pharmaceutical compositions comprising a compound provided herein, and a pharmaceutical carrier, excipient or diluent. The pharmaceutical composition can comprise one or more of the compounds described herein. It will be understood that compounds provided herein useful in the pharmaceutical compositions and treatment methods disclosed herein, can be pharmaceutically acceptable as prepared and used.

In another aspect, the present invention relates to methods for preventing, treating or ameliorating a condition from among those listed herein, particularly conditions that are associated with immune-mediated reactions, autoimmune conditions, or other conditions which are modulated by immunosuppression. Examples of these conditions are multiple sclerosis, type-1 diabetes mellitus, rheumatoid arthritis, psoriasis, contact dermatitis, obesity, systemic lupus erythematosus, graft-versus host disease, and transplant rejection, which method comprises administering to a mammal in need thereof an amount of one or more of the compounds provided herein, or pharmaceutical composition thereof, effective to prevent, treat or ameliorate the condition.

In addition to the methods of treatment set forth above, the present invention extends to the use of any of the compounds of the invention for the preparation of medicaments that may be administered for such treatments, as well as to such compounds for the treatments disclosed and specified. In additional aspects, the present invention is directed to methods for synthesizing the compounds described herein, with representative synthetic protocols and pathways described below.

Accordingly, it is an aim of this invention to provide new compounds which can modulate the activity of the voltage gated potassium channel $K_v$ 1.3, and thus avert or treat any maladies that may be causally related to aberrations in such activity.

The invention also provides a series of compounds that can treat or alleviate maladies or symptoms of same, such as immune-mediated disorders and autoimmune diseases, that may be causally related to the activation of the Kv1.3 channel.

The invention also provides a series of compounds that can treat a disease or condition, wherein the disease or condition is selected from: Acute disseminated encephalomyelitis (ADEM), Addison's disease, Allopecia areata, Alzheimers disease, Ankylosing spondylitis, Antiphospholipid antibody syndrome, Autoimmune hemolytic anemia, Autoimmune hepatitis, Autoimmune inner ear disease, Autoimmune Lymphoproliferative Syndrome (ALPS), Autoimmune polyendocrine/polyglandular syndrome, Autoimmune thrombocytoipenia purpura, Balo disease, Behcet disease, Bullous pemphigoid, Cardiomyopathy, Celiac sprue-dermatitis herpetiformis, Chronic fatigue immune dysfunction syndrome (CFIDS), Chronic inflammatory demyelinating neuropathy, Cicatrical pemphigoid, Coeliac disease, Cold agglutinin disease, CREST syndrome, Crohn's disease, Cystic fibrosis, Degos disease, Dermatomyositis, Diabetes (Type I or Juvenile onset), Early onset dementia, Eczema, Endotoxin shock, Essential mixed cryoglobulinemia, Familial Mediterranean fever, Fibromyalgia, Fibromyositis, Goodpasture's syndrome, Graves' disease, Guillain-Barre syndrome (GBS), Hashimoto's thyroidosis, Hidradenitis suppurativa, Idiopathic pulmonary fibrosis, Idiopathic thrombocytopenic purpura, IgA nephropathy, Lambert-Eaton Myasthenic Syndrome, Leukemia, Lichen planus, Meniere disease, Mixed connective tissue disease, Multiple sclerosis, Multiphasic disseminated encephalomyelitis, Myasthenia gravis, Neuromyelitis Optica, Paraneoplastic Syndromes, Pemphigus, Pemphigus vulgaris, Pernicious anaemia, Polyarteritis nodosum, Polychondritis, Polymyalgia rhematica, Polymyositis, Primary agammaglobulinemia, Primary biliary cirrhosis, Plaque Psoriasis, Psoriatic arthritis, Raynaud phenomenon, Reiter syndrome, Restenosis following angioplasty, Rheumatic fever, Rheumatoid arthritis, Rheumatoid psoriasis, Sarcoidosis, Scleroderma, Sepsis, Sezary's disease, Sjogren's syndrome, Stiffperson syndrome, Systemic lupus erythematosis (SLE), Takayasu arteritis, Temporal arteritis (also known as "giant cell arteritis"), Transplant or Allograft rejection, Ulcerative colitis, Uveitis, Vasculitis, Vitiligo, Graft vs Host disease, pustular psoriasis, and Wegener's granulomatosis.

The invention further provides a series of compounds that can treat a disease or condition, wherein the disease or condition is selected from: resistance by transplantation of organs or tissue, graft-versus-host diseases brought about by medulla ossium transplantation, rheumatoid arthritis, systemic lupus, erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonenephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

The invention further provides pharmaceutical compositions that are effective in the treatment or prevention of a variety of disease states, including the diseases associated with the central nervous system, cardiovascular conditions, chronic pulmonary obstructive disease (COPD), inflammatory bowel disease, rheumatoid arthritis, osteoarthritis, and other diseases where an immunological inflammatory component or autoimmune component is present.

In an embodiment, compounds of the present invention are used in the treatment and prophylaxis of a condition selected from Multiple sclerosis, Rheumatoid arthritis, Psoriasis, Type 1 Diabetes, Type II Diabetes, Systemic lupus nephritis, Oncology, Glomerulonephritis, Sjögrens's syndrome, Transplant rejection, Graft versus host disease, Allergic contact dermatitis, Neointimal hyperplasia/restenosis, Periodontal disease, Leprosy, and Obesity.

In another embodiment W is a single bond.
In another embodiment W is $SO_2$.
In an embodiment Q is a single bond.
In an embodiment Q is a single bond, and W is $SO_2$.
In an embodiment Q and W are single bonds.
In an embodiment $G^2$-Y—W together is from 3-6 atoms in length.
In an embodiment $G^2$-Y—W together is 3 atoms in length.
In an embodiment $G^2$-Y—W together is 4 atoms in length.
In an embodiment $G^2$-Y—W together is 5 atoms in length.
In an embodiment $G^2$-Y—W together is 6 atoms in length.
In an embodiment $G^2$-Y—W together is 3 atoms in length and W is a single bond.
In an embodiment $G^2$-Y—W together is 3 atoms in length and W is $SO_2$.
In an embodiment $G^2$-Y—W together is 3 atoms in length and Q is a single bond.
In an embodiment $G^2$-Y—W together is 4 atoms in length and W is a single bond.
In an embodiment $G^2$-Y—W together is 4 atoms in length and W is $SO_2$.
In an embodiment $G^2$-Y—W together is 4 atoms in length and Q is a single bond.
In an embodiment $G^2$-Y—W together is 5 atoms in length and W is a single bond.
In an embodiment $G^2$-Y—W together is 5 atoms in length and W is $SO_2$.
In an embodiment $G^2$-Y—W together is 5 atoms in length and Q is a single bond.
In an embodiment $G^2$-Y—W together is 6 atoms in length and W is a single bond.
In an embodiment $G^2$-Y—W together is 6 atoms in length and W is $SO_2$.
In an embodiment $G^2$-Y—W together is 6 atoms in length and Q is a single bond.

In certain embodiments -G²-Y—W— is selected from one of the following:

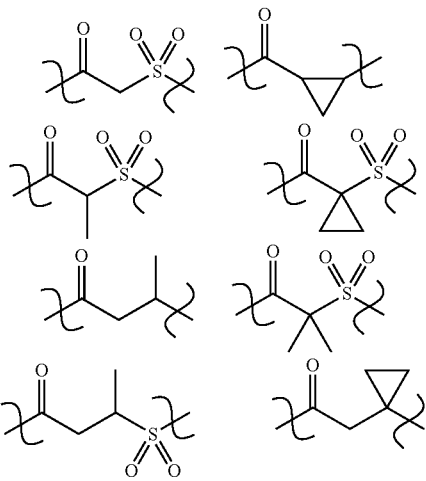

In an embodiment V is an optionally substituted phenyl group.

In an embodiment V is an optionally substituted phenyl group, and Q is a single bond.

In an embodiment V is an optionally substituted phenyl group, and W is SO₂.

In an embodiment V is an optionally substituted phenyl group, Q is a single bond, and W is SO₂.

In an embodiment V is an optionally substituted phenyl group, Q and W are single bonds.

Accordingly, in a further embodiment the invention relates to compounds of formula (Ia):

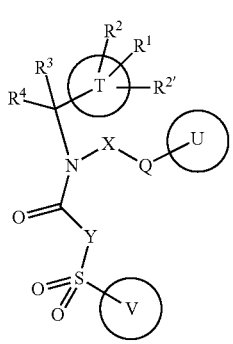

(Ia)

wherein:
X is selected from a single bond, an alkylene group having 1 to 6 carbon atoms optionally substituted with 1 or 2 substituents selected from fluoro or $C_1$-$C_6$-alkyl,
Y is selected from an alkylene group having 1 to 6 carbon atoms optionally substituted one or two times with $C_3$-$C_8$-cycloalkyl or $C_1$-$C_3$-alkyl; or a 3-8-membered cycloalkylene group,
Q is selected from O, NH or a single bond,
V is an aryl group optionally substituted with 1 to 3 substitutents selected from Hal, NO₂, CN, SO₂—$C_1$-$C_6$ alkyl, NMe₂, $C_1$-$C_6$-alkyl, O—$C_1$-$C_6$-alkyl, —(CH₂)$_m$—O—$C_1$-$C_6$-alkyl, —$C_1$-$C_6$-halo-alkyl, O—$C_1$-$C_6$-halo-alkyl or a 5-6-membered heteroaromatic group,
U is cycloalkyl, cycloalkenyl, heterocyclyl or heteroaryl, each of the above groups being optionally substituted with 1 to 3 substitutents selected from Hal, NO₂, CN, —SO₂—$C_1$-$C_6$-alkyl, —S—$C_1$-$C_6$-alkyl, NMe₂, $C_1$-$C_6$-alkyl, —C(O)O—$C_1$-$C_6$-alkyl, O—$C_1$-$C_6$-alkyl, —(CH₂)$_m$—O—$C_1$-$C_6$-alkyl, —$C_1$-$C_6$-halo-alkyl, or a 5-6-membered heteroaromatic group being optionally substituted by Hal,
T denotes phenyl, triazolyl, thiazolyl, oxazolyl, oxadiazolyl, or pyrazolyl,
R¹ is Hal, —$C_1$-$C_6$-alkyl, O—$C_1$-$C_6$-alkyl, —(CH₂)$_m$—O—$C_1$-$C_6$-alkyl, O—$C_1$-$C_6$-halo-alkyl, —(CH₂)$_m$—O—$C_1$-$C_6$-halo-alkyl, —SO₂—$C_1$-$C_6$-alkyl, —(CH₂)$_m$—SO₂—$C_1$-$C_6$-alkyl, —SO₂—$C_1$-$C_6$-halo-alkyl, —(CH₂)$_m$—SO₂—$C_1$-$C_6$-halo-alkyl, —SO₂-3-8-cycloalkyl, —(CH₂)$_m$—SO₂-3-8-cycloalkyl, cyano or —$C_1$-$C_6$-halo-alkyl,
R² and R²' are independently from one another H, Hal, —$C_1$-$C_6$-alkyl, —O—$C_1$-$C_6$-alkyl, —(CH₂)$_m$—O—$C_1$-$C_6$-alkyl, O—$C_1$-$C_6$-halo-alkyl, —(CH₂)$_m$—O—$C_1$-$C_6$-halo-alkyl, —SO₂—$C_1$-$C_6$-alkyl, —(CH₂)$_m$—SO₂—$C_1$-$C_6$-alkyl, —SO₂—$C_1$-$C_6$-halo-alkyl, —(CH₂)$_m$—SO₂—$C_1$-$C_6$-halo-alkyl, —SO₂-3-8-cycloalkyl, —(CH₂)$_m$—SO₂-3-8-cycloalkyl, —$C_1$-$C_6$-halo-alkyl, or
R¹ and R² are linked to form with the ring T to which they are attached a 7-12-membered fused heterocyclyl or 7-12-membered fused cycloalkyl, each of which may be optionally substituted with 1 to 3 Hal, —$C_1$-$C_6$-halo-alkyl, NO₂, CN, $C_1$-$C_6$-alkyl, —(CH₂)$_m$—O—$C_1$-$C_6$-alkyl, or —O—$C_1$-$C_6$-alkyl,
R³ is $C_1$-$C_6$-alkyl, $C_1$-$C_6$-haloalkyl, —(CH₂)$_m$—O—$C_1$-$C_6$-alkyl, or —(CH₂)$_m$—O—$C_1$-$C_6$-haloalkyl; a 3-8-membered cycloalkyl group, optionally substituted with 1 to 3 substitutents independently selected from Hal, —$C_1$-$C_6$-halo-alkyl, or $C_1$-$C_6$-alkyl; or a 3-8-membered heterocyclic group, optionally substituted with 1 to 3 substituents independently selected from Hal, —$C_1$-$C_6$-halo-alkyl, NO₂, CN, $C_1$-$C_6$-alkyl, —(CH₂)$_m$—O—$C_1$-$C_6$-alkyl, —(CH₂)$_m$—SO₂—$C_1$-$C_6$-alkyl, —SO₂—$C_1$-$C_6$-alkyl, —O—$C_1$-$C_6$-alkyl, —(CH₂)$_m$—O—$C_1$-$C_6$-halo-alkyl, —(CH₂)$_m$—SO₂—$C_1$-$C_6$-halo-alkyl, —SO₂—$C_1$-$C_6$-halo-alkyl, —O—$C_1$-$C_6$-halo-alkyl, —C(O)—$C_1$-$C_6$-alkyl, or —C(O)O—$C_1$-$C_6$-alkyl,
R⁴ denotes H, $C_1$-$C_6$-alkyl, or forms together with R³ a 3-8-membered cycloalkyl ring, optionally substituted with Hal, —$C_1$-$C_6$-halo-alkyl, NO₂, CN, $C_1$-$C_6$-alkyl, —(CH₂)$_m$—O—$C_1$-$C_6$-alkyl, —O—$C_1$-$C_6$-alkyl, —C(O)—$C_1$-$C_6$-alkyl, or —C(O)O—$C_1$-$C_6$-alkyl, and
each m is independently selected from 1, 2, 3, or 4 preferably 1 or 2;
as well as pharmaceutically acceptable salts thereof, or is an enantiomeric mixture of 2 enantiomers in all ratios, and/or as a mixture of diastereoisomers in all ratios.

In relation to compounds of formula (Ia) the following further definitions may apply:

In an embodiment X is an alkylene group having 1 to 4 carbon atoms, optionally substituted with 1 or 2 substituents selected from fluoro or $C_1$-$C_6$-alkyl.

In an embodiment X is selected from methylene or ethylene.

In an embodiment X is methylene.

In an embodiment X is a single bond.

In an embodiment Y is an alkylene group having 1 to 4 carbon atoms, optionally substituted one or two times with $C_3$-$C_8$-cycloalkyl or $C_1$-$C_3$-alkyl.

In an embodiment Y is selected from methylene, ethylene, propylene, isopropylene, or tertbutylene. In an embodiment Y is

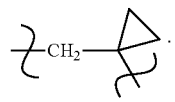

In an embodiment Y is

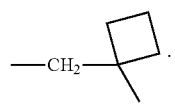

In an embodiment Y is a 3-8-membered cycloalkylene group, or 3-8-membered cycloalkenylene.

In an embodiment Y is a 3-membered cycloalkylene.

In an embodiment Y is

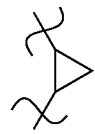

In an embodiment Y is

In an embodiment Y—W is

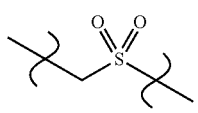

In an embodiment Y—W is

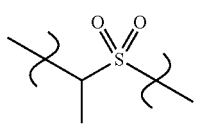

In an embodiment Y—W is

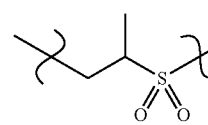

In an embodiment Y—W is

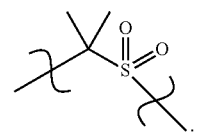

In an embodiment Y—W is

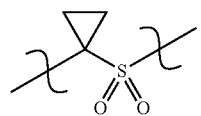

In an embodiment Q is a single bond.

Accordingly the invention contemplates compounds of the following general formulae:

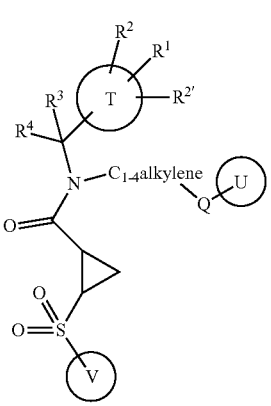
(Ia$^I$)

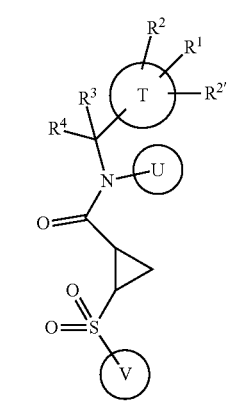
(Ia$^{II}$)

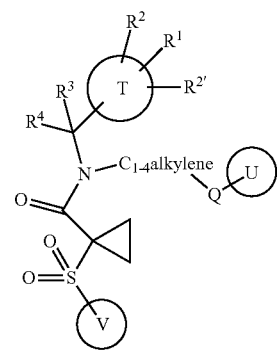
(Ia$^{III}$)

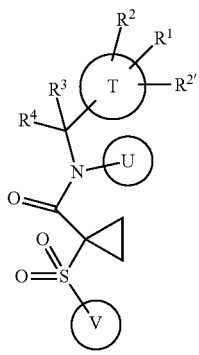
(Ia^IV)

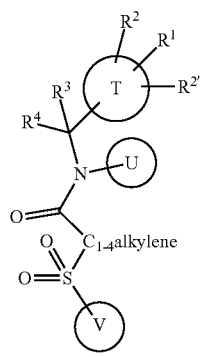
(Ia^V)

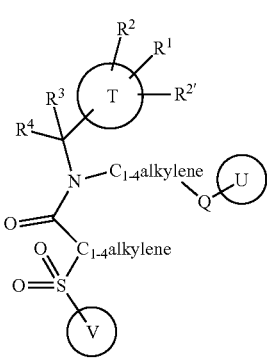
(Ia^VI)

wherein $R^1$, $R^2$, $R^{2'}$, $R^3$ and $R^4$, T, Q, U and V are as defined above for compounds of formula (Ia).

In an embodiment the compound of the invention is a compound of formula (Ia^I).

In an embodiment the compound of the invention is a compound of formula (Ia^II).

In an embodiment the compound of the invention is a compound of formula (Ia^III).

In an embodiment the compound of the invention is a compound of formula (Ia^IV).

In an embodiment the compound of the invention is a compound of formula (Ia^V).

In an embodiment the compound of the invention is a compound of formula (Ia^VI).

In an embodiment the compound of the invention is a compound of formula (Ia^I), (Ia^III), (Ia^VI), wherein Q is a single bond.

In further embodiments the invention contemplates the following general formulae:

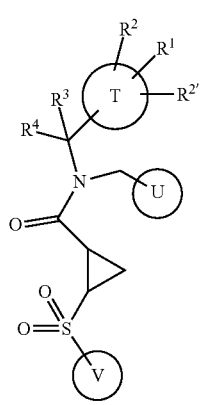
(Ia^Ia)

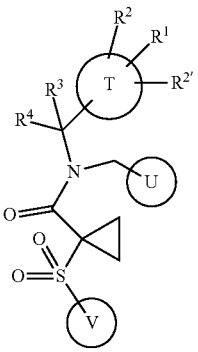
(Ia^IIIa)

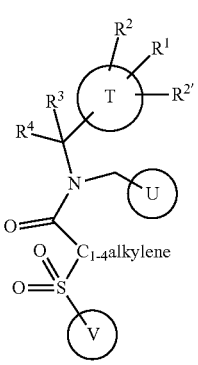
(Ia^VIa)

wherein $R^1$, $R^2$, $R^{2'}$, $R^3$ and $R^4$, T, U and V are as defined above for compounds of formula (Ia).

In an embodiment the compound of the invention is a compound of formula (Ia^Ia).

In an embodiment the compound of the invention is a compound of formula (Ia^IIIa).

In an embodiment the compound of the invention is a compound of formula (Ia^VIa).

In still further embodiments the invention contemplates the following further general formulae:

(Ia<sup>VIa'</sup>)

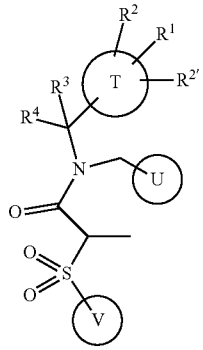

(Ia<sup>VIa''</sup>)

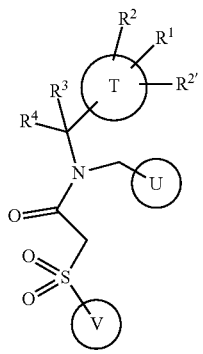

(Ia<sup>VIa'''</sup>)

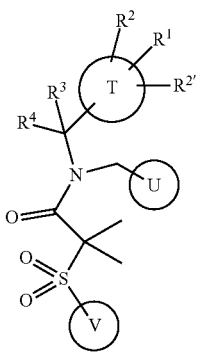

(Ia<sup>VIa''''</sup>)

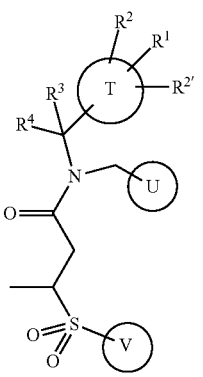

wherein $R^1$, $R^2$, $R^{2'}$, $R^3$ and $R^4$, T, U and V are as defined above for compounds of formula (Ia).

In a further embodiment, where W is a single bond, the invention relates to compounds of formula (Ib) and salts thereof:

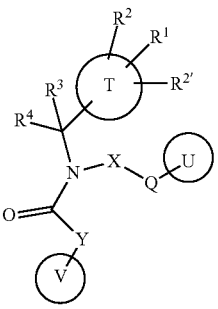

(Ib)

wherein:
X selected from a single bond, an alkylene group having 1 to 6 carbon atoms optionally substituted with 1 or 2 substituents selected from fluoro or $C_1$-$C_6$-alkyl,
Y is a 3-membered cycloalkylene group,
Q is selected from O, NH or a single bond,
V is an aryl group optionally substituted with 1 to 3 substitutents selected from Hal, $NO_2$, CN, $SO_2$—$C_1$-$C_6$ alkyl, $NMe_2$, $C_1$-$C_6$-alkyl, O—$C_1$-$C_6$-alkyl, —$(CH_2)_m$—O—$C_1$-$C_6$-alkyl, —$C_1$-$C_6$-halo-alkyl, O—$C_1$-$C_6$-halo-alkyl or a 5-6-membered heteroaromatic group,
U is cycloalkyl, cycloalkenyl, heterocyclyl or heteroaryl, each of the above groups being optionally substituted with 1 to 3 substitutents selected from Hal, $NO_2$, CN, —$SO_2$—$C_1$-$C_6$-alkyl, —S—$C_1$-$C_6$-alkyl, $NMe_2$, $C_1$-$C_6$-alkyl, —C(O)O—$C_1$-$C_6$-alkyl, O—$C_1$-$C_6$-alkyl, —$(CH_2)_m$—O—$C_1$-$C_6$-alkyl, —$C_1$-$C_6$-halo-alkyl, or a 5-6-membered heteroaromatic group being optionally substituted by Hal,
T denotes phenyl, triazolyl, thiazolyl, oxazolyl, oxadiazolyl, or pyrazolyl,
$R^1$ is Hal, —$C_1$-$C_6$-alkyl, O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, cyano or —$C_1$-$C_6$-halo-alkyl,
$R^2$ and $R^{2'}$ are independently from one another H, Hal, —$C_1$-$C_6$-alkyl, —O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, —$C_1$-$C_6$-halo-alkyl, or
$R^1$ and $R^2$ are linked to form with the ring T to which they are attached a 7-12-membered fused heterocyclyl or 7-12-membered fused cycloalkyl, each of which may be optionally substituted with 1 to 3 Hal, —$C_1$-$C_6$-halo-alkyl, $NO_2$, CN, $C_1$-$C_6$-alkyl, —$(CH_2)_m$—O—$C_1$-$C_6$-alkyl, or —O—$C_1$-$C_6$-alkyl,
$R^3$ is $C_1$-$C_6$-alkyl, $C_1$-$C_6$-haloalkyl, —$(CH_2)_m$—O—$C_1$-$C_6$-alkyl, or —$(CH_2)_m$—O—$C_1$-$C_6$-haloalkyl; a 3-8-membered cycloalkyl group, optionally substituted with 1 to 3 substitutents independently selected from Hal, —$C_1$-$C_6$-halo-alkyl, or $C_1$-$C_6$-alkyl; or a 3-8-membered heterocyclic group, optionally substituted with 1 to 3 substituents independently selected from Hal, —$C_1$-$C_6$-halo-alkyl, $NO_2$, CN, $C_1$-$C_6$-alkyl, —$(CH_2)_m$—O—$C_1$-$C_6$-alkyl, —$(CH_2)_m$—$SO_2$—$C_1$-$C_6$-alkyl, —$SO_2$—$C_1$-$C_6$-alkyl, —O—$C_1$-$C_6$-alkyl, —$(CH_2)_m$—O—$C_1$-$C_6$-halo-alkyl, —$(CH_2)_m$—$SO_2$—$C_1$-$C_6$-halo-alkyl, —$SO_2$—$C_1$-$C_6$-halo-alkyl, —O—$C_1$-$C_6$-halo-alkyl, —C(O)—$C_1$-$C_6$-alkyl, or —C(O)O—$C_1$-$C_6$-alkyl, $R^4$ denotes H, $C_1$-$C_6$-alkyl, or forms together with $R^3$ a 3-8-membered cycloalkyl ring, optionally substituted with Hal, —$C_1$-$C_6$-halo-alkyl, $NO_2$, CN, $C_1$-$C_6$-alkyl, —$(CH_2)_m$—O—$C_1$-$C_6$-alkyl, —O—$C_1$-$C_6$-alkyl, —C(O)—$C_1$-$C_6$-alkyl, or —C(O)O—$C_1$-$C_6$-alkyl, and each m is independently selected from 1, 2, 3, or 4, as well as pharmaceutically acceptable salts thereof, or is an enantiomeric mixture of 2 enantiomers in all ratios, and/or as a mixture of diastereoisomers in all ratios.

In an embodiment Q is a single bond.

In an embodiment Q and X are single bonds.

In an embodiment the present invention contemplates the following further general formulae:

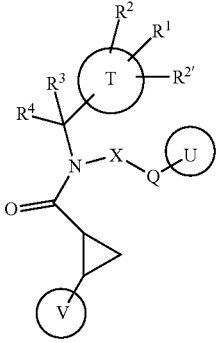

(Ib$^I$)

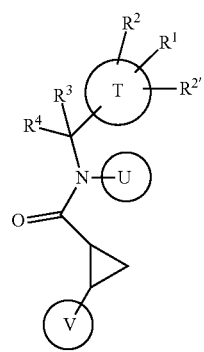

(Ib$^{II}$)

wherein $R^1$, $R^2$, $R^{2'}$, $R^3$ and $R^4$, T, X, Q, U and V are as defined above for compounds of formula (Ib).

With reference to formula (Ib$^I$), the following further definitions may apply:

In an embodiment X is $C_1$-$C_4$ alkylene.

In an embodiment X is methylene, ethylene, propylene or isopropylene,

In an embodiment X is methylene or ethylene.

In an embodiment X is methylene.

In an embodiment the compounds of the invention may be represented by the following general formula (Ib$^{Ia}$):

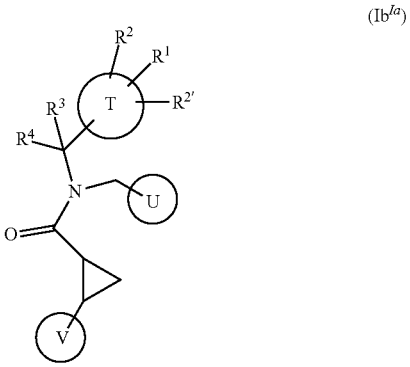

(Ib$^{Ia}$)

In still further embodiments the invention relates to compounds of formula (Ic) and salts thereof:

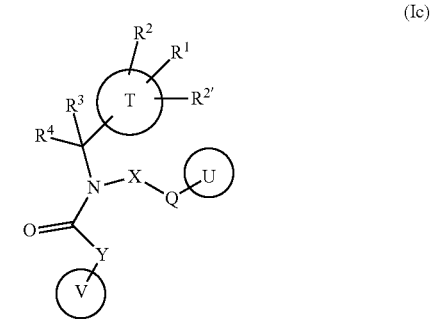

(Ic)

wherein:
X is selected from a single bond, an alkylene group having 1 to 6 carbon atoms optionally substituted with 1 or 2 substituents selected from fluoro or $C_1$-$C_6$-alkyl,
Y is an alkylene group having 1 to 6 carbon atoms,
Q is selected from O, NH or a single bond,
V is an aryl group optionally substituted with 1 to 3 substitutents selected from Hal, $NO_2$, CN, $SO_2$—$C_1$-$C_6$ alkyl, $NMe_2$, $C_1$-$C_6$-alkyl, O—$C_1$-$C_6$-alkyl, —$(CH_2)_m$—O—$C_1$-$C_6$-alkyl, —$C_1$-$C_6$-halo-alkyl, O—$C_1$-$C_6$-halo-alkyl or a 5-6-membered heteroaromatic group,
U is cycloalkyl, cycloalkenyl, heterocyclyl or heteroaryl, each of the above groups being optionally substituted with 1 to 3 substituents selected from Hal, $NO_2$, CN, —$SO_2$—$C_1$-$C_6$-alkyl, —S—$C_1$-$C_6$-alkyl, $NMe_2$, $C_1$-$C_6$-alkyl, —C(O)O—$C_1$-$C_6$-alkyl, O—$C_1$-$C_6$-alkyl, —$(CH_2)_m$—O—$C_1$-$C_6$-alkyl, —$C_1$-$C_6$-halo-alkyl, or a 5-6-membered heteroaromatic group being optionally substituted by Hal,
T is a phenyl, a triazolyl, a thiazolyl, an oxazolyl, an oxadiazolyl, or pyrazolyl group,
$R^1$ is Hal, —$C_1$-$C_6$-alkyl, O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, cyano or —$C_1$-$C_6$-halo-alkyl,
$R^2$ and $R^{2'}$ are independently from one another H, Hal, —$C_1$-$C_6$-alkyl, —O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, —$C_1$-$C_6$-halo-alkyl, or R$^1$ and R$^2$ are linked to form with the ring T to which they are attached a 7-12-membered fused heterocyclyl or 7-12-membered fused cycloalkyl, each of which may be optionally substituted with 1 to 3 Hal, —C$_1$-C$_6$-haloalkyl, NO$_2$, CN, C$_1$-C$_6$-alkyl, —(CH$_2$)$_m$—O—C$_1$-C$_6$-alkyl, or —O—C$_1$-C$_6$-alkyl, R$^3$ is C$_1$-C$_6$-alkyl, C$_1$-C$_6$-haloalkyl, —(CH$_2$)$_m$—O—C$_1$-C$_6$-alkyl, or —(CH$_2$)$_m$—O—C$_1$-C$_6$-haloalkyl; a 3-8-membered cycloalkyl group, optionally substituted with 1 to 3 substitutents independently selected from Hal, —C$_1$-C$_6$-halo-alkyl, or C$_1$-C$_6$-alkyl; or a 3-8-membered heterocyclic group, optionally substituted with 1 to 3 substitutents independently selected from Hal, —C$_1$-C$_6$-halo-alkyl, NO$_2$, CN, C$_1$-C$_6$-alkyl, —(CH$_2$)$_m$—O—C$_1$-C$_6$-alkyl, —(CH$_2$)$_m$—SO$_2$—C$_1$-C$_6$-alkyl, —SO$_2$—C$_1$-C$_6$-alkyl, —O—C$_1$-C$_6$-alkyl, —(CH$_2$)$_m$—O—C$_1$-C$_6$-halo-alkyl, —(CH$_2$)$_m$—SO$_2$—C$_1$-C$_6$-halo-alkyl, —SO$_2$—C$_1$-C$_6$-halo-alkyl, —O—C$_1$-C$_6$-halo-alkyl, —C(O)—C$_1$-C$_6$-alkyl, or —C(O)O—C$_1$-C$_6$-alkyl, R$^4$ denotes H, C$_1$-C$_6$-alkyl, or forms together with R$^3$ a 3-8-membered cycloalkyl ring, optionally substituted with Hal, —C$_1$-C$_6$-halo-alkyl, NO$_2$, CN, C$_1$-C$_6$-alkyl, —(CH$_2$)$_m$—O—C$_1$-C$_6$-alkyl, —O—C$_1$-C$_6$-alkyl, —C(O)—C$_1$-C$_6$-alkyl, or —C(O)O—C$_1$-C$_6$-alkyl, each m is independently selected from 1, 2, 3, or 4, as well as pharmaceutically acceptable salts thereof, or is an enantiomeric mixture of 2 enantiomers in all ratios, and/or as a mixture of diastereoisomers in all ratios.

In an embodiment Q is a single bond.

In an embodiment Q and X are single bonds.

In an embodiment the present invention contemplates the following further general formulae:

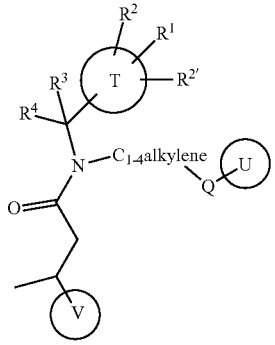

(Ic$^I$)

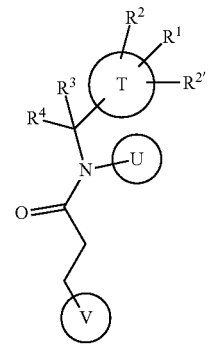

(Ic$^{II}$)

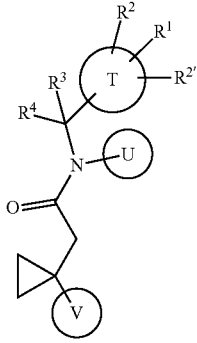

(Ic$^{III}$)

(Ic$^{IV}$)

(Ic$^V$)

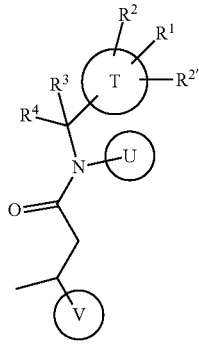

(Ic$^{VI}$)

wherein R$^1$, R$^2$, R$^{2'}$, R$^3$ and R$^4$, T, Q, U and V are as defined above for compounds of formula (Ia).

In an embodiment in relation to formulae (Ic$^I$), (Ic$^{II}$), and (Ic$^{IIII}$) Q is a single bond.

In still a further embodiment the invention contemplates the following further general formula:

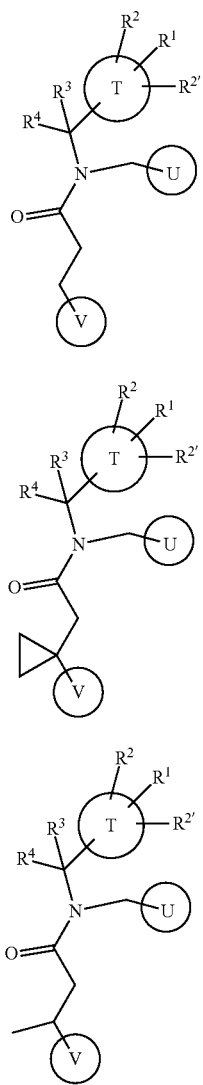

(Ic$^{Ia}$)

(Ic$^{IIa}$)

(Ic$^{IIIa}$)

wherein R$^1$, R$^2$, R$^{2'}$, R$^3$ and R$^4$, T, U and V are as defined above for compounds of formula (Ia).

With reference to Formulae (I), (Ia), (Ib) or (Ic) and each sub formula, the following further definitions may apply:

In an embodiment R$^4$ is H or C$_1$-C$_4$ alkyl.

In an embodiment R$^4$ is H.

In an embodiment R$^4$ is C$_1$-C$_4$ alkyl.

In an embodiment R$^4$ is methyl.

In an embodiment R$^3$ is optionally substituted C$_1$-C$_4$ alkyl, or optionally substituted C$_3$-C$_6$ cycloalkyl.

In an embodiment R$^3$ and R$^4$ are independently C$_1$-C$_3$-alkyl.

In an embodiment R$^3$ and R$^4$ are both methyl.

In an embodiment R$^4$ is hydrogen and R$^3$ is tetrahydrofuranyl, azetidinyl, piperadinyl, or tetrahydropyranyl.

In an embodiment, the present invention provides compounds of Formulae (I), (Ia), (Ib) or (Ic) and each sub formula wherein R$^4$ denotes H or Me and R$^3$ is selected from the following groups:

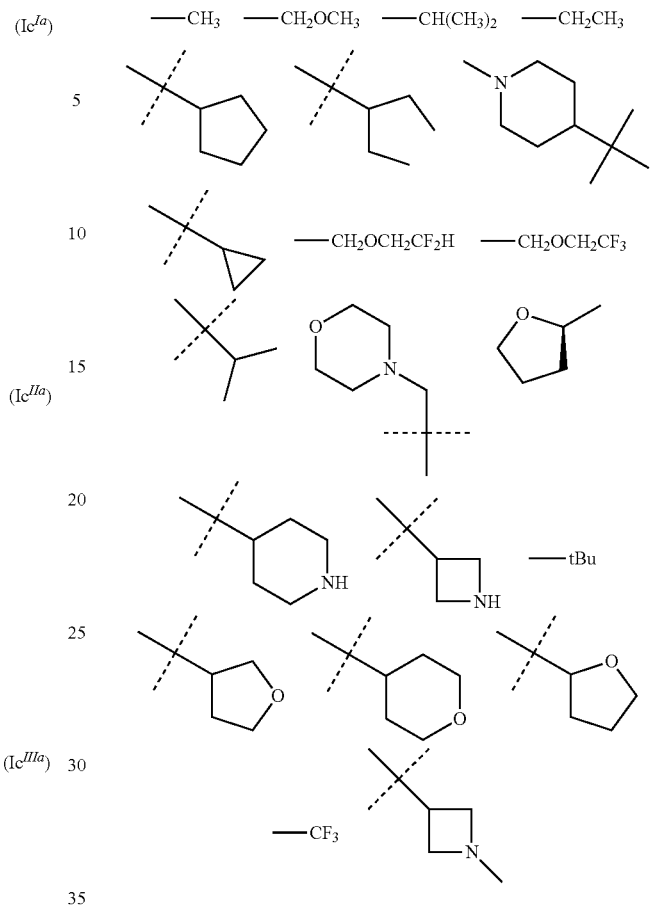

wherein the above-mentioned groups may be further substituted by 1 to 3 substituents independently selected from Hal, —C$_1$-C$_6$-halo-alkyl, NO$_2$, CN, C$_1$-C$_6$-alkyl, —(CH$_2$)$_m$—O—C$_1$-C$_6$-alkyl, —(CH$_2$)$_m$—SO$_2$—C$_1$-C$_6$-alkyl, —SO$_2$—C$_1$-C$_6$-alkyl, —O—C$_1$-C$_6$-alkyl, —(CH$_2$)$_m$—O—C$_1$-C$_6$- halo-alkyl, —(CH$_2$)$_m$—SO$_2$—C$_1$-C$_6$-halo-alkyl, —SO$_2$—C$_1$-C$_6$-halo-alkyl, or —O—C$_1$-C$_6$-halo-alkyl, or R$^4$ forms together with R$^3$ a 3 membered cycloalkyl ring.

In an embodiment with specific reference to compounds of formula (Ia), (Ib), (Ic) and sub formula thereof, R$^4$ is H and R$^3$ is C$_1$-C$_6$ alkyl, cyclopropyl, or a 3-8-membered heterocyclic group.

In an embodiment with specific reference to compounds of formula (Ia), (Ib), (Ic) and sub formula thereof, R$^4$ is H and R$^3$ is C$_1$-C$_6$ alkyl or cyclopropyl.

In an embodiment with specific reference to compounds of formula (Ia), (Ib), (Ic) and sub formula thereof, R$^4$ is H and R$^3$ is cyclopropyl.

In an embodiment with specific reference to compounds of formula (Ia), (Ib), (Ic) and sub formula thereof, R$^4$ is H and R$^3$ is ethyl.

In an embodiment with specific reference to compounds of formula (Ia), (Ib), (Ic) and sub formula thereof, R$^4$ is H and R$^3$ is isopropyl.

In an embodiment with specific reference to compounds of formula (Ia), (Ib), (Ic) and sub formula thereof, R$^4$ is H and R$^3$ is methyl.

In an embodiment U is a 5-6-membered cycloalkyl group, a 5-12-membered heterocyclyl or a 5-6 membered heteroaryl, each of the above groups being optionally substituted with 1 to 3 substituents selected from Hal, NO$_2$, CN, SO$_2$, NMe$_2$, C$_1$-C$_6$-alkyl, O—C$_1$-C$_6$-alkyl, —(CH$_2$)$_m$—O—C$_1$-C$_6$-alkyl, —C(O)O—C$_1$-C$_6$-alkyl, —SO$_2$—C$_1$-C$_6$-alkyl, —S—C$_1$-C$_6$-alkyl, —C$_1$-C$_6$-halo-alkyl, or a 5-6-membered heteroaromatic group being optionally substituted by Hal.

In an embodiment U is selected from pyridinyl, pyrazinyl, pyridazinyl, pyrimidinyl, imidazolyl, pyrazolyl, tetrahydropyranyl, cyclohexyl, 8-azabicyclo[3.2.1]octan-3-yl, triazolyl and piperidinyl, each of the above groups being optionally substituted with 1 to 3 substitutents selected from Hal, NO$_2$, CN, SO$_2$, NMe$_2$, C$_1$-C$_6$-alkyl, O—C$_1$-C$_6$-alkyl, —(CH$_2$)$_m$—O—C$_1$-C$_6$-alkyl, —C(O)O—C$_1$-C$_6$-alkyl, —SO$_2$—C$_1$-C$_6$-alkyl, —S—C$_1$-C$_6$-alkyl, —C$_1$-C$_6$-haloalkyl, or a 5-6-membered heteroaromatic group being optionally substituted by Hal.

In an embodiment U is selected from pyridinyl, pyridazinyl and pyrazolyl, each of the above groups being optionally substituted with 1 to 3 substitutents selected from CF$_3$, —SO$_2$—C$_1$-C$_6$-alkyl, C$_1$-C$_6$-alkyl or Hal.

In an embodiment, U is selected from pyridinyl, pyridazinyl and pyrazolyl, each of the above groups being optionally substituted with a substitutent selected from CF$_3$, —SO$_2$Me, methyl or F.

In a further embodiment, with specific reference to compounds of Formula (I), (Ia), (Ib), (Ic) and sub formula thereof the present invention provides wherein U is selected from:

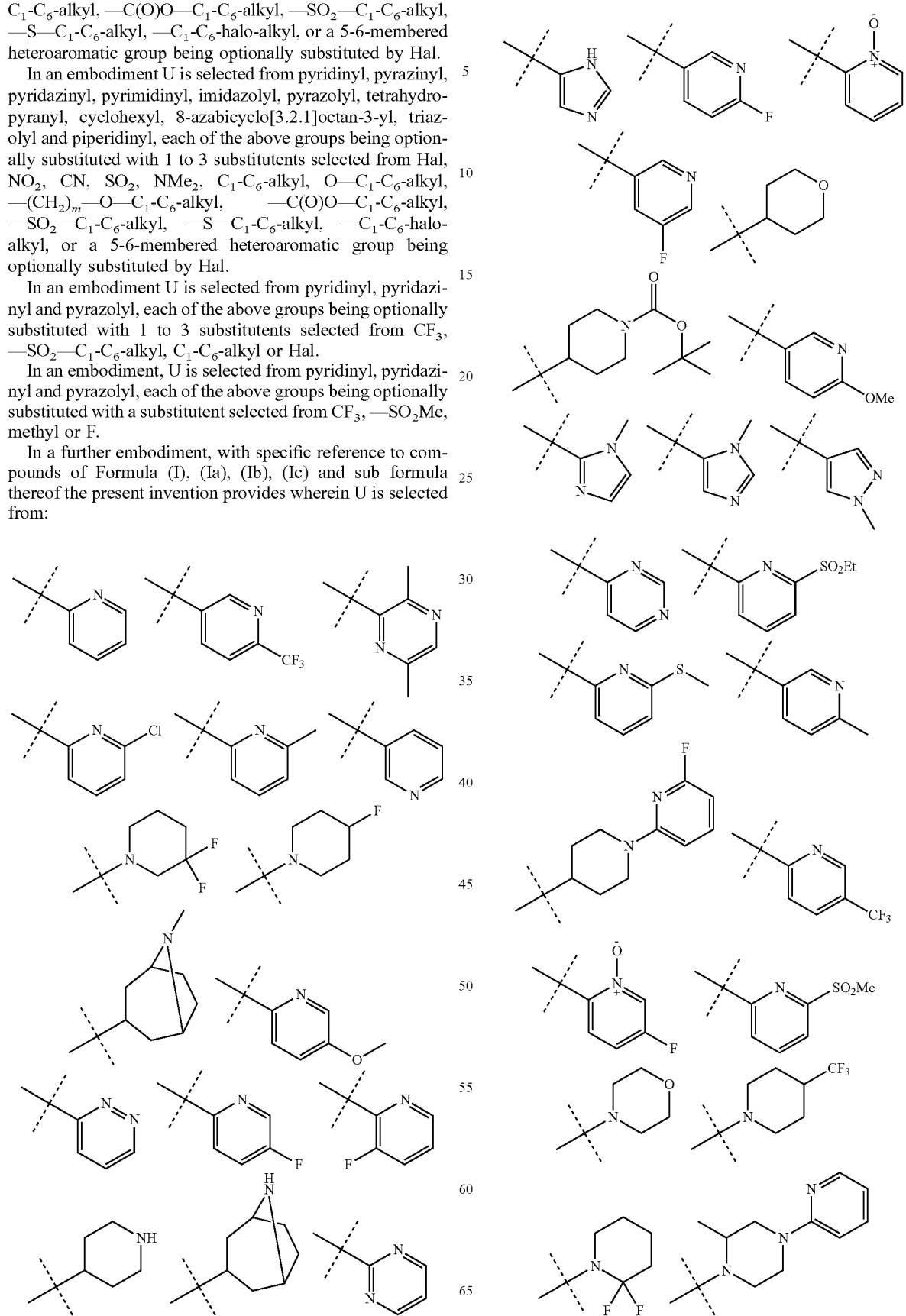

-continued

-continued

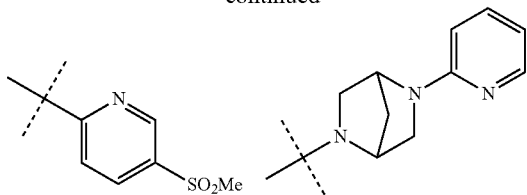

In a further embodiment, with specific reference to compounds of Formula (I), (Ia), (Ib), (Ic) and sub formula thereof the present invention provides wherein U is selected from:

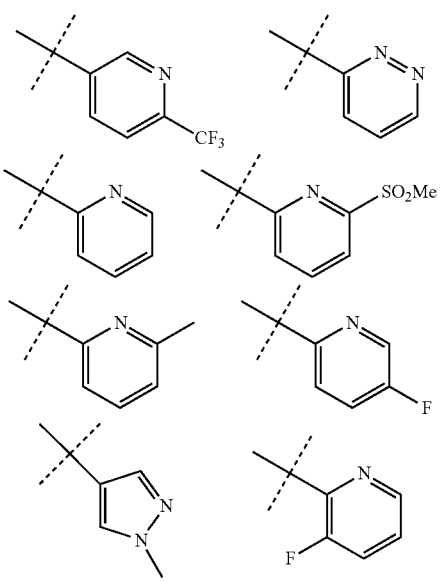

In an embodiment V is an aryl group optionally substituted with 1 to 3 substitutents selected from Hal, —$C_1$-$C_6$-halo-alkyl, O—$C_1$-$C_6$-halo-alkyl or $SO_2$— $C_1$-$C_6$ alkyl.

In an embodiment V is a phenyl group optionally substituted with 1 to 3 substitutents selected from Hal, $NO_2$, CN, $SO_2$—$C_1$-$C_6$ alkyl, $NMe_2$, $C_1$-$C_6$-alkyl, O—$C_1$-$C_6$-alkyl, —$(CH_2)_m$—O—$C_1$-$C_6$-alkyl, —$C_1$-$C_6$-halo-alkyl, O—$C_1$-$C_6$-halo-alkyl or a 5-6-membered heteroaromatic group.

In an embodiment V is a phenyl group optionally substituted with 1 to 3 substitutents selected from Hal, —$C_1$-$C_6$-halo-alkyl, O—$C_1$-$C_6$-halo-alkyl or $SO_2$—$C_1$-$C_6$ alkyl.

In an embodiment V is a phenyl group optionally substituted with 1 or 2 substituents selected from F, Cl, —$CF_3$, —$OCF_3$, —$OCHF_2$ or —$SO_2Me$.

In an embodiment V is a phenyl group optionally substituted by F.

In a further embodiment, with specific reference to compounds of Formula (I), (Ia), (Ib), (Ic) and sub formula thereof the present invention provides wherein V is selected from:

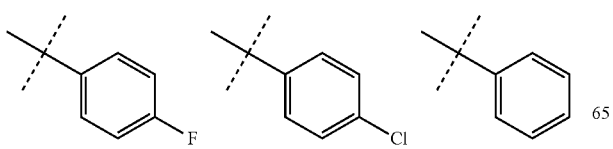

-continued

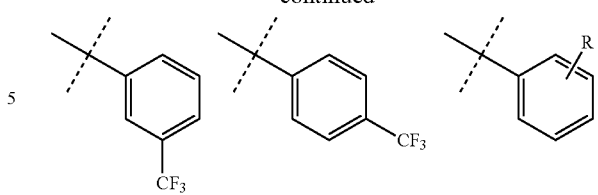

Wherein R denotes Hal, $NO_2$, CN, $SO_2$—$C_1$-$C_6$ alkyl, $NMe_2$, $C_1$-$C_6$-alkyl, O—$C_1$-$C_6$-alkyl, —$(CH_2)_m$—O—$C_1$-$C_6$-alkyl, $CF_3$, or a 5-6-membered heteroaromatic group.

In a further embodiment, with specific reference to compounds of Formula (I), (Ia), (Ib), (Ic) and sub formula thereof the present invention provides wherein V is selected from:

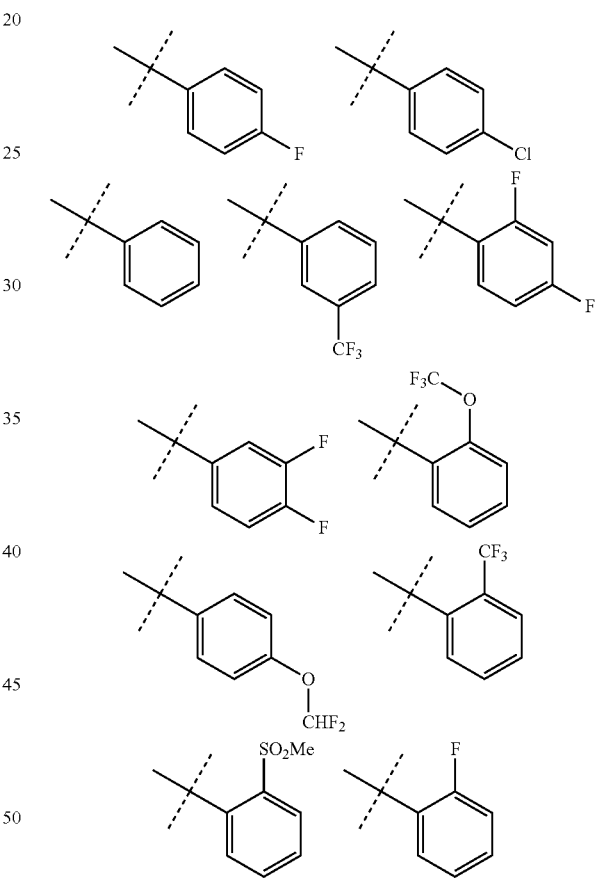

In a further embodiment, with specific reference to compounds of Formula (I), (Ia), (Ib), (Ic) and sub formula thereof the present invention provides wherein V is selected from:

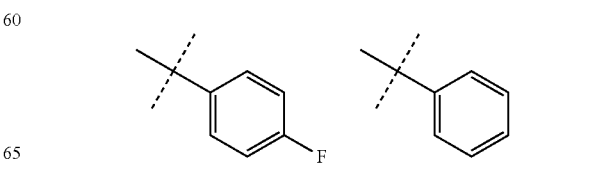

In an embodiment T is phenyl, triazolyl, oxadiazolyl or diazolyl.

In an embodiment T is phenyl.

In an embodiment $R^1$ is O—$C_1$-$C_6$-alkyl, Hal, —(CH$_2$)$_m$—O—$C_1$-$C_6$-alkyl, —$C_1$-$C_6$-alkyl, O—$C_1$-$C_6$-halo-alkyl, —SO$_2$—$C_1$-$C_6$-alkyl, —$C_1$-$C_6$-halo-alkyl, —SO$_2$-3-8-cycloalkyl, or cyano, in which m is 1.

In an embodiment $R^2$ and $R^{2'}$ are H or Hal.

In an embodiment $R^2$ is H or Hal and $R^{2'}$ is H.

In an embodiment $R^1$ is O—$C_1$-$C_6$-alkyl, Hal, —(CH$_2$)$_m$—O—$C_1$-$C_6$-alkyl, —$C_1$-$C_6$-alkyl, O—$C_1$-$C_6$-halo-alkyl, —SO$_2$—$C_1$-$C_6$-alkyl, —$C_1$-$C_6$-halo-alkyl, —SO$_2$-3-8-cycloalkyl, or cyano, in which m is 1, $R^2$ is H or Hal and $R^{2'}$ is H.

In an embodiment $R^1$ and $R^2$ are linked to form with the ring T to which they are attached a dihydrobenzofuranyl, an indanyl,

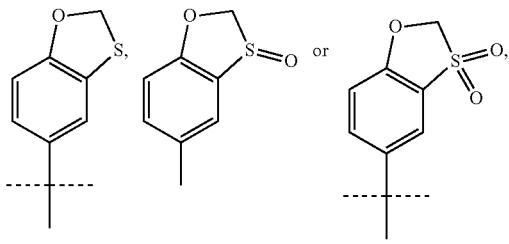

each of these groups being optionally substituted with 1 to 3 Hal, —$C_1$-$C_6$-halo-alkyl, NO$_2$, CN, $C_1$-$C_6$-alkyl, —(CH$_2$)$_m$—O—$C_1$-$C_6$-alkyl, or —O—$C_1$-$C_6$-alkyl.

In an embodiment $R^1$ and $R^2$ are linked to form with the ring T to which they are attached a dihydrobenzofuranyl, an indanyl,

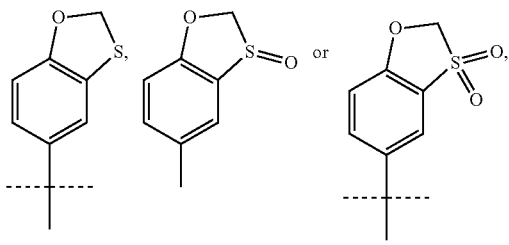

each of these groups being optionally substituted by 1 to 3 —$C_1$-$C_6$-alkyl.

In an embodiment T is phenyl, triazolyl, oxadiazolyl or diazolyl; $R^1$ is O—$C_1$-$C_6$-alkyl, Hal, —(CH$_2$)$_m$—O—$C_1$-$C_6$-alkyl, —$C_1$-$C_6$-alkyl, O—$C_1$-$C_6$-halo-alkyl, —SO$_2$—$C_1$-$C_6$-alkyl, —$C_1$-$C_6$-halo-alkyl, —SO$_2$-3-8-cycloalkyl, or cyano, in which m is 1; $R^2$ is H or Hal and $R^{2'}$ is H; or $R^1$ and $R^2$ are linked to form with the ring T to which they are attached a dihydrobenzofuranyl, an indanyl,

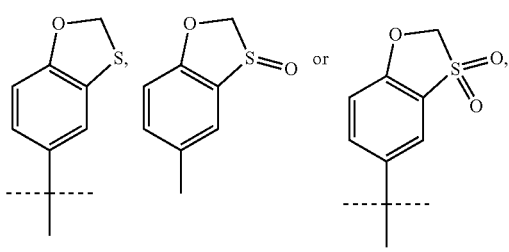

each of these groups being optionally substituted by 1 to 3 —$C_1$-$C_6$-alkyl.

In an embodiment T is phenyl, $R^1$ is O—$C_1$-$C_6$-halo-alkyl, —SO$_2$—$C_1$-$C_6$-alkyl or Hal, and $R^2$ and $R^{2'}$ are H; or $R^1$ and $R^2$ are linked to form with the ring T to which they are attached

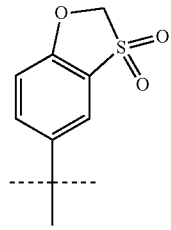

which is optionally substituted with 1 or 2 —$C_1$-$C_6$-alkyl.

In a further embodiment, with specific reference to compounds of Formula (I), (Ia), (Ib), (Ic) and sub formula thereof the present invention provides wherein the group

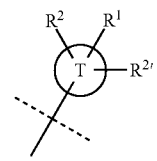

is selected from:

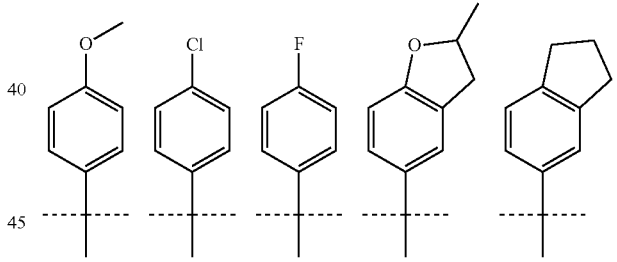

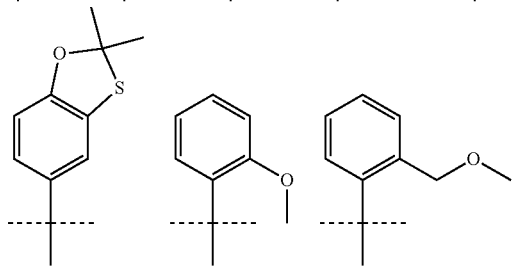

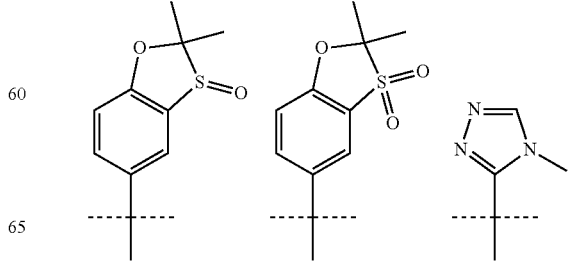

-continued
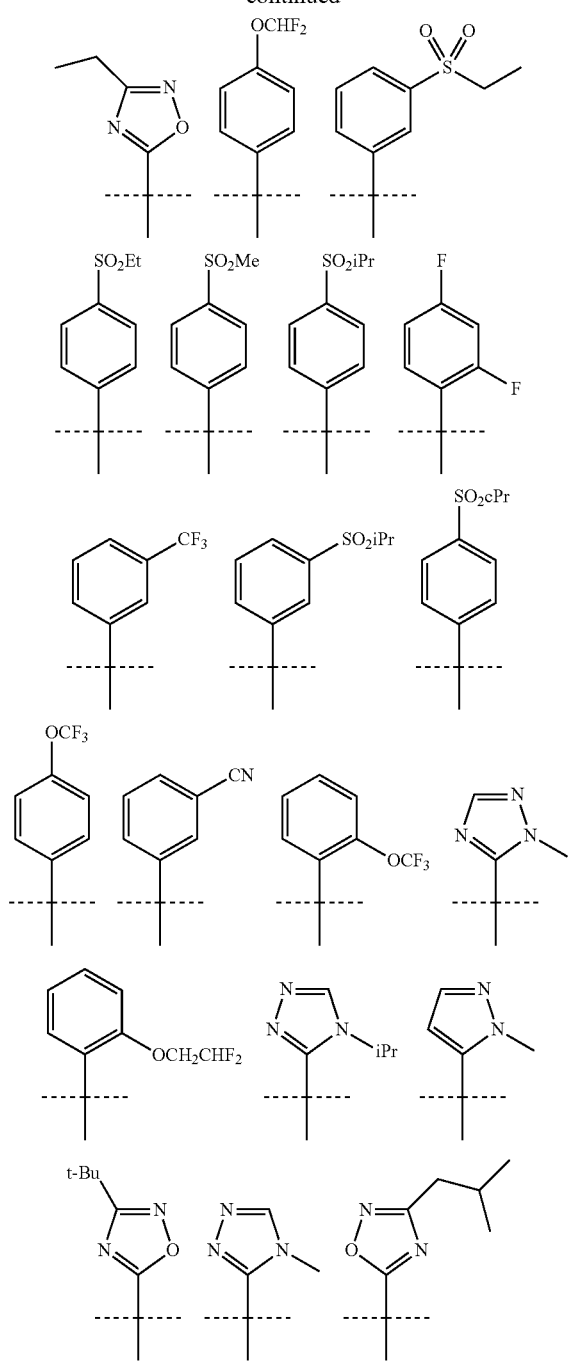
In a further embodiment, with specific reference to compounds of Formula (I), (Ia), (Ib), (Ic) and sub formula thereof the present invention provides wherein the group
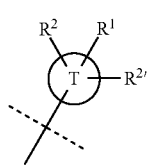
is selected from:
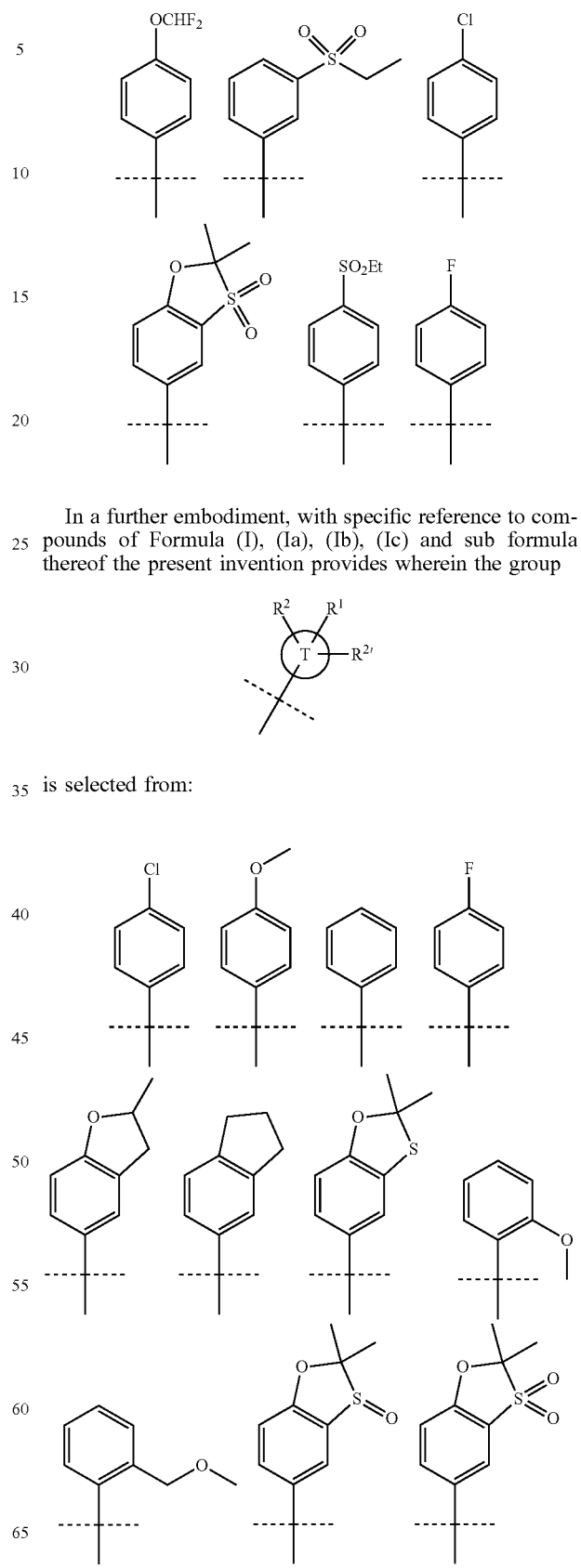
In a further embodiment, with specific reference to compounds of Formula (I), (Ia), (Ib), (Ic) and sub formula thereof the present invention provides wherein the group
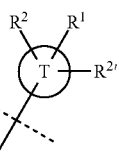
is selected from:

-continued

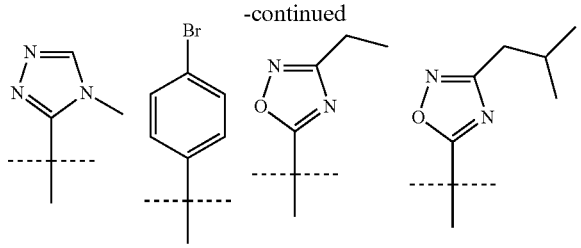

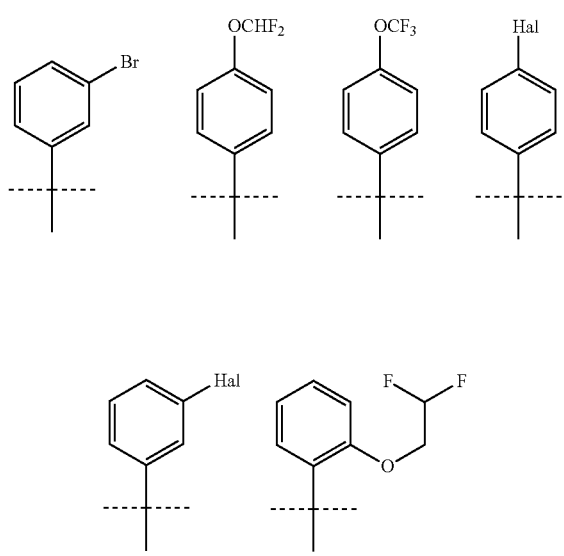

In an embodiment, T is a phenyl ring wherein at least one of $R^1$, $R^2$ or $R^{2'}$ is in para position with regard to the rest of the molecule.

In an embodiment, T is a phenyl ring wherein at least one of $R^1$, $R^2$ or $R^{2'}$ is in meta position with regard to the rest of the molecule.

In an embodiment, T is a phenyl ring wherein at least one of $R^1$, $R^2$ or $R^{2'}$ is in ortho position with regard to the rest of the molecule.

In one aspect, the present invention provides compounds of Formula (I) and related Formulae wherein
Hal preferably denotes F, Cl or Br, most preferably F, and/or
A 3-8-membered cycloalkyl group preferably is a cyclopropyl, a cyclobutyl, or a cyclopentyl, and/or
A 3-8-membered cycloalkylene group preferably is cyclopropylene, a cyclobutylene, or a cyclopentylene, and/or
A 3-8-membered heterocyclic group preferably has 1 to 3 carbon atoms which is replaced by a group selected from O, S, N, SO, SO$_2$, CO. A 3-8-membered heterocyclic group preferably denotes one of the following groups:

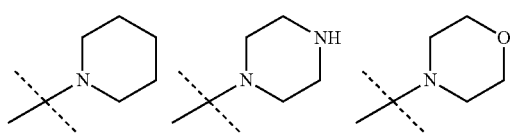

and/or
A 7-12 membered heterocyclic ring preferably denotes a bicyclic ring having 7 to 12 carbon atoms wherein the 2 rings are fused or bridged, and wherein 1 to 3 carbon atoms may be replaced by a group selected from O, S, N, SO, SO$_2$, CO. A 7-12 membered heterocyclic ring preferably denotes one of the following groups:

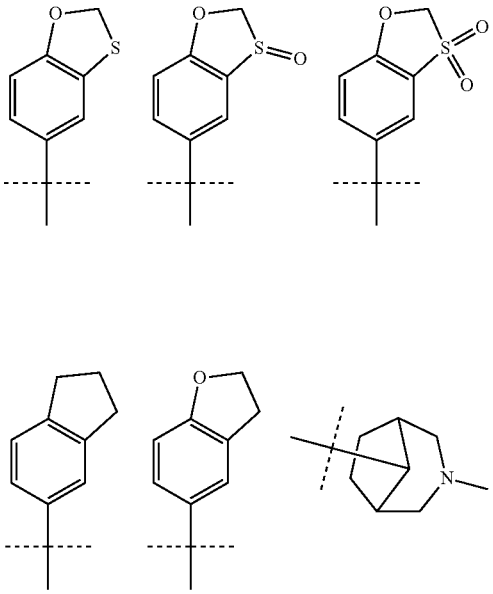

and/or
A 5-6-membered heteroaromatic group denotes an aromatic ring having 5 or 6 members and containing 1 to 3 heteroatoms selected from N, O or S. A 5-6-membered heteroaromatic group preferably denotes one of the following groups:

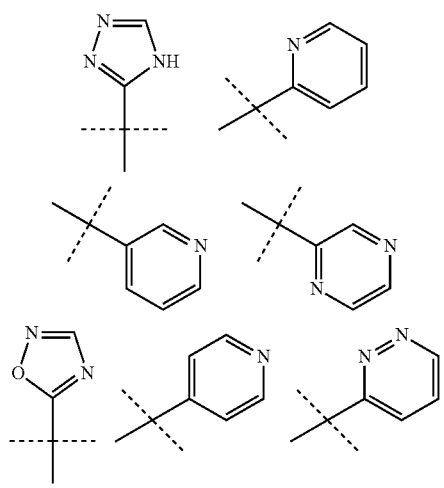

wherein these groups may be substituted according to the definitions provided above, and/or
A $C_1$-$C_6$-halo-alkyl denotes a linear or branched alkyl having 1 to 6 carbon atom wherein 1 to 6H atom is replaced by a halogen, preferably a F atom.

In another aspect, the present invention provides compounds of Formula (II):

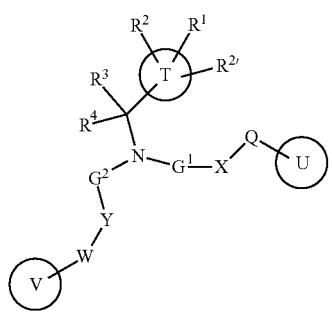

(II)

Wherein
G¹ denotes a single bond,
G² denotes a CO group,
X is selected from a single bond, an alkylene group having 1 to 6 carbon atoms optionally substituted with 1 or 2 substituents selected from fluoro or $C_1$-$C_6$-alkyl,
Y is selected from an alkylene group having 1 to 6 carbon atoms optionally substituted one or two times with $C_3$-$C_8$-cycloalkyl or $C_1$-$C_3$-alkyl; or a 3-8-membered cycloalkylene group,
Q is selected from O, NH or a single bond,
W is selected from SO, $SO_2$ or a single bond,
U is cycloalkyl, cycloalkenyl, heterocyclyl or heteroaryl, each of the above groups being optionally substituted with 1 to 3 substitutents selected from Hal, $NO_2$, CN, —$SO_2$—$C_1$-$C_6$-alkyl, —S—$C_1$-$C_6$-alkyl, $NMe_2$, $C_1$-$C_6$-alkyl, —C(O)O—$C_1$-$C_6$-alkyl, O—$C_1$-$C_6$-alkyl, —$(CH_2)_m$—O—$C_1$-$C_6$-alkyl, —$C_1$-$C_6$-halo-alkyl, or a 5-6-membered heteroaromatic group being optionally substituted by Hal,
V is an aryl group optionally substituted with 1 to 3 substitutents selected from Hal, $NO_2$, CN, $SO_2$—$C_1$-$C_6$ alkyl, $NMe_2$, $C_1$-$C_6$-alkyl, O—$C_1$-$C_6$-alkyl, —$(CH_2)_m$—O—$C_1$-$C_6$-alkyl, —$C_1$-$C_6$-halo-alkyl, O—$C_1$-$C_6$-halo-alkyl or a 5-6-membered heteroaromatic group,
T denotes phenyl, triazolyl, thiazolyl, oxazolyl, oxadiazolyl, or pyrazolyl,
$R^1$ is H, Hal, —$C_1$-$C_6$-alkyl, O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, cyano or —$C_1$-$C_6$-halo-alkyl,
$R^2$ and $R^{2'}$ are independently from one another H, Hal, —$C_1$-$C_6$-alkyl, —O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, —$C_1$-$C_6$-halo-alkyl, or
$R^1$ and $R^2$ are linked to form with the ring T to which they are attached a 7-12-membered fused heterocyclyl or 7-12-membered fused cycloalkyl, and optionally substituted with 1 to 3 Hal, —$C_1$-$C_6$-halo-alkyl, $NO_2$, CN, a linear or branched alkyl group having 1 to 6 carbon atoms, —$(CH_2)_m$—O—$C_1$-$C_6$-alkyl, or —O—$C_1$-$C_6$-alkyl,
$R^3$ is $C_1$-$C_6$-alkyl,
$R^4$ is $C_1$-$C_6$-alkyl,
m is selected from 1, 2, 3 or 4, preferably 1 or 2,
Hal is F, Cl, Br, or I,
wherein -$G^2$-Y—W together is at least 3 atoms in length, as well as pharmaceutically acceptable salts thereof, or is an enantiomeric mixture of 2 enantiomers in all ratios, and/or as a mixture of diastereoisomers in all ratios.

In an embodiment $R^3$ is $C_1$-$C_3$-alkyl.
In an embodiment $R^4$ is $C_1$-$C_3$-alkyl.
In an embodiment $R^3$ and $R^4$ are $C_1$-$C_3$-alkyl.
In an embodiment $R^3$ is methyl.
In an embodiment $R^4$ is methyl.
In an embodiment $R^3$ and $R^4$ are methyl.
In some embodiments $G^1$, $G^2$, X, Y, Q, W, U, V, T, $R^1$, $R^2$, $R^{2'}$, m and Hal are as defined above for a compound of Formula (I), (Ia), (Ib) or (Ic).

In an embodiment with specific reference to formula (II) $R^3$ and $R^4$ are methyl and T is phenyl and $R^1$, $R^2$, and $R^{2'}$ are all H.

In other aspects, in the kit or set, pharmaceutical composition, method or use of the present invention described above a compound of Formula (II) may be present or used instead of a compound of Formula (I).

"Alkyl" refers to monovalent alkyl groups which may be straight chained or branched. In certain embodiments an alkyl group has 1 to 6 carbon atoms (i.e., $C_1$-$C_6$-alkyl). In certain embodiments an alkyl group has 1 to 4 carbon atoms (i.e., $C_1$-$C_4$-alkyl). In certain embodiments an alkyl group has 1 to 3 carbon atoms (i.e., $C_1$-$C_3$-alkyl). Examples of such alkyl groups include methyl, ethyl, n-propyl, iso-propyl, n-butyl, iso-butyl, n-hexyl, and the like.

"Alkylene" refers to divalent alkyl groups which may be straight chained or branch chained. In certain embodiments the alkenylene group has 1 to 6 carbon atoms. In certain embodiments 1 to 4 carbon atoms. In certain other embodiments 1 to 3 carbon atoms. In still further embodiments 1 or 2 carbon atoms. Examples of such alkylene groups include methylene (—$CH_2$—), ethylene (—$CH_2CH_2$—), and the propylene isomers (e.g., —$CH_2CH_2CH_2$— and —$CH(CH_3)CH_2$—), and the like.

"Aryl" refers to an aromatic carbocyclic group having a single ring (eg. phenyl) or multiple condensed rings (eg. naphthyl or anthryl), preferably having from 6 to 14 carbon atoms. Examples of aryl groups include phenyl, naphthyl and the like.

"Cycloalkyl" refers to cyclic alkyl groups having a single cyclic ring or multiple condensed or fused rings, preferably incorporating 3 to 12 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, indanyl, 1,2,3,4-tetrahydronapthalenyl and the like.

"Cycloalkenyl" refers to cyclic alkenyl groups having a single cyclic ring or multiple condensed or fused rings, and at least one point of internal unsaturation, preferably incorporating 3 to 8 carbon atoms. Examples of suitable cycloalkenyl groups include, for instance, cyclobut-2-enyl, cyclopent-3-enyl, cyclohex-4-enyl, cyclooct-3-enyl, indenyl and the like.

"Hal" or "halogen" refers to fluoro, chloro, bromo and iodo.

"Heteroaryl" or "Heteroaromatic" refers to a monovalent aromatic heterocyclic group which fulfils the Hückel criteria for aromaticity (ie. contains $4n+2\pi$ electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl).

"Heterocyclyl" or "Heterocyclic" refers to a monovalent saturated or unsaturated group having a single ring or multiple condensed or fused rings, preferably from 1 to 8 carbon atoms and from 1 to 4 hetero atoms selected from nitrogen, sulfur, SO, $SO_2$, oxygen, selenium or phosphorous within the ring. In one embodiment, the heteroatoms are selected from nitrogen, sulfur, SO, $SO_2$ and oxygen.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are nontoxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures in all ratios, including racemic mixtures, thereof. The compounds may also therefore appear as an enantiomerically enriched mixture of two enantiomers in all ratios, and/or as a mixture of diastereoisomers in all ratios. Such isomers may be prepared by asymmetric synthesis, for example using chiral intermediates, or mixtures may be resolved by conventional methods, eg., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

It would be appreciated that in certain embodiments a hydrogen atom may be replaced with an isotope of hydrogen. For example, deuterium may be used to replace a metabolically labile hydrogen to improve the pharmacokinetics. Alternatively, tritium may be incorporated into a compound for diagnostic or analytical purposes, including but not limited to biodistribution studies.

"Therapeutically effective amount" means the amount of a compound that, when administered to a subject for treating a disease, is sufficient to effect such treatment for the disease. The "therapeutically effective amount" includes that amount of a compound or composition that will elicit the biological or medical response of a subject that is being sought by a medical doctor or other clinician. The "therapeutically effective amount" can vary depending on the compound, the disease and its severity, and the age, weight, etc., of the subject to be treated.

"Preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term "prophylaxis" is related to "prevention", and refers to a measure or procedure the purpose of which is to prevent, rather than to treat or cure a disease.

"Treating" or "treatment" of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

"Compounds of the present invention", and equivalent expressions, are meant to embrace compounds of the Formula(e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

The inhibition data shown for the compounds of the list below was calculated using the steady state current amplitude at the end of the depolarising pulse in patch clamp evaluations (as described in the Biology Protocols: 1. Electrophysiology).

GENERAL DESCRIPTION OF CHEMISTRY

Figure 1:
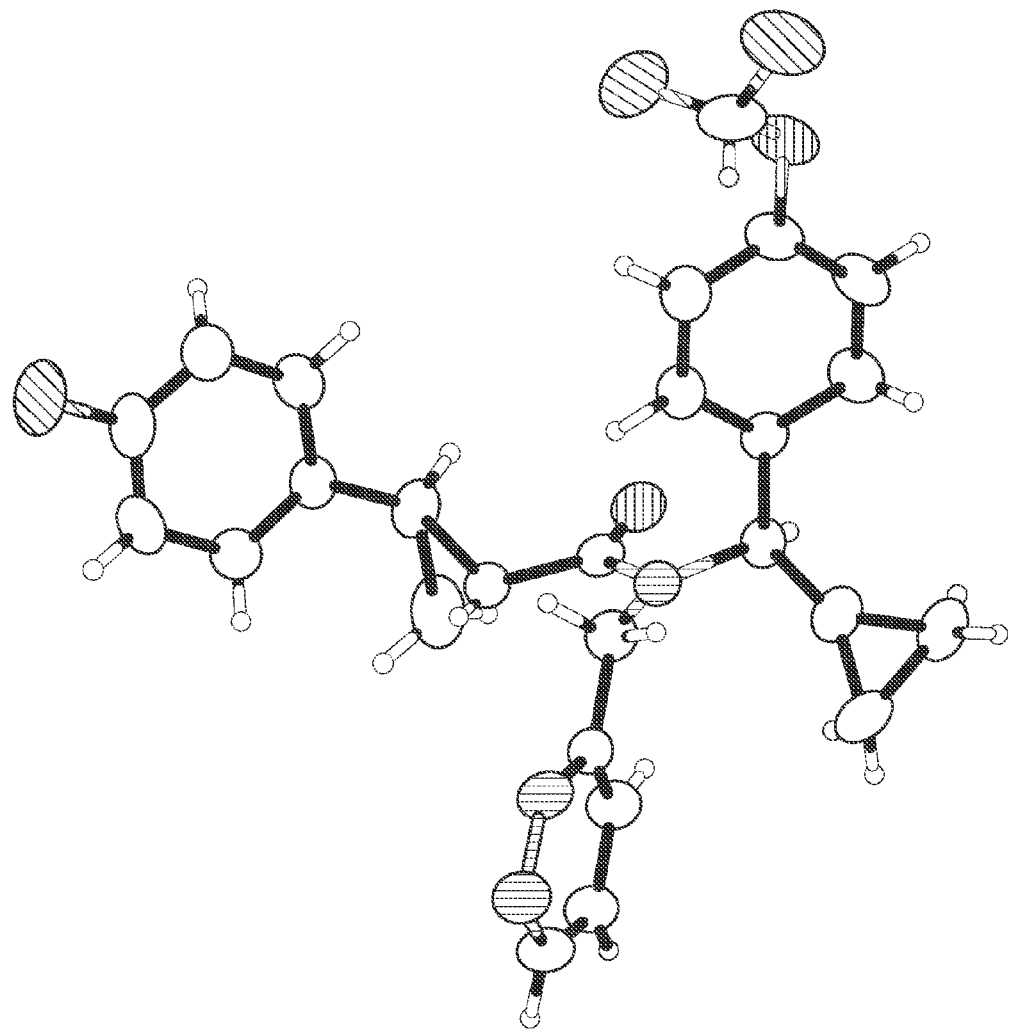
FIG. 1 depicts the crystal structure of (1R,2R)-2-(4-Fluoro-phenyl)-cyclopropanecarboxylic acid [(R)-cyclopropyl-(4-difluoromethoxy-phenyl)-methyl]-pyridazin-3-ylmethyl-amide.

Compounds of Formula (I) can be made by the reaction of the compounds of Formula 5, wherein $R^1$, $R^2$, $R^{2'}$, $R^3$, $R^4$, $G^1$, X, Q, T and U are as above defined, with a compound of Formula 8, wherein $G^1$, Y, W and V are as above defined, and wherein LG denotes a suitable leaving group, as depicted in scheme 1. LG preferably denotes an halogen, preferably chlorine or bromine, a sulfonate, or denotes an activated acid derivative obtained by the reaction of a carboxylic acid in the presence of an amide coupling agent. The amide coupling agents include EDCI, BOP, PyBOP, HOBt, HATU, T3P, DCC. They can be used in a suitable solvent, as for example dichloromethane or dimethylformamide at room temperature. Under preferred conditions, the secondary amines 5 is converted to compounds of Formula (I) by reaction with an activated acid such as an acid chloride, in dichloromethane at room temperature, or a mixed anhydride or a N-succinimide ester in ethanol at room temperature or by reaction with an acid in the presence of an amide coupling reagent selected from EDCI, BOP, PyBOP, HOBt, HATU, T3P, DCC in dichloromethane or dimethylformamide at room temperature.

Alternatively, compounds of Formula (I) can be synthesised by reacting a compound of Formula 7, wherein $R^1$, $R^2$, $R^{2'}$, $R^3$, $R^4$, $G^2$, Y, W, T and V are as above defined, with a compound of Formula 9, wherein $G^1$, X, Q, U are as above define and wherein LG denotes a suitable leaving group. Examples of such alkanes having LG groups are alkyl halides or alkyl sulfonates. The reaction of compounds of Formula 7 with compounds of Formula 9 is preferably performed in the presence of a base such as sodium hydride, potassium tert-butoxide, potassium carbonate preferably in dimethylformamide or acetonitrile. The temperature of the reaction is between room temperature and 100° C., preferably between 20 and 60° C. Optionally, a phase transfer catalyst, such as tetra-n-butylammonium bromide can be used. Preferred conditions are the use of acetone or acetonitrile with heating at 45-100° C.

Scheme 1:

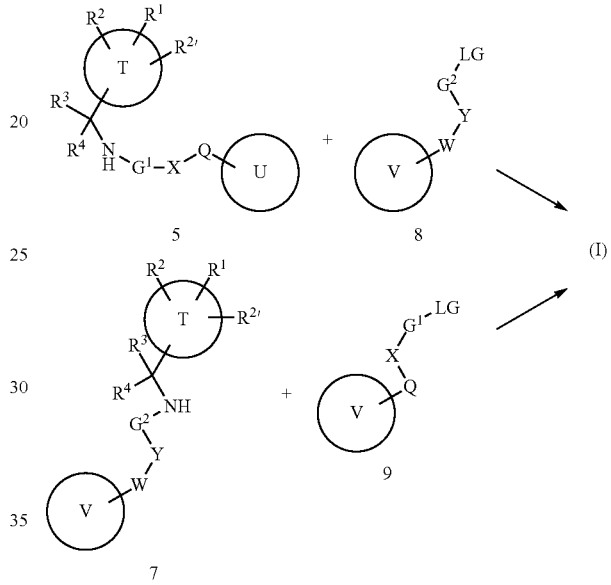

When $R^4$ is H, the compounds of Formula 5 can be synthesised by reacting ketones 1, wherein $R^1$, $R^2$, $R^{2'}$, $R^3$ and T are as above defined, with amines 2, wherein $G^1$, X, Q and U are as above defined, according to scheme 2. This reaction is preferably performed by reductive amination via an imine intermediate.

Alternatively, when $G^1$ is a single bond, compounds of Formula 5, wherein $R^1$, $R^2$, $R^{2'}$, $R^3$, $R^4$, X, Q, T and U are as defined above, may be synthesised by reacting a compound of Formula 3, wherein $R^1$, $R^2$, $R^{2'}$, $R^3$, $R^4$ and T are as above defined, with the aldehyde of Formula 4, wherein Q and U are as above defined, and wherein X' denotes a linear or branched alkyl having 1 to 6 carbon atom or a cyclic alkyl having 3 to 8 carbon atoms wherein 1 —CH$_2$— group, in this linear, branched or cyclic alkyl, is replaced by a —CO— group. Scheme 2.

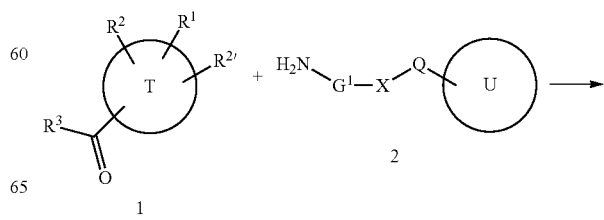

Scheme 3.

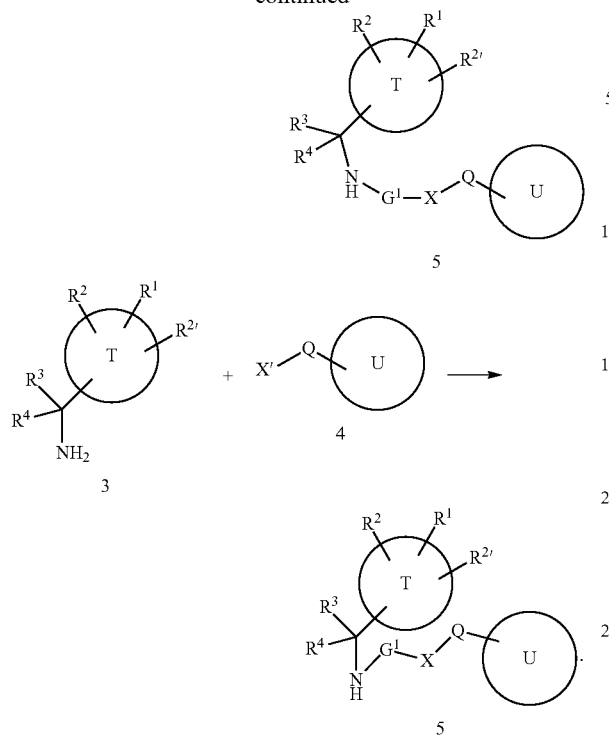

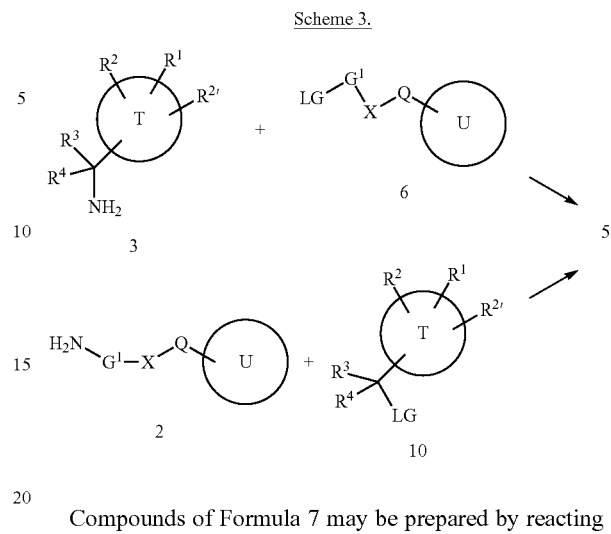

$R^4 = H$
$G^1 = $ a bond

The reductive amination reaction described in scheme 2 can occur in a single pot reaction using borohydride reagents, including but not limited to sodium cyanoborohydride, sodium acetoxyboro-hydride and sodium borohydride in halogenated solvents such as dichloromethane or 1,2-dichloroethane, or alcohols such as methanol, typically at room temperature for 0.5-12 hours.

The reaction can also occur in two steps. Firstly by the formation of imine in the presence of an acid including but not limited to p-toluenesulfonic acid, or Amberlyst resin and also a dehydrating reagent, such as but not limited to magnesium sulphate, sodium sulphate, molecular sieves or TiCl$_4$ using for example dichloromethane, ethanol, ethyl acetate or dimethyl sulfoxide as solvent. This step may be performed in a Dean Stark apparatus using toluene at 90-110° C. In a second step, the imine can be converted to the secondary amine using borohydride reagents as described above.

Secondary amines 5 may be prepared by the alkylation of primary amines 2 with a compound of Formula 6 or the amine 3 with a compound of Formula 10, wherein LG in Formulae 6 and 10 denotes a suitable leaving group. Such suitable leaving groups may be selected from halogen, preferably chlorine or bromine, or a sulfonate group, preferably selected from mesylate, tosylate, benzyl sulphonyl, a perfluoroalkyl sulfonate such as mono, di or trifluoromethyl sulfonate or triflate. The reaction is preferably performed in the presence of a base, such as potassium carbonate or triethylamine, in solvents preferably selected from dichloromethane, acetonitrile, dimethyl sulfoxide, at temperatures ranging from room temperature to 100° C., As disclosed in scheme 3.

Compounds of Formula 7 may be prepared by reacting a compound of Formula 3, wherein $R^1$, $R^2$, $R^{2'}$, $R^3$, $R^4$ and T are as above defined, with a compound of Formula 8, wherein $G^2$, Y, W, and V are as above defined, and wherein LG is as defined above, as mentioned in scheme 4.

Scheme 4:

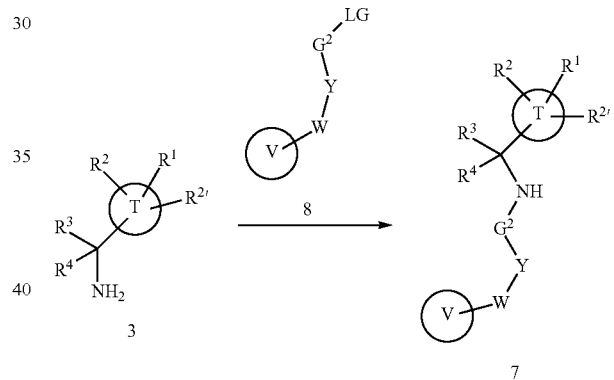

Amines of Formula 3 can be acylated with compounds of Formula 8, using techniques well known in the art. For this purpose, LG in the compounds of Formula 8 is preferably an activated acid obtained by reaction of a COOH group in the presence of an amide coupling reagent. The amide coupling reagents include EDCI, BOP, PyBOP, HOBt, HATU, T3P, DCC. They can be used in a suitable solvent, as for example dichloromethane or dimethylformamide at room temperature.

Amines 3 wherein $R^4$ is H can be prepared by functional group transformations well known in the art. Non-limiting examples are provided in Scheme 5. Ketones 11 can be condensed with hydroxylamine, for instance in ethanol at 80-100° C. for 1-2 days to give 12, which can in turn be reduced to amine 3 using for example Raney nickel in methanol at 80-100° C. for 2-6 hours, or by hydrogenation using palladium on charcoal for instance in ethanol at room temperature for 1-12 hours. Aldehydes 13 can be treated with metallated alkyl species such as Grignard reagents or alkyl lithiums to give secondary alcohols 14 for instance in diethylether or tetrahydrofuran at −78° C. for 1-4 hours, which can be converted to azides 15 using techniques known in the art, for instance by reaction with sodium azide in chloroform and sulfuric acid at 0° C. to room temperature. The azides can be reduced to the amines 3 for example by catalytic hydrogenation with palladium on charcoal in methanol at room temperature or by using PPh₃/H₂O (Staudinger conditions). Reaction of benzonitriles 16 with Grignard reagents or alkyl lithiums for example diethyl ether or tetrahydrofuran at room temperature to 50° C. for 1-4 hours can give imines 17, which may be reduced for instance with sodium borohydride in methanol at room temperature or lithium aluminium hydride in dimethyl formamide at room temperature or borane-THF complex in tetrahydrofuran at −20° C. to room temperature to give the amines 3.

Procedure), cHex (cyclohexane), HPLC (high performance liquid chromatography), hr (hour), IPA (isopropyl alcohol), int. (intermediate), LCMS (liquid chromatography—mass spectrometry), MHz (Megahertz), MeOH (methanol), min (minute), mL (milliliter), mmol (millimole), mM (millimolar), mp (melting point), MS (mass spectrometry), MTBE (methyl tert-butyl ether), MW (microwave), NMM (N-methyl morpholine), m (multiplet), NMR (Nuclear Magnetic Resonance), NBS (N-bromo succinimide), PBS (phosphate buffered saline), PDA (photodiode array), PMB (paramethoxybenzyl), cPr (cyclo-propyl), iPr (iso-propyl), PTLC (preparative thin layer chromatography), Rt (retention time), RT (room temperature), TBAF (tetra-butylammonium fluo-

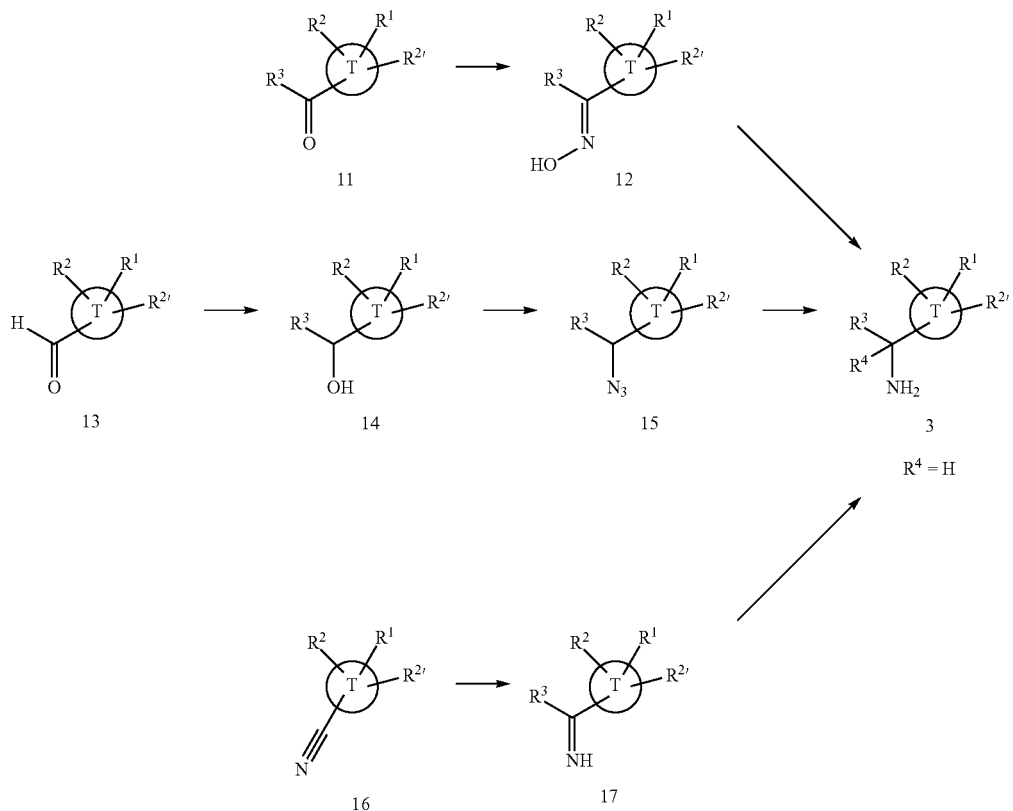

Scheme 5.

Chemistry Protocols

The following abbreviations refer to the abbreviations used below:

AcOH (acetic acid), CAN (acetonitrile) BINAP (2,2'-bis (disphenylphosphino)-1,1'-binaphthalene), dba (dibenzylidene acetone), bs (broad singlet), iBu (iso-butyl), tBu (tert-Butyl), tBuOK (potassium tert-butoxide), m-CPBA (meta-chloroperbenzoic acid); CDI (1,1'-Carbonyldiimidazole), cond. (conditions), DAST (diethylaminosulfurtrifluoride), DBU (1,8-dizabicyclo[5.4.0]undec-7-ene), DCM (dichloromethane), DEA (diethylamine), DIAD (diisobutylazodicarboxylate), DIEA (di-isopropyl ethylamine), DMA (dimethyl acetamide), DMAP (4-dimethylaminopyridine), DMSO (dimethyl sulfoxide), DMF (N,N-dimethylformamide), DPPA (diphenylphosphoryl azide), d (doublet), EDC.HCl (1-ethyl-3-(3-dimethylaminopropyl) carbodiimide hydrochloride), eq. (equivalents), EtOAc (ethyl acetate), EtOH (ethanol), g (gram), Gen. (General ride), TBTU (N,N,N',N'-tetramethyl-O-(benzotriazol-1-yl) uronium tetrafluoroborate), T3P (propane phosphonic acid anhydride), TEA (triethyl amine), TFA (trifluoroacetic acid), THF (tetrahydrofuran), t (triplet), PetEther (petroleum ether), TBME (tert-butyl methyl ether), TLC (thin layer chromatography), TMS (trimethylsilyl), TMSI (trimethylsilyl iodide), UV (ultraviolet), # of iso. (number of stereoisomers).

The compounds of invention have been named according to the standards used in the program ACD/Name Batch from Advanced Chemistry Development Inc., ACD/Labs (7.00 Release). Product version: 7.10, build: 15 Sep. 2003. NMR, HPLC and MS data provided in the examples described below are registered on:

NMR: Bruker DPX-300 (300 MHz) or Varian Gemini 2000 (300 MHz) using residual signal of deuterated solvent as internal reference.

HPLC: Method 1—Waters Alliance 2695, column Waters XBridge C8 3.5 µm 4.6×50 mm, conditions: solvent A ($H_2O$ with 0.1% TFA), solvent B (ACN with 0.05% TFA), gradient 5% B to 100% B over 8 min, UV detection with PDA Water 996 (230-400 nm).

LCMS: Method 2—Agilent 1100 Series LC/MSD, column Phenomenex Gemini-NX C18 5 µm, Zorbax Eclipse XBD-C8 or Luna 5 µm C8, 150×4.6 mm, with mobile phase 80% ACN, 15% $H_2O$, 5% buffer (3:1 MeOH/$H_2O$, 315 mg $HCO_2NH_4$, 1 mL AcOH) and MS detection (ESI method).

UPLC: Method 3—Waters Acquity, column Waters Acquity UPLC BEH C18 1.7 µm 2.1×50 mm, conditions: solvent A (10 mM ammonium acetate in water+5% ACN), solvent B (ACN), UV detection (PDA, 230-400 nm) and MS detection (SQ detector, positive and negative ESI modes, cone voltage 30 V). Gradient 5% B to 100% B over 3 min or gradient 40% B to 100% B over 3 min.

MD Autoprep: preparative HPLC purifications are performed with a mass directed auto-purification Fractionlynx from Waters equipped with a Sunfire Prep C18 OBD column 19×100 mm or 30×100 mm 5 m, unless otherwise reported. All HPLC purifications were performed with a gradient of ACN/$H_2O$ or ACN/$H_2O$/HCOOH (0.1%).

Preparative Chiral Separation of Example Compounds: preparative SFC/HPLC purifications were performed using the columns and conditions listed below (250×20 mm).

A=SFC Chiralpak 1A (35-40° C., 10-20% MeOH or EtOH in heptane, 60-80 mL/min)

B=SFC Chiralpak 1C (40° C., 15-30% MeOH, EtOH or IPA in heptane (with up to 0.1% DEA), 60-100 mL/min)

C=SFC Chiralpak AD-H (40° C., 7% EtOH in heptane, 60 mL/min)

D=SFC ChiralCel ODH (40° C., 10-20% MeOH or EtOH in heptane (with up to 0.1% DEA), 60-80 mL/min)

E=HPLC ChiralCel ODH (20% IPA in heptane, with 0.1% DEA, 10 mL/min)

F=HPLC Chiralpak 1C (20-50% EtOH or IPA in heptane with 0.1% DEA, 10-20 mL/min)

G=HPCL Chiralpak 1A (100% EtOH or 20% EtOH or IPA in heptane with either 0.1% DEA or 0.37% DCM and 0.19% acetone, 10 mL/min)

H=HPLC Chiralpak AYH (20% IPA in heptane 10 mL/min)

I=SFC Chiralcel OJH (35-40° C., 20% MeOH in heptane, 60-80 mL/min)

J=HPLC Chiralpak AYH (20% EtOH in heptane with 0.1% DEA, 10 mL/min)

EXAMPLES AND GENERAL PROCEDURES

General Procedures

General Procedure A: Reductive Amination of Aldehydes/Ketones to Sec-Amines Using Triacetoxyborohydride To a solution of aldehyde/ketone (1 eq.) and amine (1-2.5 eq.) in anhydrous DCE (~0.1M), sodium triacetoxyborohydride (1.5-3.0 eq.) and with or without acetic acid (2-3 eq.) were added sequentially and the resulting reaction mixture was stirred under a nitrogen atmosphere at RT until completion. The crude reaction mixture was diluted with EtOAc and the organics washed with a $NaHCO_3$ (aq.) solution or 1M NaOH followed by distilled water. The organic layer was separated, dried ($MgSO_4$) and concentrated under reduced pressure to provide the crude product, which was used without purification to the next step or purified by MD Autoprep or by silica-gel column chromatography using increasing gradient of EtOAc or/and MeOH in hexane or DCM as eluant to afford the secondary amine.

General Procedure B: Reductive Amination of Aldehydes/Ketones to Sec-Amines Using p-Toluenesulfonic Acid and Dean-Stark Apparatus To a solution of aldehyde/ketone (1 eq.) and amine (1-4 eq.) in toluene (2-5 M) was added p-toluenesulfonic acid (0.1 eq.) and resulting mixture was heated to reflux under Dean-Stark conditions. After the formation of the imine intermediate (TLC/LCMS), solvent was removed under reduced pressure and the resulting residue was dissolved in MeOH or DCM. Sodium borohydride or sodium triacetoxyborohydride was added and reaction mixture was stirred at RT under a nitrogen atmosphere. Upon completion of the reaction (LCMS), the solvent was removed under reduced pressure and the resulting residue was diluted with EtOAc or DCM and the organics washed with saturated $NH_4Cl$ (aq.) solution or 1M NaOH followed by distilled water. The organic layer was separated, dried ($MgSO_4$) and concentrated under reduced pressure to give the crude product, which was used without purification to the next step or purified by MD Autoprep or by flash chromatography (silica-gel, EtOAc) to afford the secondary amine.

General Procedure C: Preparation of t-Amides from Acid Chlorides

Triethylamine or diisopropylethylamine (2 eq.) was added to a solution of sec-amine (1 eq.) in anhydrous DCM or $Et_2O$ (0.1-0.3M) and the resulting solution was stirred at RT under a nitrogen atmosphere for 5 min. Acid chloride (1.5-2.5 eq.) was added and the reaction mixture was stirred until completion (LCMS). The reaction mixture was diluted with EtOAc or diethyl ether and washed thoroughly with $NaHCO_3$ (aq.) solution followed by distilled water. The organic layer was separated, dried ($MgSO_4$) and concentrated under reduced pressure. The crude material was purified using either PTLC or silica-gel flash chromatography using increasing gradient of EtOAc or/and MeOH in hexane or DCM as eluant.

General Procedure D: Preparation of Tertiary-Amides from Acids

To a solution of sec-amine (1 eq.) with or without triethylamine (1-1.5 eq.) and acid (1-6 eq.) in anhydrous DCE (0.22-0.28M) at 0° C. or RT, was added 1-propylphosphonic acid cyclic anhydride (T3P) (1-4 eq.) under a nitrogen atmosphere. The mixture was allowed to stir at RT or reflux until reaction completion (LCMS). The reaction was quenched by the addition of 1M NaOH and extracted with EtOAc or DCM. Organic layer was washed sequentially with 1M NaOH and then with 1M HCl, filtered, dried ($MgSO_4$) and concentrated under reduced pressure, to obtain a yellow oil, which was purified using PTLC and/or silica-gel flash chromatography or was used without purification to the next step or by MD Autoprep.

General Procedure E: Formation of Sulfonamides

To a mixture of potassium carbonate (2 eq.) in anhydrous acetonitrile (0.1-0.4 M) were added the sec-amine (1 eq.) and the sulfonyl chloride (1.5-2.5 eq.) sequentially under nitrogen atmosphere. The resulting mixture was heated to reflux until reaction completion (LCMS). Solvent was removed under reduced pressure and the reaction mixture was diluted with EtOAc and washed thoroughly with NaHCO$_3$ (aq.) solution followed by distilled water. The organic layer was separated, dried (MgSO$_4$) and concentrated under reduced pressure. The crude material was purified using either PTLC or silica-gel flash chromatography using increasing gradient of EtOAc or/and MeOH in hexane or DCM as eluant.

General Procedure F: Deprotection of Acetal

A solution of acetal (1 eq.) in a mixture of CH$_3$CN/H$_2$O/TFA (1/1/0.04) (0.1-0.5 M) was stirred at RT for 18 hr. The reaction was diluted with DCM and was then washed sequentially with 1M HCl, 1M NaOH and brine. The organic was dried (MgSO$_4$), filtered and concentrated under reduced pressure and the crude material purified by column chromatography or used directly to the next step without further purification.

General Procedure G: Swern-Oxidation of Alcohols to Aldehydes

Oxalyl chloride (1.5 eq.) was added slowly to a solution of anhydrous dimethylsulfoxide (3.0 eq.) in anhydrous DCM (0.17-2.0M) at −78° C. under a nitrogen atmosphere and stirred for 30 min. To the resulting mixture, was added the alcohol (1 eq.) dissolved in anhydrous DCM (0.2-0.4M) and the reaction mixture was stirred at −78° C. for 45 min. Anhydrous triethylamine (6 eq.) was added drop-wise and reaction was stirred at −78° C. for 30 min and then at RT for 30 min. The DCM was removed under reduced pressure and residue was dissolved in diethyl ether and washed with NH$_4$Cl (aq.) solution. The organic layer was separated and the aqueous layer was again extracted with diethyl ether. The organic layers were combined, dried (MgSO$_4$), filtered and concentrated under reduced pressure to give the crude product, which was purified by column chromatography.

General Procedure H: Alkylation of Sec-Amines

To the solution of sec-amine (1 eq.) in anhydrous DCM (~0.14M) was added sequentially DIPEA (1.2-1.5 eq.) and chloroacetylchloride (1.1-1.4 eq.) and the resulting mixture was stirred at RT under a nitrogen atmosphere until completion. The reaction was quenched with water and extracted with DCM. The combined organics were dried (MgSO$_4$) and concentrated under reduced pressure. Crude material was purified using PTLC and/or silica-gel column chromatography.

General Procedure I: Preparation of t-Amides

To a solution of amide (1 eq.) and amine (2-2.5 eq.) in anhydrous DMF (0.11-0.12M) was added Na$_2$CO$_3$ (2-2.5 eq.) and sodium iodide (1-1.1 eq.) sequentially and the resulting mixture was stirred at 65° C. overnight. The reaction mixture was cooled to RT and diluted with diethyl ether and washed with water. Organic layer was separated, dried (MgSO$_4$) and concentrated under reduced pressure. Crude material was purified using silica-gel column chromatography.

General Procedure J: Preparation of Acid Chlorides

A suspension of acid in thionyl chloride (0.4-0.6M) was stirred at RT overnight or refluxed for 1 h. Excess thionyl chloride was removed under reduced pressure at RT and traces were removed under reduced pressure. A clear oil of acid chloride was obtained, which was used without further purification.

Or

To a solution of the acid and DMF (cat) in anhydrous DCM at 0° C. was added a solution of oxalyl chloride (3 eq.) in anhydrous DCM, dropwise. The reaction mixture was stirred for 1 hr at 0° C., before warming to RT and stirring for a further 1 hr. The reaction mixture was concentrated under reduced pressure and used without further purification.

General Procedure K: Reductive Amination of Ketones with Amine.HCl to Sec-Amines Using Ti(OiPr)$_4$ and NaBH$_3$(CN)

To a suspension of the amine.HCl salt (1.5 eq.) in THF was added DIPEA (1.5 eq.), the ketone (1 eq.) and Ti(OiPr)$_4$ and the reaction mixture heated to 50° C. in a sealed tube ON. The reaction mixture was cooled to RT and a solution of NaBH$_3$(CN) (2 eq.) in MeOH was added and the reaction mixture heated to 50° C. ON. The reaction mixture was cooled and diluted with Et$_2$O and quenched with NaOH (1M). The biphasic solution was filtered through Celite and the phases separated before extracting the aqueous phase with EtOAc (2×). The combined extracts were dried (MgSO$_4$) and concentrated under reduced pressure to provide the crude product which was used without purification in the next step or purified by silica-gel column chromatography using the appropriate solvent.

General Procedure L: Reductive Amination of Aldehydes/Ketones to Sec-Amines Using Sodium Borohydride To a solution of the ketone/aldehyde (1 eq.) and the amine (1.eq) in THF (0.2M) at RT was added MgSO$_4$ (2.5 eq.). The reaction was monitored by LCMS/TLC for completion of imine formation (heated to 60° C. if required). Upon completion the reaction mixture was filtered through Celite and concentrated under reduced pressure. The imine was taken up in MeOH (0.2M) and NaBH$_4$ was added at RT. The reaction was monitored by LCMS/TLC. Upon complete reduction of the imine the reaction mixture was diluted with NH$_4$Cl (sat. aq.) and the product extracted with DCM (3×). The combined extracts were dried (MgSO$_4$) and concentrated under reduced pressure to provide the crude product which was used without purification in the next step or purified by silica-gel column chromatography using the appropriate solvent.

General Procedure M: Preparation of t-Amides from Acid Chlorides in Pyridine

To a solution of the acid chloride (1.5 eq.) in pyridine (0.2M) was added a solution of the amine (1 eq.) in pyridine followed by DMAP (0.2 eq.). The reaction mixture was stirred until complete (by LCMS or TLC). The reaction mixture was concentrated under reduced pressure and diluted with Et$_2$O. The organics were washed with H$_2$O (3×) and NH$_4$Cl (sat. aq., 1×) before stirring vigorously with K$_2$CO$_3$ (2M) for 1 hr. The phases were then separated and the organics dried (MgSO$_4$) and concentrated under reduced pressure. The crude material was purified by either PTLC or silica-gel flash column chromatography using the appropriate solvent.

General Procedure N: Liberation of N-Tert-Butoxycarbonyl Protected Amines Using TMSI To a solution of the N-tert-butoxycarbonyl derivative in CHCl$_3$ (0.2M) at RT was added TMSI, dropwise. The solution was stirred for 5 minutes at RT before quenching by addition of a couple of drops of MeOH followed by NaHCO$_3$ (sat. aq.). The product was extracted into DCM (3×) and the combined extracts dried (MgSO$_4$) and concentrated under reduced pressure. The crude material was purified by PTLC and/or silica-gel flash column chromatography using the appropriate solvent.

General Procedure O: Liberation of N-Tert-Butoxycarbonyl Protected Amines Using TFA To solution of the N-tert-butoxycarbonyl derivative in DCM or DCE (0.5M) was added TFA at RT and the reaction mixture stirred. The reaction progress was monitored by TLC/LCMS and upon completion the reaction was quenched by addition of NaHCO$_3$ (sat. aq.). The product was extracted with DCM (3×) and the combined extracts dried (MgSO$_4$) and concentrated under reduced pressure. The crude material was either used without purification in the next step or purified by either PTLC or silica-gel flash column chromatography using the appropriate solvent.

Note: for particularly unreactive analogues microwave irradiation of the above solution at 120° C. for 5 minutes produced the desired product.

General Procedure P: Liberation of N-Tert-Butoxycarbonyl Protected Amines Using HCl The N-tert-butoxycarbonyl derivative was dissolved in a solution of HCl in Et$_2$O. After several minutes a precipitate formed and LCMS was used to monitor the reaction progress. Upon completion the precipitate was collected by vacuum filtration and the product re-crystallised from DMC/Et$_2$O.

General Procedure Q: N-Methylation Via Reductive Amination of an Amine and Formaldehyde with Sodium Triacetoxyborohydride or Sodium Cyanoborohydride To a solution of the amine in MeOH (0.2M) was added AcOH and formaldehyde (37% in H$_2$O). The reaction mixture was stirred at RT for 30 min before addition of NaHB(OAc)$_3$ or NaBH$_3$(CN). The reaction was monitored by LCMS/TLC and following completion was quenched with NaHCO$_3$ (sat. aq.). The product was extracted with EtOAc (3×) and the combined extracts dried (MgSO$_4$) and concentrated under reduced pressure. The crude material was purified by either PTLC or silica-gel flash column chromatography using the appropriate solvent.

General Procedure R: Pyridine N-Oxide Formation Using m-CPBA

To a solution of the pyridine analogue in DCM (0.1M) at 0° C. was added m-CPBA (1.2 eq.) and the reaction mixture warmed to RT. The reaction progress was monitored by TLC/LCMS and upon completion the reaction mixture was diluted with EtOAc and washed with NaOH (1M, 3×), brine (1×), dried (MgSO$_4$) and concentrated under reduced pressure. The crude product was purified by pTLC or silica-gel flash column chromatography using the appropriate solvent.

General Procedure S: Amine Formation Using CH$_3$CO$_2$NH$_4$ and NaBH$_3$(CN)

To a solution of the ketone analogue in MeOH (0.1M) was added ammonium acetate (10 eq.) and NaBH$_3$(CN) (4 eq.). The reaction mixture was heated at reflux for 18 hours. The reaction mixture was cooled to RT and concentrated under reduced pressure and the crude residue partitioned between 1M NaOH and EtOAc. The layers were separated and the aqueous further extracted with EtOAc (2×). The extracts were combined, dried over MgSO$_4$, filtered and concentrated under reduced pressure. The crude product was purified by silica-gel flash column chromatography using the appropriate solvent.

General Procedure T: Conversion of 6-Bromopyridine to 6-Alkylsulfone

Step i) To a suspension of NaH 60% in mineral oil (1.2 eq) in dry DMF (0.1M) under N$_2$ at RT was added the appropriate thiol (1.2 eq.) drop-wise. After stirring at this temperature for 10 min. a solution of the 6-bromopyridine analogue in dry DMF (0.1M) was added drop-wise and the reaction heated to 60° C. The reaction was monitored by LCMS/TLC and following completion was quenched with sat.NH$_4$Cl. The product was extracted with EtOAc (3×) and the combined extracts dried (MgSO$_4$) and concentrated under reduced pressure. The crude material was purified by either PTLC or silica-gel flash column chromatography using the appropriate solvent to obtain the thiopyridine intermediate.

Step ii) To a solution of the thiopyridine intermediate in dry DCM (0.1M) under N$_2$ at 0° C. was added m-CPBA (2 eq) portion-wise. The reaction was monitored by LCMS/TLC and following completion was quenched with sat..NaHCO$_3$. The product was extracted with EtOAc (3×) and the combined extracts dried (MgSO$_4$) and concentrated under reduced pressure. The crude material was purified by either PTLC or silica-gel flash column chromatography using the appropriate solvent

General Procedure U: Preparation of t-Amides Using HATU

To a solution of acid (1.05 eq.) and DIPEA (2.1 eq.) in anhydrous DMF (8 mL per 200 mg acid) at 0° C. under a nitrogen atmosphere was added HATU (1.1 eq.) followed by amine (1 eq.). The mixture was stirred at this temperature for 3 hr. and then brought to ambient temperature and stirred for 16 hr. Once complete the reaction was diluted with EtOAc and extracted with water×1, sat. NaHCO$_3$×1 and brine×1, the combined organics were then dried (MgSO$_4$), filtered, concentrated under reduced pressure and purified by column chromatography eluting with 5% diethyl ether in DCM.

General Procedure Y: Reductive Amination of Aldehydes/Ketones to Sec-Amines Using Sodium Cyanoborohydride To a solution of the ketone/aldehyde (1 eq.) and the amine (0.9 eq) in DCE (0.2M) at RT was added a solution of sodium cyanoborohydride (4 eq) in MeOH (0.8 M) in three portions within 2 hours and reaction mixture was stirred overnight at RT. The reaction was quenched by addition of sodium bicarbonate (sat. aq.) and extracted with EtOAc. The organic layer was washed with brine, dried over MgSO$_4$ and concentrated under reduced pressure. The crude material was purified by silica-gel flash chromatography using 10% MeOH in 1/1 DCM/Diethyl ether mixture as eluent.

General Procedure AD: Modified Reductive Amination with Acetone

To a solution of amine (1 eq.) in anhydrous THF (1 mL per 100 mg amine) was added acetone (4 eq.) followed by Ti(OPr$^i$)$_4$ (1.4 eq.) and the vessel sealed and heated to 40° C. for 2 hr. After this time the volatiles were removed under a stream of nitrogen and methanol (1 mL per 200 mg amine) was added to the residue. To this was added acetone (1 eq.) followed by NaBH$_3$CN (2 eq.) and the vessel sealed and heated to 40° C. for 2 hr. Once complete the mixture was diluted with EtOAc and quenched with minimal sat. NaHCO$_3$ solution, the mixture was then filtered through Celite washing with EtOAc. The filtrate was then extracted with sat. NaHCO$_3$ solution×1 and the organics dried (MgSO$_4$), concentrated under reduced pressure and the crude material used.

Intermediate a 1-cyclopropyl-1-(4-methoxyphenyl)-N-(pyridin-2-ylmethyl)methanamine

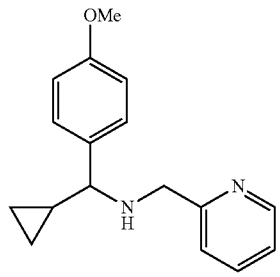 [SMILES: COc1ccc(C(NCc2ccccn2)C2CC2)cc1]

Cyclopropyl-4-methoxyphenyl ketone (1 g, 5.67 mmol) and 2-(aminomethyl) pyridine (1.18 mL, 11.35 mmol), were reacted according to General Procedure A to afford the title compound as a pale yellow oil. $^1$H NMR (CDCl$_3$) δ 8.56-8.55 (m, 1H), 7.63-7.57 (dt, J=1.5, 7.8 Hz, 1H), 7.33-7.29 (m, 2H), 7.19-7.12 (m, 2H), 6.91-6.87 (m, 2H), 3.81 (s, 3H), 3.81-3.68 (m, 2H), 2.77 (d, J=9.0 Hz, 1H), 1.65 (bs, 1H), 1.19-1.16 (m, 1H), 0.66-0.56 (m, 1H), 0.43-0.27 (m, 2H), 0.21-0.14 (m, 1H). MS (ES$^+$) m/z 269.2 (M+H)$^+$.

Intermediate b 1-cyclopropyl-1-(4-chlorophenyl)-N-(pyridin-2-ylmethyl)methanamine

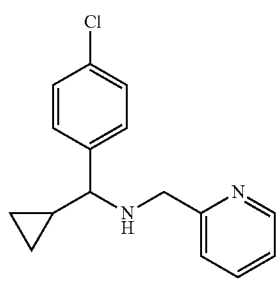 [SMILES: Clc1ccc(C(NCc2ccccn2)C2CC2)cc1]

4-Chlorophenyl cyclopropylketone (500 mg, 2.77 mmol) and 2-(aminomethyl) pyridine (1.151 mL, 11.17 mmol) were reacted according to General Procedure B to afford title compound as a pale yellow oil. $^1$H NMR (CDCl$_3$) δ 8.57 (m, 1H), 7.63-7.57 (m, 1H), 7.35-7.29 (m, 4H), 7.17-7.12 (m, 2H), 3.79-3.66 (m, 2H), 2.79 (d, J=8.91 Hz, 1H), 1.14-1.05 (m, 1H), 0.67-0.59 (m, 1H), 0.43-0.29 (m, 2H), 0.22-0.15 (m, 1H). LCMS (Method 2) m/z 273.2 (M+H)$^+$.

Intermediate c

Enantiomer A of 1-cyclopropyl-1-(4-chlorophenyl)-N-(pyridin-2-ylmethyl)methanamine

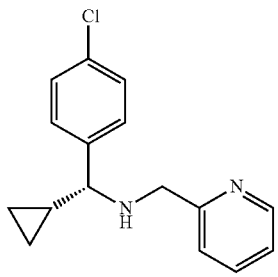

Enantiomer A of 4-chlorophenyl(cyclopropyl)methanamine (purified from the racemate of 4-chlorophenyl(cyclopropyl)methanamine by preparative HPLC using a Chiralpak AYH 250×20 mm column (Daicel) (eluent EtOH DEA 0.1% v/v, flow 10 ml min, 427 mg, 2.35 mmol) and pyridine-2-carboxaldehyde (201 mg, 1.87 mmol), were reacted according to General Procedure A to afford the titled compound (433 mg, 85%) as a yellow oil. $^1$HNMR (CDCl$_3$) δ 8.56 (d, J=4.5 Hz, 1H), 7.63-7.57 (m, 1H), 7.35-7.28 (m, 4H), 7.17-7.12 (m, 2H), 3.77-3.66 (m, 2H), 2.79 (d, J=9.0 Hz, 1H), 2.38 (bs, 1H), 1.13-1.03 (m, 1H), 0.67-0.58 (m, 1H), 0.43-0.28 (m, 2H), 0.21-0.14 (m, 1H). MS (ES$^+$) m/z 273.2 (M+H$^+$).

Intermediate d

Enantiomer B of 1-cyclopropyl-1-(4-chlorophenyl)-N-(pyridin-2-ylmethyl)methanamine

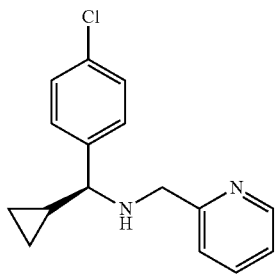 [SMILES: Clc1ccc([C@@H](NCc2ccccn2)C2CC2)cc1]

Enantiomer B of 4-chlorophenyl(cyclopropyl)methanamine (purified from the racemate of 4-chlorophenyl(cyclopropyl)methanamine by preparative HPLC using a Chiralpak AYH 250×20 mm column (Daicel) (eluent EtOH DEA 0.1% v/v, flow 10 ml min, 419 mg, 2.31 mmol) and pyridine-2-carboxaldehyde (201 mg, 1.87 mmol), were reacted according to General Procedure A to give the titled compound (499 mg, 98%) as a yellow oil. ¹HNMR (CDCl₃) δ 8.56 (d, J=4.5 Hz, 1H), 7.63-7.57 (m, 1H), 7.35-7.28 (m, 4H), 7.17-7.12 (m, 2H), 3.77-3.66 (m, 2H), 2.79 (d, J=9.0 Hz, 1H), 2.38 (bs, 1H), 1.13-1.03 (m, 1H), 0.67-0.58 (m, 1H), 0.43-0.28 (m, 2H), 0.21-0.14 (m, 1H). MS (ES⁺) m/z 273.2 (M+H⁺).

Intermediate i 1-cyclopentyl-1-(4-fluorophenyl)-N-(pyridin-2-ylmethyl)methanamine

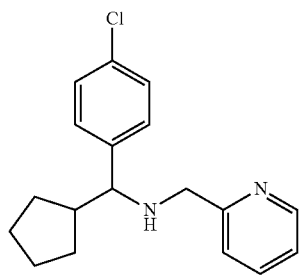 [SMILES: Clc1ccc(C(NCc2ccccn2)C2CCCC2)cc1]

Cyclopentyl(4-fluorophenyl)methanamine hydrochloride (200 mg, 0.87 mmol) and 2-pyridinecarboxaldehyde (93 mg, 0.87 mmol) were reacted according to General Procedure A (however triethylamine (0.12 mL, 0.87 mmol) was stirred for 10 min with the amine hydrochloride prior to addition of aldehyde) to give the title compound as a yellow oil (251 mg, quantitative). ¹H NMR (CDCl₃) δ 8.58-8.56 (m, 1H), 7.61 (td, J=7.7, 1.8 Hz, 1H), 7.33-7.25 (m, 2H), 7.17-6.99 (m, 4H), 3.69 (d, J=14.2 Hz, 1H), 3.59 (d, J=14.2 Hz, 1H), 3.32 (d, J=8.3 Hz, 1H), 2.18-1.22 (m, 8H), 1.10-1.01 (m, 1H). HPLC (Method 1) Rt 2.72 min (Purity: 95.1%). UPLC/MS (Method 3) 285.2 (M+H⁺).

Intermediate l 1-(2-methyl-2,3-dihydro-1-benzofuran-5-yl)-N-(pyridin-2-ylmethyl)propan-1-amine

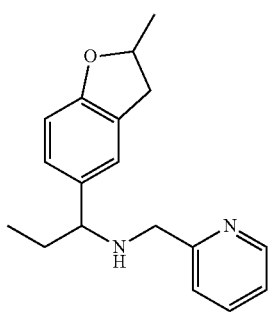 [SMILES: CCC(NCc1ccccn1)c1ccc2c(c1)CC(C)O2]

1-(2-Methyl-2,3-dihydro-benzofuran-5-yl)-propylamine (178 mg, 0.93 mmol) and 2-pyridinecarboxaldehyde (100 mg, 0.93 mmol), were reacted according to General Procedure A to give the title compound as a yellow oil (190 mg, 72%). ¹H NMR (d₆-DMSO) δ 8.46-8.44 (m, 1H), 7.75-7.69 (m, 1H), 7.40-7.38 (m, 1H), 7.23-7.19 (m, 1H), 7.13 (s, 1H), 6.98-6.96 (m, 1H), 6.65-6.62 (m, 1H), 4.93-4.82 (m, 1H), 3.63-3.51 (m, 2H), 3.30-3.24 (m, 1H), 2.80-2.71 (m, 1H), 2.64-2.52 (m, 1H), 1.74-1.65 (m, 1H), 1.55-1.46 (m, 1H), 1.39-1.37 (d, J=6.2 Hz, 3H), 0.77-0.72 (t, J=7.4 Hz, 3H). HPLC (Method 1) Rt 7.76 min (Purity: 99.4%). UPLC/MS (Method 3) 283.1 (M+H⁺).

Intermediate v 1-(2,3-dihydro-1H-inden-5-yl)-N-[2-(3,6-dimethyl-pyrazin-2-yloxy)ethyl]ethanamine

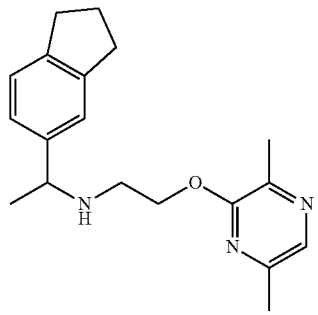 [SMILES: Cc1cnc(C)c(OCCNC(C)c2ccc3c(c2)CCC3)n1]

1-Indan-5-yl-ethylamine (107 mg, 0.66 mmol) and intermediate mm (110 mg, 0.73 mmol), were reacted according to General Procedure A to give the title compound as clear oil. ¹H NMR (CDCl₃) δ 7.83 (s, 1H), 7.20-7.07 (m, 3H), 4.44-7.32 (m, 2H), 3.82 (q, J=6.6 Hz, 1H), 2.96-2.82 (m, 6H), 2.42 (s, 3H), 2.36 (s, 3H), 2.12-2.02 (m, 2H), 1.37 (d, J=6.6 Hz, 3H). -LCMS (Method 2) m/z 312.5 (M+H⁺).

Intermediate x 1-(2,3-dihydro-1H-inden-5-yl)-N-[2-(6-chloropyridin-2-yloxy)ethyl]ethanamine

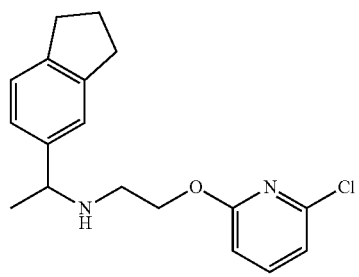 [SMILES: CC(NCCOc1cccc(Cl)n1)c1ccc2c(c1)CCC2]

5-Acetylindane (106 mg, 0.66 mmol) and intermediate kk were reacted as described according to General Procedure A to afford the titled compound as a yellow oil. ¹HNMR (CDCl₃) δ 7.51 (t, J=7.8 Hz, 1H), 7.21-7.08 (m, 3H), 6.88 (d, J=7.8 Hz, 1H), 6.65 (d, J=7.8 Hz, 1H), 4.43-4.31 (m, 2H), 3.82 (q, J=6.6 Hz, 1H), 2.94-2.79 (m, 6H), 2.12-2.02 (m, 2H), 1.76 (s, 1H), 1.37 (d, J=6.6 Hz, 3H). LCMS (Method 2) m/z 317.3 (M+H⁺).

Intermediate y 1-(2,3-dihydro-1H-inden-5-yl)-N-[2-(pyridin-2-yloxy)ethyl]ethanamine

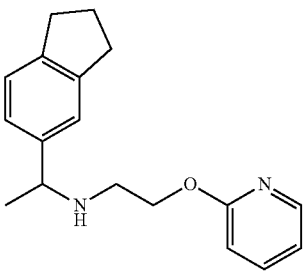 [SMILES: CC(NCCOc1ccccn1)c1ccc2c(c1)CCC2]

5-Acetylindane (214 mg, 1.34 mmol) and 2-(pyridin-2-yloxy)ethanamine (prepared according to the procedure outlined in Tetrahedron 1988, 44(1), 91-100) (448 mg, 3.24 mmol), were reacted as described according to General Procedure A to afford the titled compound (275 mg, 73%) as a yellow oil. $^1$HNMR (CDCl$_3$) δ 8.14-8.12 (m, 1H), 7.58-7.53 (m, 1H), 7.22-7.08 (m, 3H), 6.87-6.83 (m, 1H), 6.75-6.72 (m, 1H), 4.43-4.30 (m, 2H), 3.82 (q, J=6.6 Hz, 1H), 2.95-2.80 (m, 6H), 2.12-2.02 (m, 2H), 1.76 (s, 1H), 1.37 (d, J=6.6 Hz, 3H). LCMS (Method 2) m/z 283.3 (M+H)$^+$.

Intermediate bb 1-(2,3-dihydro-1H-inden-5-yl)-N-[2-(6-methylpyridin-2-yloxy)ethyl]ethanamine

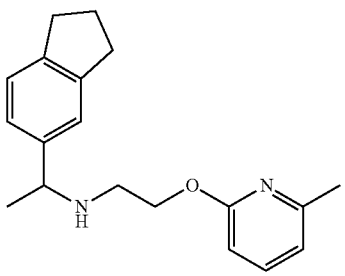 [SMILES: Cc1cccc(OCCNC(C)c2ccc3c(c2)CCC3)n1]

5-Acetylindane (214 mg, 1.34 mmol) and 2-[(6-methylpyridin-2-yl)oxy]ethanamine (prepared according to the procedure outlined in U.S. Pat. No. 3,535,328 (A), 761 mg, 5.0 mmol), were reacted as described according to General Procedure A to afford the titled compound as a yellow oil. $^1$HNMR (CDCl$_3$) δ 7.44 (dd, J=8.1, 7.2 Hz, 1H), 7.22-7.08 (m, 3H), 6.70 (d, J=7.2 Hz, 1H), 6.52 (d, J=8.1 Hz, 1H), 4.41-4.28 (m, 2H), 3.82 (q, J=6.6 Hz, 1H), 2.94-2.79 (m, 6H), 2.42 (s, 3H), 2.12-2.02 (m, 2H), 1.88 (s, 1H), 1.37 (d, J=6.6 Hz, 3H). LCMS (Method 2) m/z 297.2 (M+H)$^+$.

Intermediate cc 1-(2,2-dimethyl-1,3-benzoxathiol-5-yl)-N-(pyridin-2-ylmethyl)ethanamine

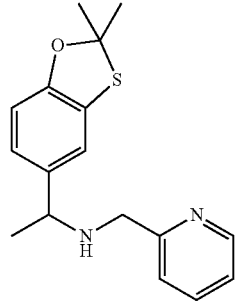 [SMILES: CC(NCc1ccccn1)c1ccc2c(c1)SC(C)(C)O2]

1-(2,2-Dimethyl-1,3-benzoxathiol-5-yl)ethanone (prepared according to procedure outlined in the Journal of Heterocyclic Chemistry, 1984, 21(2), 573-6 and 1982, 19(1), 135-9) (126 mg; 0.60 mmol), 2-(aminomethyl)pyridine (262 mg, 2.42 mmol) and p-toluenesulfonic acid monohydrate (12 mg, 0.06 mmol) were reacted according to General Procedure B, to give the title compound as a pale yellow oil (156 mg, 86%). $^1$H NMR (CDCl$_3$) δ 8.54 (ddd, J=4.9, 1.7, 0.9 Hz, 1H), 7.60 (td, J=7.7, 1.7 Hz, 1H), 7.21-7.13 (m, 3H), 6.95 (dd, J=8.2, 1.9 Hz, 1H), 6.69 (d, J=8.2 Hz, 1H), 3.82-3.71 (m, 3H), 2.47 (brs, 1H), 1.84 (s, 6H), 1.39 (d, J=6.6 Hz, 3H). HPLC (Method 1) Rt 2.84 min (Purity: 98.6%). UPLC/MS (Method 3) 301.1 (M+H)$^+$.

Intermediate dd (1S)-1-(2-methoxyphenyl)-N-(pyridin-2-ylmethyl)ethanamine

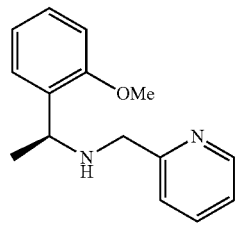 [SMILES: COc1ccccc1[C@H](C)NCc1ccccn1]

2-Pyridinecarboxaldehyde (200 mg, 1.87 mmol) and (S)-2-methoxy-α-methylbenzylamine (282 mg, 1.87 mmol), were reacted according to General Procedure A to give the title compound as a yellow oil (368 mg, 81%). $^1$H NMR (CDCl$_3$) δ 8.54 (m, 1H), 7.60 (td, J=7.7, 1.8 Hz, 1H), 7.41 (dd, J=7.5, 1.6 Hz, 1H), 7.26-7.19 (m, 2H), 7.12 (m, 1H), 6.96 (m, 1H), 6.87 (d, J=8.2 Hz, 1H), 4.24 (q, J=6.7 Hz, 1H), 3.82 (s, 3H), 3.78 (s, 2H), 2.33 (brs, 1H), 1.42 (d, J=6.7 Hz, 3H). HPLC (Method 1) Rt 2.11 min (Purity: 99.1%). UPLC/MS (Method 3) 243.0 (M+H)$^+$.

Intermediate ee (1R)-1-(2-methoxyphenyl)-N-(pyridin-2-ylmethyl)ethanamine

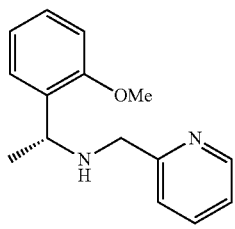 [SMILES: COc1ccccc1[C@@H](C)NCc1ccccn1]

2-Pyridinecarboxaldehyde (200 mg, 1.87 mmol) and (R)-2-methoxy-α-methylbenzylamine (282 mg, 1.87 mmol) were reacted according to General Procedure A to give the title compound as a yellow oil (368 mg, 81%). $^1$H NMR (CDCl$_3$) δ 8.54 (ddd, J=4.9, 1.6, 0.8 Hz, 1H), 7.60 (td, J=7.7, 1.8 Hz, 1H), 7.42 (dd, J=7.5, 1.7 Hz, 1H), 7.26-7.19 (m, 2H), 7.12 (m, 1H), 6.96 (td, J=7.4, 1.0 Hz, 1H), 6.86 (dd, J=8.2, 0.8 Hz, 1H), 4.22 (q, J=6.6 Hz, 1H), 3.82 (s, 3H), 3.77 (s, 2H), 2.33 (brs, 1H), 1.41 (d, J=6.6 Hz, 3H). HPLC (Method 1) Rt 2.05 min (Purity: 98.8%). UPLC/MS (Method 3) 243.1 (M+H)$^+$.

Intermediate ff

1-[2-(methoxymethyl)phenyl]-N-(pyridin-2-ylmethyl)ethanamine

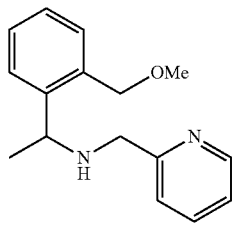 [SMILES: COCc1ccccc1C(C)NCc1ccccn1]

1-[2-(Methoxymethyl)phenyl]ethanone (prepared according to procedure outlined in the Journal of Organic Chemistry, 1970, 35(8), 2532-8) (205 mg, 1.25 mmol), 2-(aminomethyl)pyridine (135 mg, 1.25 mmol) and p-toluenesulfonic acid monohydrate (24 mg, 0.12 mmol), were reacted according to General Procedure B to give the title compound as a yellow oil (276 mg, 86%). $^1$H NMR (CDCl$_3$) δ 8.58-8.52 (m, 1H), 7.66 (d, J=7.8, 1H), 7.61 (td, J=7.7, 1.8, 1H), 7.39-7.28 (m, 2H), 7.19 (ddd, J=12.4, 8.2, 3.1, 3H), 4.45 (s, 2H), 4.24 (q, J=6.5, 1H), 3.78 (s, 2H), 3.33 (s, 3H), 1.44 (d, J=6.5, 3H). HPLC (Method 1) Rt 2.34 min (Purity: 96.2%). UPLC/MS (Method 3) 257.1 (M+H)$^+$.

Intermediate gg 1-(2,3-dihydro-H-inden-5-yl)-N-(pyridin-2-ylmethyl)ethanamine

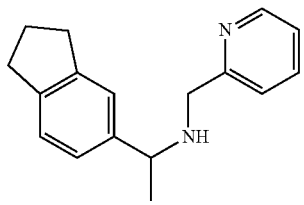 [SMILES: CC(NCc1ccccn1)c1ccc2c(c1)CCC2]

5-Acetylindane (1.0 g, 6.24 mmol) and 2-(aminomethyl)pyridine (639 μl, 6.24 mmol) were reacted according to General Procedure B to give the title compound as a yellow oil. $^1$H NMR (d$_6$-DMSO) δ 8.47-8.45 (m, 1H), 7.76-7.70 (m, 1H), 7.41-7.39 (m, 1H), 7.24-7.06 (m, 4H), 3.71-3.65 (m, 1H), 3.59 (s, 2H), 2.85-2.79 (m, 4H), 2.02-1.98 (m, 2H), 1.26 (d, J=6.6 Hz, 3H). HPLC (Method 1) Rt 2.39 min (Purity: 91.7%). UPLC/MS (Method 3) 253.1 (M+H)$^+$.

Intermediate hh 3-(4-Fluorophenyl)butanal

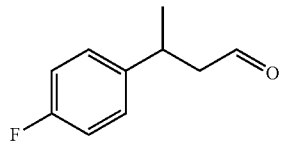

3-(4-Fluorophenyl)butan-1-ol (2.01 g, 11.94 mmol), oxalyl chloride (1.60 mL, 18.34 mmol), DMSO (2.60 mL, 36.61 mmol) and TEA (10.00 mL, 74.46 mmol), were reacted according to General Procedure G to afford the titled compound (1.69 g, 85%) as a yellow oil. $^1$HNMR (CDCl$_3$) δ 9.69 (t, J=1.8 Hz, 1H), 7.21-7.14 (m, 2H), 7.02-6.95 (m, 2H), 3.36 (sextet, J=7.2 Hz, 1H), 2.77-2.60 (m, 2H), 1.29 (d, J=7.2 Hz, 3H).

Intermediate kk

2-[(6-chloropyridin-2-yl)oxy]ethanamine

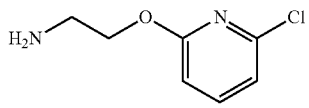 [SMILES: NCCOc1cccc(Cl)n1]

To a solution of ethanolamine (1.00 g, 16.4 mmol) in anhydrous 1,4-dioxane (20 mL) at RT was added NaH (60% in oil) (655 mg, 16.4 mmol) portion-wise. The reaction mixture was heated to reflux (100° C.) for 30 mins, then cooled to RT and 2,6-dichloropyridine (2.423 g, 16.4 mmol) was then added. The reaction mixture was again heated to reflux (100° C.) for 3 hr, then cooled to RT, quenched with water and extracted with diethyl ether. The combined organic extracts were dried (MgSO$_4$), filtered and concentrated under reduced pressure to afford crude 2-[(6-chloropyridin-2-yl)oxy]ethanamine which was purified by flash chromatography eluting initially with 1:1 EtOAc:hexane to remove any remaining 2,6-dichloropyridine then eluted with 1:9 MeOH:DCM to obtain pure 2-[(6-chloropyridin-2-yl)oxy]ethanamine as a pale yellow oil (1.846 g, 65% yield). $^1$H NMR (CDCl$_3$) δ 7.50 (t, J=7.8 Hz, 1H), 6.88 (d, J=7.8 Hz, 1H), 6.66 (d, J=7.8 Hz, 1H), 4.31 (t, J=5.4 Hz, 2H), 3.05 (t, J=5.4 Hz, 2H), 1.35 (br s, 2H).

Intermediate ll

2-[(3,6-dimethylpyrazin-2-yl)oxy]ethanol

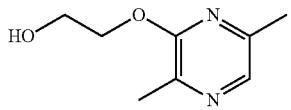

To a solution of ethylene glycol (1.00 g, 16.11 mmol) in anhydrous DMF (10 mL) at RT was added NaH (60% in oil) (222 mg, 6.04 mmol) portion-wise. The reaction mixture was stirred for 5 min before addition of 3-chloro-2,5-dimethylpyrazine (574 mg, 4.03 mmol). The mixture was heated to 50° C. for 20 hr, then cooled to RT, quenched with water and extracted with. The combined organic extracts were dried (MgSO$_4$), filtered and concentrated under reduced pressure. The crude material was purified by flash chromatography eluting with 1:4 EtOAc:hexane to afford the titled compound as a pale yellow solid. $^1$H NMR (CDCl$_3$) δ 7.87 (s, 1H), 4.50-4.47 (m, 2H), 3.98-3.93 (m, 2H), 3.44 (t, J=5.7 Hz, 1H), 2.42 (s, 3H), 2.38 (s, 3H). LCMS (Method 2) m/z 169.3 (M+H)$^+$.

Intermediate mm:
[(3,6-dimethylpyrazin-2-yl)oxy]acetaldehyde

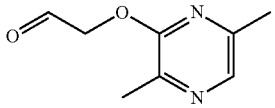

Intermediate ll (150 mg, 0.89 mmol) was reacted according to General Procedure G and the crude aldehyde was used as such without further purification. LCMS (Method 2) m/z 167.3 (M+H)$^+$.

Intermediate nn 3-(4-fluorophenyl)butanoyl chloride

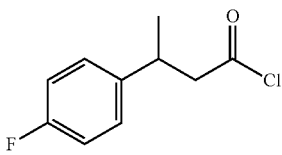

3-(4-Fluorophenyl)butanoic acid (2 g, 9.97 mmol) and thionyl chloride (20 mL) were reacted according to General Procedure J to afford the titled compound (quantitative conversion) as a clear oil, which was used without further purification.

Intermediate qq 2-(4-fluorophenyl)cyclopropanecarbonyl chloride

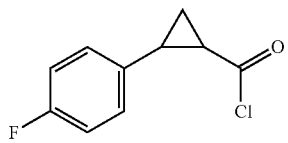 [SMILES: O=C(Cl)C1CC1c1ccc(F)cc1]

2-(4-fluorophenyl)cyclopropanecarboxylic acid (2 g, 10.07 mmol) and thionyl chloride (20 mL) were reacted according to General Procedure J to afford the titled compound as a clear oil, which was used without further purification.

Intermediate uu cyclopropyl(2,2-dimethyl-1,3-benzoxathiol-5-yl)methanone

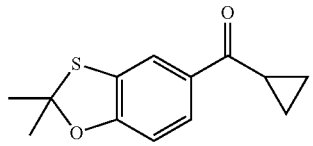 [SMILES: CC1(C)Oc2ccc(C(=O)C3CC3)cc2S1]

To a solution of cyclopropancarbonyl chloride (2.6 g, 25.26 mmol) in anhydrous DCM (20 mL) at −10° C. under a nitrogen atmosphere was added AlCl$_3$ (1.7 g, 12.63 mmol) portion-wise and the mixture was stirred until homogeneous. The solution was then added to a solution of 2,2-dimethyl-1,3-benzoxathiole (prepared according to procedure outlined in the Journal of Heterocyclic Chemistry, 1984, 21 (2), 573-6 and 1982, 19(1), 135-9) (2.1 g, 12.63 mmol) in anhydrous DCM (20 mL) at −10° C. After stirring for 30 min at −10° C., the mixture was poured into 5M NaOH. The aqueous phase was extracted twice with DCM. The combined organics were dried (MgSO$_4$), filtered and concentrated under reduced pressure to give an oil. The oil was purified by column chromatography using 5% to 20% EtOAc in n-heptane to give title compound as a white solid (542 mg, 18%). $^1$H NMR (CDCl$_3$) δ 7.80 (d, J=1.9 Hz, 1H), 7.74 (dd, J=8.3, 1.9 Hz, 1H), 6.82 (d, J=8.3 Hz, 1H), 2.60-2.53 (m, 1H), 1.86 (s, 6H), 1.22-1.17 (m, 2H), 1.02-0.96 (m, 2H). HPLC (Method 1) Rt 4.15 min (Purity: 86.9%).

Intermediate vv cyclopropyl(2,2-dimethyl-3,3-dioxido-1,3-benzoxathiol-5-yl)methanone

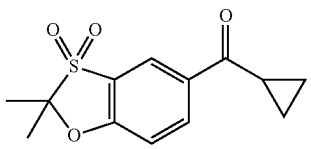 [SMILES: CC1(C)Oc2ccc(C(=O)C3CC3)cc2S1(=O)=O]

To a solution of Intermediate uu (542 mg, 2.31 mmol) in glacial AcOH (10 mL) at 0° C. was added H₂O₂ (2.62 mL, 23.13 mmol). After stirring for 30 min at RT, H₂O₂ (5.2 mL, 46.26 mmol) was added and the reaction was stirred at RT for 18 hr. DCM was added and the organic phase was washed with water, 1N NaOH, saturated solution of sodium thiosulfate, dried (MgSO₄), filtered and concentrated under reduced pressure to give the title compound as a white solid (625 mg, quantitative). ¹H NMR (CDCl₃) δ 8.04 (d, J=1.9 Hz, 1H), 7.89 (dd, J=8.7, 1.9 Hz, 1H), 6.76 (d, J=8.7 Hz, 1H), 2.30-2.22 (m, 1H), 1.44 (s, 6H), 0.95-0.90 (m, 2H), 0.78-0.72 (m, 2H). HPLC (max plot) 93.7%; Rt 3.40 min. UPLC/MS (Method 3) 267.0 (M+H)⁺.

Intermediate ww (E)-cyclopropyl(2,2-dimethyl-3,3-dioxido-1,3-benzoxathiol-5-yl)methanone oxime

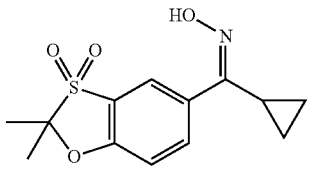 [SMILES: CC1(C)Oc2ccc(/C(=N\O)C3CC3)cc2S1(=O)=O]

A solution of Intermediate vv (625 mg, 2.35 mmol) in hydroxylamine (10 mL) and EtOH (10 mL) was heated at 90° C. for 2 days. The mixture was then cooled to RT, water was added and the mixture was extracted four times with DCM. The combined organics were washed with water, dried (MgSO₄), filtered and concentrated under reduced pressure. n-Heptane was added and the solid was triturated, sonicated and filtered to give the title compound as a white solid (578 mg, 88%). UPLC/MS (Method 3) 282.0 (M+H)⁺.

Intermediate xx 1-cyclopropyl-1-(2,2-dimethyl-3,3-dioxido-1,3-benzoxathiol-5-yl)methanamine

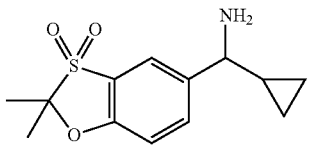 [SMILES: CC1(C)Oc2ccc(C(N)C3CC3)cc2S1(=O)=O]

A solution of Intermediate ww (578 mg, 2.05 mmol) in MeOH (20 mL) was hydrogenated in H-Cube® (Thalesnano) with Raney nickel 1 mL/min 60 bars at 90° C. under recycling condition for 3 hr. The mixture was then concentrated under reduced pressure and the titled compound was isolated as HCl salt (white solid) after exposure to HCl (1.25N in diethyl ether) (380 mg, 61%). HPLC (max plot) 90.5%; Rt 3.40 min. UPLC/MS (Method 3) 251.0 (M+H)⁺.

Intermediate yy 1-cyclopropyl-1-(2,2-dimethyl-3,3-dioxido-1,3-benzoxathiol-5-yl)-N-(pyridin-2-ylmethyl)methanamine

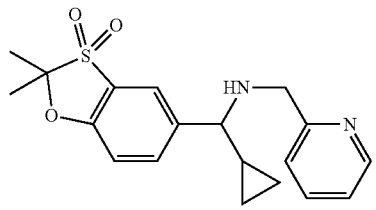 [SMILES: CC1(C)Oc2ccc(C(NCc3ccccn3)C3CC3)cc2S1(=O)=O]

Intermediate xx (195 mg, 0.64 mmol) and 2-pyridinecarboxaldehyde (69 mg; 0.64 mmol) were reacted according to General Procedure A (however triethylamine (0.089 mL, 0.64 mmol) was stirred for 10 min with the amine hydrochloride prior to addition of aldehyde) to give the title compound as a yellow oil (180 mg, 78%). ¹H NMR (CDCl₃) δ 8.57-8.55 (m, 1H), 7.79-7.62 (m, 3H), 7.19-6.99 (m, 3H), 3.89-3.70 (m, 2H), 2.88 (d, J=9.0 Hz, 1H), 1.75 (s, 6H), 1.19 (brs, 1H), 0.75-0.17 (m, 4H). HPLC (Method 1) Rt 2.26 min (Purity: 86.3%). UPLC/MS (Method 3) 359.1 (M+H)⁺.

Intermediate zz 1-(4-methyl-4H-1,2,4-triazol-3-yl)-N-(pyridin-2-ylmethyl)ethanamine

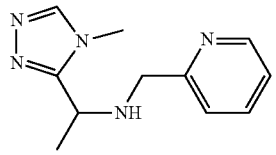 [SMILES: CC(NCc1ccccn1)c1nncn1C]

1-(4-Methyl-4H-[1,2,4]triazol-3-yl)-ethylamine dihydrochloride (140 mg; 0.70 mmol) and 2-pyridinecarboxaldehyde (83 mg, 0.77 mmol) were reacted according to General Procedure A to give the title compound as an oil. UPLC/MS (Method 3) 218.1 (M+H)⁺.

Intermediate aaa 1-(3-ethyl-1,2,4-oxadiazol-5-yl)-N-(pyridin-2-ylmethyl)ethanamine

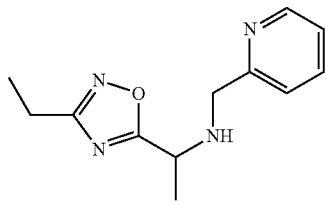 [SMILES: CCc1noc(C(C)NCc2ccccn2)n1]

1-(3-ethyl-1,2,4-oxadiazol-5-yl)ethanamine (180 mg, 0.71 mmol) and 2-pyridinecarboxaldehyde (83 mg, 0.78 mmol), were reacted according to General Procedure A to give the title compound as an oil (87 mg, 53%). $^1$H NMR (d$_6$-DMSO) δ 8.56-8.54 (m, 1H), 7.64 (dt, J=1.8, 7.7 Hz, 1H), 7.30-7.28 (m, 1H), 7.19-7.15 (m, 1H), 4.19 (q, J=6.9 Hz, 1H), 4.00-3.88 (m, 2H), 3.10-2.70 (br s, 1H) 2.75 (q, J=7.6 Hz, 2H), 1.58 (d, J=6.9 Hz, 3H), 1.32 (t, J=7.6 Hz, 3H). UPLC/MS (Method 3) 233.1 (M+H)$^+$.

Intermediate ab

Enantiomer A of 1-(4-fluorophenyl)-N-[2-(4-fluoropiperidin-1-yl)ethyl]-2-methylpropan-1-amine

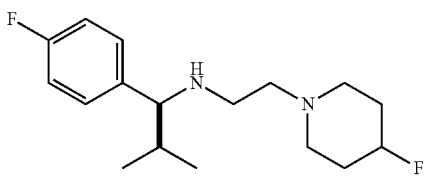 [SMILES: CC(C)[C@H](NCCN1CCC(F)CC1)c1ccc(F)cc1]

Step 1: 2-chloro-N-[(1 S)-1-(4-fluorophenyl)-2-methylpropyl]acetamide

To a solution of intermediate bk (0.50 g, 167 mmol) in anhydrous DCM (10 mL) at RT was added DIPEA (610 μL, 129 mmol)) followed by chloro acetylchloride (280 μL, 113 mmol. The reaction progress was monitored by LCMS and TLC, upon completion the reaction mixture was diluted with EtOAc and washed with NH$_4$Cl (½ sat. aq., 2×) and brine (1×), dried (Na$_2$SO$_4$) and concentrated under reduced pressure. The crude product was purified by flash silica gel chromatograph (20% EtOAc/hexane, Rf=0.24) to give the intermediate shown as a white solid (94%, 683 mg). LCMS (Method 2) m/z 244.3 (M+H)$^+$.

Step 2: N-[(1 S)-1-(4-fluorophenyl)-2-methylpropyl]-2-(4-fluoropiperidin-1-yl)acetamide A solution of the amide (332 mg, 243 mmol), NaI (620 mg, 150 mmol), Na$_2$CO$_3$ (296 mg, 106 mmol) and 4-fluoropiperidine.HCl (385 mg, 140 mmol) in anhydrous DMF was flushed with N$_2$, stoppered and heated to 60° C. ON. The reaction mixture was diluted with EtOAc and washed with NH$_4$Cl (½ sat. aq., 3×) and brine (1×), dried (Na$_2$SO$_4$) and concentrated under reduced pressure. The crude product was purified by flash silica gel chromatography (60% EtOAc/hexane, Rf=0.34) to give the intermediate shown as a yellow oil (97%, 408 mg). LCMS (Method 2) m/z 311.2 (M+H)$^+$.

Step 3: Enantiomer A of 1-(4-fluorophenyl)-N-[2-(4-fluoropiperidin-1-yl)ethyl]-2-methylpropan-1-amine To a 0° C. solution of the amide (389 mg, 310 mmol) in anhydrous THF (5 mL) was added LiAlH$_4$ (133 mg, 351 mmol) and the reaction mixture warmed to 50° C. Reaction progress was monitored by LCMS and upon completion was quenched by cooling to 0° C., diluting with EtOAc (10 mL) and slow addition of NaK tartrate (1M) solution. A grey solid formed and the reaction mixture was for 3 days during which time the solids dissolved. The product was extracted into EtOAc (3×) and the pooled extracts were dried (Na$_2$SO$_4$) and concentrated under reduced pressure. The crude product was purified by flash silica gel chromatography (4% MeOH/EtOAc, Rf=0.24) to give the title compound as a yellow oil (82%, 408 mg). LCMS (Method 2) m/z 297.2 (M+H)$^+$.

Intermediate ac

Cyclopropyl-(3-ethanesulfonyl-phenyl)-methyl]-(2,2-difluoro-2-pyridin-2-yl-ethyl)-amine

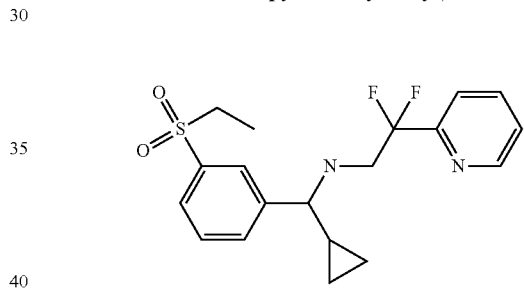

Tetraethyl orthotitanate (2.84 mL, 13.4 mmol) was added into a solution of cyclopropyl[3-(ethylsulfonyl)phenyl]methanone (2.0 g; 8.4 mmol) and 2,2-difluoro-2-pyridin-2-yl-ethylamine benzenesulfonate (3.18 g, 10.1 mmol) in anhydrous THF (16 mL) at RT. The resulting mixture was heated at reflux for 2 hours, and then cooled to RT. Sodium borohydride (952 mg, 25.2 mmol) was added and the resulting mixture was stirred at RT until completion. The reaction mixture was poured in MeOH (20 mL) under vigorous stirring, and then the resulting suspension was filtered off and rinsed with MTBE. A 1N aqueous solution of NaOH (100 mL) was added to the filtrate under vigorous stirring and the precipitate was removed by filtration. The resulting biphasic filtrate was separated and the aqueous layer was extracted with MTBE. The combined organic layers were washed with water and brine, dried (Na$_2$SO$_4$) and concentrated under reduced pressure. After purification by flash chromatography (silica, petroleum ether/EtOAc 1:1), the title compound was obtained as a colourless oil (790 mg, 25%). UPLC/MS (max plot) 90.3%; Rt 1.54 min; (MS+) 381.4 ([M+H]$^+$).

Intermediate ad

N-[(4-chlorophenyl)(cyclopropyl)methyl]-8-methyl-8-azabicyclo[3.2.1]octan-3-amine

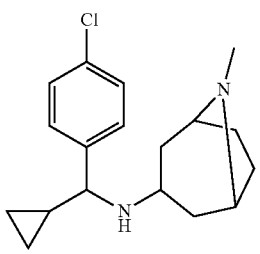 [SMILES: CN1C2CCC1CC(NC(c1ccc(Cl)cc1)C1CC1)C2]

To a solution of 4-chlorobenzaldehyde (400 mg, 2.84 mmol) and 8-methyl-8-azabicyclo[3.2.1]octan-3-amine (413 mg, 2.98 mmol) in anhydrous THF (6 mL) was added magnesium sulphate (685 mg, 5.69 mmol) and the resulting reaction mixture was stirred at RT for 4 hours. Reaction mixture was filtered and filtrate was concentrated under reduced pressure to obtain imine-intermediate as light brown oil (748 mg). Cyclopropyl bromide (5.69 mmol) was dissolved in dry diethyl ether (6 mL) under nitrogen atmosphere at −78° C. and treated with tert-BuLi. After 10 minutes, cooling was removed and the mixture was stirred at room temperature for 1 hr. Reaction mixture was again cooled to −78° C. and a solution of imine-intermediate in dry diethyl ether (4 mL) was added slowly. Cooling was removed and reaction was stirred at room temperature for 24 hr. The crude reaction mixture was diluted with EtOAc and the organics washed with ammonium chloride (aqueous) solution followed by brine. The organic layer was separated, dried (MgSO$_4$) and concentrated under reduced pressure to provide the title compound (800 mg), which was used without purification to the next step. $^1$H NMR (CDCl$_3$) δ 7.29-7.21 (m, 4H), 3.08-3.0 (m, 2H), 2.87 (d, J=8.4 Hz, 1H), 2.67-2.61 (m, 1H), 2.23 (s, 3H), 2.03-1.38 (m, 9H), 1.02-0.88 (m, 1H), 0.63-0.53 (m, 1H), 0.43-0.33 (m, 1H), 0.32-0.18 (m, 1H). MS (ES$^+$) m/z 305.2 (M+H$^+$).

Intermediate ae 1-(4-ethanesulfonyl-phenyl)-propylamine

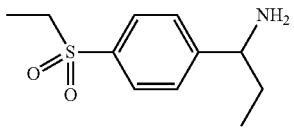

Step 1: 1-(4-ethylsulfanyl-phenyl)-propan-1-one

Aluminium chloride (8.78 g, 65.8 mmol) was added into a solution of propionyl chloride (4.86 mL, 55.7 mmol) in anhydrous DCM (35 mL) cooled at 5° C. The resulting solution was stirred at 5° C. for 15 minutes, and then added dropwise over 5 minutes into a solution of (ethylthio) benzene in anhydrous DCM (35 mL) cooled at −10° C. After 1.5 hours at −10° C., the reaction mixture was poured into a mixture of a 5N aqueous solution of HCl (100 mL) and crushed ice, and then was extracted with DCM (2×100 mL). The combined organic layers were washed with a saturated solution of NaHCO$_3$ and brine, then dried (MgSO$_4$) and concentrated under reduced pressure to give the title compound as a greenish solid (8.7 g, 88%), use without further purification. $^1$H NMR (300 MHz, DMSO-d$_6$) δ 7.94-7.81 (m, 2H), 7.45-7.34 (m, 2H), 3.04 (m, 4H), 1.28 (t, J=7.3 Hz, 3H), 1.07 (t, J=7.2 Hz, 3H). UPLC/MS (max plot) 100%; Rt 1.78 min; (MS+) 195.1 ([M+H]$^+$).

Step 2: 1-(4-ethanesulfonyl-phenyl)-propan-1-one

A solution of oxone monopersulfate (58.8 g, 94.0 mmol) in water (160 mL) was added over 5 minutes into a solution of 1-(4-ethylsulfanyl-phenyl)-propan-1-one (8.7 g, 44.8 mmol) in EtOAc (80 mL). The resulting mixture was stirred at RT for 4 hours under vigorous stirring. The layers were separated and the aqueous layer was extracted with EtOAc (300 mL). The combined organic layers were washed with water (200 mL) and brine (200 mL), and then dried (MgSO$_4$) and concentrated under reduced pressure to give 8.86 g of an off-white solid. The solid was triturated in Et$_2$O, and then filtered off and dried under reduced pressure to give the title compound as a white solid (7.8 g, 77%). $^1$H NMR (300 MHz, DMSO-d6) δ 8.29-8.11 (m, 2H), 8.11-7.95 (m, 2H), 3.38 (q, J=7.4 Hz, 2H), 3.13 (q, J=7.1 Hz, 2H), 1.19-1.01 (m, 6H). HPLC (max plot) 99.7%; Rt 2.90 min. UPLC/MS (max plot) 100%; Rt 1.09 min; (MS+) 244.3 ([M+NH$_4$]$^+$).

Step 3: allyl-[1-(4-ethanesulfonyl-phenyl)-propyl]-amine

A solution of 1-(4-ethanesulfonyl-phenyl)-propan-1-one (5.80 g, 25.6 mmol) and allylamine (3.85 mL, 51.3 mmol) was prepared in anhydrous THF (70 mL), and then tetraethyl orthotitanate (8.6 mL, 41.0 mmol) was added. The resulting mixture was heated at 60° C. for 2 hours, and then stirred at RT for 15 hours. The reaction mixture was cooled down to 5° C. and NaBH$_4$ (1.94 g, 51.3 mmol) was added portionwise over 5 min. The resulting mixture was stirred for 2 hours allowing temperature to warm up to RT, and then MeOH (60 mL) was added drop-wise over 15 min. The mixture was diluted with a 1N aqueous solution of HCl (100 mL) and washed twice with MTBE (2×50 mL). The aqueous layer was basified with a 1N aqueous solution of NaOH and extracted with MTBE (2×100 mL). The organic layers were combined, washed with brine, dried (MgSO$_4$) and concentrated under reduced pressure to give the title compound as a colourless oil (3.67 g, 54%), used without further purification. UPLC/MS (max plot) 98.3%; Rt 1.11 min; (MS+) 268.2 ([M+H]$^+$).

Step 4: 1-(4-ethanesulfonyl-phenyl)-propylamine

A mixture of bis(dibenzylideneacetone)palladium (387 mg, 0.67 mmol) and 14-bis(diphenylphosphino)butane (287 mg, 0.67 mmol) was prepared in THF (20 mL) under nitrogen and stirred at RT for 15 minutes. The preformed catalyst and thiosalicylic acid (2.28 g, 14.8 mmol) were added into a solution of allyl-[1-(4-ethanesulfonyl-phenyl)-propyl]-amine (3.60 g, 13.5 mmol) in THF (20 mL). The resulting mixture was stirred at 60° C. for 3 hours until completion. The reaction mixture was diluted a 1N aqueous solution of HCl, and then washed with EtOAc. The aqueous layer was basified with a 1N aqueous solution of NaOH, and then extracted with EtOAc (3×100 mL). The organic layers were combined, dried (MgSO$_4$) and concentrated under reduced pressure to give 2.55 g of a yellow oil. After purification by flash chromatography (silica, THF), the racemic title compound was obtained as a pale yellow oil (2.1 g, 69%). Refer to Table 1 for separation of enantiomers.

Intermediate af 1-(4-methanesulfonyl-phenyl)-propylamine

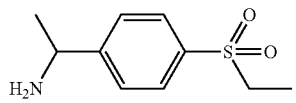

The title compound was prepared following procedures described for Intermediate ae (steps 1 to 4), but starting from (methylthio)benzene in step 1. After purification by flash chromatography (silica, THF), the racemic title compound was obtained as a pale yellow oil (3.65 g). Refer to Table 1 for separation of enantiomers.

Intermediate aq tert-Butyl 3-[amino(4-fluorophenyl)methyl]azetidine-1-carboxylate

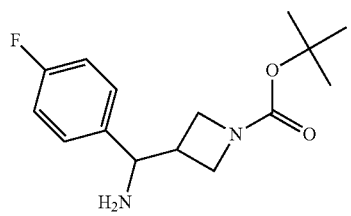 [SMILES: CC(C)(C)OC(=O)N1CC(C(N)c2ccc(F)cc2)C1]

Step 1: tert-Butyl 3-(4-fluorobenzoyl)azetidine-1-carboxylate

To a solution of 1-Bromo-4-fluorobenzene (20 g, 0.0984 mol) in dry tetrahydrofuran (200 mL) was added n-Butyl lithium (76.8 mL, 0.1229 mol, 1.6 M solution in hexane) in drops at −78° C. under nitrogen and stirred at same temperature for 1 hr. To this reaction mixture, tert-Butyl 3-{[methoxy (methyl) amino]carbonyl}azetidine-1-carboxylate (20 g, 0.0819 mol) in tetrahydrofuran (75 mL) was added at −78° C. The reaction mixture was stirred for 1 hr at −78° C. The reaction mixture was quenched with ice and extracted with ethyl acetate (2×100 mL) and dried over sodium sulphate. The solvent was evaporated and the residue was purified by column chromatography by using silica gel (60-120 mesh) using pet ether and ethyl acetate (80:20) as an eluent to afford (23 g, 95%) of the title compound as a pale brown liquid. TLC: Pet ether/Ethyl acetate: (5/5), R$_f$=0.6; $^1$H NMR (400 MHz, DMSO-d$_6$): δ 7.98-7.94 (m, 2H), 7.39-7.34 (m, 2H), 4.41-4.34 (m, 1H), 4.12 (s, 2H), 3.95 (s, 2H), 1.36 (s, 9H).

Step 2: tert-Butyl 3-[(E)-(4-fluorophenyl)(hydroxyimino)methyl]azetidine-1-carboxylate To a solution of tert-Butyl 3-(4-fluorobenzoyl) azetidine-1-carboxylate (14 g, 0.0501 mol) in a mixture of methanol (120 mL) and water (20 mL) was added sodium acetate (10.2 g, 0.1253 mol) followed by hydroxyl amine hydrochloride (6.9 g, 0.1002 mol) at RT. The reaction mixture was stirred at RT for 12 hr. After completion of the reaction, the reaction mixture was concentrated under reduced pressure. The residue was dissolved with ethyl acetate (200 mL), washed with an aqueous solution of sodium bicarbonate (10%, 100 mL), water (100 mL), brine solution (100 mL) and dried over sodium sulphate. The solvent was evaporated and the crude material was purified by column chromatography by using pet ether and ethyl acetate (50:50) as an eluent to afford (13 g, 88%) of the title compound as a white solid. TLC: Pet ether/Ethyl acetate: (7/3), R$_f$=0.2; $^1$H NMR (400 MHz, DMSO-d6): δ 11.38 (s, 1H), 7.41-7.38 (m, 2H), 7.25-7.20 (m, 2H), 4.12-4.08 (t, J=8.2 Hz, 1H), 4.04-3.95 (m, 2H), 3.82-3.76 (m, 2H), 1.37 (s, 9H).

Step 3: tert-Butyl 3-[amino(4-fluorophenyl)methyl]azetidine-1-carboxylate

To a solution of tert-Butyl 3-[(E)-(4-fluorophenyl)(hydroxyimino)methyl]azetidine-1-carboxylate (12 g, 0.0407 mol) in methanol (300 mL) was added palladium on carbon (10%, 3.6 g). This reaction mixture was hydrogenated under 20 Kg of pressure of Hydrogen for 12 hr at RT. The reaction mixture was filtered off catalyst and the filtrate was concentrated. The resulted residue was purified by acid-base work up [the residue was taken in an aqueous solution of citric acid (10%, 50 mL) and washed with ethyl acetate (2×100 mL). The separated aqueous layer was basified with an aqueous solution of sodium bicarbonate (10%, 40 mL) and extracted with DCM (2×100 mL). The DCM layer was washed with brine solution, dried over sodium sulphate and evaporated under reduced pressure] to afford (8.5 g, 74%) of the title compound as a white solid. TLC: Pet ether/Ethyl acetate: (1/1), R$_f$=0.2; $^1$H NMR (400 MHz, DMSO-d6): δ 7.39-7.36 (m, 2H), 7.12-7.08 (m, 2H), 3.87-3.85 (d, J=8.9 Hz, 1H), 3.81-3.79 (d, J=5.9 Hz, 2H), 3.57 (s, 1H), 3.46-3.43 (t, J=7.6 Hz, 1H), 2.67-2.50 (m, 1H), 2.02 (s, 2H) 1.36 (s, 9H); LCMS: 181 [M−100]$^+$ Intermediate ah tert-butyl-3-{amino[4-(difluoromethoxy)phenyl]methyl}azetidine

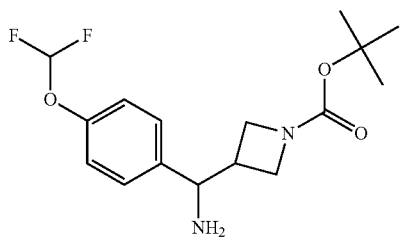 [SMILES: CC(C)(C)OC(=O)N1CC(C(N)c2ccc(OC(F)F)cc2)C1]

Step 1: 3-(4-Benzyloxy-benzoyl)-azetidine-1-carboxylic acid tert-butyl ester

To a stirred solution of 1-(Benzyloxy)-4-bromobenzene (32.3 g, 0.12 mol) in dry THF (250 mL) was added n-Butyl lithium (83 mL, 0.13 mol, 1.6 M solution in hexane) in drops at −78° C. under nitrogen and the reaction mixture was stirred at same temperature for 1 hr. To this reaction mixture, a solution of tert-butyl 3-{[methoxy(methyl)amino]carbonyl}azetidine-1-carboxylate (25 g, 0.10 mol) in dry THF (150 mL) was added in drops. The reaction mixture was stirred at −78° C. for 1 hr. After completion of reaction, the reaction mixture was quenched with ice water and extracted with ethyl acetate (2×200 mL). The combined organic layer washed with water (200 mL), brine (100 mL) and dried over sodium sulphate. The solvent was concentrated under reduced pressure; the crude product was slurred with pet ether (100 mL) and ethyl acetate (50 mL). The solids were filtered to afford (30 g, 75%) of the titled compound as white solid. TLC-Pet ether/Ethyl acetate (8:2), $R_f$=0.7; $^1$H NMR (400 MHz, DMSO-$d_6$) δ 7.84-7.82 (t, J=8.0 Hz, 2H), 7.46-7.31 (m, 5H), 7.14-7.10 (m, 2H), 5.20 (s, 2H), 4.35-4.28 (m, 1H), 4.10 (s, 2H), 3.93 (s, 2H), 1.36 (s, 9H).

Step 2: tert-butyl 3-[hydroxy(4-hydroxyphenyl)methyl]azetidine-1-carboxylate To a solution 3-(4-benzyloxy-benzoyl)-azetidine-1-carboxylic acid tert-butyl ester (48 g, 0.01 mol) in methanol (600 mL) was added 10% Pd/C (5 g) and the reaction mixture was hydrogenated at 5.0 kg/cm$^{-1}$ pressure of hydrogen at RT for 8 hr. After the completion of reaction, the reaction mixture was filtered through celite bed to remove the catalyst and the filtrate was concentrated under reduced pressure. The crude product was purified by column chromatography by using pet ether and ethyl acetate as an eluent to afford (40 g, 98%) of the titled compound as white solid. TLC-Pet ether/Ethyl acetate (5:5), $R_f$=0.5; $^1$H NMR (400 MHz, DMSO-$d_6$) δ 9.26 (s, 1H), 7.11-7.08 (m, 2H), 6.69-6.66 (m, 2H), 5.31-5.30 (d, J=4.0 Hz, 1H), 4.50-4.47 (dd, J=4.0 Hz, 8.0 Hz, 1H), 3.74 (s, 2H), 3.62 (s, 1H), 3.54-3.50 (t, J=16.0 Hz, 1H), 2.69-2.64 (m, 1H), 1.39 (s, 9H).

Step 3: tert-butyl 3-[[4-(difluoromethoxy)phenyl](hydroxy)methyl]azetidine-1-carboxylate To a stirred solution of tert-butyl 3-[hydroxy (4-hydroxyphenyl) methyl]azetidine-1-carboxylate (40 g, 0.143 mol) in a mixture of acetonitrile (400 mL) and potassium hydroxide (in water 400 mL) (160 g, 0.91 mol) in a 1 Ltr pressure vessel, was added diethyl(bromodifluromethyl) phosphonate (84 g, 0.09 mol) at −78° C. under nitrogen. The vessel was sealed and mixture was warmed to RT over a period of 30 min. After completion of reaction, mixture was diluted with diethyl ether (400 mL) and stirred for 15 min. The organic layer separated and washed with water (200 mL), brine (100 mL) and dried over sodium sulphate. The solvent was concentrated under reduced pressure. The crude product was purified by column chromatography by using pet. ether and ethyl acetate as an eluent to afford (22 g, 50%) of the titled compound as white solid. TLC-Pet ether/Ethyl acetate (5:5), $R_f$=0.3; $^1$H NMR (400 MHz, DMSO-$d_6$) δ 7.39-7.00 (m, 5H), 5.56 (s, 1H), 4.65-4.62 (dd, J=4.0 Hz, 12 Hz, 1H), 3.76-3.61 (m, 4H), 2.74-2.70 (t, J=16 Hz, 1H), 1.36 (s, 9H).

Step 4: tert-butyl 3-[4-(difluoromethoxy)benzoyl]azetidine-1-carboxylate

To a stirred solution of oxalyl chloride (24.2 g, 0.19 mol) in DCM (200 mL) was added DMSO (29.9 g, 0.38 mol) in drops at −78° C. under nitrogen. After 15 min, a solution of tert-butyl 3-[[4-(difluoromethoxy)phenyl](hydroxy)methyl]azetidine-1-carboxylate (21 g, 0.06 mol) in DCM was added in drops at −78° C. The reaction mixture was stirred at same temperature for 3 hr. and was added triethylamine (54 mL, 0.38 mol) at −78° C. in drops. The reaction mixture was stirred for additional 2 hr. and quenched with aqueous solution of sodium bicarbonate solution (10%, 200 mL) and extracted with DCM (2×200 mL). The combined organic layer was washed with aqueous solution of citric acid (1%, 200 mL), water (200 mL), brine (100 mL) and dried over sodium sulphate. The solvent was concentrated under reduced pressure to afford (20 g, 96%) of the titled compound as white solid. TLC-Pet ether/Ethyl acetate (4:6), $R_f$=0.2; $^1$H NMR (400 MHz, DMSO-$d_6$) δ 7.84-7.82 (t, J=8.0 Hz, 2H), 7.46-7.31 (m, 5H), 7.14-7.10 (m, 2H), 5.20 (s, 2H), 4.35-4.28 (m, 1H), 4.10 (s, 2H), 4.39 (s, 2H), 1.36 (s, 9H).

Step 5: tert-butyl 3-[[4-(difluoromethoxy)phenyl](hydroxyimino)methyl]azetidine-1-carboxylate To a stirred solution of tert-butyl 3-[4-(difluoromethoxy)benzoyl]azetidine-1-carboxylate (20 g, 0.06 mol) in methanol (150 mL) and water (50 mL) was added sodium acetate (12.5 g, 0.15 mol) followed by hydroxyl amine hydrochloride (8.4 g, 0.12 mol) at RT. The reaction mixture was stirred at RT for 12 hr. The reaction mixture was concentrated under reduced pressure and the residue was diluted ethyl acetate (2×200 mL) was washed with aqueous sodium bicarbonate solution (10%, 200 mL), water (100 mL), brine (100 mL) and dried over sodium sulphate. The solvent was concentrated under reduced pressure to afford (20 g, 96%) of the titled compound as an off white solid. TLC-Pet ether/Ethyl acetate (5:5), $R_f$=0.3; $^1$H NMR (400 MHz, DMSO-$d_6$) δ 11.18 (s, 1H), 7.54-7.09 (m, 5H), 4.11-3.76 (m, 5H), 1.34 (s, 9H).

Step 6: tert-butyl 3-{amino[4-(difluoromethoxy)phenyl]methyl}azetidine-1-carboxylate To a solution of tert-butyl 3-[(Z)-[4-(difluoromethoxy)phenyl](hydroxyimino)methyl]azetidine-1-carboxylate (20 g, 0.05 mol) in methanol (500 mL) was added 10% Pd/C (3 g) and the reaction mixture was hydrogenated under 20 bar pressure of hydrogen at RT for 48 hr. The reaction mixture was filtered through celite bed to remove the catalyst and the filtrate was concentrated under reduced pressure to afford (16 g, 86%) of the titled compound as colourless liquid. TLC-Pet ether/Ethyl acetate (4:6), $R_f$=0.2; $^1$H NMR (400

MHz, DMSO-d$_6$) δ 7.34-6.99 (m, 5H), 3.87-3.85 (d, J=8.0 Hz, 3H), 3.79 (s, 1H), 3.57-3.44 (m, 1H), 2.65-2.59 (m, 1H), 2.06-2.03 (d, J=12.0 Hz, 2H), 1.34 (s, 9H); LCMS: (Method 1) 282.5 [M+100]$^+$ Refer to Table 1 for separation of enantiomers.

Intermediate ai tert-butyl 4-(amino (4-(difluoromethoxy) phenyl) methyl) piperidine-1-carboxylate and Intermediate as: tert-Butyl 4-[4-(difluoromethoxy) benzoyl]piperidine-1-carboxylate

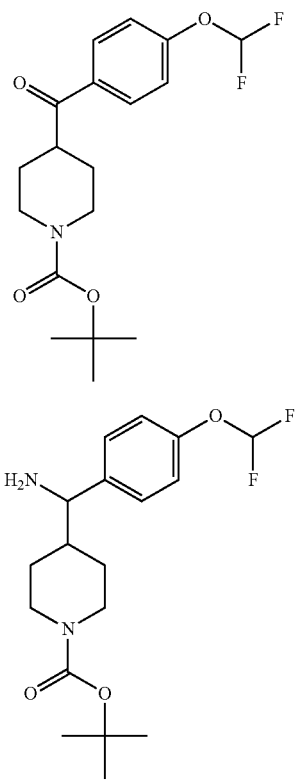

Intermediate as

Intermediate ai

The title compounds were prepared following the procedures described for Intermediate ah (steps 1-6), but 1-(Benzyloxy)-4-bromobenzene (23 g, 0.08 mol) and tert-butyl 4-{[methoxy (methyl) amino]carbonyl}piperidine-1-carboxylate (20 g, 0.07 mol) were used in Step 1.

Intermediate as (Step 4) was achieved as a white solid. TLC-Pet ether/Ethyl acetate (4:6), R$_f$=0.2; $^1$H NMR (400 MHz, DMSO-d$_6$) δ 7.80 (s, 1H), 7.71-7.00 (d, J=4.0 Hz, 1H), 7.66-7.64 (d, J=8.0 Hz, 1H), 7.59-7.57 (t, J=16.0 Hz, 1H), 3.95-3.85 (m, 2H), 3.71-3.22 (m, 1H), 3.28-3.22 (m, 2H) 2.53-2.48 (m, 2H), 2.03-1.99 (m, 2H), 1.74-1.71 (m, 1H), 1.59-1.53 (m, 1H), 1.35 (bs, 9H), 1.22-1.19 (m, 1H), 1.09-0.99 (m, 3H), 0.97-0.96 (m, 1H).

Intermediate ai (Step 6) was achieved as a colourless liquid. TLC-Pet ether/Ethyl acetate (4:6), R$_f$=0.2; $^1$H NMR (400 MHz, DMSO-d$_6$) δ 7.34-6.99 (m, 5H), 3.95-3.92 (d, J=12.0 Hz, 1H), 3.87-3.84 (d, J=12.0 Hz, 1H), 3.55-3.53 (d, J=8.0 Hz, 1H), 2.59-2.48 (m, 2H), 1.97 (s, 1H), 1.78-1.75 (d, J=12.0 Hz, 2H) 1.51-1.46 (m, 1H), 1.35 (s, 9H), 1.21-1.16 (m, 1H), 1.04-0.89 (m, 2H). LCMS (Method 1) 254.4 (M–100)

Intermediate aj

{1-[4-(difluoromethoxy) phenyl]-2-methylpropyl}amine

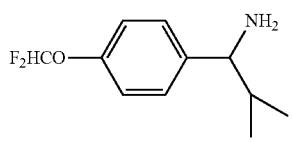

Step-1: 1-[4-(difluoromethoxy) phenyl]-2-methylpropan-1-ol

To a stirred solution of 4-difluoromethoxy benzaldehyde (23 g, 0.1334 mol) in dry THF (400 mL) under N$_2$, was added isopropyl magnesium chloride (2.0 M in THF) (20.59 g, 100.1 mL, 0.2002 mol) slowly at 0° C. The reaction mixture was stirred at RT for 3 hr. TLC confirmed the completion of the reaction mixture. The reaction mixture was again cooled to 0° C. and quenched with saturated NH$_4$Cl solution and extracted with (2×1000 mL) of ethyl acetate. The organic layer was separated, dried over Na$_2$SO$_4$ and evaporated. The crude was passed through silica gel column (60-120 mesh), pet ether/ethyl acetate as elutent to afford (13 g, 45%) of the titled compound as pale yellow liquid. TLC-pet ether/ethyl acetate: (8/2): R$_f$=0.5; $^1$H NMR (DMSO-d$_6$, 400 MHz) δ 7.31-7.29 (d, J-11.2 Hz, 2H), 7.37-7.00 (t, 1H), 7.10-7.08 (d, J-8.6 Hz, 2H), 5.13-5.12 (d, J-4.4 Hz, 1H), 4.25-4.22 (t, 1H), 1.79-1.746 (m, 1H), 0.94-0.84 (d, 3H), 0.81-0.71 (d, 3H).

Step-2: 1-(1-azido-2-methylpropyl)-4-(difluoromethoxy) benzene

To an ice-cooled solution of 1-[4-(difluoromethoxy) phenyl]-2-methylpropan-1-ol (6.75 g, 0.0312 mol) in 21 mL of 56% sulphuric acid and 21 mL of chloroform was added sodium azide (6.1 g, 0.0937 mol) in portions at 0° C. and the mixture was stirred at RT for 5 hr. The reaction was completed by TLC. The reaction mixture was diluted with ice cold water (75 mL) and extracted with DCM (2×75 mL). The separated organic layer was washed with brine solution and dried over Na$_2$SO$_4$ and evaporated. The crude was passed through chromatography using silica gel (60-120 mesh) using pet ether/ethyl acetate as an elutent to afford (5.9 g, 79%) of the titled compound as pale yellow oil. TLC-pet ether/ethyl acetate: (8/2): R$_f$=0.7; LCMS (Method 1) 214.3 (M–27) $^1$H NMR (DMSO-d$_6$, 400 MHz) δ 7.39-7.37 (d, J-8.6 Hz, 2H), 7.44-7.07 (t, 1H), 7.21-7.18 (d, J-8.6 Hz, 2H), 4.46-4.44 (d, J-8.2 Hz, 1H), 1.97-1.92 (m, 1H), 0.95-0.93 (d, 3H), 0.81-0.70 (d, 3H).

Step-3: {1-[4-(difluoromethoxy) phenyl]-2-methylpropyl}amine

To a stirred solution of 1-(1-azido-2-methylpropyl)-4-(difluoromethoxy) benzene (20 g) in methanol (500 mL) was added 10% Pd on carbon (2.0 g) under N$_2$ bubbling. The reaction was carried out at 5 kg/cm$^2$ pressure of H$_2$ at RT for 12 hr. The catalyst was collected by filtration and washed with methanol. The combined filtrate concentrated under reduced pressure. The resulted residue was purified by acid-base work up. ie; The reaction mixture was taken with 10% citric acid solution and washed with ethyl acetate (2×75 mL). The separated aqueous layer was basified with 25% ammonia solution and extracted with ethyl acetate (2×50 mL), washed with brine, dried over $Na_2SO_4$ and evaporated under reduced pressure to afford (15 g, 84%) of the titled compound as a yellow liquid. Refer to Table 1 for separation of enantiomers.

Intermediate ak

{cyclopropyl[4-(difluoromethoxy)phenyl]methyl}amine

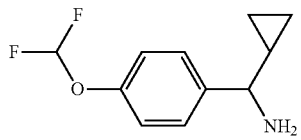

The title compound was prepared following the procedure described for Intermediate aj (steps 1-3), using 4-difluoromethoxy benzaldehyde (40 g, 0.234 mol) and cPrMgBr (0.5 M in THF) in step 1. The title compound was achieved as a yellow liquid (17 g, 60%). TLC-chloroform/methanol: (9/1): $R_f$=0.1; LCMS (Method 1): 197 [M−16]$^+$; $^1$H NMR (DMSO-$d_6$, 400 MHz) δ 7.44-7.41 (2H, d, J-11.32 Hz), 7.11-7.08 (2H, d, J-11.28 Hz), 7.36-6.99 (1H, t), 3.17-3.15 (1H, d), 2.2-1.93 (2H, bs), 0.94-0.89 (1H, m), 0.46-0.41 (1H, m), 0.35-0.27 (2H, m), 0.26-0.22 (1H, m).

Intermediate al cyclopropyl-C-[3-(propane-2-sulfonyl)-phenyl]}-methylamine and Intermediate az: cyclopropyl-[3-(propane-2-sulfonyl)-phenyl]}-methanone Intermediate al

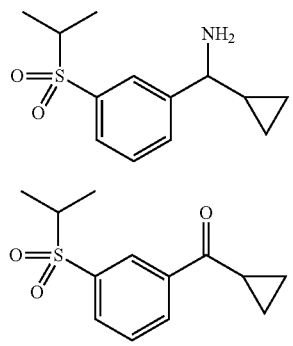

Intermediate az

Step 1: 1-bromo-3-(isopropylthio)benzene

2-Bromopropane (5.46 mL, 58.2 mmol) was added dropwise into a mixture of 3-bromothiophenol (6.29 mL, 52.9 mmol) and $K_2CO_3$ (10.96 g, 79.3 mmol) in anhydrous DMF (100 mL), and then stirred at RT overnight. The reaction mixture was diluted with water (200 mL) and extracted with MTBE (3×150 mL). The combined organic layers were washed with brine, dried ($MgSO_4$) and concentrated under reduced pressure to give the title compound as a colourless oil (12.44 g, quantitative), used without further purification. UPLC/MS (max plot) 100%; Rt 2.23 min; (MS+) no signal.

Step 2:
cyclopropyl-(3-isopropylsulfanyl-phenyl)-methanone

A 2.5M solution of butyllithium in toluene (21.53 mL, 53.8 mmol) was added dropwise over 8 minutes into a solution of 1-bromo-3-(isopropylthio)benzene (12.44 g, 53.8 mmol) in anhydrous toluene (125 mL) at RT and the resulting mixture was stirred overnight, and then 1 hour at 40° C. The reaction mixture was cooled at −30° C. and cyclopropanecarbonitrile (4.46 mL, 59.2 mmol) was added dropwise over 10 minutes. The resulting orange suspension was stirred at −30° C. for 30 minutes and was then allowed to warm up to 0° C. for 1.5 hours. The reaction mixture was diluted with a 5N aqueous solution of HCl (32.3 mL) over 20 minutes keeping temperature below 10° C., and then stirred at 40° C. for 2 hours and at RT for 72 hours. The layers were separated and the organic one was washed with water, dried ($Na_2SO_4$) and concentrated under reduced pressure to give the title compound as a yellow oil (10.38 g, 88%), used without further purification. UPLC/MS (max plot) 89.9%; Rt 1.97 min; (MS+) 221.3 ([M+H]$^+$).

Step 3

C-cyclopropyl-C-[3-(propane-2-sulfonyl)-phenyl]-methylamine (Intermediate al) and cyclopropyl-[3-(propane-2-sulfonyl)-phenyl]}-methanone (Intermediate az)

The title compounds were prepared following procedures described for Intermediate ae (steps 2 to 4), but starting from cyclopropyl-(3-isopropylsulfanyl-phenyl)-methanone in step 2. Refer to Table 1 for separation of enantiomers.

Intermediate am

Cyclopropyl [3-(ethylsulfonyl) phenyl]methanone

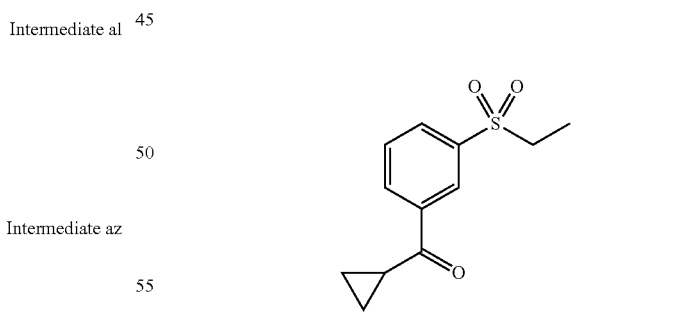

Step 1: Preparation of cyclopropyl [3-(ethylthio) phenyl]methanone

The title compound was prepared following the procedure described for Intermediate al (step 2), but starting from 3-Bromo-1-ethanesulfanylbenzene (25.40 g; 116.98 mmol). The crude material (23.40 g; crude yield: 96.98%) was obtained as greenish oil, which was used directly without further purification. UPLC/MS: (Method 3) MS(ES$^+$) 207;

$^1$H NMR (DMSO, 300 MHz) δ 7.89-7.83 (m, 2H), 7.61-7.56 (m, 1H), 7.52-7.46 (m, 1H), 3.10-3.00 (m, 2H), 2.95-2.85 (m, 1H), 1.30-1.22 (m, 3H), 1.08-1.00 (m, 4H).

Step 2: Preparation of cyclopropyl [3-(ethylsulfonyl) phenyl]methanone

The title compound was prepared following the procedure described for Intermediate ae (step 2), but starting from cyclopropyl [3-(ethylthio) phenyl]methanone (18.43 g; 80.40 mmol). The crude title product was obtained as orange oil, which was used directly without further purification [18.28 g; crude yield: 95%; purity: 95%; corrected yield: 91%]. UPLC/MS: (Method 3) MS(ES$^+$) 239. $^1$H NMR (DMSO, 300 MHz) δ 8.50-8.45 (m, 2H), 8.24-8.19 (m, 1H), 7.95-7.88 (m, 1H), 3.50-3.42 (m, 2H), 3.10-3.00 (m, 1H), 1.22-1.12 (m, 7H).

Intermediate an

C-cyclopropyl-C-(4-ethanesulfonyl-phenyl)]-methyl-amine

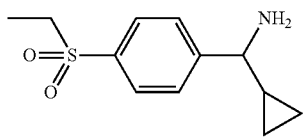 [SMILES: CCS(=O)(=O)c1ccc(C(N)C2CC2)cc1]

The title compounds were prepared following procedures described for Intermediate ae (steps 1 to 4), but starting from cyclopropanecarbonyl chloride in step 1. After purification by flash chromatography (silica, THF), the racemic title compound was obtained as a colourless oil (2.51 g, 16% over 4 steps). Refer to Table 1 for separation of enantiomers.

Intermediate ao

C-cyclopropyl-C-[4-(propane-2-sulfonyl)-phenyl]}-methylamine

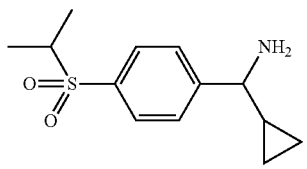

The title compounds were prepared following procedures described for Intermediate ae (steps 1 to 4), but starting from (isopropylthio)benzene and cyclopropanecarbonyl chloride in step 1. After purification by flash chromatography (silica, THF), the racemic title compound was obtained as a colourless oil (5.26 g, 30% over 4 steps).

To a solution of tert-Butyl 3-(4-fluorobenzoyl) azetidine-1-carboxylate (14 g, 0.0501 mol) in a mixture of methanol (120 mL) and water (20 mL) was added sodium acetate (10.2 g, 0.1253 mol) followed by hydroxyl amine hydrochloride (6.9 g, 0.1002 mol) at RT. The reaction mixture was stirred at RT for 12 hr. After completion of the reaction, the reaction mixture was concentrated under reduced pressure. The residue was dissolved with ethyl acetate (200 mL), washed with an aqueous solution of sodium bicarbonate (10%, 100 mL), water (100 mL), brine solution (100 mL) and dried over sodium sulphate. The solvent was evaporated and the crude material was purified by column chromatography by using pet ether and ethyl acetate (50:50) as an eluent to afford (13 g, 88%) of the title compound as a white solid. TLC: Pet ether/Ethyl acetate: (7/3), R$_f$=0.2; $^1$H NMR (400 MHz, DMSO-d6): δ 11.38 (s, 1H), 7.41-7.38 (m, 2H), 7.25-7.20 (m, 2H), 4.12-4.08 (t, J=8.2 Hz, 1H), 4.04-3.95 (m, 2H), 3.82-3.76 (m, 2H), 1.37 (s, 9H).

Refer to Table 1 for separation of enantiomers.

Intermediate ar

C-Cyclopropyl-C-(3-ethanesulfonyl-phenyl)-methyl-amine

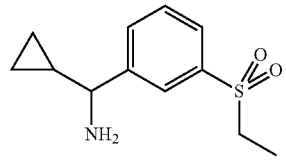 [SMILES: CCS(=O)(=O)c1cccc(C(N)C2CC2)c1]

Step 1: C-Cyclopropyl-C-(3-ethylsulfanyl-phenyl)-methylamine hydrochloride

To a 500 mL three necked flask under nitrogen containing 3-Bromo-1-ethanesulfanylbenzene 3 (20.00 g; 92.11 mmol; 1.00 eq) in dry toluene (200 mL; 20V) at RT was added rapidly a solution of n-butyllithium (36.84 mL; 92.11 mmol; 1.00 eq; 2.5M in toluene). Reaction mixture was stirred at RT overnight (Monitoring of lithium-bromine exchange was performed by quenching a sample with CO$_2$ and by injecting resulting carboxylic acid in UPLC/MS: 7% of starting material 3 was left). Reaction mixture was stirred at 40° C. for 4 hr to get lithium-bromine exchange completion.

Temperature was brought down to −30° C. and cyclopropanecarbonitrile (7.64 mL; 101.32 mmol; 1.10 eq) was added drop wise over 10 minutes. Resulting nice orange light suspension was stirred at −30° C. for 2 hr and was then allowed to warm up to 0° C. until completion (Monitoring of reaction was done by quenching sample with HCl (1N) and following ketimine and ketone formation by UPLC/MS).

Ethanol (100 mL; 5V) was added in one portion and sodium borohydride (6.97 g; 184.22 mmol; 2.00 eq) was added to the resulting colourless solution keeping temperature below 10° C. Reaction mixture was stirred at RT over the week-end after what new batch of sodium borohydride (6.97 g; 184.22 mmol; 2.00 eq.) was added to get completion after 5 h. Reaction mixture was poured in a large beaker containing HCl (5N, 100 mL; careful important foaming). Phases were separated and aqueous phase was washed with MTBE (2×150 mL) and then basified with NaOH (5N). Aqueous phase was then extracted with MTBE (3×150 mL) and combined organic phase was washed with brine, dried over Na$_2$SO$_4$, filtered and concentrated to afford colourless oil (m=12.05 g)

This oil was dissolved in 250 mL of diethyl ether at RT and then HCl (2N) in diethyl ether was added drop wise. Resulting white suspension was filtered and dried under reduced pressure to give title product [14.21 g; crude yield:

63%; purity: 100%; corrected yield 63%] as white powder. UPLC/MS: (Method 3) MS(ES+) 207 [M-NH$_2$]+.

Step 2: Preparation of C-Cyclopropyl-C-(3-ethane-sulfonyl-phenyl)-methylamine

To a solution of C-Cyclopropyl-C-(3-ethylsulfanyl-phenyl)-methylamine (12.00 g; 49.22 mmol; 1.00 eq) in acetic acid (120 mL; 10V) was added perchloric acid (4.20 mL; 49.22 mmol; 1.00 eq; 70%) in one portion. Then reaction mixture was cooled down to 15° C. and hydrogen peroxide (50.27 mL; 492.21 mmol; 10.00 eq; 30%) was added drop wise over 10 min (exothermic at the beginning of addition) keeping temperature at 20° C. Then solution was stirred at RT for 15 min after what exotherm brought temperature at 30° C., ice bath was used to maintain temperature at 25° C. for 5 hr until nearly completion. The reaction was quenched with an excess of NaOH (5N) and the product extracted with dichloromethane. After drying over Na$_2$SO$_4$, filtration and concentration, resulting yellow oil (m=10 g) was purified by chromatoflash (SiO$_2$, THF) to give the title product [8.00 g; crude yield: 68%; purity: 91%; corrected yield 62%] as colourless oil (traces of THF by NMR). UPLC/MS: (Method 3) MS(ES+) 239 [M-NH$_2$]+

Refer to Table 1 for separation of enantiomers.

Intermediate at tert-butyl 3-{amino[4-(trifluoromethoxy)phenyl]methyl}azetidine-1-carboxylate

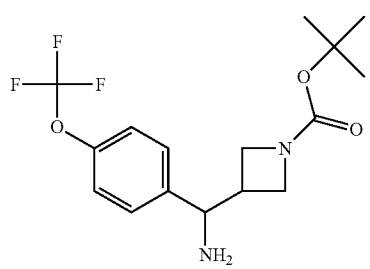 [SMILES: CC(C)(C)OC(=O)N1CC(C(N)c2ccc(OC(F)(F)F)cc2)C1]

The title compound was prepared following procedures described for Intermediate ag (steps 1-3), but starting from 1-bromo-4-(trifluoromethoxy)benzene (20 g, 0.0786 mol). The titled compound was achieved as a white solid. TLC-Pet ether/Ethyl acetate (1:1), R$_f$=0.3; $^1$H NMR (400 MHz, DMSO-d$_6$) δ 7.48-7.46 (m, 2H), 7.28-7.26 (d, J=8.0 Hz, 2H), 3.91-3.89 (d, J=8.0 Hz, 1H), 3.84-3.79 (bs, 2H), 3.59 (bs, 1H), 3.49-3.45 (t, J=8.0 Hz, 1H), 2.67-2.61 (m, 1H), 1.97 (bs, 2H), 1.34 (s, 9H). LCMS: (Method 1) 291.01 [M−56]

Intermediate au

C-[(4-cyclopropanesulfonyl-phenyl)-C-cyclopropyl]-methylamine

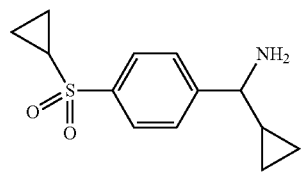 [SMILES: NC(c1ccc(S(=O)(=O)C2CC2)cc1)C1CC1]

The title compounds were prepared following procedures described for Intermediate ae (steps 1 to 4), but starting from (cyclopropylthio)benzene and cyclopropanecarbonyl chloride in step 1. After purification by flash chromatography (silica, THF), the racemic title compound was obtained as a white solid (2.77 g, 21% over 4 steps). Refer to Table 1 for separation of enantiomers.

Intermediate av (1R,2R)-2-(4-fluorophenyl)cyclopropanecarbonyl fluoride

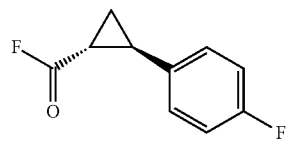 [SMILES: O=C(F)[C@@H]1C[C@H]1c1ccc(F)cc1]

Intermediate da (1 gm, 5.55 mmol) was dissolved in DCM (3 mL) and DAST (880 μl, 6.66 mmol) was added to the solution at RT under stirring and nitrogen atmosphere. Reaction was stirred for 1 hr. and then quenched by the addition of aqueous solution of sodium bicarbonate and extracted with DCM. Organic layer was separated, dried (MgSO$_4$) and concentrated under reduced pressure to get the crude light brown thick oily material which was used without any purification.

Intermediate aw 4-(azido(3-(ethylsulfonyl)phenyl)methyl)tetrahydro-2H-pyran

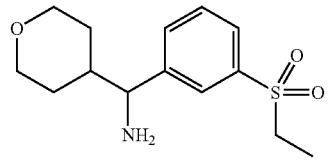 [SMILES: CCS(=O)(=O)c1cccc(C(N)C2CCOCC2)c1]

Step 1: (3-(ethylthio)phenyl)(tetrahydro-2H-pyran-4-yl)methanol

To a solution of 1-Bromo-3-(ethylthio)benzene (720.9 mg, 3.32 mmol) in dry THF (5 mL) under N$_2$ at −78° C. was added 1.9M n-BuLi in cyclohexane (2 mL, 3.80 mmol) drop-wise. The reaction was stirred at this temperature for 10 mins before addition of 4-formyltetrahydropyran (350 μL, 3.36 mmol) drop-wise. The cooling bath was removed and the reaction allowed to achieve ambient temperature over 1 hour. TLC (1:9 EtOAc/hexanes) showed the reaction complete. The reaction was quenched with sat.NH$_4$Cl and extracted with Et$_2$O. The extracts were combined, dried over MgSO$_4$, filtered and concentrated under reduced pressure. The crude material was purified by column chromatography eluting with 15-30% EtOAc/hexanes to afford (3-(ethylthio)phenyl)(tetrahydro-2H-pyran-4-yl)methanol (719.1 mg, 2.85 mmol, 86%)

Step 2: (3-(ethylsulfonyl)phenyl)(tetrahydro-2H-pyran-4-yl)methanol

To a solution of (3-(ethylthio)phenyl)(tetrahydro-2H-pyran-4-yl)methanol (709.1 g, 2.81 mmol) in dry DCM (10 mL) under $N_2$ at 0° C. was added mCPBA (5.88 g 26.25 mmol) portion-wise. The reaction was stirred at this temperature for 1 hour. LCMS showed the reaction complete. The reaction was quenched with sat.NaHCO$_3$ and extracted with EtOAc. The extracts were combined, dried over MgSO$_4$, filtered and concentrated under reduced pressure. The crude material was purified by column chromatography eluting with 30-80% EtOAc/hexanes to afford (3-(ethylsulfonyl)phenyl)(tetrahydro-2H-pyran-4-yl)methanol (654.9 mg, 2.30 mmol, 82%)

Step 3: 4-(azido(3-(ethylsulfonyl)phenyl)methyl)tetrahydro-2H-pyran

To a solution of (3-(ethylsulfonyl)phenyl)(tetrahydro-2H-pyran-4-yl)methanol (304.2 g, 1.07 mmol) in a mixture of dry toluene and dry THF (7 mL, 2:5) under $N_2$ at 0° C. was added sequentially DPPA (350 µL, 1.62 mmol) and DBU (250 µL, 1.67 mmol) drop-wise. After stirring for 10 min at this temperature, the cooling bath was removed and the reaction allowed to achieve ambient temperature over 1 hour before heating to 80° C. overnight. LCMS showed the reaction complete. The reaction was cooled to RT, quenched with sat.NH$_4$Cl and extracted with EtOAc. The extracts were combined and washed with H$_2$O (×2) and brine, dried over MgSO$_4$, filtered and concentrated under reduced pressure. The crude material was purified by column chromatography eluting with 30-45% EtOAc/hexanes to afford 4-(azido(3-(ethylsulfonyl)phenyl)methyl)tetrahydro-2H-pyran (294.7 mg, 0.95 mmol, 89%)

Step 4: 4-(azido(3-(ethylsulfonyl)phenyl)methyl)tetrahydro-2H-pyran

To a solution of 4-(azido(3-(ethylsulfonyl)phenyl)methyl)tetrahydro-2H-pyran (290.7 mg, 0.940 mmol) in MeOH (5 mL) under $N_2$ was added 10% Pd/C (33.4 mg, ~11% w/w). The vessel was placed under H$_2$ atm. and stirred at RT for 2 hours. LCMS showed the reaction complete. The reaction was filtered through Celite and concentrated under reduced pressure. The crude material was purified by column chromatography eluting with 3-15% MeOH/DCM to afford the title compound (210.2 mg, 0.74 mmol, 79%). MS (ES$^+$) m/z 284.2 (M–H)$^+$.

Intermediate ax

Cyclopropyl(2-(2,2-difluoroethoxy)phenyl)benzonitrile

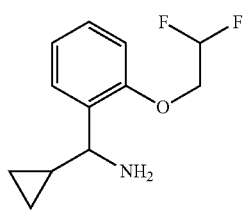 [SMILES: NC(c1ccccc1OCC(F)F)C1CC1]

Step 1: Synthesis of 2-(2,2-difluoroethoxy)benzonitrile

To the solution of 2-cyanophenol (5 g, 42.0 mmol) and 2,2-difluoroethanol (5.166 g, 63 mmol) in toluene (120 mL) was added triphenylphosphine (14.312 g, 54.6 mmol) and reaction mixture was stirred for 5 min at room temperature. Diisopropyl azodicarboxylate (11.64 mL, 57.6 mmol) was added to the reaction and stirring was continued overnight. Reaction was quenched by the addition of saturated NH$_4$Cl solution and extracted with DCM. The organic layer was separated, dried (MgSO$_4$), filtered and concentrated under reduced pressure to give the crude product, which was purified by silica gel column chromatography using 15% EtOAc in hexane as eluant to afford the title compound as colourless oil (7 g, 91%). $^1$H NMR (CDCl$_3$) δ 7.62-7.54 (m, 2H), 7.13-6.97 (m, 2H), 6.37-5.98 (m, 1H), 4.36-4.26 (m, 2H).

Step 2: Synthesis of cyclopropyl(2-(2,2-difluoroethoxy)phenyl)benzonitrile 2-(2,2-difluoroethoxy)benzonitrile (2 g, 10.9 mmo) was dissolved in THF (15 mL) and added dropwise to the cyclopropylmagnesium bromide solution (30.6 mL, 15.3 mmol) at RT under nitrogen atmosphere. After complete addition, reaction was heated to 50° C. and stirred for 4 hr. Reaction was cooled to RT and MeOH (25 mL) was added followed by the sequential addition of sodium borohydride (826 mg). Reaction was quenched by the slow addition of saturated NH$_4$Cl solution and extracted with ethyl acetate. The organic layer was separated, dried (MgSO$_4$), filtered and concentrated under reduced pressure to give the crude material, which was purified by column chromatography to afford title compound as white solid (1.3 g, 52%). $^1$H NMR (CDCl$_3$) δ 7.48-6.81 (m, 4H), 6.31-5.92 (m, 1H), 4.26-4.16 (m, 2H), 3.47 (d, J=8.7 Hz, 1H), 1.66-1.17 (m, 1H), 0.66-0.57 (m, 1H), 0.49-0.20 (m, 3H). MS (ES$^+$) (Method 2) m/z 226.2 (M–H)$^+$.

Intermediate ay

Cyclopropyl(2-(trifluoromethoxy)phenyl)benzonitrile

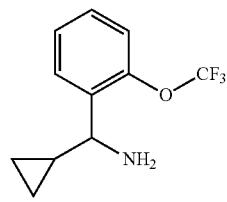 [SMILES: NC(c1ccccc1OC(F)(F)F)C1CC1]

2-(2,2-difluoroethoxy)benzonitrile (as per Intermediate ax, step 1) (2 g, 10.7 mmo) was dissolved in THF (15 mL) and added dropwise to the cyclopropylmagnesium bromide solution (32.1 mL, 16.0 mmol) at RT under nitrogen atmosphere. After complete addition, reaction was heated to 50° C. and stirred for overnight. Reaction was cooled to RT and MeOH (25 mL) was added followed by the sequential addition of sodium borohydride (809 mg). Reaction was quenched by the slow addition of saturated NH$_4$Cl solution and extracted with ethyl acetate. The organic layer was separated, dried (MgSO$_4$), filtered and concentrated under reduced pressure to give pale yellow gummy material, which was used without any purification. MS (ES⁺) (Method 2) m/z 230.2 (M–H)⁺.

Intermediate fa

1-[4-(propane-2-sulfonyl)-phenyl]-propan-1-one

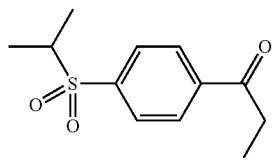 [SMILES: CCC(=O)c1ccc(S(=O)(=O)C(C)C)cc1]

The title compound was prepared following procedures described for Intermediate ae (steps 1 and 2), but starting from (isopropylthio)benzene in step 1. After purification by flash chromatography (silica, cHex/EtOAc 6:4), followed by trituration in Et$_2$O, the title compound was obtained as a white powder (2.1 g, 26% over 2 steps). $^1$H NMR (300 MHz, DMSO-d$_6$) δ 8.33-8.11 (m, 2H), 8.07-7.89 (m, 2H), 3.59-3.43 (m, 1H), 3.14 (q, J=7.1 Hz, 2H), 1.24-1.02 (m, 9H). HPLC (max plot) 99.3%; Rt 3.21 min. UPLC/MS (max plot) 100%; Rt 1.24 min; (MS+) 258.3 ([M+NH$_4$]⁺).

Intermediate fb 4-(3-trifluoromethyl-benzoyl)-piperidine-1-carboxylic acid tert-butyl ester

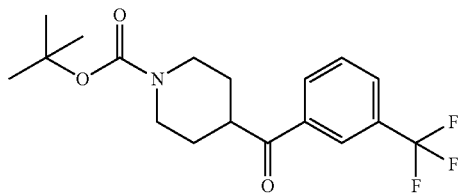 [SMILES: CC(C)(C)OC(=O)N1CCC(C(=O)c2cccc(C(F)(F)F)c2)CC1]

A solution of 1-bromo-3-trifluoromethyl-benzene (1.70 g, 7.56 mmol) in anhydrous Et$_2$O (7 mL) was added dropwise over 5 minutes into a 1.6M solution of butyllithium in hexanes (4.72 mL, 7.56 mmol) in anhydrous Et$_2$O (35 mL) cooled at –78° C. After 15 minutes at –78° C., a solution of tert-butyl 4-[methoxy(methyl)amino]carbonyl-piperidine-1-carboxylate (2.06 g, 7.56 mmol) in anhydrous Et$_2$O (7 mL) was added dropwise over 5 min. After 1 hour at –78° C., the cooling bath was removed and water (25 mL) was added and the mixture was allowed to come back at RT. The resulting mixture was diluted with Et$_2$O (30 mL) and the layers were separated. The organic layer was washed with water (2×25 mL) and brine (25 mL), dried (Na$_2$SO$_4$) and concentrated under reduced pressure to give 2.44 g of a pale yellow oil. This oil was dissolved in MeOH (12 mL), then water (6 mL) was added slowly. The precipitate was filtered off, washed twice with a mixture of MeOH/water (2:1) and dried under reduced pressure to give the title compound as a white powder (1.31 g, 49%). $^1$H NMR (300 MHz, DMSO-d$_6$) δ 8.31 (d, J=7.9 Hz, 1H), 8.23 (s, 1H), 8.03 (d, J=7.8 Hz, 1H), 7.80 (dd, J=7.9, 7.8 Hz, 1H), 3.97 (d, J=12.8 Hz, 2H), 3.73 (tt, J=11.3, 3.5 Hz, 1H), 2.92 (br s, 2H), 1.77 (dd, J=12.7, 1.6 Hz, 2H), 1.49-1.31 (m, 11H). UPLC/MS (Method 3) (MS–) 356.5 ([M–H]⁻).

Intermediate fc

N-{cyclopropyl[4-(difluoromethoxy)phenyl]methyl}-2-(3,3-difluoropiperidin-1-yl)ethanamine

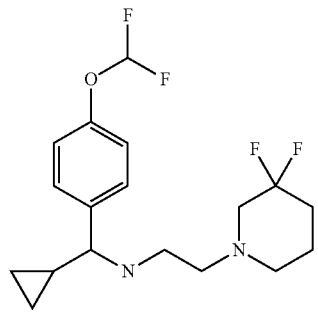 [SMILES: FC(F)Oc1ccc(C(NCCN2CCCC(F)(F)C2)C2CC2)cc1]

The title compound was prepared following procedures described for intermediate ab (steps 1-3) using Intermediate ak (1.2 g, 5.63 mmol), (48 over 3 steps). LCMS (Method 2) (ES⁺) 361.2 [M+H]⁺.

Intermediate fd (1R)-1-(4-methoxyphenyl)-N-(pyridin-2-ylmethyl)ethanamine

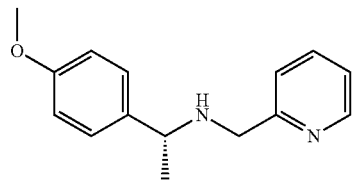 [SMILES: COc1ccc([C@@H](C)NCc2ccccn2)cc1]

(R)-(+)-1-(4-Methoxyphenyl)ethylamine (153.6 mg, 1.02 mmol), 2-pyridinecarbaldehyde (100 μL, 1.05 mmol) and sodium triacetoxyborohydride (345.2 mg, 1.63 mmol) were reacted as described under General Procedure A to give the title compound (215.6 mg, 87.2%) as pale yellow oil. $^1$H NMR (300 MHz, CDCl$_3$) δ 8.56-8.47 (m, 1H), 7.63-7.57 (m, 1H), 7.37-7.08 (m, 4H), 6.90-6.85 (m, 2H), 3.84-3.72 (m, 6H), 1.39 (d, J=6.6 Hz, 3H). LCMS (Method 2) (ES⁺) m/z 243.3 (M+H⁺)

Intermediate fe (1S)-1-(4-methoxyphenyl)-N-(pyridin-2-ylmethyl)ethanamine

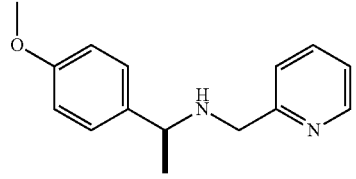 [SMILES: COc1ccc([C@H](C)NCc2ccccn2)cc1]

(S)-(−)-1-(4-Methoxyphenyl)ethylamine (150.9 mg, 1.00 mmol), 2-pyridinecarbaldehyde (100 μL, 1.05 mmol) and sodium triacetoxyborohydride (341.7 mg, 1.61 mmol) were reacted as described under General Procedure A to give the title compound (217.7 mg, 89.8%) as pale yellow oil. $^1$H NMR (300 MHz, CDCl$_3$) δ 8.56-8.47 (m, 1H), 7.63-7.57 (m, 1H), 7.37-7.08 (m, 4H), 6.90-6.85 (m, 2H), 3.84-3.67 (m, 6H), 1.39 (d, J=6.6 Hz, 3H). LCMS (Method 2) (ES$^+$) m/z 243.3 (M+H$^+$)

Intermediate fg 1-(2,3-dihydro-1H-inden-5-yl)-N-{[6-(trifluoromethyl)pyridin-3-yl]methyl}ethanamine

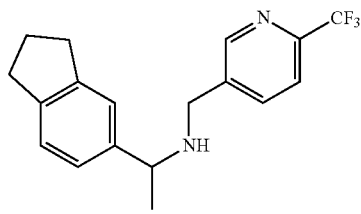 [SMILES: CC(NCc1ccc(C(F)(F)F)nc1)c1ccc2c(c1)CCC2]

1-Indan-5-yl-ethylamine (170 mg, 1.054 mmol), 6-(trifluoromethyl)pyridine-3-carboxaldehyde (203 mg, 1.159 mmol), sodium triacetoxyborohydride (447 mg, 2.108 mmol) and acetic acid (190 mg, 3.163 mmol) were reacted using General Procedure A. The crude material was purified by flash chromatography (silica-gel, EtOAc/DCM 3:7) to give the title compound (60 mg, 18%) as pale yellow oil. $^1$H NMR (300 MHz, CDCl$_3$) δ 8.62 (s, 1H), 7.83 (dd, J=1.5, 8.1 Hz, 1H), 7.61 (d, J=8.1 Hz, 1H), 7.20-7.16 (m, 2H), 7.07 (dd, J=1.5, 8.1 Hz, 1H), 3.79-3.68 (m, 3H), 2.90 (t, J=7.5 Hz, 4H), 2.13-2.03 (m, 2H), 1.37 (d, J=6.6 Hz, 3H). LCMS (Method 2) (ES$^+$) m/z 321.2 (M+H$^+$).

Intermediate fh

4-[amino-(3-ethanesulfonyl-phenyl)-methyl]-piperidine-1-carboxylic acid tert-butyl ester

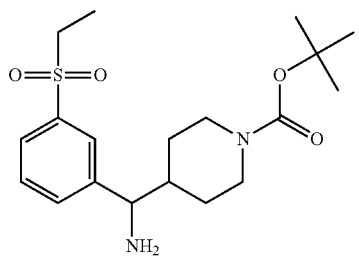 [SMILES: CCS(=O)(=O)c1cccc(C(N)C2CCN(C(=O)OC(C)(C)C)CC2)c1]

Step 1:
4-(3-ethylsulfanyl-bezoyl)-piperidine-1-carboxylic acid tert-butyl ester The title compound was prepared following procedures described for intermediate ai (Step 1), to afford the titled compound as colourless liquid. TLC-Pet ether/Ethyl acetate (8:2), R$_f$=0.7; $^1$H NMR (400 MHz, DMSO-d$_6$) δ 7.80 (s, 2H), 7.79-7.69 (dd, J=7.7, 1.0 Hz, 1H), 7.58-7.55 (m, 1H), 7.49-7.45 (t, J=14 Hz, 1H) 3.96-3.93 (d, J=12 Hz, 2H) 3.62 (s, 1H) 3.06-3.01 (m, 2H) 2.93-2.91 (t, 2H) 1.75-1.72 (d, J=11.6 Hz, 2H) 1.41-1.35 (m, 11H) 1.25-1.23 (m, 3H).

Step 2: 4-(3-ethanesulfonyl-bezoyl)-piperidine-1-carboxylic acid tert-butyl ester The title compound was prepared following procedures described for General Procedure Q using 4-(3-ethylsulfanyl-bezoyl)-piperidine-1-carboxylic acid tert-butyl ester (11 g, 0.025 mol). The titled compound (8 g, 66%) was achieved as an off white solid. TLC-Pet ether/Ethyl acetate (5:5), R$_f$=0.5; $^1$H NMR (400 MHz, DMSO-d$_6$) δ 8.36-8.34 (dd, J=8.0, 1.1 Hz, 2H), 8.15-8.12 (m, 1H), 7.83-7.81 (t, J=8.0 Hz, 1H), 4.02-3.98 (dd, J=14.8, 6.8 Hz, 2H) 3.74-3.71 (m, 1H) 3.52-3.67 (m, 2H) 2.91 (bs, 2H) 1.79-1.76 (d, J=12 Hz, 2H) 1.42-1.39 (m, 11H) 1.12-1.08 (t, J=16 Hz, 3H).

Step 3: 4-[amino-(3-ethanesulfonyl-phenyl)-methyl]-piperidine-1-carboxylic acid tert-butyl ester The title compound was prepared following procedures described for intermediate ai (Steps 5 and 6), using 4-(3-ethylsulfanyl-benzoyl)-piperidine-1-carboxylic acid tert-butyl ester (8 g, 0.020 mol). The titled compound was achieved as a colourless liquid (2.5 g, 52%). TLC-Pet ether/Ethyl acetate (4:6), R$_f$=0.2; $^1$H NMR (400 MHz, DMSO-d$_6$) δ 7.80 (s, 1H), 7.71-7.00 (d, J=4.0 Hz, 1H), 7.66-7.64 (d, J=8.0 Hz, 1H), 7.59-7.57 (t, J=16.0 Hz, 1H), 3.95-3.85 (m, 2H), 3.71-3.22 (m, 1H), 3.28-3.22 (m, 2H) 2.53-2.48 (m, 2H), 2.03-1.99 (m, 2H), 1.74-1.71 (m, 1H), 1.59-1.53 (m, 1H), 1.35 (bs, 9H), 1.22-1.19 (m, 1H), 1.09-0.99 (m, 3H), 0.97-0.96 (m, 1H). LCMS: (Method 1) 282.5 [M+100].

Intermediate fi 1-(2,4-difluorophenyl)-1-(1-methylpiperidin-4-yl)methanamine

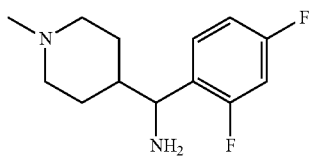 [SMILES: CN1CCC(C(N)c2ccc(F)cc2F)CC1]

Step 1: 1-(2,4-difluorophenyl)-N-hydroxy-1-(1-methylpiperidin-4-yl)methanimine 1-(2,4-difluorophenyl)-N-hydroxy-1-(piperidin-4-yl)methanimine hydrochloride was reacted according to General Procedure Q to give the title compound.

Step 2: 1-(2,4-difluorophenyl)-1-(1-methylpiperidin-4-yl)methanamine 1-(2,4-difluorophenyl)-N-hydroxy-1-(1-methylpiperidin-4-yl)methanimine (1 eq.) was dissolved in the smallest amount of THF (1 mL per 150 mg oxime) and the mixture cooled to 0° C. before addition of 70% aqueous formic acid (5 mL per 150 mg oxime). Once added the mixture was allowed to attain ambient temperature and zinc powder (30 eq.) was added portion wise over 15 min. The reaction mixture was stirred until complete (1.5 hr) at room temperature. Once complete the mixture was filtered through Celite and washed with EtOAc. The filtrate was neutralized with a concentrated ammonia solution to pH 8 and then extracted with 10% MeOH in DCM (×3). The combined organics were then dried (MgSO$_4$), concentrated under reduced pressure to yield 1.368 g, 88% of 1-(2,4-difluorophenyl)-1-(1-methyl-piperidin-4-yl)methanamine. LCMS (Method 2) 241.3 [M+H]$^+$ Intermediate fi 1-[4-(difluoromethoxy)phenyl]-2-methoxyethanamine

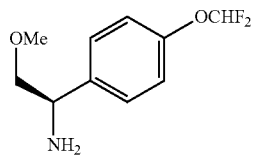 [SMILES: COC[C@H](N)c1ccc(OC(F)F)cc1]

Step 1: 1-(difluoromethoxy)-4-ethenylbenzene

To a solution of methyl triphenylphosphonium iodide (2.348 g) in anhydrous diethyl ether (40 mL) under a nitrogen atmosphere was added KOBu$^t$ (0.913 g) portion-wise. The mixture was stirred for 5 minutes, after which time 4-difluoromethoxybenzaldehyde (1 g) was added drop-wise as a solution in anhydrous diethyl ether (10 mL), once added the mixture was stirred until complete. Once complete most of the diethyl ether was removed under reduced pressure, being very careful not to remove the alkene, pentane (100 mL) was then added. The mixture was filtered through a plug of silica gel eluting with 5% diethyl ether in pentane. The collection of alkene was monitored by TLC and once no further alkene was coming through the filtration was stopped and the diethyl ether and pentane mixture removed under reduced pressure, again being careful not to remove the volatile alkene. This gave ~500 mg of 1-(difluoromethoxy)-4-ethenylbenzene, ~50% yield which contained small amounts of diethyl ether and pentane and was used as such in Step 2.

Step 2: benzyl l{1-[4-(difluoromethoxy)phenyl]-2-hydroxyethyl}carbamate

Synthesis of benzyl l{1-[4-(difluoromethoxy)phenyl]-2-hydroxyethyl}carbamate was performed as outlined in J. Am. Chem. Soc., 1998, p 1207 using 1-(difluoromethoxy)-4-ethenylbenzene to give 401 mg, 40% yield.

Step 3: benzyl {1-[4-(difluoromethoxy)phenyl]-2-methoxyethyl}carbamate

To a solution of benzyl {1-[4-(difluoromethoxy)phenyl]-2-hydroxyethyl}carbamate (1 eq.) in anhydrous acetone (1 mL per 50 mg alcohol) was added MeI (5 eq.) followed by Ag$_2$O (5 eq.) under nitrogen. The vessel was sealed to prevent MeI evaporation and stirred for 1 day. After this time additional MeI (2 eq.) was added and the vessel sealed again and stirred for 2 days. After this time the mixture was filtered through Celite washing with EtOAc, the filtrate was concentrated under reduced pressure and the crude material purified by column chromatography eluting with 30% EtOAc in hexanes, giving the title compound in quantitative yield (265 mg).

Step 4: 1-[4-(difluoromethoxy)phenyl]-2-methoxyethanamine

To a solution of benzyl {1-[4-(difluoromethoxy)phenyl]-2-methoxyethyl}carbamate (1 eq.) in methanol (4 mL per 150 mg Cbz protected amine) under a nitrogen atmosphere was added Pd/C (10% by weight). The atmosphere was then changed to hydrogen and the mixture left to stir until complete (0.5 hr). Once complete the mixture was filtered through Celite to give 177 mg, 94% of the crude material 1-[4-(difluoromethoxy)phenyl]-2-methoxyethanamine. LCMS (Method 2) 218.2 (M+H)$^+$ Intermediate fk 1-[4-(propan-2-yl)-4H-1,2,4-triazol-3-yl]-N-{[6-(trifluoromethyl)pyridin-3-yl]methyl}ethanamine

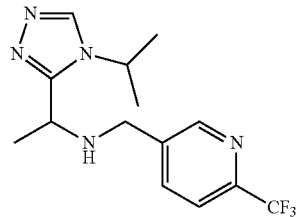 [SMILES: CC(NCc1ccc(C(F)(F)F)nc1)c1nncn1C(C)C]

To a suspension of 1-[4-(propan-2-yl)-4H-1,2,4-triazol-3-yl]ethanamine dihydrochloride hydrochloride (300 mg, 1.32 mmol) and 6-(trifluoromethyl)nicotinaldehyde (210 mg, 1.20 mmol) in anhydrous THF was added K$_2$CO$_3$ (0.183 mg, 1.32 mmol) and stirred for 1 hour. The reaction was quenched by addition of MeOH, filtered and NaBH$_4$ (181 mg, 4.78 mmol) was added and the reaction mixture stirred until complete by LCMS. The reaction was partitioned between EtOAc and NaHCO$_3$ (sat. aq.). The organic phase was loaded straight onto a column and eluted with 100% EtOAc to give 80 mg (21%) of the title compound. MS (ES$^+$) m/z 314.3 (M+H$^+$)

TABLE 1

Separation of Chiral Intermediates

| Racemic Building Block | Source | Seperation Conditions (column, eluent, flow rate) | First Eluting arbitrary stereochemical assignment | Second Eluting arbitrary stereochemical assignment |
|---|---|---|---|---|
| 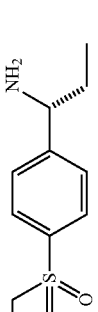 | Intermediate ae | HPLC Chiralpak AY—H, EtOH/ 0.1% Et₂NH | 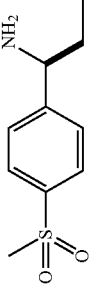 Intermediate bc | 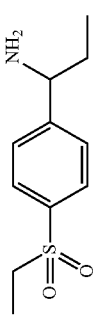 Intermediate bd |
| 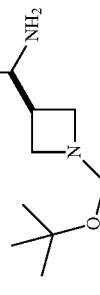 | Intermediate af | HPLC Chiralpak AY—H, EtOH/ 0.1% Et₂NH | 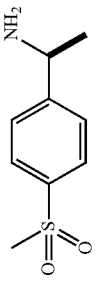 Intermediate be | 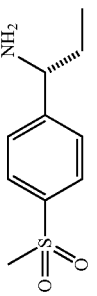 Intermediate bf |
| 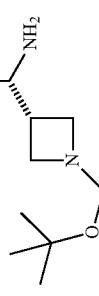 | alpha-Methyl-4-(methylsulphonyl) benzylamine from ABCR GmbH & Co. KG | HPLC Chiralpak AY—H, 250 × 20 mm, 50% Heptane – 50% EtOH + 0.1% DEA; 10 ml/min | 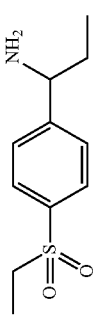 Intermediate bg | 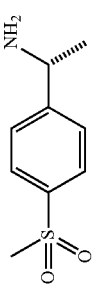 Intermediate bh |
| 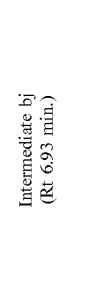 | Intermediate ah | SFC Prep 80, Column-Phenomenex Lux-C4 (250 × 30) mm, 5 micron, Mobile phase: CO₂:0.5% DEA in IPA (60:40), Total Flow-40 g/min, Cycle time: 15 min., Injection volume: 250 µl (75 mg/injection) Total Run time: 20 min and | 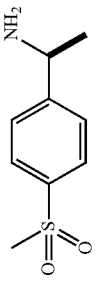 Intermediate bi (Rt 4.35 min.) | 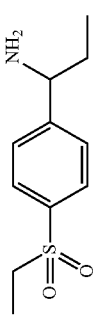 Intermediate bj (Rt 6.93 min.) |

TABLE 1-continued

Separation of Chiral Intermediates

| Racemic Building Block | Source | Separation Conditions (column, eluent, flow rate) | First Eluting arbitrary stereochemical assignment | Second Eluting arbitrary stereochemical assignment |
|---|---|---|---|---|
| 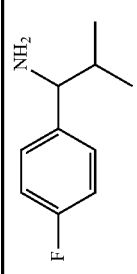 | 1-(4-fluoro-phenyl)-2-methyl-propylamine purchased from Enamine Ltd | chiral prep. HPLC (condition: Chiralpak IC, 250 × 20 mm, ACN + 0.1% DEA at 10 ml/min) | 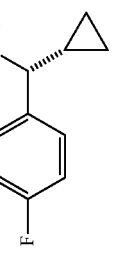<br>Intermediate bk<br>(Rt 7.93 min) | 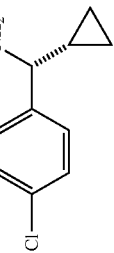<br>Intermediate bl<br>(Rt 8.72 min.) |
| 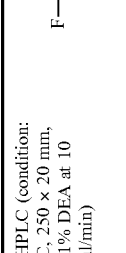 | intermediate aj | CHIRAL HPLC Method: 0.2% DEA in HEXANE:IPA: 80:20, Flow-1.0 ml/min Column. CHIRALCEL OD—H (250 × 4.6) mm, 5 μm | <br>Intermediate bm<br>(Rt: 4.8 min.) | <br>Intermediate bn<br>(Rt 6.5 min.) |
| 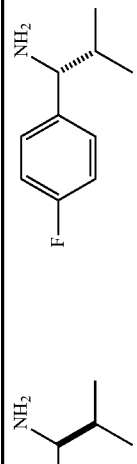 | 4-fluorophenyl)(cyclopropyl)methanamine from Enamine Ltd. | HPLC Chiralpak IC, 250 × 20 mm, ACN + 0.1% DEA at 10 ml/min | 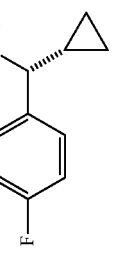<br>Intermediate bo<br>(Rt 8.40 min.) | 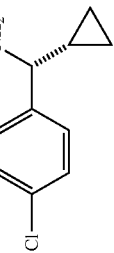<br>Intermediate bp<br>(Rt 8.90 min.) |
| 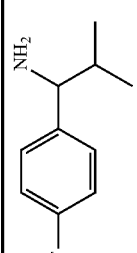 | (4-chlorophenyl)(cyclopropyl)methanamine hydrochloride from Enamine Ltd. | HPLC Chiralpak AY—H, 250 × 20 mm, EtOH + 0.1% DEA, 10 ml/min | 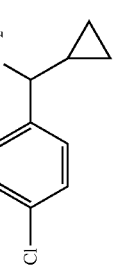<br>Intermediate bq<br>(Rt 7.18 min.) | 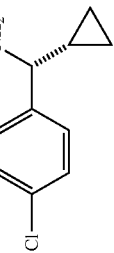<br>Intermediate br<br>(Rt 8.75 min.) |

TABLE 1-continued

Separation of Chiral Intermediates

| Racemic Building Block | Source | Seperation Conditions (column, eluent, flow rate) | First Eluting arbitrary stereochemical assignment | Second Eluting arbitrary stereochemical assignment |
|---|---|---|---|---|
| | Intermediate ak | HPLC CHIRALCEL OD—H (250 × 21) mm, 0.2% DEA in HEXANE:IPA: 90:10, Flow-12.0 ml/min, 20 min/injection | Intermediate bt | Intermediate bs (Rt 9.154 min.) |
| | Intermediate al | HPLC Chiralpak AY—H, heptane/EtOH/Et₂NH 50:50:0.1 | | |
| | Intermediate an | HPLC Chiralpak AY—H, EtOH/ 0.1% Et₂NH | Intermediate bu | Intermediate bv |
| | Intermediate ao | chiral HPLC (Chiralpak AY—H, EtOH/0.1% Et₂NH): | Intermediate bw | Intermediate bx |
| | | | Intermediate by | Intermediate bz |

TABLE 1-continued

Separation of Chiral Intermediates

| Racemic Building Block | Source | Seperation Conditions (column, eluent, flow rate) | First Eluting arbitrary stereochemical assignment | Second Eluting arbitrary stereochemical assignment |
|---|---|---|---|---|
| [ethylsulfonyl-phenyl-cyclopropyl-methanamine structure] | Intermediate ar | Chiralpak AY—H, 250 × 20 mm, 5 um using Heptane/EtOH/DEA (60/40/0.1) as eluent (feed concentration: 114 mg/ml; flow 10 ml/min) | [structure] Intermediate cb | [structure] Intermediate ca |
| [cyclopropylsulfonyl-phenyl-cyclopropyl-methanamine structure] | Intermediate au | HPLC Chiralpak AY—H, EtOH/ 0.1% Et$_2$NH | [structure] Intermediate cd | [structure] Intermediate cc |
| [methyltriazolyl-isobutyl-methanamine structure] | 1-(1-methyl-1H-1,2,4-triazol-5-yl)-1-propanamine from ABCR GmbH & Co. KG | HPLC Chiralpak IC, 250 × 20 mm, 5 um, Heptane/EtOH + 0.1% DEA: 60/40 10 ml/min | [structure] Intermediate gc (Rt 10.28 min.) | [structure] Intermediate gd (Rt 12.45 min.) |

TABLE 1-continued

Separation of Chiral Intermediates

| Racemic Building Block | Source | Seperation Conditions (column, eluent, flow rate) | First Eluting arbitrary stereochemical assignment | Second Eluting arbitrary stereochemical assignment |
|---|---|---|---|---|
| 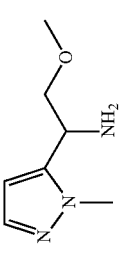 | 2-Methoxy-1-(1-methyl-1H-pyrazol-5-yl)ethanamine, from ABCR GmbH & Co. KG | HPLC Chiralpak IC, 250 × 20 mm, ACN + 0.1% DEA at 10 ml/min | 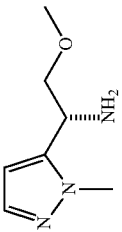 Intermediate ge (Rt 10.35 min) | 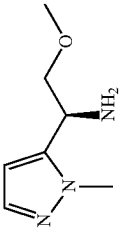 Intermediate gf (Rt 12 min.) |
| 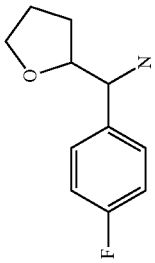 | (4-fluorophenyl)(oxolan-2-yl)methanamine, purchased from Enamine Ltd | HPLC CHIRALCEL OD—H (250 × 21) mm, 0.1% DEA in HEXANE:IPA: 90:10 | 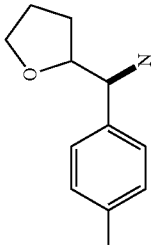 Intermediate gh | 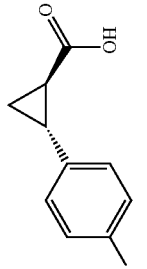 Intermediate gi |
| 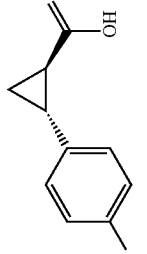 | trans-2-(4-fluorophenyl) cyclopropanecarboxylic acid | HPLC Chiralpak ADH (250 × 20) mm (Daicel), hetane/EtOH/formic acid 90/10/01 v/v/v, 0.7 mL/min), | 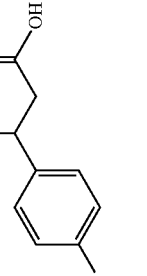 Intermediate gj | 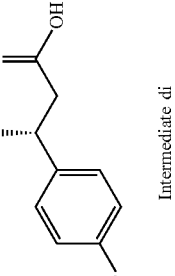 Intermediate da |
| trans-racemate  | 3-(4-Fluorophenyl) butanoic acid | HPLC Chiralpak OJH, 250 × 20 mm column (Daicel) (eluent heptane/ EtOH/iPrOH (90/5/5) v/v/v + 0.1% (v/v) Formic acid, flow 10 mL/min, |  Intermediate gh |  Intermediate di |

TABLE 2

Acid to Acid Chloride Intermediates

| Structure | Int. # | Gen. Proc. | Structure | Int. # |
|---|---|---|---|---|
| (4-fluorophenyl cyclopropane carboxylic acid) | da | J | (4-fluorophenyl cyclopropane carbonyl chloride) | ea |
| (2,4-difluorophenyl cyclopropane carboxylic acid) racemate | db | J | (2,4-difluorophenyl cyclopropane carbonyl chloride) racemate | eb |
| (3,4-difluorophenyl cyclopropane carboxylic acid) racemate | dc | J | (3,4-difluorophenyl cyclopropane carbonyl chloride) racemate | ec |

TABLE 2-continued

Acid to Acid Chloride Intermediates

| Structure | Int. # | Gen. Proc. | Structure | Int. # |
|---|---|---|---|---|
| 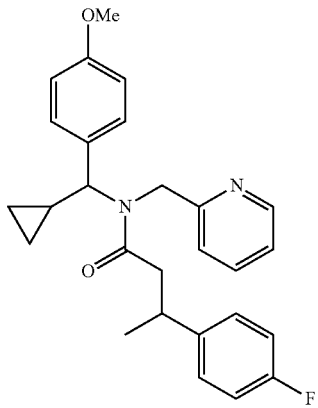 [SMILES: COc1ccc(C(C2CC2)N(Cc2ccccn2)C(=O)CC(C)c2ccc(F)cc2)cc1] racemate | de | J | 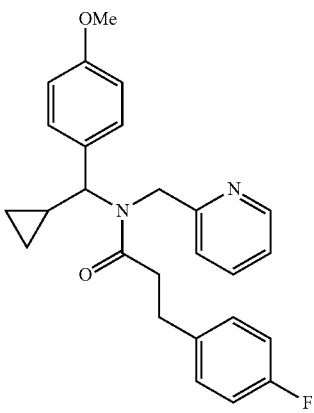 [SMILES: COc1ccc(C(C2CC2)N(Cc2ccccn2)C(=O)CCc2ccc(F)cc2)cc1] racemate | ed |
| (OH, CF₃ acid) | df | J | (Cl, OCF₃ acid chloride) racemate | ef |

Where indicated the chiral acids or acid chlorides are racemic mixtures of enantiomers, otherwise chiral acids or chiral acid chlorides are enantiopure and the absolute stereochemistry is not known.

Example 1

N-[cyclopropyl(4-methoxyphenyl)methyl]-3-(4-fluorophenyl)-N-(pyridin-2-ylmethyl)butanamide Intermediate a (25 mg, 0.09 mmol) was reacted with Intermediate nn (46.7 mg, 0.23 mmol) in presence of triethylamine (26 µl, 0.19 mmol) according to General Procedure C to afford the title compound (34 mg, 84%) as clear oil. $^1$H NMR (CDCl$_3$) δ 8.52-8.37 (m, 1H), 7.65-7.43 (m, 1H), 7.30-6.70 (m, 10H), 5.19-4.96 (m, 1H), 4.55-4.12 (m, 2H), 3.81-3.77 (m, 3H), 3.57-3.47 (m, 1H), 2.79-2.35 (m, 2H), 1.33-1.23 (m, 4H), 1.20-0.15 (m, 4H). $^1$H NMR (d$_6$-DMSO, 110° C.) δ 8.42 (br s, 1H), 7.61-7.56 (m, 1H), 7.27-6.99 (m, 8H), 6.84-6.81 (m, 2H), 4.72-4.67 (m, 2H), 4.34 (t, J=17.7 Hz, 1H), 3.75 (s, 3H), 3.42-3.32 (m, 1H), 2.80-2.43 (m, 2H), 1.28-1.12 (m, 4H), 0.68-0.61 (m, 1H), 0.32-0.12 (m, 3H). LCMS (Method 2) Rt 2.346 min (98.2% purity), m/z 433.3 (M+H)$^+$.

Example 2

N-[cyclopropyl(4-methoxyphenyl)methyl]-3-(4-fluorophenyl)-N-(pyridin-2-ylmethyl)propanamide Intermediate a (30 mg, 0.11 mmol) was reacted with 3-(4-fluorophenyl)propanoyl chloride (41.7 mg, 0.22 mmol) in presence of triethylamine (31.2 µl, 0.22 mmol) according to General Procedure C to afford the title compound (32 mg, 68%) as clear oil. $^1$H NMR (CDCl$_3$) δ 8.49-8.41 (m, 1H), 7.56-7.50 (m, 1H), 7.26-7.05 (m, 6H), 6.99-6.89 (m, 2H), 6.84-6.78 (m, 2H), 5.20-5.11 (m, 1H), 4.51-4.09 (m, 2H), 3.79 (br s, 3H), 3.06-2.90 (m, 2H), 2.75-2.47 (m, 2H), 1.04-0.95 (m, 1H), 0.79-0.66 (m, 1H), 0.39-0.28 (m, 2H), 0.12-0.04 (m, 1H). LCMS (Method 2) Rt 2.192 min (96.6% purity), m/z 419.2 (M+H)+.

Example 3

(3R)—N-[cyclopropyl(4-chlorophenyl)methyl]-3-(4-fluorophenyl)-N-(pyridin-2-ylmethyl)butanamide

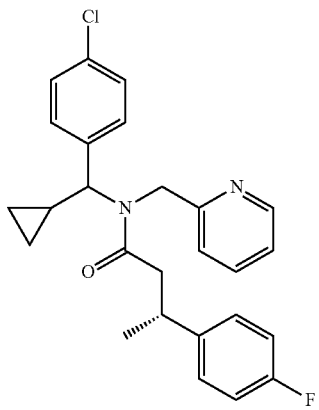 [SMILES: C[C@H](CC(=O)N(Cc1ccccn1)C(c1ccc(Cl)cc1)C1CC1)c1ccc(F)cc1]

Intermediate b (30 mg, 0.11 mmol) was reacted with Intermediate ei (44 mg, 0.22 mmol) in presence of triethylamine (31 μl, 0.22 mmol) according to General Procedure C to afford the title compound (42 mg, 88%) as clear oil. 1H NMR (CDCl3) δ 8.53-8.36 (m, 1H), 7.65-7.44 (m, 1H), 7.33-6.82 (m, 10H) 5.21-4.96 (m, 1H), 4.57-4.06 (m, 2H), 3.58-3.42 (m, 1H), 2.74-2.28 (m, 2H), 1.33-1.24 (m, 4H), 0.98-0.82 (m, 1H), 0.76-0.56 (m, 1H), 0.40-0.18 (m, 2H). HPLC (Method 2) Rt 2.831 min (100% purity). MS (ES+) m/z 437.3 (M+H+).

Example 4

(3S)—N-[cyclopropyl(4-phenyl)methyl]-3-(4-fluorophenyl)-N-(pyridin-2-ylmethyl)butanamide

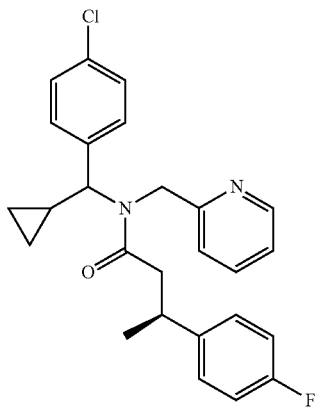 [SMILES: C[C@@H](CC(=O)N(Cc1ccccn1)C(c1ccc(Cl)cc1)C1CC1)c1ccc(F)cc1]

Intermediate b (30 mg, 0.11 mmol) was reacted with Intermediate oo (44 mg, 0.22 mmol) in presence of triethylamine (31 μl, 0.22 mmol) according to General Procedure C to afford the title compound (43 mg, 90%) as clear oil. 1H NMR (CDCl3) δ 8.52-8.36 (m, 1H), 7.65-7.43 (m, 1H), 7.33-6.82 (m, 10H) 5.21-4.96 (m, 1H), 4.57-4.05 (m, 2H), 3.58-3.42 (m, 1H), 2.74-2.28 (m, 2H), 1.33-1.24 (m, 4H), 0.98-0.82 (m, 1H), 0.78-0.55 (m, 1H), 0.40-0.18 (m, 2H). HPLC (Method 2) Rt 2.809 min (100% purity). MS (ES+) m/z 437.3 (M+H+).

Example 5

Diastereomer A of (3R)—N-[1-cyclopropyl(4-chlorophenyl)methyl]-3-(4-fluorophenyl)-N-(pyridin-2-ylmethyl)butanamide, and Example 6: Diastereomer B of (3R)—N-[1-cyclopropyl(4-chlorophenyl)methyl]-3-(4-fluorophenyl)-N-(pyridin-2-ylmethyl)butanamide

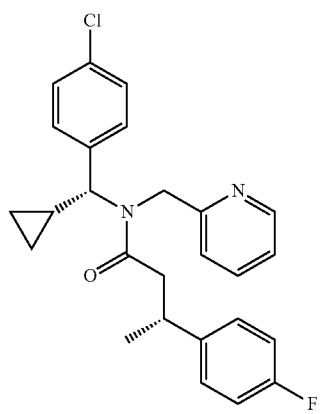

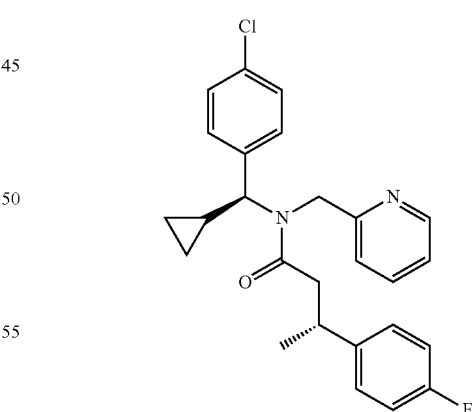

Example 3 was a diastereomeric mixture and was resolved by on Prep LC 4000 with 2777C Sample Manager PAL (loop: 5 ml) and Waters Fraction collector III, equipped with Waters 2487 Dual Detector using Chiralpak ADH 250×20 mm (Daicel) (eluent hexane EtOH DEA 85/15/01 v/v/v, flow 10 ml min) to afford compound 5 (first eluting) and compound 6 (second eluting).

Example 7

Diastereomer A of (3S)—N-[1-cyclopropyl(4-chlorophenyl)methyl]-3-(4-fluorophenyl)-N-(pyridin-2-ylmethyl)butanamide, and Example 8: diastereomer B of (3S)—N-[1-cyclopropyl(4-chlorophenyl)methyl]-3-(4-fluorophenyl)-N-(pyridin-2-ylmethyl)butanamide

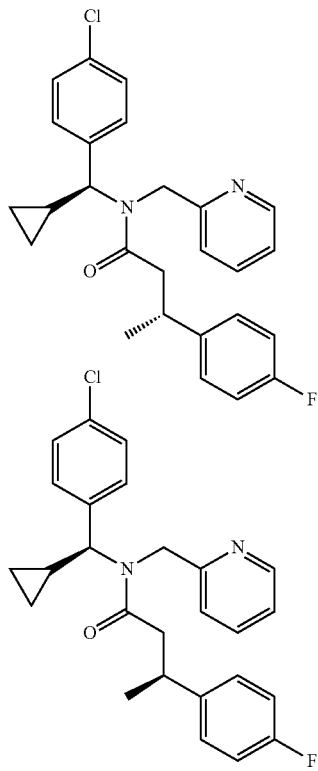

7

8

Example 4 was a diastereomeric mixture and was resolved by on Prep LC 4000 with 2777C Sample Manager PAL (loop: 5 ml) and Waters Fraction collector III, equipped with Waters 2487 Dual Detector using Chiralpak IA 250×20 mm (eluent hexane ISOH 50/50 v/v, flow 10 ml min) to afford compound 7 (first eluting) and compound 8 (second eluting).

Example 9

N-[cyclopropyl(4-chlorophenyl)methyl]-3-(4-fluorophenyl)-N-(pyridin-2-ylmethyl)propanamide

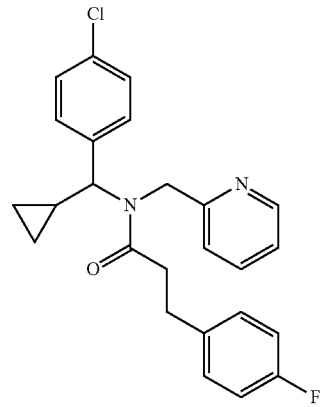 [SMILES: O=C(CCc1ccc(F)cc1)N(Cc1ccccn1)C(c1ccc(Cl)cc1)C1CC1]

Intermediate b (30 mg, 0.11 mmol) was reacted with 3-(4-fluorophenyl)propanoyl chloride (41 mg, 0.22 mmol) in presence of triethylamine (31 µl, 0.22 mmol) according to General Procedure C to afford the title compound (40 mg, 86%) as clear oil. $^1$H NMR (CDCl$_3$) δ 8.49-8.38 (m, 1H), 7.58-7.50 (m, 1H), 7.28-6.90 (m, 10H) 5.19-5.11 (m, 1H), 4.53-4.07 (m, 2H), 3.05-2.95 (m, 2H), 2.70-2.51 (m, 2H), 1.18-0.92 (m, 1H), 0.86-0.68 (m, 1H), 0.58-0.49 (m, 1H), 0.40-0.27 (m, 2H). LCMS (Method 2) Rt 2.605 min (100% purity), m/z 423.3 (M+H)$^+$.

Example 10

N-[(4-chlorophenyl)(cyclopropyl)methyl]-2-(4-fluorophenyl)-N-(pyridin-2-ylmethyl)cyclopropanecarboxamide

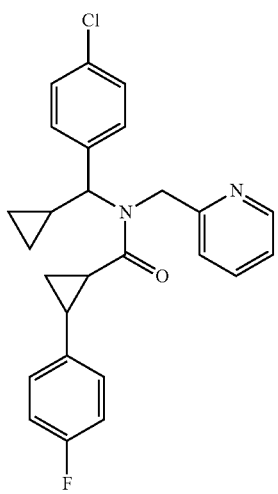 [SMILES: O=C(C1CC1c1ccc(F)cc1)N(Cc1ccccn1)C(c1ccc(Cl)cc1)C1CC1]

Intermediate b (23 mg, 0.08 mmol) was reacted with Intermediate qq (33.5 mg, 0.17 mmol) in presence of triethylamine (23.5 µl, 0.17 mmol) according to General Procedure C to afford the title compound (28 mg, 76%) as clear oil. $^1$H NMR (CDCl$_3$) δ 8.44-8.35 (m, 1H), 7.65-6.80 (m, 11H), 5.22-5.07 (m, 1H), 4.78-4.28 (m, 2H), 2.52-2.43 (m, 1H), 1.88-1.66 (m, 2H), 1.30-1.05 (m, 2H), 0.90-054 (m, 2H), 0.48-0.12 (m, 2H). LCMS (Method 2) Rt 2.652 min (98.4% purity), m/z 435.2 (M+H)$^+$.

Example 13

Diastereomer C of N-[(4-chlorophenyl)(cyclopropyl)methyl]-2-(4-fluorophenyl)-N-(pyridin-2-ylmethyl)cyclopropanecarboxamide

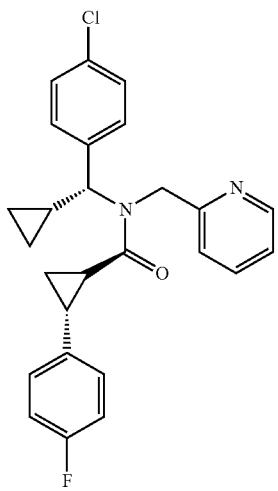

Intermediate d (75 mg, 0.28 mmol), Intermediate gj (63 mg, 0.35 mmol), triethylamine (74 μl, 0.42 mmol) and T3P (330 μl, 0.55 mmol) were reacted according to General Procedure D to afford the titled compound (77 mg, 64%) as a pale yellow oil. $^1$H NMR (CDCl$_3$) δ 8.48-8.35 (m, 1H), 7.67-7.42 (m, 1H), 7.39-7.23 (m, 5H), 7.16-6.96 (m, 1H), 6.90-6.79 (m, 4H), 5.21-5.15 (m, 1H), 4.78-4.36 (m, 2H), 2.50-2.44 (m, 1H), 1.84-1.78 (m, 1H), 1.74-1.66 (m, 1H), 1.25-1.07 (m, 2H), 0.82-0.74 (m, 1H), 0.69-0.61 (m, 1H), 0.48-0.23 (m, 2H). HPLC (Method 2) Rt 2.638 min (100% purity). MS (ES$^+$) m/z 435.2 (M+H$^+$).

Example 14

Diastereomer D of N-[(4-chlorophenyl)(cyclopropyl)methyl]-2-(4-fluorophenyl)-N-(pyridin-2-ylmethyl)cyclopropanecarboxamide

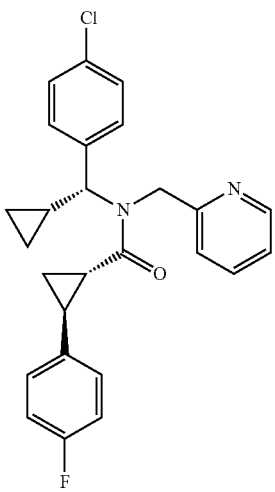 [SMILES: O=C([C@H]1C[C@@H]1c1ccc(F)cc1)N(Cc1ccccn1)[C@@H](c1ccc(Cl)cc1)C1CC1]

Intermediate d (73 mg, 0.27 mmol), Intermediate da (60 mg, 0.33 mmol), triethylamine (74 μl, 0.42 mmol) and T3P (330 μL, 0.55 mmol) were reacted according to General Procedure D to afford the titled compound (74 mg, 64%) as a pale yellow oil. $^1$H NMR (CDCl$_3$) δ 8.44-8.42 (m, 1H), 7.68-7.53 (m, 1H), 7.39-7.36 (m, 2H), 7.31-7.20 (m, 3H), 7.14-7.05 (m, 1H), 6.95-6.83 (m, 4H), 5.20-5.07 (m, 1H), 4.79-4.29 (m, 2H), 2.51-2.45 (m, 1H), 1.90-1.83 (m, 1H), 1.80-1.70 (m, 1H), 1.28-1.06 (m, 2H), 0.80-0.70 (m, 1H), 0.62-0.53 (m, 1H), 0.44-0.33 (m, 1H), 0.29-0.16 (m, 1H). HPLC (Method 2) Rt 2.697 min (100% purity). MS (ES$^+$) m/z 435.2 (M+H$^+$).

Example 21

N-[cyclopentyl(4-fluorophenyl)methyl]-3-(4-fluorophenyl)-N-(pyridin-2-ylmethyl)propanamide

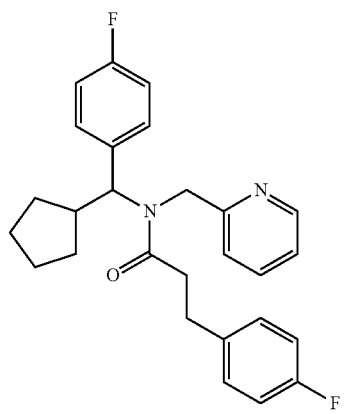 [SMILES: O=C(CCc1ccc(F)cc1)N(Cc1ccccn1)C(c1ccc(F)cc1)C1CCCC1]

Intermediate i (125 mg, 0.44 mmol), 3-(4-fluorophenyl)propionic acid (148 mg, 0.88 mmol), triethylamine (0.12 mL, 0.88 mmol) and T3P (0.84 mL, 1.32 mmol) were reacted according to General Procedure D to give the title compound as a yellow oil. $^1$H NMR (d$_6$-DMSO) δ 8.35-8.31 (m, 1H), 7.46-6.92 (m, 10H), 6.57-6.38 (m, 1H), 5.58-4.90 (m, 1H), 4.60-4.46 (m, 2H), 3.23-2.68 (m, 4H), 2.48-2.36 (m, 1H), 1.61-1.36 (m, 6H), 1.26-0.87 (m, 2H). HPLC (Method 1) Rt 3.80 min (Purity: 99.9%). UPLC/MS (Method 3) 435.2 (M+H)$^+$.

Example 24

3-(4-fluorophenyl)-N-[1-(2-methyl-2,3-dihydro-1-benzofuran-5-yl)propyl]-N-(pyridin-2-ylmethyl)propanamide

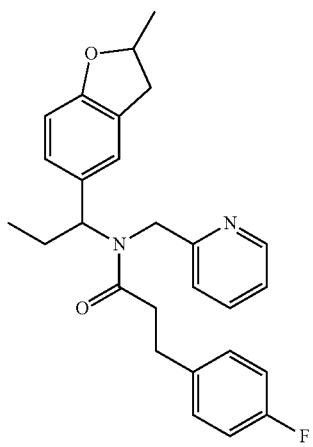 [SMILES: CCC(c1ccc2c(c1)CC(C)O2)N(Cc1ccccn1)C(=O)CCc1ccc(F)cc1]

Intermediate 1 (60 mg, 0.21 mmol), 3-(4-fluorophenyl)propionic acid (54 mg, 0.32 mmol), T3P (178 μl, 0.32 mmol) and triethylamine (29 μl, 0.21 mmol) were reacted according to General Procedure D to give the title compound as a colourless oil (51 mg). $^1$H NMR (d$_6$-DMSO) δ 8.42-8.33 (m, 1H), 7.56-7.46 (m, 1H), 7.38-6.94 (m, 7H), 6.81-6.76 (m, 1H), 6.58-6.52 (m, 1H), 5.65-4.96 (m, 1H), 4.89-4.77 (m, 1H), 4.48-4.22 (m, 2H), 3.24-2.81 (m, 4H), 2.70-2.52 (m, 2H), 1.93-1.66 (m, 2H), 1.33-1.31 (m, 3H), 0.77-0.70 (m, 3H). HPLC (Method 1) Rt 3.36 min (Purity: 100.0%). UPLC/MS (Method 3) 433.4 (M+H)+.

Compound 39: Diastereomer A of N-[1-(2,3-dihydro-1H-inden-5-yl)ethyl]-3-(4-fluorophenyl)-N-{[6-(trifluoromethyl)pyridin-3-yl]methyl}butanamide & Compound 40: Diastereomer B of N-[1-(2,3-dihydro-1H-inden-5-yl)ethyl]-3-(4-fluorophenyl)-N-{[6-(trifluoromethyl)pyridin-3-yl]methyl}butanamide

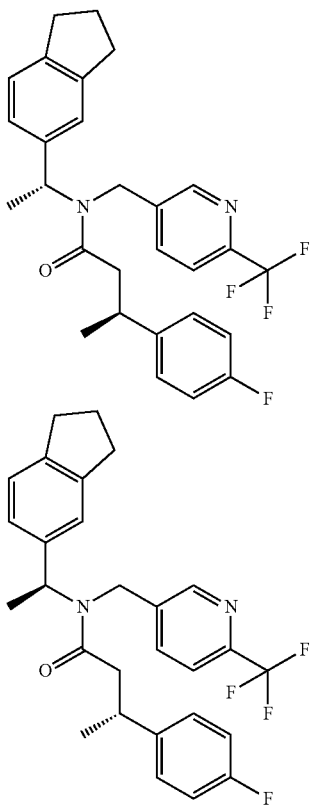

Intermediate fg (50 mg, 0.156 mmol) was reacted with Intermediate nn (79 mg, 0.390 mmol) in presence of TEA (44 µl, 0.312 mmol) using General Procedure C to afford racemic compounds 39 and 40 (arbitrarily assigned above). The crude material was purified over PTLC (silica-gel, DCM) Compound 39 (25 mg, 33%) was eluted first as clear oil. ¹H NMR (300 MHz, DMSO, 110° C.) δ 8.31 (bs, 1H), 7.57-7.45 (m, 2H), 7.36-7.27 (m, 3H), 7.09-6.96 (m, 4H), 5.66 (bs, 1H), 4.51-4.36 (m, 2H), 3.43-3.33 (m, 1H), 2.86-2.73 (m, 5H), 2.16-1.88 (m, 3H), 1.40 (d, J=7.2 Hz, 3H), 1.27 (d, J=6.9 Hz, 3H). ¹H NMR (300 MHz, CDCl₃) δ 8.38-8.21 (m, 1H), 7.52-6.72 (m, 9H), 6.16-5.18 (m, 1H), 4.54-4.14 (m, 2H), 3.57-3.48 (m, 1H), 2.96-2.38 (m, 5H), 2.24-1.86 (m, 2H), 1.37-1.27 (m, 7H). HPLC (Method 2) Rt 3.670 min (96% purity). MS (ES+) m/z 485.2 (M+H+) Compound 40 was eluted second (28 mg, 37%) as clear oil. ¹H NMR (300 MHz, CDCl₃) δ 8.28-8.14 (m, 1H), 7.42-6.55 (m, 9H), 6.14-5.15 (m, 1H), 4.41-4.22 (m, 2H), 3.60-3.48 (m, 1H), 2.99-2.38 (m, 5H), 2.06-1.95 (m, 2H), 1.53 (d, J=7.2 Hz, 3H), 1.37 (d, J=6.9 Hz, 3H), 1.31-1.25 (m, 1H). HPLC (Method 2) Rt 3.562 min (97.9% purity). MS (ES+) m/z 485.2 (M+H+).

Example 41

N-[1-(2,3-dihydro-1H-inden-5-yl)ethyl]-3-(4-fluorophenyl)-N-[2-(3,6-dimethylpyrazin-2-yloxy)ethyl]butanamide

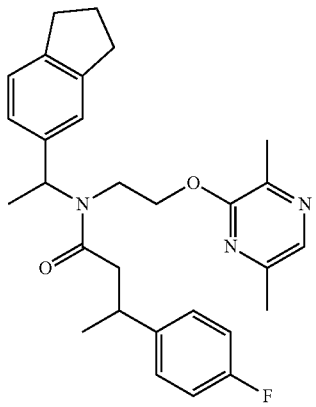 [SMILES: Cc1cnc(C)c(OCCN(C(=O)CC(C)c2ccc(F)cc2)C(C)c2ccc3c(c2)CCC3)n1]

Intermediate v (70 mg, 0.23 mmol) was reacted with Intermediate nn (113 mg, 0.56 mmol) in presence of triethylamine (63 µl, 0.45 mmol) according to General Procedure C to afford the title compound (75 mg, 70%) as clear oil. ¹H NMR (CDCl₃) δ 7.86-7.80 (m, 1H), 7.25-6.76 (m, 7H), 6.05-4.97 (m, 1H), 4.42-3.12 (m, 5H), 2.91-2.58 (m, 5H), 2.36-2.28 (m, 6H), 2.12-1.98 (m, 2H), 1.68-1.26 (m, 7H). LCMS (Method 2) Rt 4.153 min (95% purity), m/z 476.5 (M+H)+.

Example 44

N-[1-(2,3-dihydro-1H-inden-5-yl)ethyl]-3-(4-fluorophenyl)-N-[2-(6-chloropyridin-2-yloxy)ethyl]butanamide

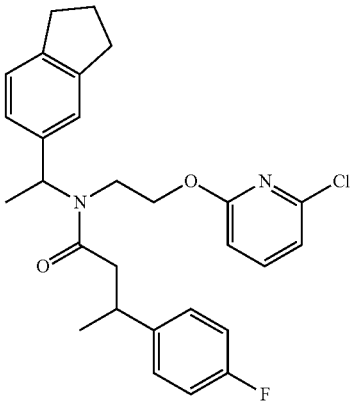 [SMILES: CC(CC(=O)N(CCOc1cccc(Cl)n1)C(C)c1ccc2c(c1)CCC2)c1ccc(F)cc1]

Intermediate x (67 mg, 0.21 mmol), Intermediate nn and (75 mg, 0.38 mmol), DIPEA (60 µl, 0.35 mmol) were reacted according to General Procedure C to afford the titled compound (93 mg, 91%) as a yellow oil. ¹H NMR (CDCl₃)

δ 7.53-7.44 (m, 1H), 7.30-7.04 (m, 4H), 6.99-6.72 (m, 4H), 6.55-6.50 (m, 1H), 6.07-4.97 (m, 1H), 4.38-4.19 (m, 1H), 4.12-3.84 (m, 1H), 3.80-3.09 (m, 3H), 2.95-2.74 (m, 5H), 2.70-2.59 (m, 1H), 2.12-1.98 (m, 2H), 1.67-1.29 (m, 6H). LCMS (Method 2) Rt 5.132 min (98% purity), m/z 481.2 (M+H)+.

Example 45

N-[1-(2,3-dihydro-1H-inden-5-yl)ethyl]-3-(4-fluorophenyl)-N-[2-(6-chloropyridin-2-yloxy)ethyl]propanamide

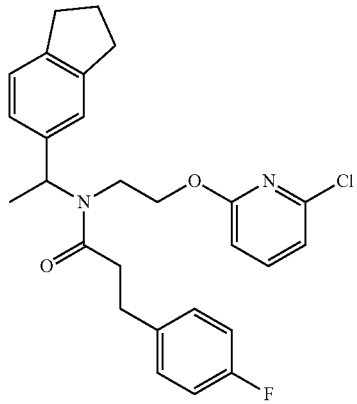 [SMILES: CC(c1ccc2c(c1)CCC2)N(CCOc1cccc(Cl)n1)C(=O)CCc1ccc(F)cc1]

Intermediate x (66 mg, 0.21 mmol), 3-(4-fluorophenyl) propanoyl chloride, (58 mg, 0.31 mmol) and DIPEA (50 μl, 0.29 mmol) were reacted according to General Procedure C to afford the titled compound (83 mg, 86%) as a yellow oil. 1H NMR (CDCl3) δ 7.51-7.44 (m, 1H), 7.27-7.12 (m, 4H), 7.03-6.85 (m, 4H), 6.56-6.48 (m, 1H), 6.10-5.02 (m, 1H), 4.43-4.24 (m, 1H), 4.09-3.20 (m, 3H), 3.09-2.98 (m, 2H), 2.94-2.72 (m, 6H), 2.11-2.00 (m, 2H), 1.62-1.51 (m, 3H). LCMS (Method 2) Rt 4.592 min (98% purity), m/z 467.3 (M+H)+.

Example 46

N-[1-(2,3-dihydro-1H-inden-5-yl)ethyl]-3-(4-fluorophenyl)-N-[2-(pyridin-2-yloxy)ethyl]butanamide

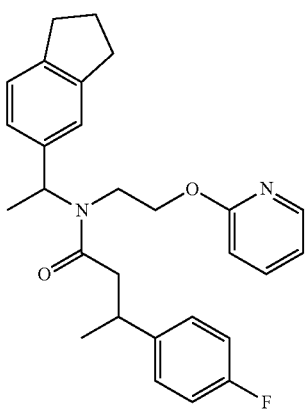 [SMILES: CC(CC(=O)N(CCOc1ccccn1)C(C)c1ccc2c(c1)CCC2)c1ccc(F)cc1]

Intermediate y (69 mg, 0.24 mmol), Intermediate nn (71 mg, 0.35 mmol) and DIPEA (60 μl, 0.35 mmol) were reacted according to General Procedure C to afford the titled compound (98 mg, 90%) as a pale yellow oil. 1H NMR (CDCl3) δ 8.10-8.04 (m, 1H), 7.58-7.49 (m, 1H), 7.28-7.04 (m, 4H), 6.99-6.76 (m, 4H), 6.64-6.59 (m, 1H), 6.04-4.96 (m, 1H), 4.38-4.23 (m, 1H), 4.18-4.02 (m, 1H), 3.87-3.14 (m, 3H), 2.98-2.58 (m, 6H), 2.11-1.98 (m, 2H), 1.64-1.29 (m, 6H). LCMS (Method 2) Rt 3.979 min (100% purity), m/z 447.3 (M+H)+.

Example 47

N-[1-(2,3-dihydro-1H-inden-5-yl)ethyl]-3-(4-fluorophenyl)-N-[2-(pyridin-2-yloxy)ethyl]propanamide

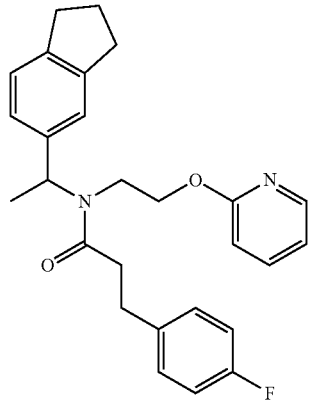

Intermediate y (71 mg, 0.25 mmol), 3-(4-fluorophenyl) propanoyl chloride (72 mg, 0.39 mmol) and DIPEA (60 μl, 0.35 mmol) were reacted according to General Procedure C to afford the titled compound (99 mg, 91%) as a yellow oil. 1H NMR (CDCl3) δ 8.11-7.97 (m, 1H), 7.56-7.50 (m, 1H), 7.24-7.13 (m, 4H), 7.04-6.92 (m, 3H), 6.91-6.81 (m, 1H), 6.65-6.57 (m, 1H), 6.07-5.03 (m, 1H), 4.45-4.29 (m, 1H), 4.16-3.22 (m, 3H), 3.07-2.97 (m, 2H), 2.94-2.71 (m, 6H), 2.10-1.99 (m, 2H), 1.60-1.52 (m, 3H). LCMS (Method 2) Rt 3.568 min (100% purity), m/z 433.3 (M+H)+.

Example 49

3-(4-fluorophenyl)-N-[(1R)-1-(4-methoxyphenyl) ethyl]-N-(pyridin-2-ylmethyl)butanamide

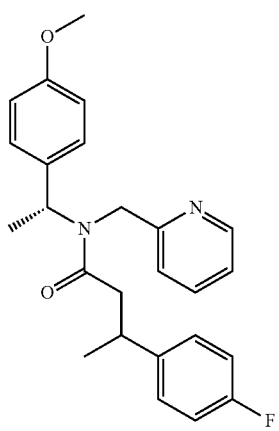 [SMILES: COc1ccc([C@@H](C)N(Cc2ccccn2)C(=O)CC(C)c2ccc(F)cc2)cc1]

Intermediate fd (45.6 mg, 0.19 mmol) was reacted with Intermediate nn (45 μL, 0.28 mmol) in presence of TEA (60 μL, 0.43 mmol) as described under General Procedure C to afford the crude material. The compound was purified by silica gel column chromatography (EtOAc/DCM 2:8) to give the title compound (64.1 mg, 83%) as a clear oil. $^1$H NMR (300 MHz, CDCl$_3$) δ 8.50-8.36 (m, 1H), 7.58-7.39 (m, 1H), 7.28-6.64 (m, 10H), 6.15-5.16 (m, 1H), 4.93-4.00 (m, 2H), 3.79-3.76 (m, 3H), 3.59-3.43 (m, 1H), 2.98-2.36 (m, 2H), 1.50-1.22 (m, 6H). MS (ES$^+$) m/z 407.3 (M+H$^+$).

Example 51

N-[1-(2,3-dihydro-1H-inden-5-yl)ethyl]-4-phenyl-N-[2-(pyridin-2-yloxy)ethyl]butanamide

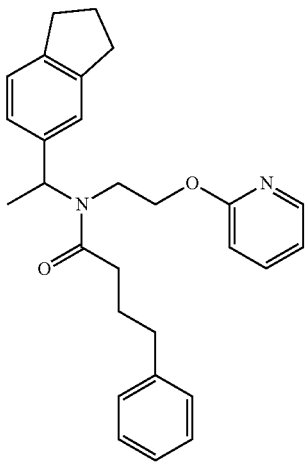 [SMILES: CC(c1ccc2c(c1)CCC2)N(CCOc1ccccn1)C(=O)CCCc1ccccc1]

Intermediate y (72 mg, 0.25 mmol), 3-phenylpropanoyl chloride (76 mg, 0.41 mmol) and DIPEA (65 μl, 0.38 mmol) were reacted according to General Procedure C to afford the titled compound (96 mg, 88%) as a yellow oil. $^1$H NMR (CDCl$_3$) δ 8.11-8.08 (m, 1H), 7.57-7.49 (m, 1H), 7.30-6.95 (m, 8H), 6.88-6.80 (m, 1H), 6.67-6.59 (m, 1H), 6.11-4.99 (m, 1H), 4.48-4.28 (m, 1H), 4.20-3.98 (m, 1H), 3.81-3.23 (m, 2H), 2.89-2.84 (m, 4H), 2.74-2.67 (m, 2H), 2.59-2.45 (m, 2H), 2.13-1.99 (m, 4H), 1.63-1.54 (m, 3H). LCMS (Method 2) Rt 4.078 min (100% purity), m/z 429.2 (M+H)$^+$.

Example 52

N-[1-(2,3-dihydro-1H-inden-5-yl)ethyl]-3-(4-fluorophenyl)-N-[2-(6-methylpyridin-2-yloxy)ethyl]butanamide

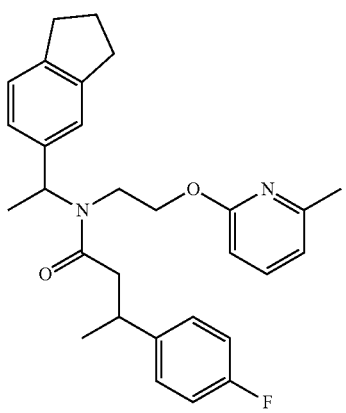 [SMILES: Cc1cccc(OCCN(C(=O)CC(C)c2ccc(F)cc2)C(C)c2ccc3c(c2)CCC3)n1]

Intermediate bb (73 mg, 0.25 mmol), Intermediate nn (71 mg, 0.35 mmol) and DIPEA (60 μl, 0.35 mmol) were reacted according to General Procedure C to afford the titled compound (103 mg, 91%) as a pale yellow oil. $^1$H NMR (CDCl$_3$) δ 7.45-7.38 (m, 1H), 7.25-7.05 (m, 4H), 6.98-6.90 (m, 2H), 6.83-6.65 (m, 2H), 6.44-6.37 (m, 1H), 6.07-4.94 (m, 1H), 4.40-3.98 (m, 2H), 3.88-3.10 (m, 3H), 2.93-2.56 (m, 6H), 2.40-2.38 (m, 3H), 2.12-1.98 (m, 2H), 1.69-1.43 (m, 3H), 1.37-1.26 (m, 3H). LCMS (Method 2) Rt 5.038 min (100% purity), m/z 461.2 (M+H)$^+$.

Example 53

N-[1-(2,3-dihydro-1H-inden-5-yl)ethyl]-3-(4-fluorophenyl)-N-[2-(6-methylpyridin-2-yloxy)ethyl]propanamide

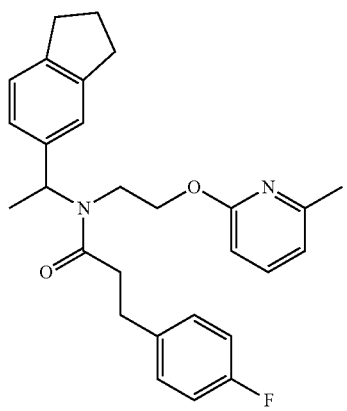 [SMILES: Cc1cccc(OCCN(C(=O)CCc2ccc(F)cc2)C(C)c2ccc3c(c2)CCC3)n1]

Intermediate bb (71 mg, 0.24 mmol), 3-(4-fluorophenyl)propanoyl chloride (66 mg, 0.35 mmol) and DIPEA (60 μl, 0.35 mmol) were reacted according to General Procedure C to afford the titled compound (74 mg, 70%) as a pale yellow oil. $^1$H NMR (CDCl$_3$) δ 7.44-7.38 (m, 1H), 7.22-7.13 (m, 4H), 7.04-6.90 (m, 3H), 6.69-6.67 (m, 1H), 6.46-6.36 (m, 1H), 6.07-5.00 (m, 1H), 4.45-4.25 (m, 1H), 4.16-3.20 (m, 3H), 3.13-2.92 (m, 2H), 2.89-2.71 (m, 6H), 2.40-2.30 (m, 3H), 2.11-2.00 (m, 2H), 1.68-1.53 (m, 3H). LCMS (Method 2) Rt 4.44 min (98% purity), m/z 447.3 (M+H)$^+$.

Example 54

N-[1-(2,2-dimethyl-1,3-benzoxathiol-5-yl)ethyl]-3-(4-fluorophenyl)-N-(pyridin-2-ylmethyl)propanamide

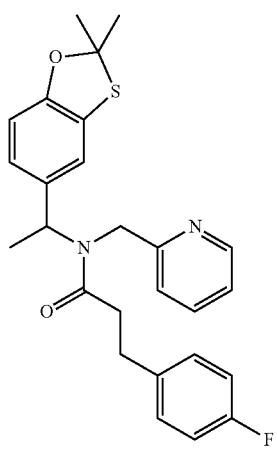 [SMILES: CC(c1ccc2c(c1)SC(C)(C)O2)N(Cc1ccccn1)C(=O)CCc1ccc(F)cc1]

Intermediate cc (83 mg, 0.28 mmol), 3-(4-fluorophenyl)propionic acid (46 mg, 0.28 mmol), triethylamine (0.04 mL, 0.28 mmol) and T3P (0.18 mL, 0.28 mmol) were reacted according to General Procedure D to give the title compound as a colourless oil (75 mg, 61%). $^1$H NMR (CDCl$_3$) δ 8.40 (d, J=4.0 Hz, 0.7H), 8.35 (d, J=4.9 Hz, 0.3H), 7.43 (td, J=7.7, 1.8 Hz, 1H), 7.17-6.62 (m, 7H), 6.56 (t, J=8.7 Hz, 1H), 6.04 (q, J=7.1 Hz, 0.6H), 5.07 (d, J=6.6 Hz, 0.4H), 4.78 (d, J=16.0 Hz, 0.4H), 4.25 (m, 1.6H), 3.64 (t, J=5.7 Hz, 0.2H), 2.95 (dt, J=19.7, 7.2 Hz, 1.8H), 2.77 (t, J=7.3 Hz, 0.6H), 2.59-2.38 (m, 1.4H), 1.74 (s, 5H), 1.49 (s, 1H), 1.37 (d, J=7.0 Hz, 1H), 1.26 (d, J=7.2 Hz, 2H). HPLC (Method 1) Rt 3.61 min (Purity: 97.8%). UPLC/MS (Method 3) 451.3 (M+H)$^+$.

Example 55

3-(4-fluorophenyl)-N-[(1S)-1-(2-methoxyphenyl)ethyl]-N-(pyridin-2-ylmethyl)propanamide

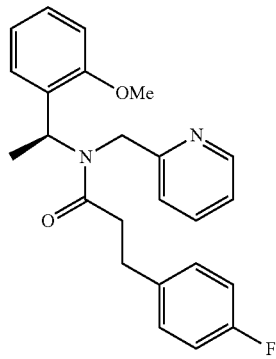 [SMILES: COc1ccccc1[C@H](C)N(Cc1ccccn1)C(=O)CCc1ccc(F)cc1]

Intermediate dd (80 mg, 0.33 mmol), 3-(4-fluorophenyl)propionic acid (56 mg, 0.33 mmol), triethylamine (0.05 mL, 0.33 mmol) and T3P (0.21 mL, 0.33 mmol) were reacted according to General Procedure D to give the title compound as a brown oil (78 mg, 60%). $^1$H NMR (CDCl$_3$) δ 8.39-8.30 (m, 1H), 7.45-7.37 (m, 1H), 7.29-7.20 (m, 2H), 7.20-6.74 (m, 7H), 6.67-6.63 (m, 1H), 6.42-5.47 (m, 1H), 4.61-4.38 (m, 2H), 3.70 (s, 3H), 3.13-2.49 (m, 4H), 1.48-1.42 (m, 3H). HPLC (Method 1) Rt 3.17 min (Purity: 99.0%). UPLC/MS (Method 3) 393.3 (M+H)$^+$.

Example 57

3-(4-fluorophenyl)-N-{1-[2-(methoxymethyl)phenyl]ethyl}-N-(pyridin-2-ylmethyl)propanamide

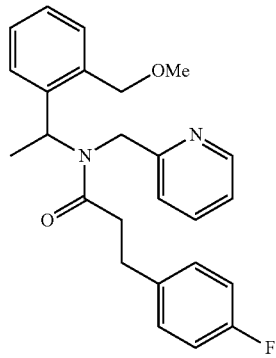 [SMILES: COCc1ccccc1C(C)N(Cc1ccccn1)C(=O)CCc1ccc(F)cc1]

Intermediate ff (80 mg; 0.31 mmol), 3-(4-fluorophenyl)propionic acid (58 mg, 0.34 mmol), T3P (348 μl, 0.62 mmol) and triethylamine (42 μl, 0.31 mmol) were reacted according to General Procedure D to give the title compound as a yellow oil. $^1$H NMR (d$_6$-DMSO) δ 8.38-8.33 (m, 1H), 7.58-7.35 (m, 2H), 7.28-7.01 (m, 8H), 6.94-6.65 (m, 1H), 6.05-5.53 (m, 1H), 4.70-4.06 (m, 4H), 3.24-3.20 (m, 3H), 2.94-2.53 (m, 4H), 1.45-1.31 (m, 3H). HPLC (Method 1) Rt 3.30 min (Purity: 100.0%). UPLC/MS (Method 3) 407.3 (M+H)$^+$.

Example 58

Enantiomer A of 3-(4-fluorophenyl)-N-{1-[2-(methoxymethyl)phenyl]ethyl}-N-(pyridin-2-ylmethyl)propanamide

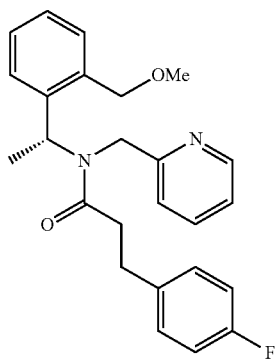 [SMILES: COCc1ccccc1[C@@H](C)N(Cc1ccccn1)C(=O)CCc1ccc(F)cc1]

Example 57 (50 mg) was separated by chiral HPLC (AD-H, 250×20 mm, 5 um) using EtOH+0.1% DEA (10 mL/min) to give the title compound (1st eluting pic) as a yellow oil (19 mg). HPLC (Method 1) Rt 3.13 min (Purity: 99.4%). UPLC/MS (Method 3) 407.2 (M+H)$^+$.

Example 61

N-[(1R)-1-(2-methoxyphenyl)ethyl]-N-(pyridin-2-ylmethyl)-3-[3-(trifluoromethyl)phenyl]propanamide

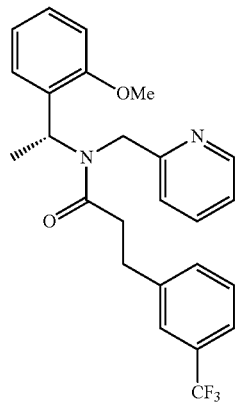 [SMILES: COc1ccccc1[C@@H](C)N(Cc1ccccn1)C(=O)CCc1cccc(C(F)(F)F)c1]

Intermediate ee (80 mg, 0.33 mmol), 3-(3-trifluoromethylphenyl)propionic acid (72 mg, 0.33 mmol), T3P (0.21 mL, 0.33 mmol) and triethylamine (0.05 mL, 0.33 mmol) were reacted according to General Procedure D to give the title compound as a brown oil (64 mg, 44%). $^1$H NMR (CDCl$_3$) δ 8.40-8.29 (m, 1H), 7.54-7.36 (m, 5H), 7.28-7.25 (m, 1H), 7.17-7.12 (m, 1H), 7.05-7.65 (m, 3H), 6.67-6.64 (m, 1H), 6.21-5.47 (m, 1H), 4.64-4.40 (m, 2H), 3.68-3.67 (m, 3H), 3.23-2.56 (m, 4H), 1.49-1.44 (m, 3H). HPLC (Method 1) Rt 3.68 min (Purity: 100.0%). UPLC/MS (Method 3) 443.3 (M+H)$^+$.

Example 62

N-[1-(2,2-dimethyl-1,3-benzoxathiol-5-yl)ethyl]-N-(pyridin-2-ylmethyl)-3-[3-(trifluoromethyl)phenyl]propanamide

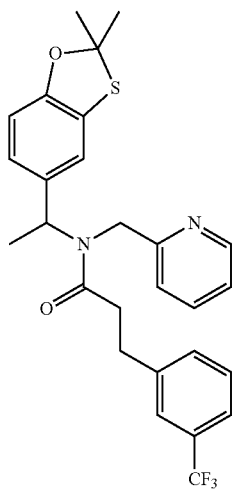 [SMILES: CC(c1ccc2c(c1)SC(C)(C)O2)N(Cc1ccccn1)C(=O)CCc1cccc(C(F)(F)F)c1]

Intermediate cc (83 mg, 0.28 mmol), 3-(3-trifluoromethylphenyl)propionic acid (60 mg, 0.28 mmol), T3P (0.18 mL, 0.28 mmol and triethylamine (0.04 mL, 0.28 mmol) were reacted according to General Procedure D to give the title compound as a yellow oil. $^1$H NMR (CDCl$_3$) δ 8.47-8.41 (m, 1H), 7.61-7.35 (m, 5H), 7.13-6.60 (m, 5H), 6.14-5.11 (m, 1H), 4.89-4.29 (m, 2H), 3.16-3.01 (m, 2H), 2.91-2.57 (m, 2H), 1.80 (s, 6H), 1.45-1.32 (m, 3H). HPLC (Method 1) Rt 3.99 min (Purity: 96.8%). UPLC/MS (Method 3) 501.4 (M+H)$^+$.

Example 63

N-[1-(2,2-dimethyl-3-oxido-1,3-benzoxathiol-5-yl)ethyl]-N-(pyridin-2-ylmethyl)-3-[3-(trifluoromethyl)phenyl]propanamide

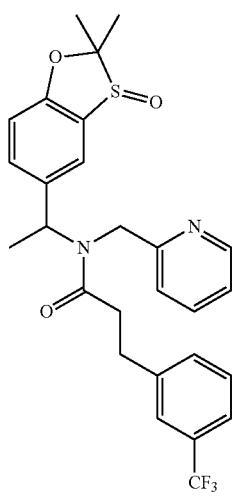 [SMILES: CC(c1ccc2c(c1)S(=O)C(C)(C)O2)N(Cc1ccccn1)C(=O)CCc1cccc(C(F)(F)F)c1]

To a solution of Example 62 (70 mg, 0.14 mmol) in glacial AcOH (5 mL) at 0° C. was added H$_2$O$_2$ (0.03 mL, 0.28 mmol). After stirring for 2 hr, H$_2$O$_2$ (0.12 mL, 1.12 mmol) was added and the stirring continued at RT overnight. Water was added and the aqueous phase was extracted with DCM. The combined organics were then extracted with 1 M NaOH, dired (MgSO$_4$), filtered and concentrated under reduced pressure. The crude mixture was purified by MD Autoprep to give the title compound as a vitreous solid. $^1$H NMR (CDCl$_3$) δ 8.41-8.29 (m, 1H), 7.79-7.30 (m, 7H), 7.22-6.79 (m, 3H), 6.23-5.18 (m, 1H), 4.87-4.29 (m, 2H), 3.26-2.61 (m, 4H), 1.81 (br s, 3H), 1.50-1.39 (m, 6H). HPLC (Method 1) Rt 3.42 min (Purity: 85.9%). UPLC/MS (Method 3) 517.3 (M+H)$^+$.

Example 64

N-[1-(2,2-dimethyl-3-oxido-1,3-benzoxathiol-5-yl)ethyl]-3-(4-fluorophenyl)-N-(pyridin-2-ylmethyl)propanamide

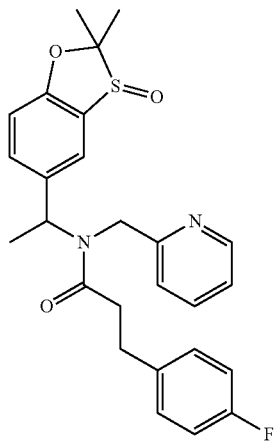 [SMILES: CC(c1ccc2c(c1)S(=O)C(C)(C)O2)N(Cc1ccccn1)C(=O)CCc1ccc(F)cc1]

To a solution of Example 54 (70 mg, 0.16 mmol) in glacial AcOH (5 mL) at 0° C. was added H$_2$O$_2$ (35 µl, 0.31 mmol). After stirring for 2 hr, H$_2$O$_2$ (0.14 mL, 1.24 mmol) was added and the stirring continued at RT overnight. Water was added and the aqueous phase was extracted with DCM. The combined organics were then extracted with 1 M NaOH, dired (MgSO$_4$), filtered and concentrated under reduced pressure. The crude was purified by MD Autoprep to give the title compound as a vitreous solid. $^1$H NMR (CDCl$_3$) δ 8.50-8.37 (m, 1H), 7.72-6.82 (m, 10H), 6.22-5.19 (m, 1H), 4.85-4.21 (m, 2H), 3.10-2.53 (m, 4H), 1.81 (s, 3H), 1.51-1.37 (m, 6H). HPLC (Method 1) Rt 2.81 min (Purity: 96.0%). UPLC/MS (Method 3) 467.3 (M+H)$^+$.

Example 65

2-[(4-fluorophenyl)sulfonyl]-N-{1-[2-(methoxymethyl)phenyl]ethyl}-N-(pyridin-2-ylmethyl)acetamide and Example 66: 1-[(4-fluorophenyl)sulfonyl]-N-{1-[2-(methoxymethyl)phenyl]ethyl}-N-(pyridin-2-ylmethyl)cyclopropanecarboxamide

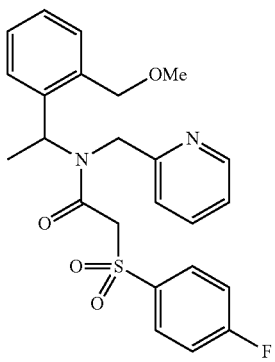

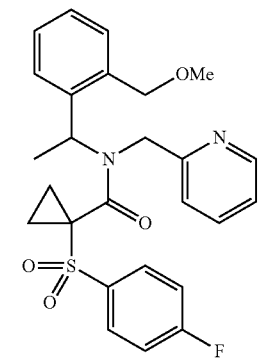

Intermediate ff (120 mg, 0.47 mmol), 1-[(4-fluorophenyl)sulfonyl]cyclopropanecarboxylic acid (prepared according to the procedure outlined in the Bulletin of the Chemical Society of Japan 1985, 58(2), 765-6) (172 mg, 0.70 mmol) containing 10% of [(4-fluorophenyl)sulfonyl]acetic acid, T3P (392 µl, 0.70 mmol) and triethylamine (65 µl, 0.47 mmol) were reacted according to General Procedure D to give Example 65 and Example 66 as brown solids. Example 65: HPLC (Method 1) Rt 2.78 min (Purity: 93.7%). UPLC/MS (Method 3) 457.1 (M+H)$^+$. Example 66: $^1$H NMR (CDCl$_3$) δ 8.44-8.43 (m, 1H), 7.69-7.64 (m, 2H), 7.48-7.38 (m, 2H), 7.30-7.07 (m, 6H), 6.75-6.72 (m, 1H), 5.80-5.70 (m, 1H), 5.12-5.00 (m, 2H), 4.66-4.62 (m, 1H), 4.27-4.23 (m, 1H), 3.36 (s, 3H), 1.95 (br s, 1H), 1.77-1.54 (m, 4H), 1.40 (d, J=7.0 Hz, 3H). HPLC (Method 1) Rt 3.11 min (Purity: 97.6%). UPLC/MS (Method 3) 483.1 (M+H)$^+$.

Example 67

N-[1-(2,3-dihydro-1H-inden-5-yl)ethyl]-3-(4-fluorophenyl)-N-(pyridin-2-ylmethyl)propanamide

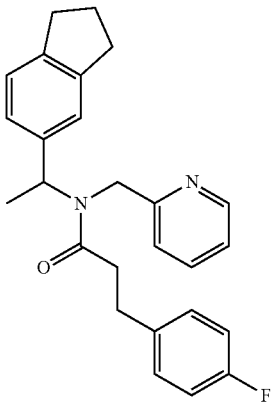 [SMILES: CC(c1ccc2c(c1)CCC2)N(Cc1ccccn1)C(=O)CCc1ccc(F)cc1]

Intermediate gg (100 mg, 0.40 mmol), 3-(4-fluorophenyl)propionic acid (73 mg, 0.44 mmol), T3P (442 µl, 0.79 mmol) and triethylamine (53 µl, 0.40 mmol) were reacted according to General Procedure D to give the title compound as a yellow oil. $^1$H NMR (d$_6$-DMSO) δ 8.48-8.46 (m, 1H), 7.67-7.58 (m, 1H), 7.32-6.94 (m, 9H), 5.94-5.31 (m, 1H), 4.69-4.01 (m, 2H), 2.99-2.65 (m, 8H), 2.02-1.91 (m, 2H), 1.39-1.24 (m, 3H). HPLC (Method 1) Rt 3.68 min.

Example 74

Diastereomer A of N-[cyclopropyl(2,2-dimethyl-3,3-dioxido-1,3-benzoxathiol-5-yl)methyl]-3-(4-fluorophenyl)-N-(pyridin-2-ylmethyl)butanamide

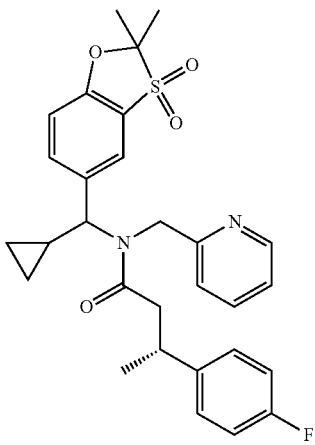 [SMILES: C[C@H](CC(=O)N(Cc1ccccn1)C(c1ccc2c(c1)S(=O)(=O)C(C)(C)O2)C1CC1)c1ccc(F)cc1]

Intermediate yy (75 mg, 0.21 mmol), Intermediate di (76 mg, 0.42 mmol), triethylamine (87 µl, 0.63 mmol) and T3P (266 mg, 0.42 mmol) were reacted according to General Procedure D to give the title compound as a white solid (41 mg, 37%). $^1$H NMR (CDCl$_3$) δ 8.52-8.33 (m, 1H), 7.69-7.44 (m, 2H), 7.23-6.74 (m, 8H), 5.12 (dd, J=10.4, 4.6 Hz, 1H), 4.55-4.12 (m, 2H), 3.56-3.46 (m, 1H), 2.71-2.44 (m, 2H), 1.71 (s, 6H), 1.34-0.23 (m, 8H). HPLC (Method 1) Rt 2.63 min (Purity: 98.4%). UPLC/MS (Method 3) 523.1 (M+H)+.

Example 76

Diastereomer A of N-[(4-chlorophenyl)(cyclopropyl)methyl]-3-[(4-fluorophenyl)sulfonyl]-N-(pyridin-2-ylmethyl)butanamide

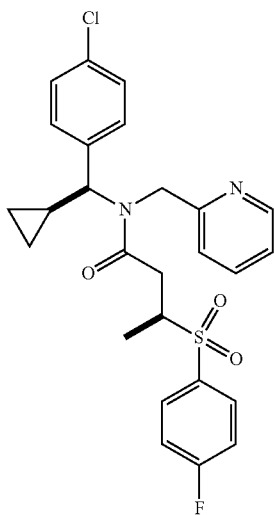 [SMILES: C[C@@H](CC(=O)N(Cc1ccccn1)[C@H](c1ccc(Cl)cc1)C1CC1)S(=O)(=O)c1ccc(F)cc1]

Intermediate b (100 mg, 0.37 mmol), Intermediate do (135 mg; 0.55 mmol), T3P (409 μl, 0.73 mmol) and triethylamine (77 μl, 0.55 mmol) were reacted according to General Procedure D to give the racemic mixture as a pale pink solid. HPLC (Method 1) Rt 3.55 min (Purity: 94.7%). UPLC/MS (Method 3) 501.1 (M+H)+. The isomers were separated by SFC Chiralpak IC at 35° C., 20 EtOH, 100 mL/min. The title compound was the first eluting isomer, eluting at 2.98 minutes.

Example 78

Diastereomer A of 3-(4-fluorophenyl)-N-[1-(4-methyl-4H-1,2,4-triazol-3-yl)ethyl]-N-(pyridin-2-ylmethyl)butanamide

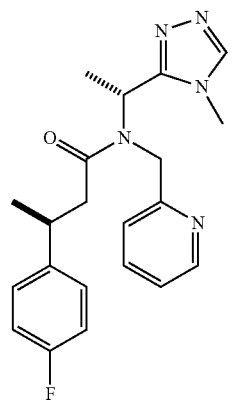 [SMILES: C[C@H](c1nncn1C)N(Cc1ccccn1)C(=O)C[C@H](C)c1ccc(F)cc1]

Intermediate zz (44 mg, 0.2 mmol), 3-(4-fluorophenyl) butanoic acid (55 mg; 0.30 mmol), T3P (226 μl, 0.41 mmol) and triethylamine (42 μl, 0.3 mmol) were reacted according to General Procedure D to give the title compound as a brown solid. $^1$H NMR (d$_6$-DMSO) δ 8.38-8.30 (m, 1H), 7.85-7.80 (m, 1H), 7.56-7.49 (m, 1H), 7.22-7.07 (m, 3H), 6.29-6.17 (m, 1H), 4.68-4.36 (m, 2H), 3.53 (s, 1.5H), 3.51-3.41 (m, 1H), 3.14 (s, 1.5H), 2.99-2.57 (m, 2H), 1.67-1.55 (m, 3H), 1.29-1.26 (m, 3H). HPLC (Method 1) Rt 2.21 min (Purity: 97.7%). UPLC/MS (Method 3) 382.2 (M+H)+. The isomers were separated by HPLC Chiralpak IC:EtOH+0.1% DEA, 10 mL/min. The title compound was the first eluting isomer, eluting at 9.44 min.

Example 80

N-[(4-chlorophenyl)(cyclopropyl)methyl]-2-[(4-fluorophenyl)sulfonyl]-N-(8-methyl-8-azabicyclo[3.2.1]octan-3-yl)acetamide

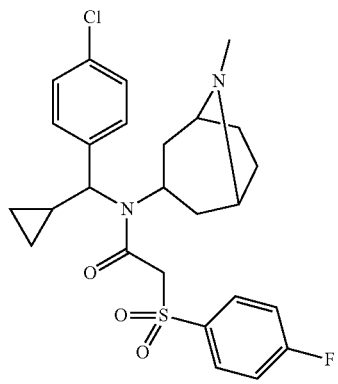 [SMILES: CN1C2CCC1CC(N(C(=O)CS(=O)(=O)c1ccc(F)cc1)C(c1ccc(Cl)cc1)C1CC1)C2]

Intermediate ad (430 mg, 1.41 mmol), (4-fluoro-benzenesulfonyl)-acetic acid (339 mg, 1.55 mmol), T3P (1.678 mL, 2.82 mmol) and triethylamine (0.393 mL, 2.82 mmol) were reacted according to General Procedure D to give the title compound as a white solid (380 mg, 53%). $^1$H NMR (CDCl$_3$) δ 7.99-7.92 (m, 2H), 7.49-7.47 (m, 2H), 7.38-7.35 (m, 2H), 7.30-7.23 (m, 2H), 4.69-4.56 (m, 1H), 4.26-4.04 (m, 3H), 3.65-3.44 (m, 2H), 3.03-2.92 (m, 1H), 2.61 (d, J=3.9 Hz, 3H), 2.26-1.84 (m, 7H), 1.86-1.75 (m, 1H), 0.99-0.90 (m, 1H), 0.81-0.71 (m, 1H), 0.63-0.55 (m, 1H), 0.49-0.41 (m, 1H). LCMS (Method 2) Rt 2.59 min (Purity: 99.4%), m/z 505.2 (M+H)+.

Example 87

3-(4-Fluorophenyl)-N-[1-(4-methyl-4H-1,2,4-triazol-3-yl)ethyl]-N-(pyridin-2-ylmethyl)butanamide

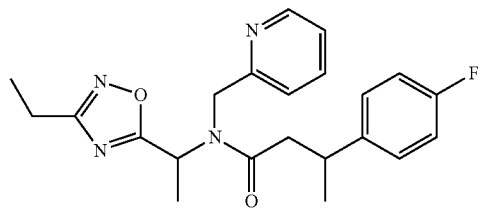 [SMILES: CCc1noc(C(C)N(Cc2ccccn2)C(=O)CC(C)c2ccc(F)cc2)n1]

Intermediate aaa (87 mg, 0.37 mmol), 3-(4-fluorophenyl)butanoic acid (102 mg; 0.56 mmol), T3P (418 μl, 0.75 mmol) and triethylamine (78 μl, 0.56 mmol) were reacted according to General Procedure D to give the title compound as a brown oil. ¹H NMR (d₆-DMSO) δ 8.59-8.52 (m, 1H), 7.78-7.59 (m, 1H), 7.24-7.18 (m, 1H), 7.15-7.09 (m, 2H), 7.03-6.90 (m, 3H), 5.94-5.30 (m, 1H), 4.96-4.46 (m, 2H), 3.50-3.40 (m, 1H), 2.94-2.46 (m, 4H), 1.76-1.56 (m, 1H), 1.54-1.47 (m, 2H), 1.35-1.31 (m, 1H), 1.27-1.20 (m, 5H). HPLC (Method 1) Rt 3.03 min (Purity: 100.0%). UPLC/MS (Method 3) 397.2 (M+H)⁺.

Example 88

N-{cyclopropyl[4-(difluoromethoxy)phenyl]methyl}-3-[(4-fluorophenyl)sulfonyl]-N-[(6-methoxypyridin-3-yl)methyl]butanamide

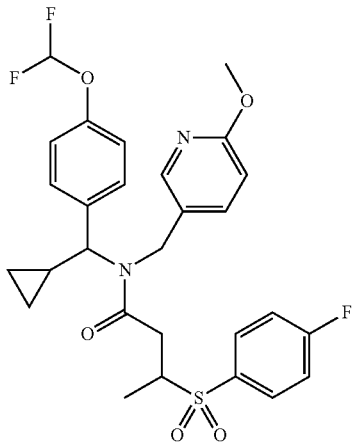 [SMILES: COc1ccc(CN(C(=O)CC(C)S(=O)(=O)c2ccc(F)cc2)C(c2ccc(OC(F)F)cc2)C2CC2)cn1]

Intermediate ak (311 mg, 0.93 mmol), Intermediate do (275 mg, 1.12 mmol) T3P (1.48 mL, 2.33 mmol) and triethylamine (0.324 mL, 1.86 mmol) were reacted according to General Procedure D to give the title compound as a yellow oil (64 mg, 12%). LCMS (Method 2) Rt 2.13 min (Purity: 99%) m/z 563.3 (M+H)⁺.

Example 89

N—{(R)-cyclopropyl[4-(difluoromethoxy)phenyl]methyl}-2-[1-(4-fluorophenyl)cyclopropyl]-N-(pyridazin-3-ylmethyl)acetamide

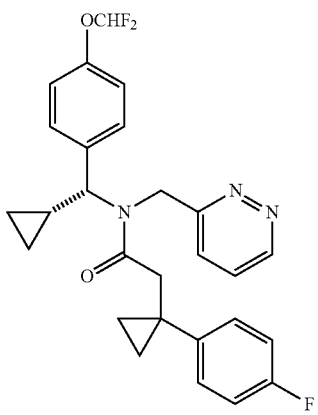 [SMILES: O=C(CC1(c2ccc(F)cc2)CC1)N(Cc1cccnn1)[C@@H](c1ccc(OC(F)F)cc1)C1CC1]

Intermediate bt (77 mg, 0.25 mmol), Intermediate eh (84 mg, 0.40 mmol) and triethylamine (0.110 mL, 0.79 mmol) were reacted in Et₂O according to General Procedure C to give the title compound as a orange/light brown oil (46 mg, 38%). LCMS (Method 2) 482.2 (M+H)⁺.

Example 91

Enantiomer A of N-{cyclopropyl[4-(difluoromethoxy)phenyl]methyl}-1-[(4-fluorophenyl)sulfonyl]-N-(pyridin-2-ylmethyl)cyclopropanecarboxamide and Example 92: Enantiomer B of N-{cyclopropyl[4-(difluoromethoxy)phenyl]methyl}-1-[(4-fluorophenyl)sulfonyl]-N-(pyridin-2-ylmethyl)cyclopropanecarboxamide

91

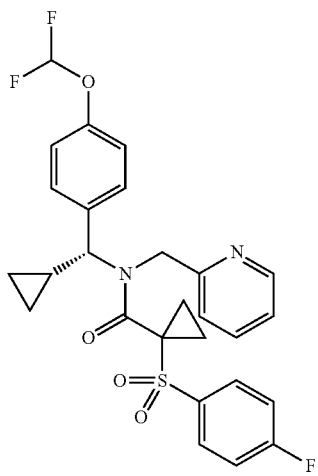

92

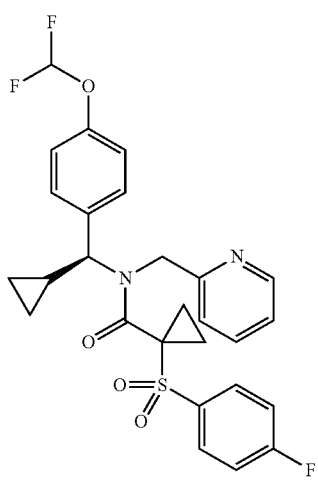

Intermediate ak (275 mg, 0.094 mmol), Intermediate ds (265 mg, 1.08 mmol), T3P (1.44 mL, 2.26 mmol) and triethylamine (0.315 mL, 1.81 mmol) were reacted according to General Procedure D to give the racemic mixture of the title compounds (143 mg, 30%). The isomers were separated by chiral HPLC according to Method G. The first eluting isomer (12.67 min, m/z 532.1 (M+H)⁺) was Enantiomer A and the second eluting isomer (29.53 min, m/z 532.1 (M+H)⁺) was Enantiomer B.

Example 93

N-[(4-chlorophenyl)(cyclopropyl)methyl]-N-(8-methyl-8-azabicyclo[3.2.1]oct-3-yl)-2-(phenylsulfonyl)acetamide

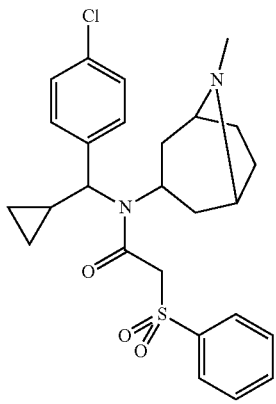 [SMILES: CN1C2CCC1CC(N(C(=O)CS(=O)(=O)c1ccccc1)C(c1ccc(Cl)cc1)C1CC1)C2]

Intermediate ad (250 mg, 0.82 mmol), Intermediate dl (197 mg, 0.984 mmol), T3P (0.978 mL, 1.64 mmol) and triethylamine (0.126 mL, 0.902 mmol) were reacted according to General Procedure D to give a racemate of the title compound as a glassy solid (250 mg, 63%). LCMS Method 2 m/z 487.3 (M+H)$^+$.

Example 94

Enantiomer A of N-[(1-(4-fluorophenyl)-2-methylpropyl]-1-[(4-fluorophenyl)sulfonyl]-N-[2-(4-fluoropiperidin-1-yl)ethyl]cyclopropanecarboxamide

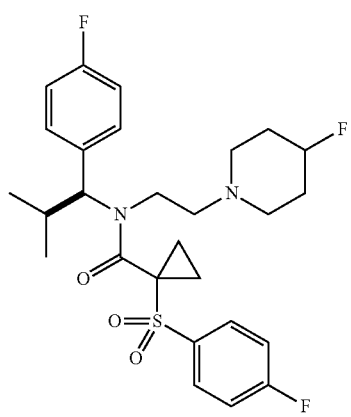 [SMILES: CC(C)[C@@H](c1ccc(F)cc1)N(CCN1CCC(F)CC1)C(=O)C1(S(=O)(=O)c2ccc(F)cc2)CC1]

Intermediate ab (104.8 mg, 0.35 mmol), Intermediate es (109 mg, 0.41 mmol) and triethylamine (0.082 mL, 0.79 mmol) were reacted in Et$_2$O according to General Procedure C to give the title compound as a yellow oil (71 mg, 38%). LCMS (Method 2) 523.2 (M+H)$^+$.

Example 95

Enantiomer A of N-[(4-chlorophenyl)(cyclopropyl)methyl]-2-[1-(4-fluorophenyl)cyclopropyl]-N-(pyridin-2-ylmethyl)acetamide

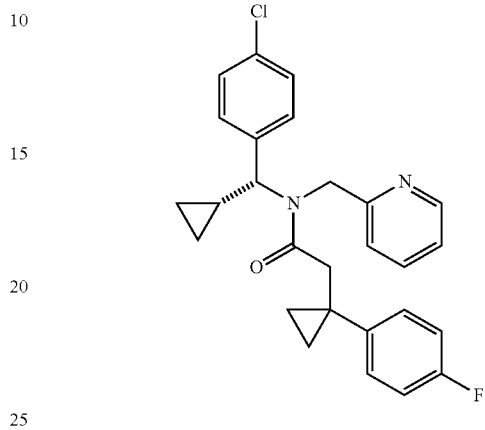

Intermediate c (65 mg, 0.24 mmol), Intermediate dh (47 mg, 0.24 mmol), T3P (0.240 mL, 0.40 mmol) and triethylamine (0.054 mL, 0.30 mmol) were reacted according to General Procedure D to give the title compound as a yellow oil (51 mg, 48%). LCMS (Method 2) 449.2 (M+H)$^+$.

Example 96

Enantiomer A of (N-[1-(3-bromophenyl)cyclopropyl]-3-(4-fluorophenyl)-N-(pyridin-2-ylmethyl)butanamide

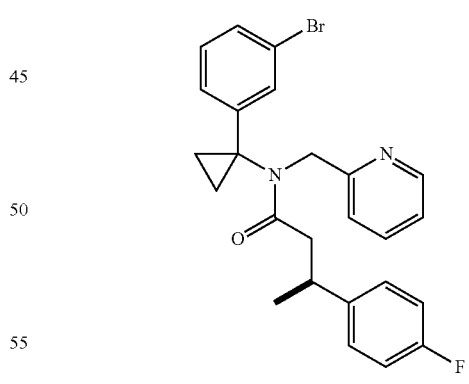

1-(3-bromophenyl)-cyclopropanamine (50 mg, 0.24 mmol)) and Intermediate oo (43 mg, 0.024 mmol), T3P (0.240 mL, 0.040) and triethylamine (0.054 mL, 0.30 mmol) were reacted according to General Procedure D to give the title compound as a yellow oil (56 mg, 50%). (LCMS (Method 2) 467.0 (M+H)

Example 97

(1R,2R)-2-(4-Fluoro-phenyl)-cyclopropanecarboxylic acid [(R)-cyclopropyl-(4-difluoromethoxy-phenyl)-methyl]-pyridazin-3-ylmethyl-amide TLC: chloroform/methanol: (9/1), $R_f$=0.1
$^1$H NMR (DMSO-$d_6$, 400 MHz) δ 7.43-7.41 (d, J=9.4 Hz, 2H), 7.35-6.98 (t, 2H), 7.10-7.08 (d, J=11.4 Hz, 1H), 3.16-3.14 (d, J=8.0 Hz 1H), 2.0-1.97 (bs, 2H), 0.92-0.89 (m, 1H), 0.44-0.41 (m, 1H), 0.33-0.29 (m, 2H), 0.26-0.23 (m, 1H).

Synthetic Scheme

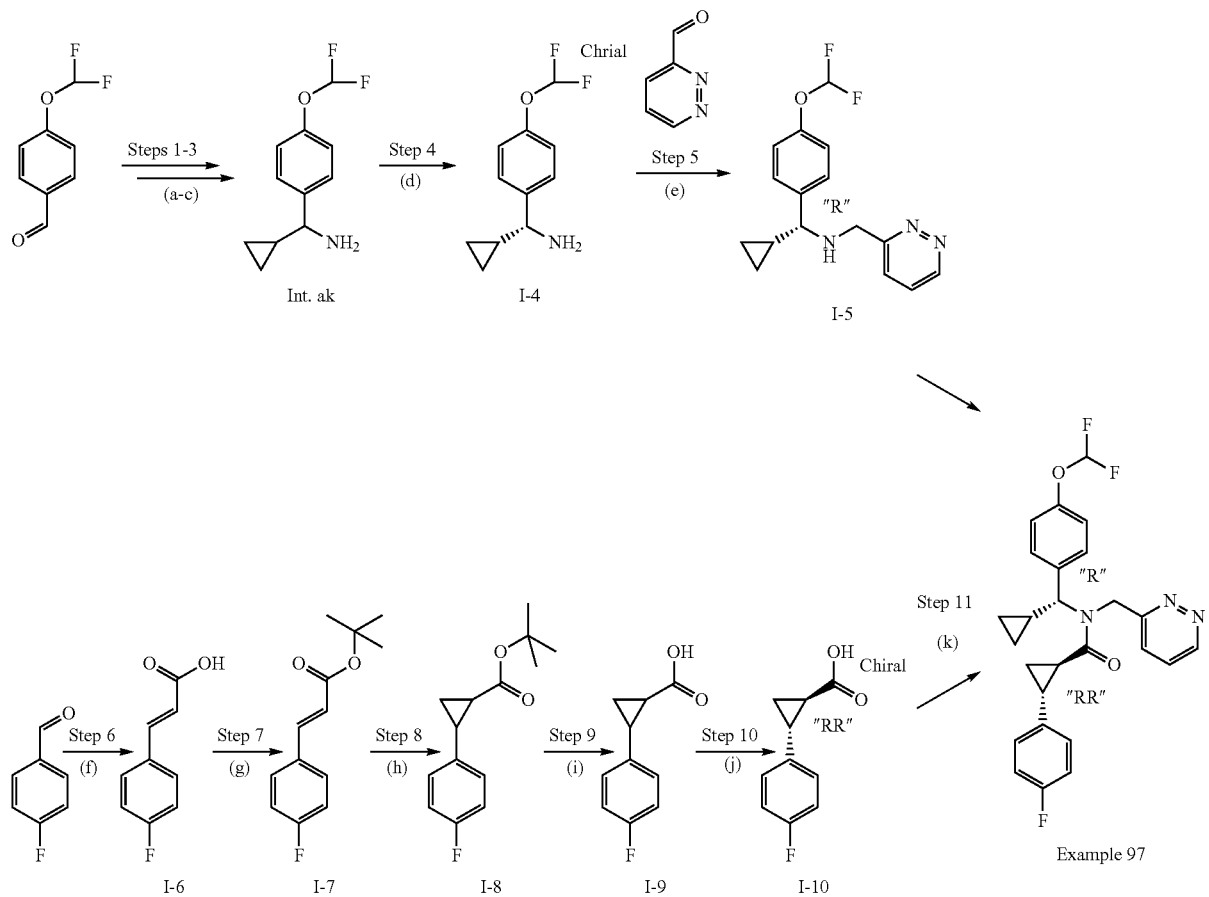

Conditions: (a) Cyclopropyl magnesium bromide, dry THF, 0° C., RT 58%. (b) Sulfuric acid, NaN₃, Chloroform, 0° C., RT, 63%. (c) Pd/C, Methanol, H₂, RT, 39%. (d) Chiral separation: Heptane/IPA/DIEA 43%. (e) Pyridazine-3-carbaldehyde, NaBH(OAc)₃, AcOH, DCE, RT, 73%. (f) Malonic acid, piperidine, pyridine, 100° C., 93%. (g) Boc2O, DMAP, t-Butanol, 80° C., 93%. (h) Trimethylsulfoxonium iodide, NaH, dry DMSO, 0° C., RT, 52%. (i) HCl 4M in dioxane, DCM, RT, 97%. (j) Chiral separation: Heptane/EtOH 90:10, 49%. (k) T₃P in EtOAc, DIEA, DCE, 60° C., 73% or 1. I-10, SoCl₂, DMF, 2. I-5, Pyr, RT, 54%.

Protocols

Steps 1-3: Preparation of Intermediate ak, C—[(R)—C-Cyclopropyl-C-(4-difluoromethoxy-phenyl)]-methylamine Method as (previously described).

HPLC: 97.6% (AUC), Rt 2.7 min. Method: A-0.1% TFA in H₂O, B-0.1% TFA in ACN, Flow 2.0 mL/min; Column: XBridge C8 (50×4.6 mm, 3.5 μm).

LCMS: 98.85% (AUC), Rt 4.5 min, MS(ES⁺) (M−16, 197). Method: A: 10 mM NH₄HCO₃; B-ACN, Flow 1.0 mL/min. Column: XBridge C8 (50×4.6 mm, 3.5 μm).

Step 4: Preparation of I-4 (Intermediate bt)

Chiral separation of ak (17.0 g) was performed under the below conditions:

Chiralcel OD-H, 250×20 mm, 5 μm; Heptane/IPA/DIEA; Concentration 42.5 mg/mL; Flow 10 mL/min to yield the 1st eluting, I-E, C—[(R)—C-Cyclopropyl-C-(4-difluoromethoxy-phenyl)]-methylamine [7.3 g; yield 43%] as a yellow liquid.

HPLC: 92.1% (AUC), Rt 2.1 min. Method: A-0.1% TFA in H₂O, B-0.1% TFA in ACN, Flow 2.0 mL/min; Column: XBridge C8 (50×4.6 mm, 3.5 μm).

Chiral HPLC: 100.0% (AUC), Rt 7.7 min. Method: Hexane/IPA/DIEA 90/10/0.1, Flow 2.0 mL/min, Column: Chiralcel OD (250×4.6 mm, 5 μm).

UPLC/MS: 87.0% (AUC), Rt 0.8 min, MS(ES⁺) (M–16, 197). Method: A: water NH₄OAc 10 mM; B-ACN, Flow 1.0 mL/min. Column: Acquity UPLC BEH C18 (2.1×50 mm, 1.7 µm)

$^1$H NMR (CDCl₃, 300 MHz) δ 7.29-7.05 (m, 2H), 6.95-6.76 (m, 2H), 6.27 (t, J=73.2 Hz, 1H), 2.98 (d, J=8.6 Hz, 1H), 1.36 (s, 2H), 0.89-0.79 (m, 1H), 0.47-0.02 (m, 4H).

Step 5: Preparation of I-5

Under N₂, to a solution of C—[(S)—C-Cyclopropyl-C-(4-difluoromethoxy-phenyl)]-methylamine (5.5 g; 25.79 mmol; 1.00 eq.) and Pyridazine-3-carbaldehyde (2.79 g; 25.79 mmol; 1.00 eq.) in DCE (90 mL) was added at RT sodium triacetoxyborohydride (10.93 g; 51.59 mmol; 2.00 eq.) followed by AcOH (4.43 mL; 77.38 mmol; 3.00 eq.) (Internal temperature increased to 35° C.). The reaction mixture was stirred at RT for 1.5 hr. until completion. The reaction was quenched carefully and slowly with a 50% aqueous saturated solution of K₂CO₃ (100 mL). The product was extracted with DCM (3×150 mL). Combined organics were dried over MgSO4, filtered and concentrated under reduced pressure giving the crude product as a brown oil m=9.2 g. It was purified by flash chromatography (SiO₂) eluting with DCM/MeOH 95:5 (Rf=0.33) to yield 6 [R)-Cyclopropyl-(4-difluoromethoxy-phenyl)-methyl]-pyridazin-3-ylmethyl-amine [5.8 g; yield 73%] as a yellow oil.

UPLC/MS: 97.5% (AUC), Rt 1.3 min, MS(ES⁺) 306.3). Method: A: water NH₄OAc 10 mM; B-ACN, Flow 1.0 mL/min. Column: Acquity UPLC BEH C18 (2.1×50 mm, 1.7 µm).

$^1$H NMR (CDCl₃, 300 MHz) δ 8.86 (dd, J=4.4, 2.2 Hz, 1H), 7.27-7.10 (m, 4H), 6.93-6.81 (m, 2H), 6.30 (t, J=74.1 Hz, 1H), 3.85-3.61 (m, 2H), 2.68 (d, J=8.9 Hz, 1H), 2.22 (bs, 1H), 0.93-0.84 (m, 1H), 0.53-0.32 (m, 1H), 0.25-0.10 (m, 2H), 0.08-0.01 (m, 1H).

Step 6: Preparation of I-6

A mixture of 4-Fluoro-benzaldehyde (200.0 g, 1.61 mol) and malonic acid (503.1 g, 4.83 mol) and piperidine (25 mL, catalytic amount) in pyridine (1 L) refluxed at 100° C. under nitrogen for 12 h. After cooling to RT, the reaction mixture was quenched by adding to ice cold solution of 6N HCL. The solid was filtered and washed with cold water and dried under reduced pressure to yield (4-Fluorophenyl)acrylic acid [250.0 g; yield 93%] as a white solid.

$^1$H NMR (DMSO-d₆, 400 MHz) δ 12.37 (br s, 1H), 7.77-7.74 (m, 2H), 7.60-7.56 (d, J=16.0 Hz, 1H), 7.26-7.21 (m, 2H), 6.51-6.47 (d, J=16.0 Hz, 1H).

Step 7: Preparation of I-7

To the mixture of (4-Fluorophenyl)acrylic acid (257.0 g, 1.55 mol) and DMAP (56.74 g, 2.01 mol) in t-Butanol (1 L) was added BOC anhydride (438.7 g, 2.01 mol) in drops. The reaction mixture was heated to 80° C. under nitrogen atmosphere for 12 h. After cooling to RT, solvent was removed under reduced pressure. The crude material was stirred with pet ether (250 mL) and the solid was filtered to yield tert-Butyl (4-fluorophenyl)acrylate [320.0 g; yield 93%] as a white solid.

$^1$H NMR (DMSO-d₆, 400 MHz) δ 7.78-7.74 (m, 2H), 7.56-7.52 (d, J=16.0 Hz, 1H), 7.26-7.21 (m, 2H), 6.50-6.46 (d, J=16.0 Hz, 1H), 1.46 (s, 9H).

Step 8: Preparation of I-8

Trimethylsulfoxonium iodide (165.7 g, 0.72 mol) was suspended in dry DMSO (700 mL). To this suspension under ice-cooling, sodium hydride (60% suspension in mineral oil) (32.4 g, 1.35 mol) was carefully added in portions over a time period of 1 h. (Note: exotherm!) Then reaction mixture was stirred at RT for 1 h. To this suspension was added a solution of tert-Butyl (4-fluorophenyl)acrylate (100.0 g, 0.42 mol) in dry DMSO (250 mL) and the mixture was stirred at RT for 12 h. The reaction mixture was carefully quenched by adding to ice-cold solution of 1.5 M HCl (500 mL) and extracted with EtOAc (3×500 mL). Combined organic layer was washed with water (500 mL), brine and dried over Na₂SO₄ and evaporated to dryness. The crude material was purified by column chromatography using silica gel (60-120 mesh) and pet ether/EtOAc as eluent to yield tert-Butyl 2-(4-fluorophenyl)cyclopropanecarboxylate [56.0 g g; yield 52%] as a white solid.

HPLC: 97.2% (AUC), Rt 5.56 min. Method: A-0.1% TFA in H2O, B-0.1% TFA in ACN, Flow 2.0 mL/min, Column: XBridge C8 (50×4.6 mm, 3.5 µm).

LCMS: 98.8% (AUC), Rt 6.99 min, MS(ES⁻) 179.0. Method: A: 10 mM NH₄HCO₃ in H2O, B: ACN, Flow 1.0 mL/min, Column: XBridge C8 (50×4.6 mm, 3.5 µm).

$^1$H NMR (DMSO-d₆, 400 MHz) δ 7.20-7.10 (m, 2H), 7.09-7.05 (m, 2H), 2.49-2.33 (m, 1H), 1.82-1.77 (m, 1H), 1.40 (s, 9H), 1.39-1.36 (m, 1H), 1.30-1.20 (m, 1H).

Step 9: Preparation of I-9

Under N₂, tert-butyl 2-(4-fluorophenyl)cyclopropanecarboxylate (12.0 g; 50.79 mmol; 1.00 eq.) was dissolved in DCM (60 mL). 4M HCl in dioxane (38.1 mL) was added. After stirring for 6 hr. at RT an HPLC indicated 65% conversion. More HCl in dioxane (20 mL) was added and the reaction was stirred O/N at RT after what an HPLC indicated full conversion and 100% a/a. The reaction mixture was evaporated to dryness at RT (first removed excess HCl) then turned the bath on at ET=50° C. to remove the solvents to yield tert-Butyl 2-(4-fluorophenyl)cyclopropanecarboxylic acid [8.93 g g; yield 97%] as a white solid as the expected racemic compound.

HPLC: 98.0% (AUC), Rt 3.55 min. Method: A-0.1% TFA in H2O, B-0.1% TFA in ACN, Flow 2.0 mL/min, Column: XBridge C8 (50×4.6 mm, 3.5 µm).

1H-NMR (300 MHz, DMSO-d6) δ 12.2-10.6 (bs, 1H), 7.15-7.05 (m, 2H), 7.05-6.95 (m, 2H), 2.61 (m, 1H), 1.88 (m, 1H), 1.67 (m, 1H), 1.39 (m, 1H).

Step 10: Preparation of I-10

Chiral separation of I-9 (10.2 g) was performed under the below conditions:

Chiralpak AD-H, 250×20 mm, 5 µm; Heptane/EtOH (90/10); Concentration 83 mg/mL; Flow 10 mL/min to yield (1R, 2R)-2-(4-Fluoro-phenyl)-cyclopropane carboxylic acid [5.0 g; yield 49%] as a white solid.

HPLC: 99.9% (AUC), Rt 3.1 min. Method: A-0.1% TFA in H₂O, B-0.1% TFA in ACN, Flow 2.0 mL/min; Column: XBridge C8 (50×4.6 mm, 3.5 µm)

UPLC/MS: 98.5% (AUC), Rt 0.7 min, MS(ES⁻) 179. Method: A: water NH₄OAc 10 mM; B-ACN, Flow 1.0 mL/min. Column: Acquity UPLC BEH C18 (2.1×50 mm, 1.7 µm).

$^1$H NMR (CDCl₃, 300 MHz) δ 7.26-6.95 (m, 4H), 2.62-2.55 (m, 1H), 1.88-1.62 (m, 2H), 1.40-1.26 (m, 1H).

Comments: The single crystal structure resolution gave as absolute configuration the following (1R, 2R)-2-(4-Fluoro-phenyl)-cyclopropane carboxylic acid.

Step 11: Preparation of Example 97

A solution of [R)-Cyclopropyl-(4-difluoromethoxy-phenyl)-methyl]-pyridazin-3-ylmethyl-amine (5.50 g; 18.01 mmol; 1.00 eq.) in DCE (110.00 mL) was cooled to 0° C. Then iPr$_2$NEt (6.13 mL; 36.03 mmol; 2.00 eq.) was added followed by (1R,2R)-2-(4-Fluoro-phenyl)-cyclopropanecarboxylic acid (3.57 g; 19.82 mmol; 1.10 eq.). The reaction mixture was stirred at 0° C. for 15 min and then 2,4,6-Tripropyl-[1,3,5,2,4,6]trioxatriphosphinane 2,4,6-trioxide (21.43 mL; 36.03 mmol; 2.00 eq.) was added dropwise (addition took 15 min). The cooling bath was removed and the mixture was heated to 60° C. (external temperature) for 5 hr. until completion. The reaction mixture was cooled to RT, quenched with a saturated solution of NaHCO$_3$ (100 mL) and phases were separated. The aqueous phase was extracted with EtOAc (2×150 mL), combined organics were washed with a saturated solution of NaHCO$_3$ (100 mL), brine (100 mL), dried over MgSO$_4$, filtered and concentrated under reduced pressure giving a brown oil m=9.07 g. The crude product was purified by flash chromatography (SiO$_2$) eluting with EtOAc-cHex 7:3 to afford (1R,2R)-2-(4-Fluoro-phenyl)-cyclopropanecarboxylic acid as a sticky beige solid m=7.5 g, difficult to handle, NMR showed 1.7% of EtOAc and traces of acetic acid.

HPLC: 99.1% (AUC), Rt 4.5 min. Method: A-0.1% TFA in H$_2$O, B-0.1% TFA in ACN, Flow 2.0 mL/min; Column XBridge C8 (50×4.6 mm, 3.5 μm).

Chiral HPLC (SFC): 100.0% (AUC), Rt 1.9 min. Method: CO2, EtOH, DIEA, Flow 4.0 mL/min, Column Chiralpak AYH (250×4.6 mm).

UPLC/MS: 98.1% (AUC), Rt 1.8 min, MS(ES$^+$) 468. Method: A: water NH$_4$OAc 10 mM; B-ACN, Flow-1.0 mL/min. Column: Acquity UPLC BEH C18 (2.1×50 mm, 1.7 μm).

An alternative procedure was used on small scale:

Acid chloride of I-10 (300 mg, 1.51 mmol) was added to a solution (1.25 M) of amine I-4 (300 mg, 0.98 mmol) in pyridine at RT under N$_2$ atmosphere and stirred overnight (~20 h). The reaction was diluted with diethyl ether (50 mL) and washed with H$_2$O (30 mL×2), aqueous NH$_4$Cl (30 mL), aqueous NaHCO$_3$ (30 mL) and brine (15 mL). The organic layer was dried (MgSO$_4$), filtered and concentrated under reduced pressure. The residue was purified by flash chromatography (small silica gel column 2.5×7 cm, eluant=1/1 hexane/diethyl ether (300 mL) to pure diethyl ether (400 mL)) to provide Example 97 as a very thick, light-brown oil (247 mg, 54% yield, 98% purity). LCMS (Method 2) 468.2 (M+H)$^+$.

$^1$H NMR (CDCl$_3$, 300 MHz) δ 9.03-8.95 (m, 1H), 7.65-6.87 (m, 10H), 6.49 (t, J=73.8 Hz, 1H), 5.26-4.30 (m, 4H), 2.52-2.46 (m, 1H), 1.94-1.57 (m, 2H), 1.390-1.10 (m, 2H), 0.87-0.05 (m, 3H).

Determination of Absolute Stereochemistry:

Trials of recrystallization were performed in order to get crystalline form. Different solvents or mixtures were tried to recrystallize the parent on 150 mg scale (2-BuOH, Et$_2$O/pentane, Et$_2$O, MIBK, 1-BuOH, DCM/pentane, ACN/H$_2$O, ACN, MTBE, diisopropylether, heptanone, diphenylether, AcOH, AcOH/H$_2$O, toluene, dibutylether). Finally after 2 weeks, recrystallisation from dibutylether occurred to afford crystals. XRPD showed crystalline form and structure was resolved via single crystal XRay analysis.

5.0 g of the beige sticky solid previously isolated was taken up in dibutyl ether (125 mL), the reaction mixture was heated until complete dissolution and then the oil bath was removed. Under stirring, seeding (100 mg of crystals of the smaller batch) was performed and crystallization occurred after a few minutes. The suspension was stirred for 5 hr. at RT and then it was put in the fridge for 2 days. The suspension was filtered, washed with dibutylether (50 mL) and dried under reduced pressure to yield (1R,2R)-2-(4-Fluoro-phenyl)-cyclopropanecarboxylic acid [(R)-cyclopropyl-(4-difluoromethoxy-phenyl)-methyl]-pyridazin-3-ylm-ethyl-amide [4.1 g; yield 84%; corrected yield 73%] as an off white solid. XRPD showed a different crystalline form than the smaller batch (see FIG. 1).

Example 98

(1R,2R)-2-(4-Fluoro-phenyl)-cyclopropanecarboxylic acid [(S)-cyclopropyl-(4-difluoromethoxy-phenyl)-methyl]-pyridazin-3-ylmethyl-amide Intermediate bs (96 mg, 0.32 mmol), Intermediate eh (94 mg, 0.47 mmol) and triethylamine (0.125 mL, 0.90 mmol) were reacted in DCM according to General Procedure C to give the title compound as a light brown glassy oil (89 mg, 61%). LCMS (Method 2) 468.2 (M+H)$^+$.

Example 99

(1R, 2R)-2-(4-Fluoro-phenyl)-cyclopropanecarboxylic acid [(R)-cyclopropyl-(3-ethanesulfonyl-phenyl)-methyl]-(6-trifluoromethyl-pyridin-3-ylmethyl)-amide Synthetic Scheme for Small Scale Synthesis (<5 g):
(Note: synthesis described gives is a mixture of two isomers (separation is discussed following large scale synthesis).

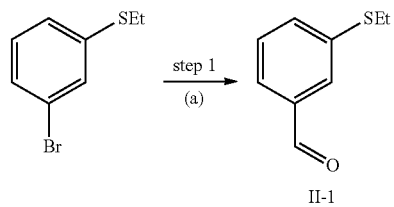

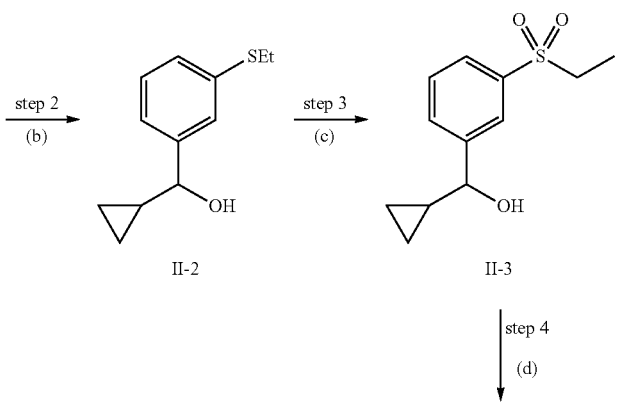

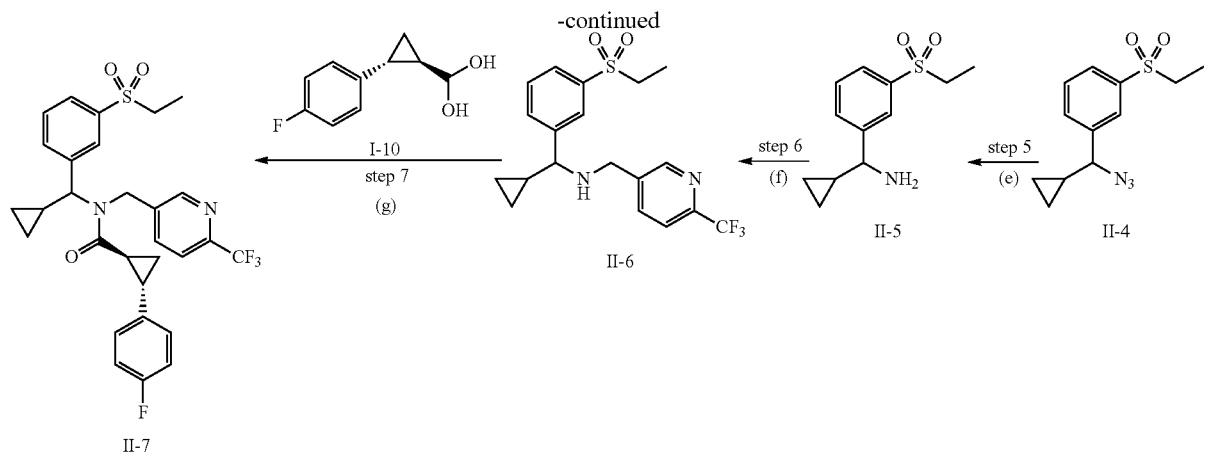

Conditions:
(a) 1. nBuLi in hexane, THF, -78° C., 2. DMF, -78° C. -> RT, 82%. (b) cPrMgBr, THF, 0° C.-> RT, 77%. (c) m-CPBA, DMC, 0° C. -> RT (96%). (d) DPPA, DBU, Toluene, 0° C.->RT-> 80° C., 94%. (e) 10% Pd/C, H₂, MeOH, RT, 88%. (f) 6-(trifluoromethyl)nicotinaldehyde, NaBH(OAc)₃, MgSO₄, 1,2-DCE, 89%. (g) 1-10, 50% T3P (in EtOAc), TEA, 1,2-DCE, 66%

Protocols

Step 1: Preparation of 3-(ethylsulfanyl)benzaldehyde (II-1)

To a solution of 3-bromo-1-ethanesulfanylbenzene (3.000 g, 13.8 mmol) in anhydrous THF at −78° C. under a nitrogen atmosphere was added 1.963M n-BuLi (7.742 ml, 15.2 mmol) dropwise and the mixture stirred at this temperature for 5 min. After this time DMF (2.14 ml, 27.6 mmol) was added dropwise and the mixture allowed to attain ambient temperature over 15 minutes. Once complete the reaction was poured into water (50 ml) and the organic layer separated. The organics were again washed with water (×1) and brine (×1) dried (MgSO₄), filtered and concentrated in vacuo to give crude aldehyde. The aldehyde was purified by column chromatography (silica-gel, 5% EtOAc/petroleum spirits, R$_f$=0.4 1/19 EtOAc/PS) to yield 1.883 g, 82% of II-1 as a pale yellow oil. ¹HNMR (300 MHz, CDCl₃) δ 9.98 (s, 1H), 7.79 (dd, J=1.5, 2.1 Hz 1H), 7.65 (ddd, J=1.2, 1.5, 7.5 Hz, 1H), 7.45 (t, J=8.1 Hz, 1H), 3.02 (q, J=7.2 Hz, 2H), 1.35 (t, J=7.5 Hz, 3H).

Step 2: Preparation of cyclopropyl[3-(ethylsulfanyl)phenyl]methanol (II-2)

To a stirred solution of II-1 (2.64 g, 15.9 mmol) in dry THF (20 ml) at 0° C. under N₂ atmosphere was added cyclopropyl magnesium bromide (0.5 M in THF, 35 ml, 17.5 mmol) dropwise. The cold bath was removed and the reaction mixture stirred at room temperature for 30 min. TLC in 10% ethyl acetate in hexane indicated the disappearance of starting aldehyde. The reaction mixture was cooled to 0° C. and quenched with sat. NH₄Cl solution and extracted with 3×25 ml of diethyl ether. The organic extracts were combined, dried over MgSO₄, filtered and concentrated under reduced pressure. The crude product was purified by column chromatography (silica-gel, 5-25% EtOAc/petroleum spirits, R$_f$=0.3 1/4 EtOAc/PS) to afford II-2 (2.55 g, 77% yield) as a pale yellow oil. ¹HNMR (300 MHz, CDCl₃) δ 7.40-7.39 (m, 1H), 7.28-7.21 (m, 3H), 3.99 (d, J=8.4 Hz, 1H), 2.97 (q, J=7.2 Hz, 2H), 1.33 (t, J=7.5 Hz, 3H), 1.26-1.17 (m, 1H), 0.66-0.36 (m, 4H).

Step 3: Preparation of cyclopropyl[3-(ethylsulfonyl)phenyl]methanol (II-3)

To a stirred solution of II-2 (2.54 g, 12.2 mmol) in dry DCM (20 ml) at 0° C. under N₂ atmosphere was added m-CPBA (5.12 g, 26.0 mmol) in 3 portions. The cold bath was removed and the reaction mixture stirred at room temperature for 1 h. LCMS indicated the reaction complete. The reaction was quenched with sat. NaHCO₃ solution and extracted with 3×25 ml of ethyl acetate. The organic extracts were combined, dried over MgSO₄, filtered and concentrated under reduced pressure. The crude product was purified by column chromatography (silica-gel, 30-50% EtOAc/petroleum spirits, R$_f$=0.1 1/1 EtOAc/PS) to afford II-3 (2.81 g, 96% yield) as a pale cloudy oil. ¹HNMR (300 MHz, CDCl₃) δ 7.99-7.98 (m, 1H), 7.83 (d, J=7.5 Hz, 1H), 7.74 (d, J=7.8 Hz, 1H), 4.10 (d, J=8.4 Hz, 1H), 3.13 (q, J=7.5 Hz, 2H), 1.29 (t, J=7.5 Hz, 3H), 1.21 (m, 1H), 0.66 (m, 2H), 0.48 (m, 2H). MS (ES⁺) m/z 258.2 (M+NH₄⁺).

Step 4: Preparation of 1-[azido(cyclopropyl)methyl]-3-(methylsulfonyl)benzene 3-[azido(cyclopropyl)methyl]phenyl methyl sulfone (II-4)

To a stirred solution of II-3 (1.40 g, 5.8 mmol) in dry PhMe (15 ml) at 0° C. under N₂ atmosphere was added DPPA (1.7 mL, 7.9 mmol) drop-wise followed by DBU (1.2 mL, 8.0 mmol) drop-wise. The cold bath was removed and the reaction mixture stirred at room temperature for 30 min before heating at 80° C. for 5 hours. LCMS indicated the reaction complete. The reaction was quenched with sat. NH₄Cl solution and extracted with 3×25 ml of ethyl acetate. The organic extracts were combined and washed with sat. NH₄Cl solution, H₂O (×2) and brine, dried over MgSO₄, filtered and concentrated under reduced pressure. The crude product was purified by column chromatography (silica-gel, 15-25% EtOAc/petroleum spirits, R$_f$=0.27 1/3 EtOAc/PS) to afford II-4 (1.45 g, 94% yield) as a clear oil.

NB: It is necessary to run a gradient elution as the azide runs just above an impurity (R$_f$=0.21 1/3 EtOAc/PS) from the reaction. The azide develops as a green spot in vanillin dip, the impurity does not develop using these conditions. ¹HNMR (300 MHz, CDCl₃) δ 7.91 (dd, J=2.1, 3.0 Hz 1H), 7.86 (ddd, J=1.5, 1.5, 7.8 Hz, 1H), 7.67 (ddd, J=7.8, 1.2, 1.2 Hz, 1H), 7.58 (dd, J=7.8, 7.8 Hz, 1H), 3.95 (d, J=8.7 Hz, 1H), 3.13 (q, J=7.5 Hz, 2H), 1.29 (m, 4H), 0.82 (m, 1H), 0.64 (m, 2H), 0.38 (m, 2H). MS (ES⁺) m/z 283.3 (M+NH₄⁺).

Step 5: Preparation of 1-cyclopropyl-1-[3-(ethylsulfonyl)phenyl]methanamine (II-5)

To a stirred solution of the II-4 (1.45 g, 5.5 mmol) in MeOH (15 ml) under N₂ atmosphere was added 10% Pd/C (136.7 mg, ~9% w/w) in one portion. The flask was evacuated and flushed with H₂(g) and the reaction mixture stirred at room temperature for 2 h. LCMS indicated the reaction complete. The reaction was filtered through Celite® and concentrated under reduced pressure to afford II-5 (1.15 g, 88% yield) as a yellow oil. ¹HNMR (300 MHz, CDCl₃) δ 7.95 (dd, J=1.8, 1.8 Hz, 1H), 7.76 (m, 2H), 7.53 (dd, J=7.8, 7.8 Hz, 1H), 3.29 (d, J=8.4 Hz, 1H), 3.12 (q, J=7.5 Hz, 2H), 1.28 (t, J=7.5 Hz, 3H), 1.06 (m, 1H), 0.64 (m, 1H), 0.51 (m, 1H), 0.34 (m, 2H). MS (ES⁺) m/z 479.2 (M+M⁺).

Step 6: Preparation of 1-cyclopropyl-1-[3-(ethylsulfonyl) phenyl]-N-{[6-(trifluoromethyl) pyridin-3-yl] methyl}methanamine (II-6)

To a stirred suspension of II-5 (1.14 g, 4.8 mmol) and anhydrous MgSO₄ (1.35 g, 11.2 mmol) in 1,2-DCE (30 ml) under N₂ atmosphere was 6-(trifluoromethyl)nicotinaldehyde (854.7 mg, 4.8 mmol) in one portion. The reaction was stirred at room temperature for 30 min before addition of NaBH(OAc)₃ (1.49 g, 7.0 mmol) in one portion. The reaction was stirred at room temperature for a further 3 h. LCMS indicated the reaction complete. The reaction was quenched with sat. NaHCO₃ solution and extracted with 3×25 mL of ethyl acetate. The organic extracts were combined, dried over MgSO₄, filtered and concentrated under reduced pressure. The crude product was purified by column chromatography (silica-gel, 30-60% EtOAc/petroleum spirits, R_f=0.20 1/1 EtOAc/PS) to afford II-6 (1.69 g, 89% yield) as a pale yellow oil. ¹HNMR (300 MHz, CDCl₃) δ 8.60 (d, J=1.5 Hz, 1H), 7.94 (dd, J=1.5, 1.5 Hz, 1H), 7.8 (m, 2H), 7.61 (m, 3H), 3.73 (q, J=), 3.77 (d, J=14.1 Hz, 1H_a), 3.70 (d, J=14.1 Hz, 1H_b), 2.96 (d, J=9 Hz, 1H), 1.29 (t, J=7.2 Hz, 3H), 1.09 (m, 1H), 0.66 (m, 1H), 0.45 (m, 1H), 0.31 (m, 2H). MS (ES⁺) m/z 399.2 (M+H⁺).

Step 7: Preparation of (1R, 2R)-2-(4-Fluoro-phenyl)-cyclopropanecarboxylic acid [(R/S)-cyclopropyl-(3-ethanesulfonyl-phenyl)-methyl]-(6-trifluoromethyl-pyridin-3-ylmethyl)-amide To a stirred solution of II-6 (229.3 mg, 0.58 mmol) and I-10 (124.4 mg, 0.69 mmol) in 1,2-DCE (5 mL) at 0° C. under N₂ atmosphere was added TEA (160 μL, 1.1 mmol) followed by T3P (50% in EtOAc, 800 μL, 1.3 mmol) drop-wise. The cold bath was removed and the reaction mixture stirred at room temperature for ~16 hours. LCMS indicated the reaction complete. The reaction was quenched with sat. NaHCO₃ solution and extracted with 3×5 ml of ethyl acetate. The organic extracts were combined, dried over MgSO₄, filtered and concentrated under reduced pressure. The crude product was purified by column chromatography (silica-gel, 5-20% EtOAc/DCM, R_f=0.48 3/17 EtOAc/DCM) to afford (1R, 2R)-2-(4-Fluoro-phenyl)-cyclopropanecarboxylic acid [(R/S)-cyclopropyl-(3-ethanesulfonyl-phenyl)-methyl]-(6-trifluoromethyl-pyridin-3-ylmethyl)-amide (214.4 mg, 66% yield) as a glassy yellow oil. ¹HNMR (300 MHz, CDCl₃) δ 8.64-8.43 (m, 1H), 7.96-7.39 (m, 6H), 7.07-6.72 (m, 4H), 5.37-4.35 (m, 3H), 4.12 (q, J=7.2 Hz, 2H), 3.15-0.32 (m, 12H). MS (ES⁺) m/z 561.3 (M+H⁺).

Synthetic Scheme for Large Scale Synthesis (25 g) of Example 99:

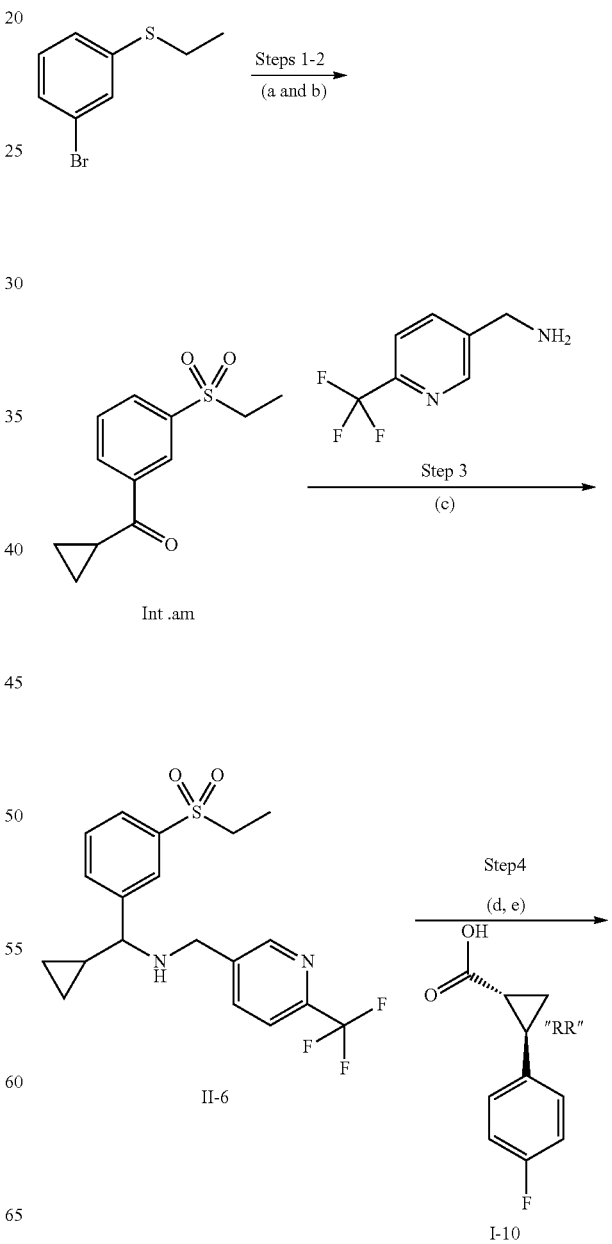

133

-continued

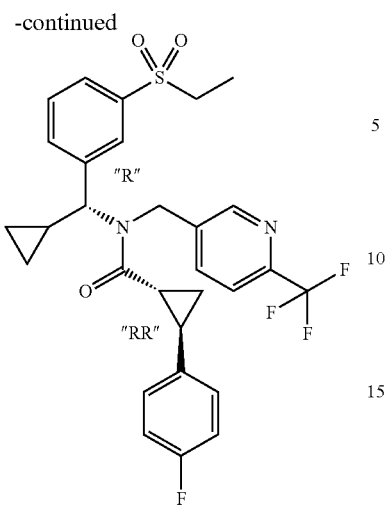

Conditions:
(a) n-butyllithium, toluene, 40° C.; Cyclopropanecarbonitrile, -30° C.; HCl 5N, 40° C., 87%. (b) Oxone, AcOEt/water, 25° C., 91%.
(c) 5-(Aminomethyl)-2-(trifluoromethyl) pyridine, Ti(OEt)$_4$, THF, reflux; NaBH$_4$, 5° C., 60%. (d) 50% T$_3$P in EtOAc, NEt$_3$, DCE, 60° C., 94%. (e) Chiral separation by SFC, 37%. Overall yeild: 17% (including chiral separation)

Protocols

Step 1-2: Preparation of cyclopropyl [3-(ethylthio)phenyl]methanone (Int. am)

Method as previously described.

UPLC/MS: 95.0% (AUC), Rt 1.13 min, MS(ES$^+$) (239). Method: A: water NH$_4$OAc 10 mM; B-ACN, Flow 1.0 mL/min. Column: Acquity UPLC BEH C18 (2.1×50 mm, 1.7 μm)

$^1$H NMR (DMSO, 300 MHz) δ 8.50-8.45 (m, 2H), 8.24-8.19 (m, 1H), 7.95-7.88 (m, 1H), 3.50-3.42 (m, 2H), 3.10-3.00 (m, 1H), 1.22-1.12 (m, 7H).

Step 3: Preparation of 1-cyclopropyl-1-[3-(ethylsulfonyl) phenyl]-N-{[6-(trifluoromethyl) pyridin-3-yl]methyl}methanamine (II-6)

To a 100 mL three necked flask under nitrogen containing cyclopropyl [3-(ethylsulfonyl) phenyl]methanone (5.00 g; 20.98 mmol; 1.00 eq.) in solution in dry THF (50 mL, 10V) was added 5-(Aminomethyl)-2-(trifluoromethyl) pyridine, (4.43 g; 25.18 mmol; 1.20 eq.) and tetraethyl orthotitanate (17.73 mL; 83.93 mmol; 4.00 eq.) in one portion. Reaction mixture was stirred at reflux for 6 h until completion (a sample was treated with an excess of NaBH$_4$ at 5° C. before injection in UPLC/MS). Reaction mixture was cooled down to 0° C. and NaBH$_4$ (1.59 g; 41.96 mmol; 2.00 eq.) was added portion wise over 5 minutes. Reaction mixture was stirred at 0° C. for 1 h until reduction completion.

Reaction mixture was quenched with an excess of methanol added dropwise (important foaming) then resulting suspension was filtered and filtrate was concentrated until 30 mL was left. Sodium hydroxide 1N (100 mL) was added and resulting thick suspension was suspended in MTBE. Filtration was done and salts were washed with MTBE. Biphasic filtrate was separated and aqueous phase was extracted with MTBE. Combined organic phase was washed with water, dried over Na$_2$SO$_4$, filtered and concentrated to give thick yellow oil which was purified by flash chromatography (SiO$_2$) eluting with (Heptane/ethyl acetate: 1/1) to give title product [5.35 g; crude yield: 64%; purity: 94%; corrected yield: 60%] as yellow clear oil. Used without further purification.

UPLC/MS: 94.0% (AUC), Rt 1.72 min, MS(ES$^+$) (399). Method: A: water NH$_4$OAc 10 mM; B-ACN, Flow 1.0 mL/min. Column: Acquity UPLC BEH C18 (2.1×50 mm, 1.7 μm)

Step 4: Preparation (1R, 2R)-2-(4-Fluoro-phenyl)-cyclopropanecarboxylic acid [(R)-cyclopropyl-(3-ethanesulfonyl-phenyl)-methyl]-(6-trifluoromethyl-pyridin-3-ylmethyl)-amide (Example 99)

To a 250 mL flask under nitrogen containing 1-cyclopropyl-1-[3-(ethylsulfonyl)phenyl]-N-{[6-(trifluoromethyl) pyridin-3-yl]methyl}methanamine (8.00 g; 20.08 mmol; 1.00 eq.) and (1R,2R)-2-(4-fluorophenyl)cyclopropanecarboxylic acid I-L (4.34 g; 24.09 mmol; 1.20 eq.) in solution in 1,2-dichloroethane (120 mL; 15V) at 0° C. was added triethylamine (5.57 mL; 40.16 mmol; 2.00 eq.) in one portion followed by 1-propylphosphonic acid cyclic anhydride T3P (28.11 g; 44.17 mmol; 2.20 eq.; 50% in ethyl acetate) which was added drop-wise over 5 minutes. The cold bath was removed and the reaction mixture was stirred at 60° C. for 14 h until completion. Reaction mixture was cooled down to 25° C. and quenched with a saturated solution of NaHCO$_3$. Phases were separated and aqueous phase was extracted with ethyl acetate. Combined organic phase was washed with a saturated solution of NaHCO$_3$, then with brine. After drying over Na$_2$SO$_4$, filtration and concentration (bath temp: 37° C.), title product [11.36 g; crude yield: quantitative; purity: 93.7%; corrected yield 93.7%] was obtained as white solid foam. Chiral purification by SFC was done directly without further purification using the conditions below:

Column: Chiralcel OD-H, 250×20 mm, 5 um; Co-solvent: 20% MeOH; Flow: 80 mL/min; Back Pressure: 120 bars; Column temperature: 30° C.

Results:

4.12 g of the title compound (Example 99) and 4.24 g of the second diastereoisomer, Example 100, were obtained as respectively first and second eluting, after injection of 11.2 g of racemic mixture.

HPLC: 98.87% (AUC), Rt 5.01 min. Method: A-0.1% TFA in H$_2$O, B-0.1% TFA in ACN, Flow 2.0 mL/min; Column: XBridge C8 (50×4.6 mm, 3.5 μm).

Chiral HPLC: 100.0% (AUC), Rt 7.7 min. Method: Hexane/IPA/DIEA 90/10/0.1, Flow 2.0 mL/min, Column: Chiralcel OD (250×4.6 mm, 5 μm).

UPLC/MS: 100% (AUC), Rt 2.11 min, MS(ES$^+$) (561). Method: A: water NH$_4$OAc 10 mM; B-ACN, Flow 1.0 mL/min. Column: Acquity UPLC BEH C18 (2.1×50 mm, 1.7 μm)

Absolute Configuration Determination

In order to establish absolute configuration of the asymmetric carbon bearing the nitrogen, racemic benzylamine intermediate II-5 (synthesis described below) was synthesized and both enantiomers were separated by chiral HPLC. Then enantiomer II-5a was coupled with 4-bromobenzoic acid and structure of resulting amide II-9 was determined by X-ray to be the (R)-enantiomer, as described below. To provide further confirmation, the (S)-enantiomer II-5b was used to synthesize an analogue of the final compound, which was compared with pure Example 99 by chiral HPLC. The stereochemistry of Example 99 was proved to be RRR.

Synthetic Scheme for Preparation of Heavy Atom-Containing Amide Analogue of II-5 for Crystallographic Determination of Absolute Stereochemistry.

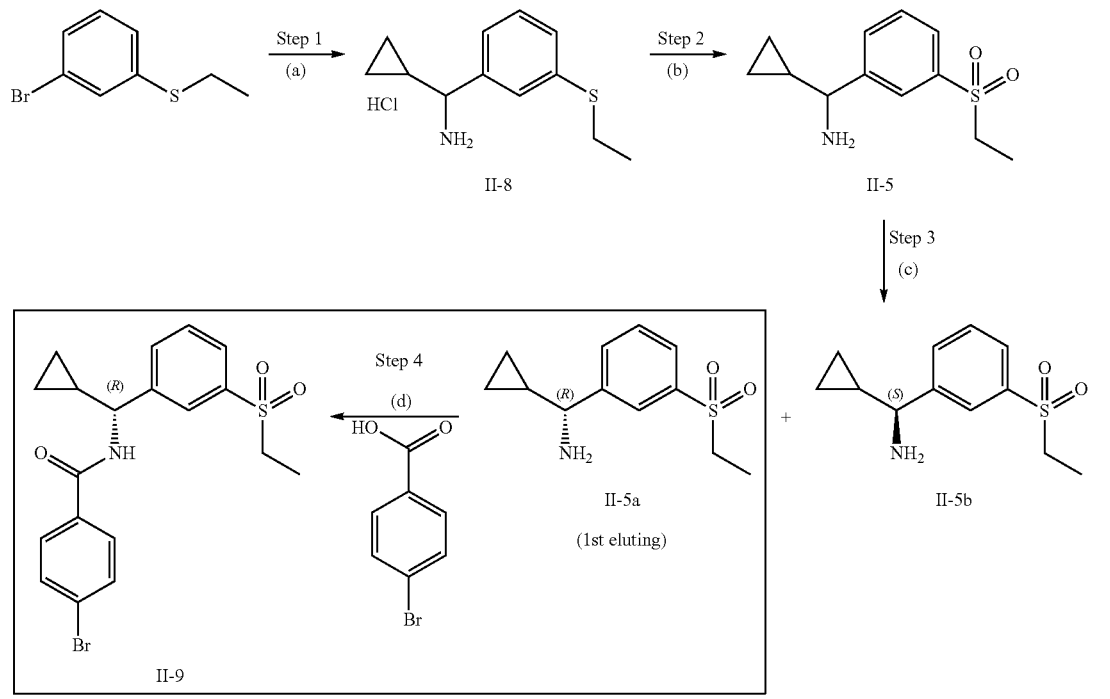

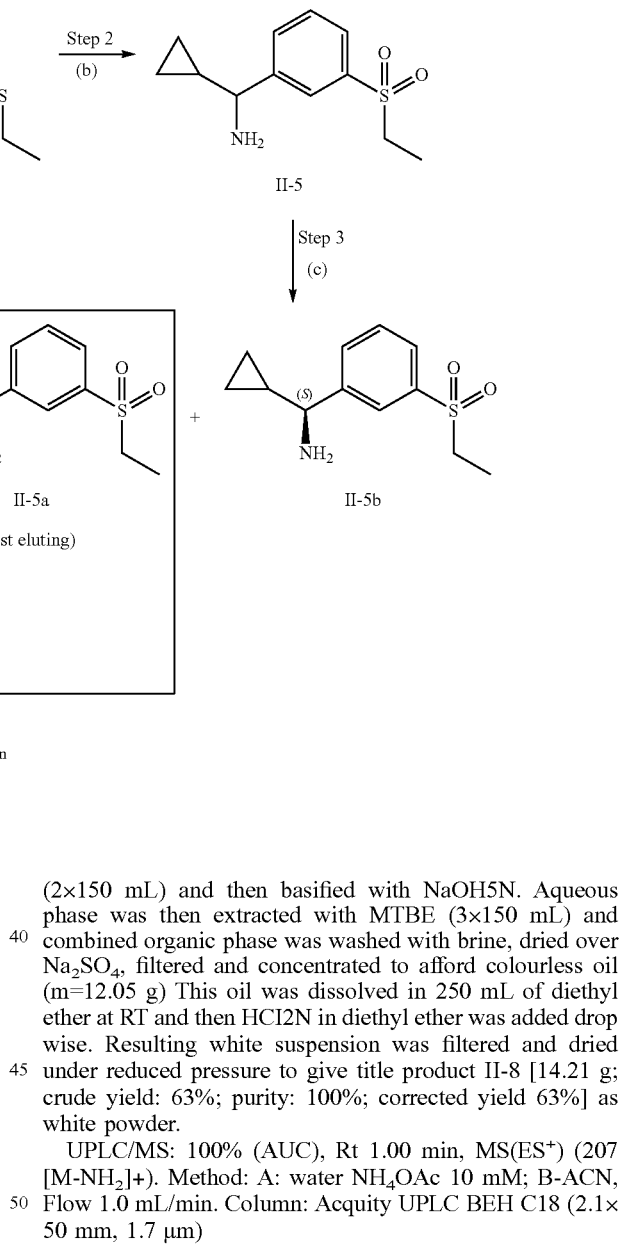

Conditions:
(a) n-butyllithium 2.5M in toluene, 40° C.; Cyclopropanecarbonitrile, -30° C.; Sodium borohydride, ethanol, RT; HCl 2N in diethyl ether, 63%. (b) Perchloric acid 70%, hydrogen peroxide 30%, Acetic acid, RT, 62%. (c) Chiralpak AY-H, 250x20mm, 5um; Heptane/EtOH/DEA (60/40/0.1). (d) 4-bromo-benzoic acid, T3P, NEt$_3$, DCE, RT, 62%.

Protocol

Step 1: Preparation of C-Cyclopropyl-C-(3-ethylsulfanyl-phenyl)-methylamine hydrochloride (II-8)

To a 500 mL three necked flask under nitrogen containing 3-Bromo-1-ethanesulfanylbenzene (20.00 g; 92.11 mmol; 1.00 eq) in dry toluene (200 mL; 20V) at RT was added rapidly a solution of n-butyllithium (36.84 mL; 92.11 mmol; 1.00 eq; 2.5M in toluene). Reaction mixture was stirred at RT overnight (Monitoring of lithium-bromine exchange was performed by quenching a sample with $CO_2$ and by injecting resulting carboxylic acid in UPLC/MS: 7% of starting material 3 was left). Reaction mixture was stirred at 40° C. for 4 h to get lithium-bromine exchange completion.

Temperature was brought down to −30° C. and cyclopropanecarbonitrile (7.64 mL; 101.32 mmol; 1.10 eq) was added drop wise over 10 minutes. Resulting nice orange light suspension was stirred at −30° C. for 2 h and was then allowed to warm up to 0° C. until completion (Monitoring of reaction was done by quenching sample with HCl (1N) and following ketimine and ketone formation by UPLC/MS).

Ethanol (100 mL; 5V) was added in one portion and sodium borohydride (6.97 g; 184.22 mmol; 2.00 eq) was added to the resulting colourless solution keeping temperature below 10° C. Reaction mixture was stirred at RT over the week-end after what new batch of sodium borohydride (6.97 g; 184.22 mmol; 2.00 eq) was added to get completion after 5 h.

Reaction mixture was poured in a large beaker containing HCI5N (100 mL; careful important foaming). Phases were separated and aqueous phase was washed with MTBE (2×150 mL) and then basified with NaOH5N. Aqueous phase was then extracted with MTBE (3×150 mL) and combined organic phase was washed with brine, dried over $Na_2SO_4$, filtered and concentrated to afford colourless oil (m=12.05 g) This oil was dissolved in 250 mL of diethyl ether at RT and then HCI2N in diethyl ether was added drop wise. Resulting white suspension was filtered and dried under reduced pressure to give title product II-8 [14.21 g; crude yield: 63%; purity: 100%; corrected yield 63%] as white powder.

UPLC/MS: 100% (AUC), Rt 1.00 min, MS(ES$^+$) (207 [M-NH$_2$]+). Method: A: water NH$_4$OAc 10 mM; B-ACN, Flow 1.0 mL/min. Column: Acquity UPLC BEH C18 (2.1× 50 mm, 1.7 μm)

Step 2: Preparation of C-Cyclopropyl-C-(3-ethanesulfonyl-phenyl)-methylamine (II-5)

To a solution of II-8 (12.00 g; 49.22 mmol; 1.00 eq) in acetic acid (120 mL; 10V) was added perchloric acid (4.20 mL; 49.22 mmol; 1.00 eq; 70%) in one portion. Then reaction mixture was cooled down to 15° C. and hydrogen peroxide (50.27 mL; 492.21 mmol; 10.00 eq; 30%) was added drop wise over 10 min (exothermic at the beginning of addition) keeping temperature at 20° C. Then solution was stirred at RT for 15 min after what exotherm brought temperature at 30° C., ice bath was used to maintain temperature at 25° C. for 5 h until nearly completion.

Quench was done with an excess of NaOH 5N and extraction was done with dichloromethane. After drying over Na$_2$SO$_4$, filtration and concentration, resulting yellow oil (m=10 g) was purified by chromatoflash (SiO$_2$, THF) to give title product II-5 [8.00 g; crude yield: 68%; purity: 91%; corrected yield 62%] as colourless oil (traces of THF by NMR).

UPLC/MS: 91% (AUC), Rt 0.57 min, MS(ES$^+$) (239 [M-NH$_2$]$^+$). Method: A: water NH$_4$OAc 10 mM; B-ACN, Flow 1.0 mL/min. Column: Acquity UPLC BEH C18 (2.1× 50 mm, 1.7 μm)

Step 3: Chiral Separation

Chiral separation was done on Chiralpak AY-H, 250×20 mm, 5 um using Heptane/EtOH/DEA (60/40/0.1) as eluent (feed concentration: 114 mg/mL; flow 10 mL/min). First eluting enantiomer II-5a (m=3.00 g) and second eluting enantiomer II-5b (m=3.47 g) were obtained.

First eluting enantiomer was arbitrary selected for next step

Step 4: Preparation of 4-Bromo-N—[(R)-cyclopropyl-(3-ethanesulfonyl-phenyl)-methyl]-benzamide (II-9)

To a stirred solution of II-5a (289 mg; 1.21 mmol; 1.00 eq) and 4-bromo-benzoic acid I-U (291.28 mg; 1.45 mmol; 1.20 eq) in DCE (4.00 mL) at RT under was added triethylamine (0.33 mL; 2.42 mmol; 2.00 eq) in one portion followed by 2,4,6-Tripropyl-[1,3,5,2,4,6]trioxatriphosphinane 2,4,6-trioxide (1.69 g; 2.66 mmol; 2.20 eq; 50% in ethyl acetate). The reaction mixture was stirred at RT until completion.

Figure 2:
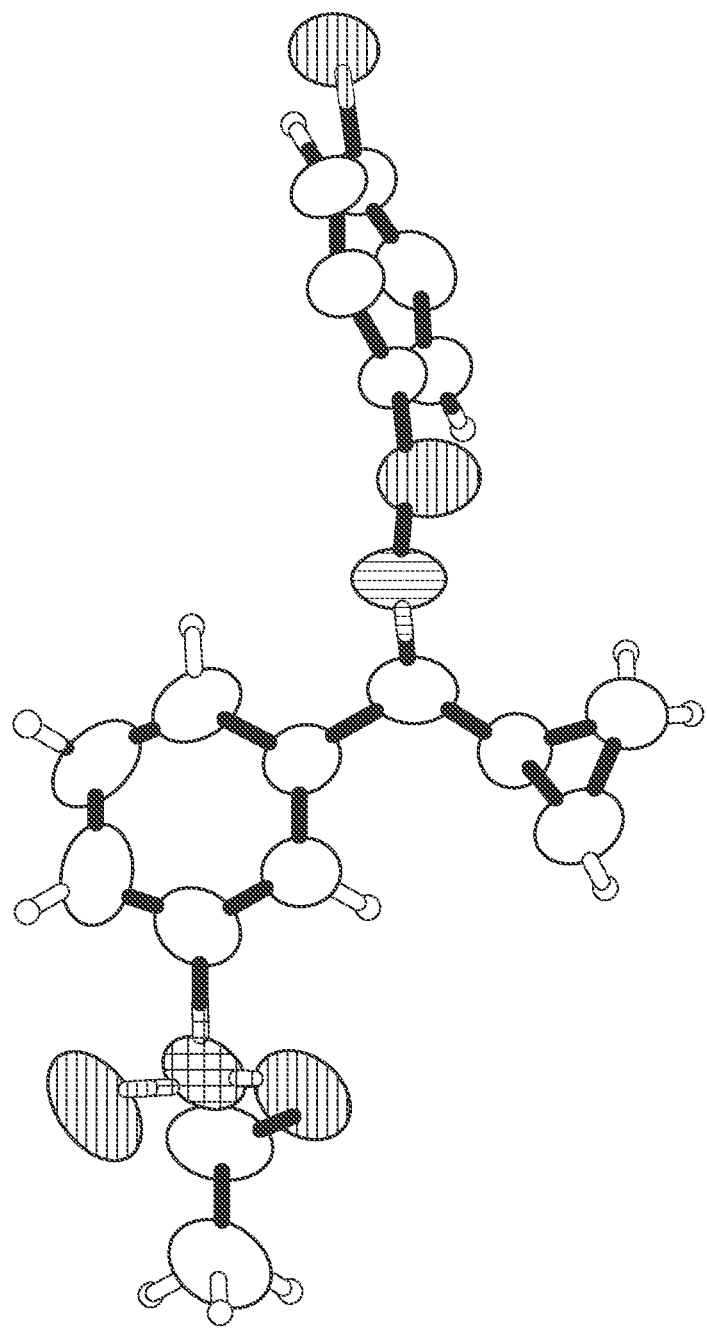
FIG. 2 depicts the crystal structure of 4-Bromo-N—[(R)-cyclopropyl-(3-ethanesulfonyl-phenyl)-methyl]-benzamide.

Reaction mixture was washed successively with a saturated solution of NaHCO$_3$, HCl (1N), water and finally with brine. After drying over Na$_2$SO$_4$, filtration and concentration, resulting off white solid was suspended in diethyl ether, filtered and dried to give title product II-9 [320 mg; crude yield: 63%; purity: 98%; corrected yield 62%] as off white solid. This product was sent for absolute configuration determination a. Results Crystal structure (see FIG. 2) was solved and showed undoubtedly the R-configuration. Therefore first eluting enantiomer II-5a was R and second eluting enantiomer II-5b was S. C—[(S)—C-Cyclopropyl-C-(3-ethanesulfonyl-phenyl)]-methylamine. II-5b was then used for the synthesis depicted below:

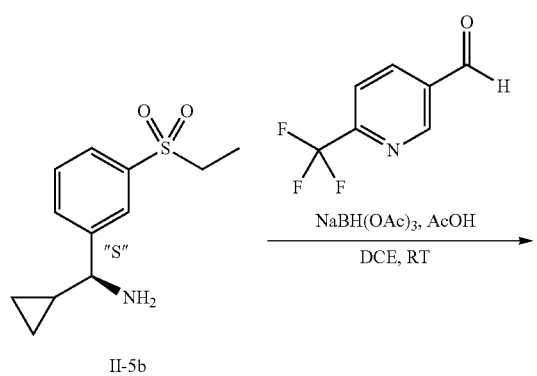

II-5b

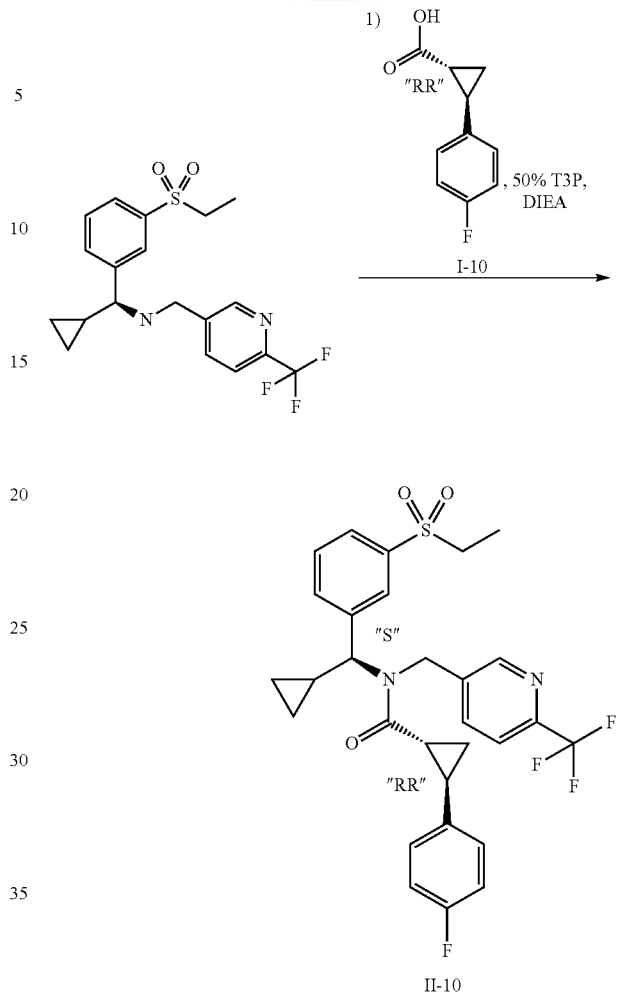

II-10

Resulting (1R, 2R)-2-(4-Fluoro-phenyl)-cyclopropanecarboxylic acid [(S)-cyclopropyl-(3-ethanesulfonyl-phenyl)-methyl]-(6-trifluoromethyl-pyridin-3-ylmethyl)-amide (II-10) was injected by chiral SFC in the same conditions than the one used for the isolation of Example 99 (Chiralcel OD-H, 250×20 mm, 5 um; Co-solvent: 20% MeOH). Under these conditions Example 99 was the first eluting and product II-10, showed to be the second eluting Example 100 (SRR).

Therefore absolute configuration of the Example 99 could be definitively attributed as RRR.

Example 100

(1R, 2R)-2-(4-Fluoro-phenyl)-cyclopropanecarboxylic acid [(S)-cyclopropyl-(3-ethanesulfonyl-phenyl)-methyl]-(6-trifluoromethyl-pyridin-3-ylmethyl)-amide Separated from a diastereomeric mixture II-7. Column: Chiralcel OD-H, 250×20 mm, 5 um; Co-solvent: 20% MeOH; Flow: 80 mL/min; Back Pressure: 120 bars; Column temperature: 30° C. (Second eluting isomer, 5.01 min). UPLC/MS (Method 3) 560.6 (M+H).

Example 101

2-(4-Fluorophenylsulfonyl)-N-(2-phenylpropan-2-yl)-N-(pyridine-2-ylmethyl)acetamide

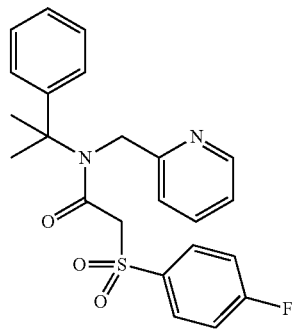 [SMILES: CC(C)(c1ccccc1)N(Cc1ccccn1)C(=O)CS(=O)(=O)c1ccc(F)cc1]

Pyridine-2-carboxaldehyde (33 μL, 0.37 mmol) and 2-phenylpropane-2-amine (53 μL, 11.35 mmol), were reacted according to General Procedure L to afford 2-Phenyl-N-(pyridine-2-ylmethyl)propane-2-amine as a light brown oil. MS (ES+) m/z 227.3 (M+H)+. 2-Phenyl-N-(pyridine-2-ylmethyl)propane-2-amine (50 mg, 0.22 mmol), Intermediate dm (58 mg, 0.27 mmol), T3P (0.265 mL, 0.44 mmol) and triethylamine (0.037 mL, 0.27 mmol) were reacted according to General Procedure D to give the title compound as a pale yellow solid (75 mg, 79%). LCMS (Method 2) 427.2 (M+H)+.

The remaining examples are described in Tables 3-12. It will be understood that the $R_{10}$ groups installed during the reductive aminations described in General Procedures A, B, K, L, Y, AD resulting from the corresponding commercially available amine, aldehyde or ketone unless otherwise specified. The $R_{10}$ groups in these tables are identified below:

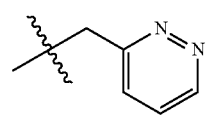
a

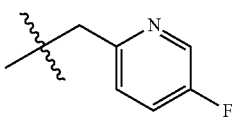
b

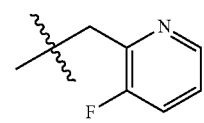
c

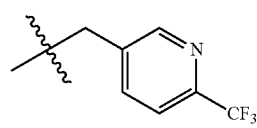
d

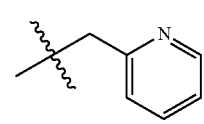
e

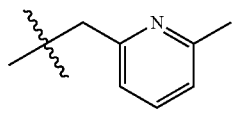
f

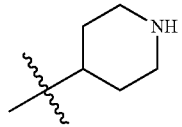
g

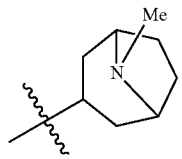
h

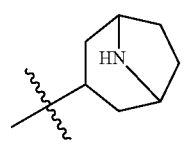
i

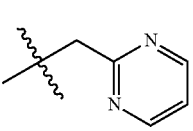
j

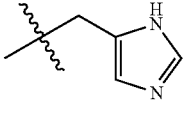
k

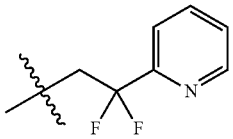
m

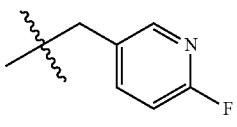
n

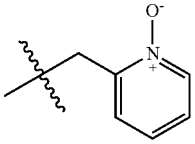
o

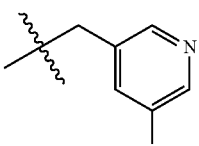
q

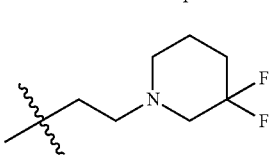
r

| | | | |
|---|---|---|---|
| s | 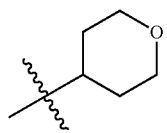 | aa | 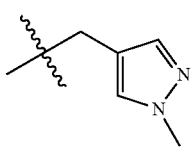 |
| u | 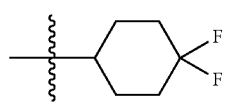 | ab | 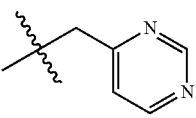 |
| v | 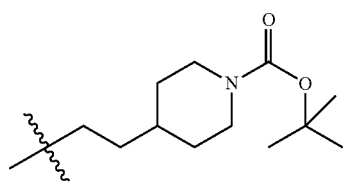 | ac | 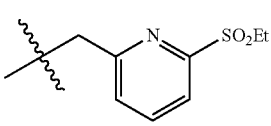 |
| w | 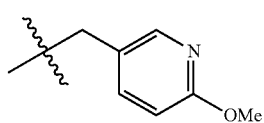 | ad | 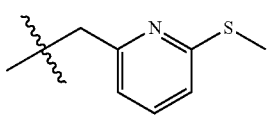 |
| x | 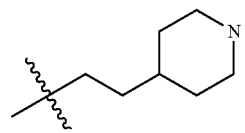 | ae | 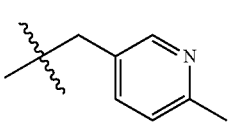 |
| y | 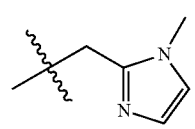 | af | 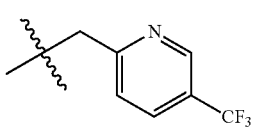 |
| z | 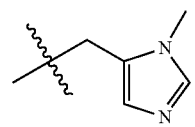 | ag | 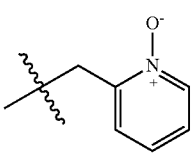 |
LCMS conditions in Tables 3-12 are denoted as: [a] LCMS (Method 2) and [b] UPLC (Method 3).

TABLE 3

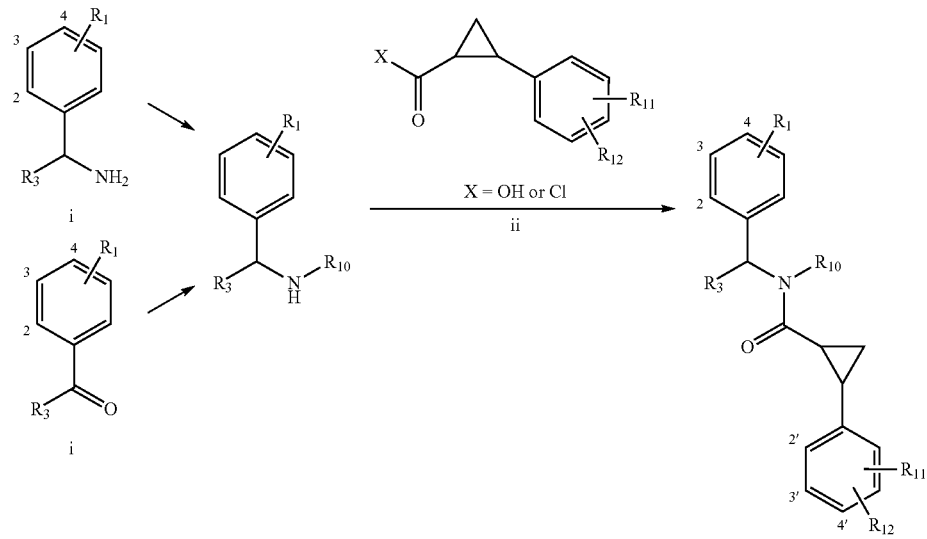

| Example | $R_1$ | $R_3$ | $R_{10}$ | $R_{11}$ | $R_{12}$ | Int. i | Int. ii | Procedures | MS [M + H] | LCMS RT (min.) | SFC/ HPLC cond. | # of iso. |
|---|---|---|---|---|---|---|---|---|---|---|---|---|
| 110 | 4-OCHF$_2$ | iPr | b | 4'-F | — | bm | ea | Gen. A, C | 487.3 [a] | | | 1 |
| 111 | 4-OCHF$_2$ | iPr | b | 4'-F | — | bn | ea | Gen. A, C | 487.3 [a] | | | 1 |
| 112 | 4-OCHF$_2$ | iPr | ag | 4'-F | — | bm | ea | Gen. A, C, R | 503.3 [a] | | | 1 |
| 113 | 4-OCHF$_2$ | iPr | a | 4'-F | — | bn | ea | Gen. A, C | 470.2 [a] | | | 1 |
| 114 | 4-OCHF$_2$ | iPr | a | 4'-F | — | bm | ea | Gen. A, C | 470.2 [a] | | | 1 |
| 115 | 4-OCHF$_2$ | iPr | b | 2'-F | 4'-F | bm | eb | Gen. A, C | 505.2 [a] | not separated | | 2 |
| 116 | 4-SO$_2$Et | Et | b | 4'-F | — | bc | ea | Gen. A, C | 499.2 [a] | not separated | | 2 |
| 117 | 4-SO$_2$Et | Et | b | 4'-F | — | bd | ea | Gen. A, C | 499.2 [a] | not separated | | 2 |
| 118 | 4-SO$_2$Et | Et | a | 4'-F | — | bd | ea | Gen. A, C | 482.2 [a] | not separated | | 2 |
| 119 | 4-SO$_2$Et | Et | d | 2'-F | 4'-F | bc | eb | Gen. A, C | 567.3 [a] | not separated | | 2 |
| 120 | 4-SO$_2$Me | Et | d | 4'-F | — | be | ea | Gen. A, C | 535.2 [a] | | | 1 |
| 121 | 4-SO$_2$Me | Et | d | 4'-F | — | bf | ea | Gen. A, C | 535.2 [a] | | | 1 |
| 122 | 4-SO$_2$Me | Et | b | 4'-F | — | bf | ea | Gen. A, C | 485.2 [a] | | | 1 |
| 123 | 4-SO$_2$Me | Me | a | 4'-F | — | bh | ea | Gen. A, C | 454.2 [a] | | | 1 |
| 124 | 4-SO$_2$Me | Et | a | 4'-F | — | bf | ea | Gen. A, C | 468.2 [a] | | | 1 |
| 125 | 4-SO$_2$Me | Et | a | 4'-F | — | be | ea | Gen. A, C | 468.2 [a] | | | 1 |
| 126 | 4-SO$_2$Me | Me | d | 4'-F | — | bg | da | Gen. A, D | 521.3 [a] | | | 1 |
| 127 | 4-SO$_2$Me | Et | d | 2'-F | 4'-F | be | db | Gen. A, D | 553.3 [a] | not separated | | 2 |
| 128 | 4-SO$_2$Me | Et | d | 2'-F | 4'-F | bf | eb | Gen. A, C | 553.6 [b] | 32.15 | F | 1 |
| 129 | 4-SO$_2$Me | Et | d | 2'-F | 4'-F | bf | eb | Gen. A, C | 553.6 [b] | 27.33 | F | 1 |
| 130 | 4-SO$_2$iPr | Et | a | 4'-F | — | fa | ea | Gen. S, A, M | 496.3 [a] | not separated | | 2 |

TABLE 4

| Example | $R_1$ | $R_2$ | $R_{10}$ | Int. i | Procedures | MS [M + H] | LCMS RT (min.) | Chiral Separation Silica Gel F-C or SFC/HPLC cond. | # of iso. |
|---|---|---|---|---|---|---|---|---|---|
| 140 | 4-OCHF$_2$ | — | s | ai | Gen. A, C, N, Q | 517.3 [a] | | | 2 |
| 141 | 4-OCHF$_2$ | — | b | ai | Gen. A, C, N | 528.3 a | 1.866 | Silica Gel F-C | 1 |
| 142 | 4-OCHF$_2$ | — | b | ai | Gen. A, C, N, Q | 542.3 a | 1.832 | Silica Gel F-C | 1 |
| 143 | 3-SO$_2$Et | — | b | fh | Gen. A,C, O, Q | 568.2 [a] | | | 1 |
| 144 | 4-F | 2-F | b | fi | Gen. A, C | 512.3 [a] | | | 1 |
| 145 | 4-F | 2-F | c | fi | Gen. A, C | 512.3 [b] | 4.42 | D | 1 |
| 146 | 3-CF$_3$ | — | b | fb | Gen. S, A, C, O, Q | 544.2 [a] | 2.423 | Silica Gel F-C | 1 |
| 147 | 3-CF$_3$ | — | b | fb | Gen. S, A, C, O, Q | 544.2 [a] | 2.391 | Silica Gel F-C | 1 |
| 148 | 3-CF$_3$ | — | q | fb | Gen. S, A, C, O, Q | 544.2 [a] | 2.195 | Silica Gel F-C | 1 |

TABLE 5

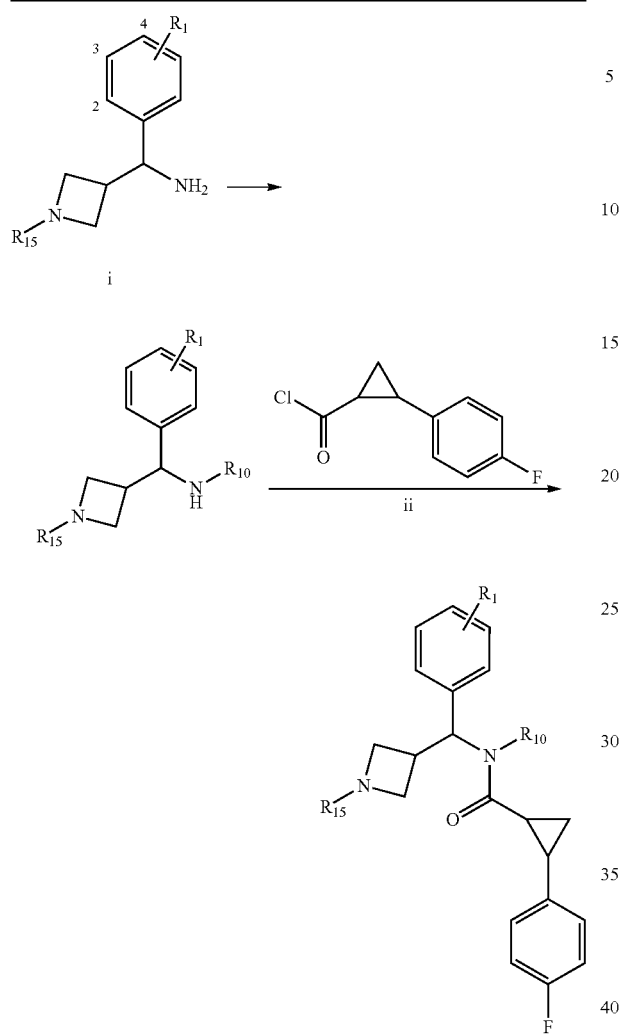

| Example | $R_1$ | $R_{15}$ | $R_{10}$ | Int. i | Procedures | MS [M + H]+ (Method 2) | LCMS RT (min.) (Method 2) |
|---|---|---|---|---|---|---|---|
| 150 | 4-OCHF$_2$ | Me | c | ah | Gen. A, C, N, Q | 514.2 | 1.916 |
| 151 | 4-OCHF$_2$ | Me | c | ah | Gen. A, C, N, Q | 514.2 | 5.023 |
| 152 | 4-OCHF$_2$ | H | b | ah | Gen. A, C, N | 500.3 | 2.205 |
| 153 | 4-OCHF$_2$ | H | b | ah | Gen. A, C, N | 500.3 | 2.180 |
| 154 | 4-OCHF$_2$ | Me | b | ah | Gen. A, C, N, Q | 514.2 | 2.200 |
| 155 | 4-F | Me | c | ag | Gen. A, C, N, Q | 466.2 | 1.936 |
| 156 | 4-F | Me | c | ag | Gen. A, C, N, Q | 466.2 | 1.589 |
| 157 | 4-F | H | c | ag | Gen. A, C, N | 452.2 | 1.809 |
| 158 | 4-F | H | b | ag | Gen. A, C, N | 452.2 | 2.026 |
| 159 | 4-OCF$_3$ | Me | b | at | Gen. A, C, N, Q | 532.3 | 2.128 |
| 160 | 4-OCHF$_2$ | Me | af | ah | Gen. A, C, N, Q | 564.3 | 2.052 |
| 161 | 4-OCHF$_2$ | Me | af | ah | Gen. A, C, N, Q | 564.3 | 2.147 |
| 162 | 4-OCF$_3$ | Me | q | at | Gen. A, C, N, Q | 532.3 | 2.216 |
| 163 | 4-OCF$_3$ | Me | q | at | Gen. A, C, N, Q | 532.3 | 2.080 |

Note:
Examples in table are single isomers seperated from diastereometic mixtures after General Procedure C by Silica Gel Flash

TABLE 6

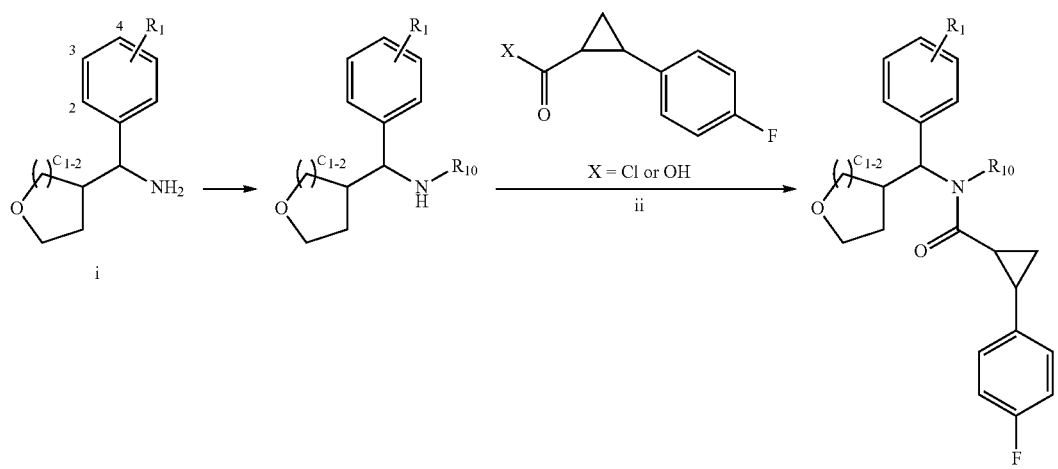

| Example | $R_1$ | n | $R_{10}$ | Int. i | Procedures | MS [M + H] | LCMS RT (min.) | Silica Gel F-C or SFC/HPLC cond. | # of iso. |
|---|---|---|---|---|---|---|---|---|---|
| 170 | 3-$SO_2$Et | 2 | c | aw | Gen. A, C | 555.2 [a] | not separated | | 2 |
| 171 | 4-F | 1 | c | gh | Gen. A, D | 467.5 [b] | 2.16 | A | 1 |
| 172 | 4-F | 1 | c | gh | Gen. A, D | 467.5 [b] | 2.57 | A | 1 |
| 173 | 4-F | 1 | a | gh | Gen. A, D | 450.5 [b] | 27.03 | F | 1 |
| 174 | 4-F | 1 | a | gh | Gen. A, D | 450.5 [b] | 34.12 | F | 1 |
| 175 | 4-F | 1 | b | gh | Gen. A, C | 467.3 [b] | 3.022 | Silica Gel F-C | 1 |
| 176 | 4-F | 1 | b | gh | Gen. A, C | 467.3 [b] | 2.837 | Silica Gel F-C | 1 |

TABLE 7

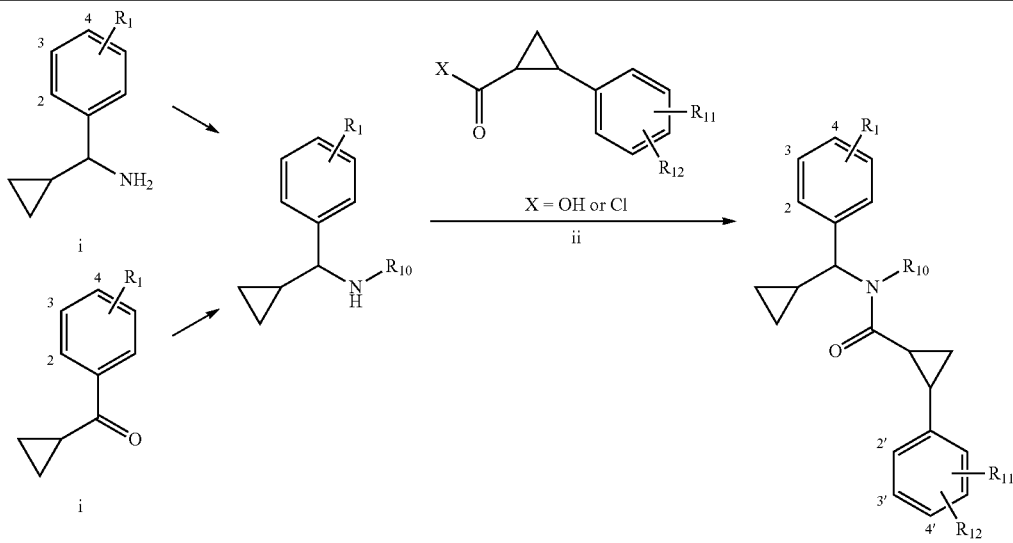

| Example | $R_1$ | $R_{10}$ | $R_{11}$ | $R_{12}$ | Int. i | Int. ii | Procedures | MS [M + H] | LCMS RT (min.) | SFC/HPLC cond. | # of iso. |
|---|---|---|---|---|---|---|---|---|---|---|---|
| 180 | 4-$OCHF_2$ | a | 3'-F | 4'-F | bt | ec | Gen. A, M | 486.2 [a] | not separated | | 2 |
| 181 | 4-$OCHF_2$ | a | 3'-F | 4'-F | bt | ec | Gen. A, M | 486.2 [b] | 3.54 | A | 1 |

TABLE 7-continued

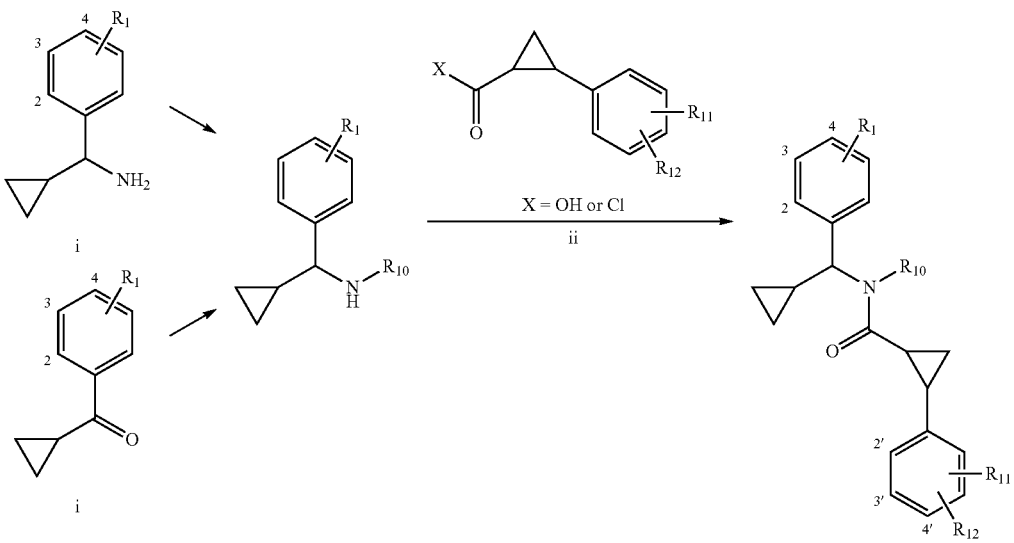

| Example | $R_1$ | $R_{10}$ | $R_{11}$ | $R_{12}$ | Int. i | Int. ii | Procedures | MS [M + H] | LCMS RT (min.) | SFC/HPLC cond. | # of iso. |
|---|---|---|---|---|---|---|---|---|---|---|---|
| 182 | 4-OCHF$_2$ | a | 2'-F | 4'-F | bt | eb | Gen. A, M | 486.2 [b] | 4.57 | A | 1 |
| 183 | 4-OCHF$_2$ | k | 4'-F | — | bt | ea | Gen. A, C, O | 456.2 [a] | | | 1 |
| 184 | 4-OCHF$_2$ | a | 3'-CF$_3$ | — | bt | ed | Gen. A, C | 518.1 [b] | 1.91 | A | 1 |
| 185 | 4-OCHF$_2$ | r | 4'-F | — | ak | ea | Int. fc, Gen. C | 523.2 [a] | not separated | | 2 |
| 186 | 4-OCHF$_2$ | r | 4'-F | — | ak | ea | Int. fc, Gen. C | 523.2 [b] | 8.2 | C | 1 |
| 187 | 4-OCHF$_2$ | y | 4'-F | — | bt | ea | Gen. A and C | 470.2 [a] | | | 1 |
| 188 | 4-OCHF$_2$ | a | 2-OCF$_3$ | — | bt | ef | Gen. A, M | 534.2 [a] | not separated | | 2 |
| 189 | 4-OCHF$_2$ | z | 4'-F | — | bt | ea | Gen. A, C | 470.2 [a] | | | 1 |
| 190 | 4-OCHF$_2$ | aa | 4'-F | — | bt | da | Gen. A, D | 470.2 [a] | | | 1 |
| 191 | 3-SO$_2$Et | m | 4'-F | — | am | ea | Int. ac, Gen. C | 543.2 [a] | not separated | | 2 |
| 192 | 3-SO$_2$Et | ab | 4'-F | — | am | ea | Gen. K, C | 494.2 [a] | not separated | | 2 |
| 193 | 3-SO$_2$Et | b | 2'-F | 4'-F | ca | eb | Gen. A, C | 529.6 [b] | 32.7 | E | 1 |
| 194 | 3-SO$_2$Et | b | 2'-F | 4'-F | ca | eb | Gen. A, C | 529.6 [b] | 25.72 | E | 1 |
| 195 | 3-SO$_2$Et | b | 2'-F | 4'-F | cb | eb | Gen. A, C | 529.6 [b] | 5.65 | B | 1 |
| 196 | 3-SO$_2$Et | b | 2'-F | 4'-F | cb | eb | Gen. A, C | 529.6 [b] | 4.15 | B | 1 |
| 197 | 3-SO$_2$Et | b | 3'-F | 4'-F | cb | ec | Gen. A, C | 529.6 [b] | 5.57 | B | 1 |
| 198 | 3-SO$_2$Et | b | 3'-F | 4'-F | cb | ec | Gen. A, C | 529.6 [b] | 3.67 | B | 1 |
| 199 | 3-SO$_2$Et | b | 3'-F | 4'-F | ca | ec | Gen. A, C | 529.6 [b] | 22.83 | F | 1 |
| 209 | 3-SO$_2$Et | b | 3'-F | 4'-F | ca | ec | Gen. A, C | 529.6 [b] | 15.87 | F | 1 |
| 210 | 3-SO$_2$Et | b | 3'-CF$_3$ | — | cb | ed | Gen. A, C | 561.6 [b] | 2.92 | B | 1 |
| 211 | 3-SO$_2$Et | b | 3'-CF$_3$ | — | cb | ed | Gen. A, C | 561.6 [b] | 4.27 | B | 1 |
| 212 | 3-SO$_2$Et | b | 3'-CF$_3$ | — | ca | ed | Gen. A, C | 561.6 [b] | 28.25 | B | 1 |
| 213 | 3-SO$_2$Et | b | 3'-CF$_3$ | — | ca | ed | Gen. A, C | 561.6 [b] | 35.35 | B | 1 |
| 214 | 3-SO$_2$Et | q | 4'-F | — | ar | ea | Gen. A, C | 511.2 [a] | not separated | | 2 |
| 215 | 3-SO$_2$Et | b | 4'-F | — | ar | ea | Gen. A, C | 511.6 [b] | 2.55 | B | 1 |
| 216 | 3-SO$_2$Et | e | 3'-CF$_3$ | — | ar | ed | Gen. A, C | 543.2 [a] | not seperated | | 4 |
| 217 | 3-SO$_2$Et | e | 3'-CF$_3$ | — | ar | ed | Gen. A, C | 543.6 [b] | 22.39 | J | 1 |
| 218 | 3-SO$_2$Et | c | 4'-F | — | ar | ea | Gen. A, C | 511.2 [a] | not separated | | 2 |
| 219 | 3-SO$_2$Et | u | 4'-F | — | ar | ea | Gen. A, M | 520.2 [a] | not separated | | 2 |
| 220 | 3-SO$_2$Et | s | 2'-OCF$_3$ | — | ca | ef | Gen. A, M | 552.2 [a] | not separated | | 2 |
| 221 | 3-SO$_2$Et | s | 2'-OCF$_3$ | — | cb | ef | Gen. A, M | 552.2 [a] | not separated | | 2 |

TABLE 7-continued

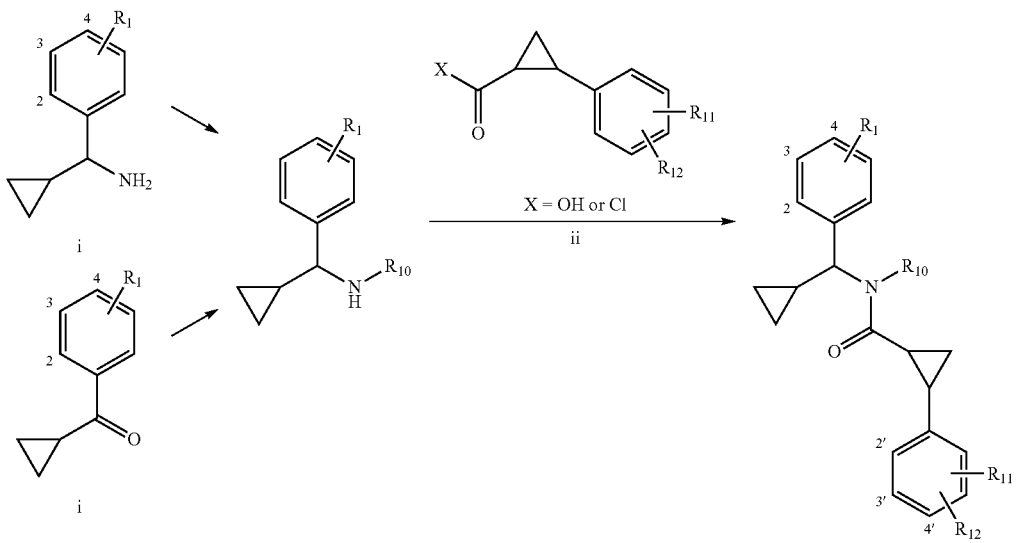

| Example | $R_1$ | $R_{10}$ | $R_{11}$ | $R_{12}$ | Int. i | Int. ii | Procedures | MS [M + H] | Chiral Separation LCMS RT (min.) | SFC/HPLC cond. | # of iso. |
|---|---|---|---|---|---|---|---|---|---|---|---|
| 222 | 3-SO$_2$Et | b | 4'-OCHF$_2$ | — | ar | eg | Gen. A, C | 559.2 [a] | not separated | | 4 |
| 223 | 3-SO$_2$Et | a | 4'-F | — | ca | ea | Gen. A, C | 494.2 [a] | | | 1 |
| 224 | 3-SO$_2$Et | a | 4'-F | — | cb | ea | Gen. A, C | 487.3 [a] | | | 1 |
| 225 | 3-SO$_2$Et | a | 3'-CF$_3$ | — | cb | ed | Gen. A, M | 544.2 [a] | not separated | | 2 |
| 226 | 3-SO$_2$Et | a | 3'-CF$_3$ | — | ca | ed | Gen. A, M | 544.2 [a] | not separated | | 2 |
| 227 | 4-SO$_2$Et | b | 3'-CF$_3$ | — | bx | ed | Gen. A, C | 561.6 [b] | 3.05 | B | 1 |
| 228 | 4-SO$_2$Et | b | 3'-CF$_3$ | — | bx | ed | Gen. A, C | 561.6 [b] | 4.15 | B | 1 |
| 229 | 4-SO$_2$Et | b | 2'-F | 4'-F | bx | eb | Gen. A, C | 529.6 [b] | 4.42 | D | 1 |
| 230 | 4-SO$_2$Et | b | 2'-F | 4'-F | bx | eb | Gen. A, C | 529.6 [b] | 5.21 | D | 1 |
| 231 | 4-SO$_2$Et | a | 4'-F | — | bx | ea | Gen. A, C | 494.2 [a] | | | 1 |
| 232 | 4-SO$_2$Et | b | 4'-F | — | bx | ea | Gen. A, C | 511.2 [a] | | | 1 |
| 233 | 4-SO$_2$Et | b | 4'-F | — | bw | ea | Gen. A, C | 511.2 [a] | | | 1 |
| 234 | 4-SO$_2$iPr | c | 4'-F | — | by | ea | Gen. A, C | 525.3 [a] | | | 1 |
| 235 | 4-SO$_2$iPr | c | 4'-F | — | bz | ea | Gen. A, C | 525.3 [a] | | | 1 |
| 236 | 4-SO$_2$iPr | a | 4'-F | — | bz | ea | Gen. A, C | 508.3 [a] | | | 1 |
| 237 | 4-SO$_2$iPr | a | 4'-F | — | by | ea | Gen. A, C | 508.3 [a] | | | 1 |
| 238 | 4-SO$_2$iPr | b | 4'-F | — | bz | ea | Gen. A, C | 525.3 [a] | | | 1 |
| 239 | 4-SO$_2$iPr | b | 4'-F | — | by | ea | Gen. A, C | 525.3 [a] | | | 1 |
| 240 | 3-SO$_2$iPr | a | 4'-F | — | bv | ea | Gen. Y, M | 508.3 [a] | | | 1 |
| 241 | 3-SO$_2$iPr | a | 4'-F | — | bu | ea | Gen. Y, M | 508.3 [a] | | | 1 |
| 242 | 3-SO$_2$iPr | b | 4'-F | — | bu | ea | Gen. A, C | 525.3 [a] | | | 1 |
| 243 | 3-SO$_2$iPr | b | 4'-F | — | bv | ea | Gen. A, C | 525.3 [a] | | | 1 |
| 244 | 3-SO$_2$iPr | q | 4'-F | — | az | ea | Gen. K, C | 525.3 [a] | not separated | | 2 |
| 245 | 3-SO$_2$iPr | c | 4'-F | — | bu | ea | Gen. A, C | 525.3 [a] | | | 1 |
| 246 | 3-SO$_2$iPr | c | 4'-F | — | bv | ea | Gen. A, C | 525.3 [a] | | | 1 |
| 247 | 3-SO$_2$iPr | ab | 4'-F | — | az | da | Gen. K, D | 508.3 [a] | not separated | | 2 |
| 248 | 4-SO$_2$cPr | a | 4'-F | — | cd | ea | Gen. A, C | 506.2 [a] | | | 1 |
| 249 | 4-SO$_2$cPr | a | 4'-F | — | ce | ea | Gen. A, C | 506.2 [a] | | | 1 |
| 250 | 4-SO$_2$cPr | b | 4'-F | — | cd | ea | Gen. A, C | 523.2 [a] | | | 1 |
| 251 | 3-CN | c | 4'-F | — | * | da | Gen. A, D | 444.1 [b] | 32.4 | H | 1 |
| 252 | 3-CN | c | 4'-F | — | * | da | Gen. A, D | 444.1 [b] | 22.82 | H | 1 |
| 253 | 4-Cl | ac | 4'-F | — | br | da | Gen. A, D, T | 527.2 [a] | | | 1 |
| 254 | 4-Cl | ad | 4'-F | — | br | da | Gen. A, D, T (Step 1) | 481.2 [a] | | | 1 |
| 255 | 4-Cl | ac | 4'-F | — | br | da | Gen. A, D, T | 513.3 [a] | | | 1 |

* 3-(aminocyclopropylmethyl)-benzonitrile

TABLE 8

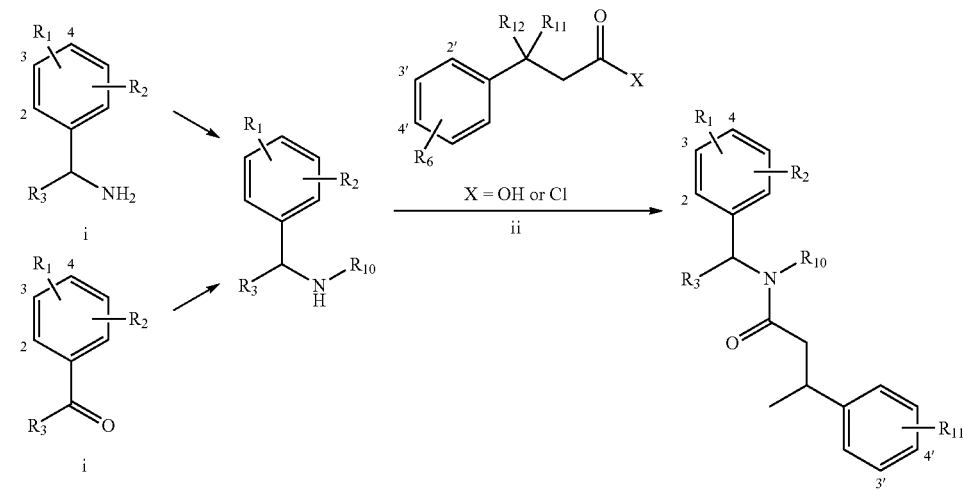

| Example | R₁ | R₂ | R₃ | R₁₀ | R₁₁ | Int. i | Int. ii | Procedures | MS [M + H] | LCMS RT (min.) | SFC/HPLC cond. | # of iso. |
|---|---|---|---|---|---|---|---|---|---|---|---|---|
| 260 | 4-OCHF₂ | — | cPr | a | 2'CF₃ | bt | ek | Gen. A, M | 520.2 [b] | 15.6 | G | 1 |
| 261 | 4-OCHF₂ | — | cPr | a | 2'CF₃ | bt | ek | Gen. A, M | 520.2 [b] | 20.2 | G | 1 |
| 262 | 4-OCHF₂ | — | cPr | a | 4'-F | ak | ei | Gen. A, M | 470.2 [a] | | | 1 |
| 263 | 4-OCHF₂ | — | cPr | d | 2'-SO₂Me | bs | dj | Gen. A, D | 597.3 [a] | not separated | | 2 |
| 264 | 4-SO₂iPr | — | cPr | b | 4'-F | bz | ei | Gen. A, C | 527.2 [a] | | | 1 |
| 265 | 3-SO₂Et | — | cPr | b | 2'-CF₃ | cb | ek | | 563.6 [b] | 36.5 | F | 1 |
| 266 | 3-SO₂Et | — | cPr | b | 2'-CF₃ | cb | ek | | 563.6 [b] | 29.5 | F | 1 |
| 267 | 3-SO₂Et | — | cPr | b | 2'-CF₃ | ca | ek | | 563.6 [b] | 6.56 | B | 1 |
| 268 | 3-SO₂Et | — | cPr | b | 2'-CF₃ | ca | ek | | 563.6 [b] | 5.22 | B | 1 |
| 269 | 4-SO₂Et | — | cPr | b | 2'-CF₃ | an | ek | Gen. A, C | 563.3 [a] | 2.94 | | 1 |
| 270 | 4-F | — | tetrahydrofuran-2-yl | b | 4'-F | gh | oo | Gen. A, C | 469.5 [b] | 1.1 | I | 1 |
| 271 | 4-F | 2-F | 1-methylpiperidin-4-yl | b | 4'-F | fi | di | Gen. A, D | 514.2 [a] | not separated | | 2 |
| 272 | 4-Cl | — | cPr | o | 4'-F | br | ei | Gen. A, C, R | 453.3 [a] | | | 1 |

TABLE 9

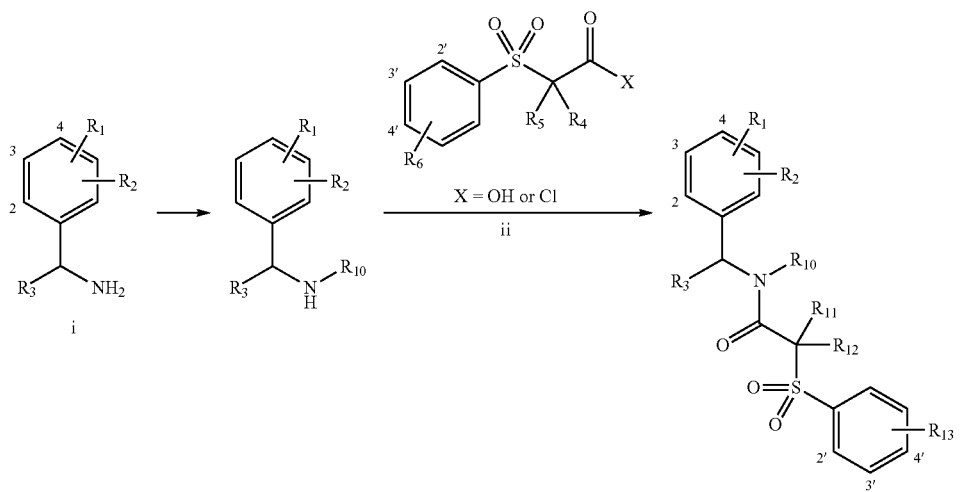

| Example | $R_1$ | $R_2$ | $R_3$ | $R_{10}$ | $R_{11}$ | $R_{12}$ | $R_{13}$ | Int. i | Int. ii | Procedures | MS [M + H] | LCMS RT (min.) | SFC/ HPLC cond. |
|---|---|---|---|---|---|---|---|---|---|---|---|---|---|
| 280 | 4-Cl | — | Me | h | H | H | 4'-F | ^ | dm | Gen. A, D | 479.2 [a] | | |
| 281 | 4-OCHF$_2$ | — | CH$_2$OMe | d | H | H | — | fj | dl | Gen. A, D | 560.2 [a] | | |
| 282 | 4-F | — | (tetrahydrofuran-2-yl) | d | H | H | — | gh | dl | Gen. A, D | 537.1 [b] | 4.9 | A |
| 283 | 4-F | — | iPr | v | H | H | 4'-F | bl | dm | Gen. A, D | 479.2 *[a] | | |
| 284 | 4-F | — | iPr | x | H | H | 4'-F | bl | dm | Gen. A, C, O | 479.2 [a] | | |
| 286 | 4-F | 2-F | (1-methylpiperidin-4-yl) | b | H | H | 4'-F | fi | dm | Gen. A, D | 550.1 [b] | 5.87 | B |
| 287 | 4-F | 2 F | (1-methylpiperidin-4-yl) | b | H | H | 4'-F | fi | dm | Gen. A, D | 550.1 [b] | 4.48 | B |
| 288 | 4-SO$_2$Me | — | Me | d | Me | Me | — | bg | ep | Gen. A, E | 569.3 [a] | | |

* Note:
MS shown as M − CO$_2$C(CH$_3$) + H

^ 4-chloro-(R)-α-methyl-benzenemethanamine

All examples are single isomers

TABLE 10

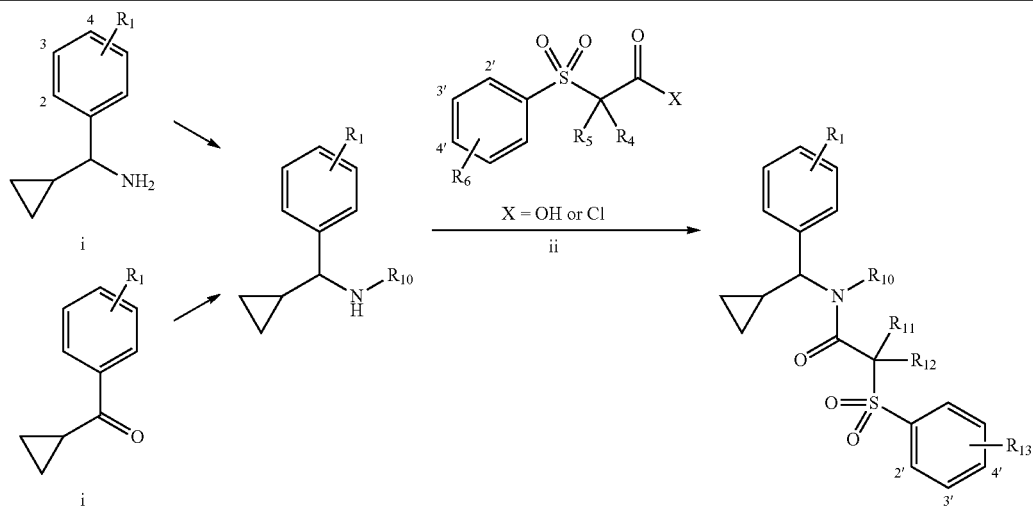

| Example # | R₁ | R₁₀ | R₁₁ | R₁₂ | R₁₃ | Int. i | Int. ii | Procedures | MS [M + H] | LCMS RT (min.) | Silica Gel F-C or SFC/ HPLC cond. | # of iso. |
|---|---|---|---|---|---|---|---|---|---|---|---|---|
| 290 | 4-Cl | b | H | H | 4'-F | br | dm | Gen. A, D | 491.2 $^a$ | | | 1 |
| 291 | 4-Cl | n | H | H | 4'-F | br | dm | Gen. A, D | 491.2 $^a$ | | | 1 |
| 292 | 4-Cl | o | H | H | 3'-CF₃ | br | dr | Gen. A, D, R | 539.2 $^a$ | | | 1 |
| 293 | 4-Cl | e | H | H | 3'-CF₃ | bq | dr | Gen. A, D | 523.2 $^a$ | | | 1 |
| 294 | 4-Cl | e | H | H | 3'-CF₃ | br | dr | Gen. A, D | 523.2 $^a$ | | | 1 |
| 295 | 4-Cl | w | H | H | 4'-F | br | dm | Gen. A, D | 503.3 $^a$ | | | 1 |
| 296 | 4-Cl | e | Me | H | 4'-F | br | eo | Gen. A, M | 487.3 $^b$ | 7.42 | B | 1 |
| 297 | 4-Cl | e | Me | H | 4'-F | br | eo | Gen. A, M | 487.3 $^b$ | 4.93 | B | 1 |
| 298 | 4-OCHF₂ | g | H | H | 4'-F | ak | dm | Gen. A, D | 497.2 $^a$ | not separated | | 2 |
| 299 | 4-OCHF₂ | d | H | H | 2'-F | bt | dn | Gen. A, D | 573.3 $^a$ | | | 1 |
| 300 | 4-OCHF₂ | d | H | H | 2'-F | bs | dn | Gen. A, D | 573.3 $^a$ | | | 1 |
| 301 | 4-OCHF₂ | d | H | H | — | bt | dl | Gen. A, D | 555.2 $^a$ | | | 1 |
| 302 | 4-OCHF₂ | d | H | H | — | bs | dl | Gen. A, D | 555.2 $^a$ | | | 1 |
| 303 | 4-OCHF₂ | c | H | H | — | bt | dl | Gen. A, D | 505.2 $^a$ | | | 1 |
| 304 | 4-OCHF₂ | c | H | H | — | bs | dl | Gen. A, D | 505.2 $^a$ | | | 1 |
| 305 | 4-OCHF₂ | a | H | H | — | bt | dl | Gen. A, D | 488.3 $^a$ | | | 1 |
| 306 | 4-OCHF₂ | a | H | H | — | bs | dl | Gen. A, D | 488.3 $^a$ | | | 1 |
| 307 | 4-OCHF₂ | a | H | H | 3'-CF₃ | bt | dr | Gen. A, D | 556.3 $^a$ | | | 1 |
| 308 | 4-OCHF₂ | a | Me | Me | 4'-F | bt | dq | Gen. A, D | 534.2 $^a$ | | | 1 |
| 309 | 4-OCHF₂ | c | H | H | 4'-F | bt | dm | Gen. A, D | 523.3 $^a$ | | | 1 |
| 310 | 4-OCHF₂ | a | H | H | 3'-CF₃ | bs | dr | Gen. A, D | 556.3 $^a$ | | | 1 |
| 311 | 4-OCHF₂ | a | Me | Me | 4'-F | bs | dq | Gen. A, M | 534.2 $^a$ | | | 1 |
| 312 | 4-OCHF₂ | d | H | H | 4'-F | ak | dm | Gen. A, D | 573.1 $^b$ | 1.8 | B | 1 |
| 313 | 4-OCHF₂ | d | H | H | 4'-F | ak | dm | Gen. A, D | 573.1 $^b$ | 2.57 | B | 1 |
| 314 | 4-OCHF₂ | e | H | H | 4'-F | ak | dm | Gen. A, D | 505.2 $^a$ | not separated | | 2 |
| 315 | 4-OCHF₂ | u | H | H | 4'-F | ak | dm | Gen. A, D | 532.3 $^b$ | 6.91 | I | 1 |
| 316 | 4-OCHF₂ | u | H | H | 4'-F | ak | dm | Gen. A, D | 532.3 $^b$ | 4.07 | I | 1 |
| 317 | 4-OCHF₂ | s | H | H | 4'-F | ak | dm | Gen. A, D | 496.3 [M − H] $^a$ | not separated | | 2 |
| 318 | 4-OCHF₂ | e | Me | Me | 4'-F | ak | dq | Gen. A, C | 533.1 $^b$ | 5.9 | A | 1 |
| 319 | 4-OCHF₂ | e | Me | Me | 4'-F | ak | dq | Gen. A, C | 533.1 $^b$ | 3.63 | A | 1 |
| 320 | 4-OCHF₂ | f | H | H | 4'-F | bt | dm | Gen. A, D | 519.2 $^a$ | | | 1 |
| 321 | 4-OCHF₂ | f | H | H | 4'-F | bs | dm | Gen. A, D | 519.2 $^a$ | | | 1 |
| 322 | 4-OCHF₂ | ae | H | H | — | bt | dl | Gen. A, D | 501.2 $^a$ | | | 1 |
| 323 | 4-OCHF₂ | ae | H | H | — | bs | dl | Gen. A, D | 501.2 $^a$ | | | 1 |
| 324 | 4-OCHF₂ | d | Me | Me | — | bs | dp | Gen. A, D | 583.3 $^a$ | | | 1 |
| 327 | 3-SO₂Et | c | H | H | — | ar | dl | Gen. A, D | 531.2 $^a$ | not separated | | 2 |
| 328 | 3-SO₂Et | e | Me | Me | — | ar | ep | Gen. A, E | 541.3 $^a$ | not separated | | 2 |
| 329 | 2-OCH₂CHF₂ | e | H | H | 4'-F | ax | em | Gen. A, C | 519.1 $^b$ | 3.59 | A | 2 |
| 330 | 2-OCH₂CHF₂ | d | H | H | 4'-F | ax | dm | Gen. A, D | 587.3 $^b$ | 5.43 | A | 1 |
| 331 | 2-OCF₃ | f | H | H | 4'-F | ay | dm | Gen. A, D | 537.3 $^b$ | 5.03 | A | 1 |
| 332 | 3-CN | d | H | H | 4'-F | * | dm | Gen. A, D | 532.1 $^b$ | 4.47 | B | 1 |
| 333 | 3-CN | d | H | H | 4'-F | * | dm | Gen. A, D | 532.1 $^b$ | 3.81 | B | 1 |

* 3-(aminocyclopropyl methyl)-benzonitrile

TABLE 11
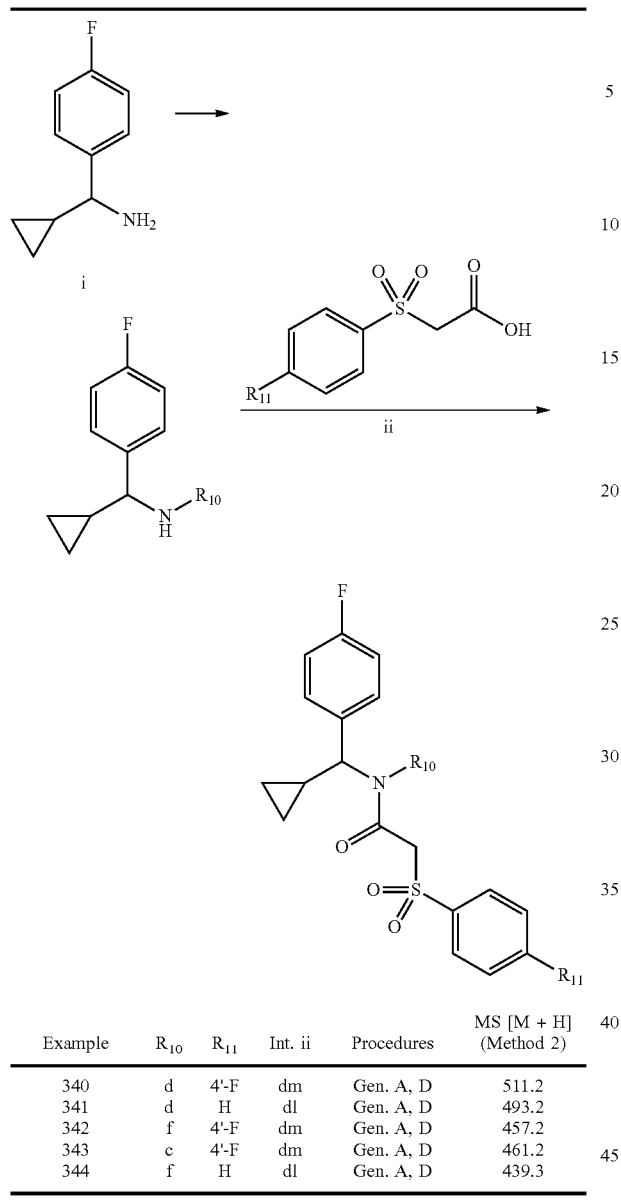
| Example | $R_{10}$ | $R_{11}$ | Int. ii | Procedures | MS [M + H] (Method 2) |
|---|---|---|---|---|---|
| 340 | d | 4'-F | dm | Gen. A, D | 511.2 |
| 341 | d | H | dl | Gen. A, D | 493.2 |
| 342 | f | 4'-F | dm | Gen. A, D | 457.2 |
| 343 | c | 4'-F | dm | Gen. A, D | 461.2 |
| 344 | f | H | dl | Gen. A, D | 439.3 |
TABLE 12
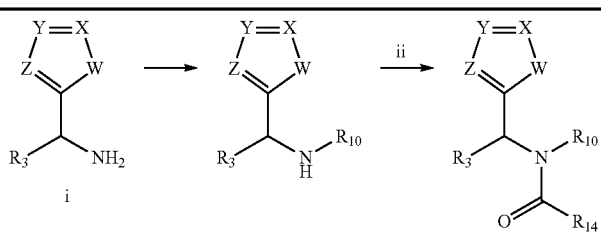
| Example # | W | X | Y | Z | $R_3$ | $R_{10}$ | $R_{14}$ | Int. i | Int. iii | Procedures | MS [M + H] | LCMS RT (min.) | SFC/HPLC cond. | Chiral Separation # of iso. |
|---|---|---|---|---|---|---|---|---|---|---|---|---|---|---|
| 350 | NMe | N | CH | N | $^i$Bu | d | bb | gc | di | Gen. A, D | 492.3 $^a$ | | | 1 |
| 351 | NMe | N | CH | N | Et | d | aa | * | da | Gen. A, D | 462.3 $^a$ | | not separated | 2 |
| 352 | NMe | N | CH | N | $^i$Bu | d | aa | gc | da | Gen. A, D | 490.2 $^a$ | | | 1 |

TABLE 12-continued

| 353 | N$^i$Pr | C | NH | N | Me | d | cc | ** | dm | Int. fk, Gen. D | 514.2 $^a$ | not separated | 2 |
| 354 | NMe | N | CH | CH | CH$_2$OMe | d | cc | gf | dm | Gen. A, D | 515.2 $^a$ | | 1 |
| 355 | O | N | C$^i$Bu | N | Me | d | aa | *** | da | Gen. A, U | 491.2 $^b$ | 2.52 | A | 1 |
| 356 | O | N | C$^i$Bu | N | Me | d | aa | *** | da | Gen. A, U | 491.2 $^b$ | 3.51 | A | 1 |

\* 1-(1-methyl-1H-1,2,4-triazol-5-yl)-1-propanamine
\*\* α-methyl-4-(1-methylethyl)-4H-1,2,4-triazole-3-methanamine
\*\*\* α-methyl-3-(1-methylethyl)-1,2,4-Oxadiazole-5-methanamine R$_5$ Groups

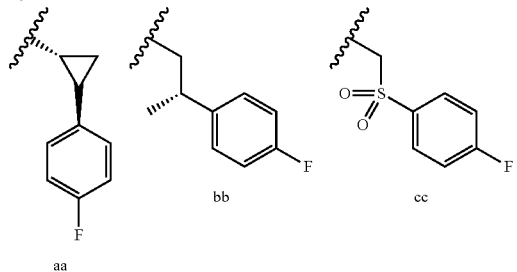

Biology Protocols

1. Electrophysiology

Kv1.x currents were measured in Kv1.3/CHO or Kv1.5/CHO cells using a planar electrode version (Nanion Technologies GMBH) of the patch-clamp technique. Whole-cell Kv1.x current transients were evoked by 500 ms depolarising voltage pulses to +40 mV from a holding potential of −80 mV applied at 10 s intervals for Kv1.5 and at 30 s intervals for Kv1.3 to allow adequate time for recovery from inactivation. Cells were continuously bathed in a buffered saline solution containing (mM): 160 NaCl, 4.5 KCl, 2 CaCl$_2$, 1 MgCl$_2$, 5 glucose, 10 HEPES, pH 7.4, 290-310 mOsm·Kg$^{-1}$. The internal (pipette) solution contained (mM): 10 NaCl, 70 KF, 75 KCl, 2 MgCl$_2$, 10 HEPES, 10 EGTA, pH 7.2, 290-310 mOsm·Kg$^{-1}$. Series resistance compensation (60-80%) was applied to cells in which the peak current amplitude exceeded 2 nA.

Compound Preparation and Potency Assessment

Compounds were initially dissolved in DMSO to 10 mM. After further dilution in DMSO, compounds were finally diluted in bath solution 1/200 (to give a final DMSO concentration of 0.5%) and applied directly to the recording chamber. Compounds were added at increasing concentrations allowing ample time for steady state block to be achieved between each concentration. Each compound was tested at 5-6 different concentrations on 2-3 cells. Compound IC$_{50}$ values were determined by fitting the average normalised reduction of either the current integral or the steady state current amplitude at the end of the 500 ms depolarising pulse obtained at each compound concentration to the Hill equation. The IC$_{50}$ data reported herein is based on the steady state calculation.

2. Effector Memory T Cell Proliferation Assay with Cytokine Read Out

Inhibition of Proliferation

Inhibition of T$_{EM}$ function in vitro was based on methods published by (Hu et al., 2007, *J. Immunol.*, 179, 4563-4570; Wulff et al., 2003, *J. Clin. Invest.*, 111, 1703-1713; Beeton et al., 2005, *Mol. Pharmacol.*, 67, 1369-1381). Peripheral blood mononuclear cells were purified from human whole blood preparations using Ficoll density centrifugation. T$_{EM}$ cells were obtained by enrichment of the CD45RA-CCR7-population using monoclonal antibodies, labelled magnetic beads and magnetic separation (Miltenyi Biotec). Enriched T$_{EM}$ cells were incubated at a concentration of 2×10$^5$ cells per well in 96-well plates in RPMI medium supplemented with 5% human serum, glutamine (Gibco) and penicillin/streptomycin (Gibco). Once plated, cells were incubated with compound at varying concentrations for 2 hours at 37° C. before being stimulated. Compound dilutions were made up in T cell medium+DMSO (to keep the concentration of DMSO constant within the dilutions) and 75 μl/well were added. After two hours, 150 μl of well contents were transferred to another 96 well plate coated with anti-human CD3 antibody (2 μg/ml overnight and then extensively washed with PBS). 72 hours later tritiated thymidine was added and proliferation of T$_{EM}$ cells measured by scintillation counting of thymidine incorporation. All incubations took place in an incubator at 37° C. and 5% CO$_2$.

Inhibition of Human Interferon Gamma (IFN-γ) and IL-17 Secretion

Peripheral blood mononuclear cells were purified from human whole blood preparations using Ficoll density centrifugation. T$_{EM}$ cells were obtained by enrichment of the CD45RA-CCR7-population using monoclonal antibodies, labelled magnetic beads and magnetic separation (Miltenyi Biotec). Enriched T$_{EM}$ cells were incubated at a concentration of 2×10$^5$ cells per well in 96-well plates in RPMI medium supplemented with 5% human serum, glutamine (Gibco) and penicillin/streptomycin (Gibco). Once plated, cells were incubated with compound dilutions for 2 hours at 37° C. before being stimulated. Compound dilutions were made up in T cell medium+DMSO (to keep the concentration of DMSO constant within the dilutions) and 75 μl/well were added. After two hours, 150 μl of well contents were transferred to another 96 well plate coated with anti-human CD3 antibody (2 μg/ml overnight and then extensively washed with PBS). 72 hours later supernatant was removed and analysed for presence of human IFNγ or IL-17 using an ELISA kit (R&D Systems) and a Fluostar optical density reader (450 nm wavelength filter). All incubations took place in an incubator at 37° C. and 5% CO$_2$.

In Vitro Inhibition of Proliferation and Cytokine Secretion by Antigen-Specific Rat T Cells Lewis rats were immunised subcutaneously with 200 μl OVA protein (Sigma) emulsion in CFA (DIFCO). 7 days later rats were challenged with OVA solution intradermally into the middle of the right ear. 24 hours later the rats were killed and inguinal lymph nodes removed. Following homogenisation (gentleMACS Dissociator (MACS Miltenyi Biotec)) and passage through a filter, cell suspensions were prepared in RPMI (supplemented with 10% FBS (heat-inactivated, Invitrogen) 1% Pen-Strep (Invitrogen), 1% Hepes 1M (Invitrogen), 1% Glutamax (Invitrogen), 1% MEM (SIGMA), 2.5 µM B-mercaptoethanol (Invitrogen), 1 µM sodium pyruvate (Invitrogen) and plated in 96 well plates at a concentration of 5×10 cells per well. Cells were left either unstimulated or stimulated with Con A (Sigma) in the presence of compound at varying concentrations and incubated at 37° C., 5% $CO_2$ for 48 hours. After this time 10 µl tritiated thymidine (1 µCi per well) was added to cell proliferation plates and incubated overnight for a further 16 hours at 37° C. and 5% CO2. Plates were frozen (−20° C.) until further use. At a convenient time, cells were harvested on filters (Filtermat A Perkin Elmer) and tritiated thymidine incorporation was measured using a Microbeta counter.

Duplicate cultures were set up under the same stimulation conditions for measurement of IFN-γ and IL-17 production. After 72 hours incubation, supernatants were removed and stored at −80° C. until cytokine analysis (IL17A & IFNg, custom Rat 2 Plex Cytokine Panel, IL17-A & IFNgamma, Kit LEGENDplex, or Kit Milliplex, MerckMillipore).

Results according to Method D1:

| Example | $IC_{50}$ (Kv1.3 ephys steady state, nM) |
|---------|---------|
| 1 | <50 |
| 2 | 50-200 |
| 5 | <50 |
| 8 | <50 |
| 9 | 50-200 |
| 10 | 50-200 |
| 13 | 50-200 |
| 14 | <50 |
| 21 | 50-200 |
| 24 | 50-200 |
| 39 | 50-200 |
| 40 | 50-200 |
| 41 | 50-200 |
| 44 | 200-1000 |
| 45 | 200-1000 |
| 46 | 50-200 |
| 47 | 50-200 |
| 51 | 50-200 |
| 52 | 200-1000 |
| 53 | 50-200 |
| 54 | 200-1000 |
| 55 | 200-1000 |
| 57 | 200-1000 |
| 61 | 50-200 |
| 62 | 200-1000 |
| 63 | 1000-2000 |
| 65 | >1000 |
| 66 | 50-200 |
| 67 | 200-1000 |
| 74 | <50 |
| 76 | <50 |
| 78 | 200-1000 |
| 80 | 200-1000 |
| 87 | 200-1000 |
| 88 | 50-200 |
| 89 | <50 |
| 91 | 200-1000 |
| 92 | 200-1000 |
| 93 | 50-200 |
| 94 | 50-200 |
| 95 | <50 |
| 96 | 50-200 |
| 97 | <50 |
| 98 | 50-200 |
| 99 | <50 |
| 100 | 50-200 |
| 101 | 200-1000 |
| 110 | <50 |
| 111 | 50-200 |
| 112 | 50-200 |
| 113 | 200-1000 |
| 114 | 50-200 |
| 115 | 50-200 |
| 116 | 200-1000 |
| 117 | 50-200 |
| 118 | 1000-2000 |
| 119 | 50-200 |
| 120 | 200-1000 |
| 121 | 50-200 |
| 122 | 50-200 |
| 123 | 200-1000 |
| 124 | 200-1000 |
| 125 | 1000-2000 |
| 126 | 200-1000 |
| 127 | 50-200 |
| 128 | 50-200 |
| 129 | 50-200 |
| 130 | 200-1000 |
| 140 | 1000-2000 |
| 141 | 200-1000 |
| 142 | 200-1000 |
| 143 | 200-1000 |
| 144 | 200-1000 |
| 145 | 200-1000 |
| 146 | 200-1000 |
| 147 | 200-1000 |
| 148 | 200-1000 |
| 150 | 200-1000 |
| 151 | 200-1000 |
| 152 | 200-1000 |
| 153 | 1000-2000 |
| 154 | 200-1000 |
| 155 | 200-1000 |
| 156 | 50-200 |
| 157 | 200-1000 |
| 158 | 200-1000 |
| 159 | 200-1000 |
| 160 | 200-1000 |
| 161 | 200-1000 |
| 162 | 200-1000 |
| 163 | 200-1000 |
| 170 | 200-1000 |
| 171 | 200-1000 |
| 172 | 50-200 |
| 173 | 50-200 |
| 174 | 50-200 |
| 175 | 200-1000 |
| 176 | 50-200 |
| 180 | 50-200 |
| 182 | 50-200 |
| 183 | 200-1000 |
| 184 | 200-1000 |
| 186 | 200-1000 |
| 187 | 200-1000 |
| 188 | 50-200 |
| 189 | 200-1000 |
| 190 | <50 |
| 191 | 50-200 |
| 192 | 200-1000 |
| 193 | 50-200 |
| 196 | 50-200 |
| 197 | 50-200 |
| 212 | 50-200 |
| 214 | 50-200 |
| 215 | 50-200 |
| 216 | 50-200 |
| 217 | 50-200 |
| 218 | 50-200 |
| 219 | 50-200 |
| 220 | 50-200 |
| 221 | 200-1000 |
| 222 | 50-200 |

| Example | IC$_{50}$ (Kv1.3 ephys steady state, nM) |
|---|---|
| 223 | 50-200 |
| 224 | 200-1000 |
| 225 | 200-1000 |
| 226 | 200-1000 |
| 227 | 50-200 |
| 228 | 50-200 |
| 229 | 50-200 |
| 230 | 50-200 |
| 231 | 50-200 |
| 232 | 50-200 |
| 233 | 50-200 |
| 234 | 200-1000 |
| 235 | 200-1000 |
| 236 | 50-200 |
| 237 | 50-200 |
| 238 | 50-200 |
| 239 | 200-1000 |
| 240 | 200-1000 |
| 241 | 200-1000 |
| 242 | 50-200 |
| 243 | 50-200 |
| 244 | 200-1000 |
| 245 | 200-1000 |
| 246 | 200-1000 |
| 247 | 50-200 |
| 248 | 200-1000 |
| 249 | 50-200 |
| 250 | 200-1000 |
| 251 | 200-1000 |
| 252 | 50-200 |
| 253 | <50 |
| 254 | 50-200 |
| 255 | <50 |
| 260 | 50-200 |
| 261 | 200-1000 |
| 262 | <50 |
| 263 | 50-200 |
| 264 | <50 |
| 265 | 50-200 |
| 269 | 50-200 |
| 270 | 50-200 |
| 271 | 200-1000 |
| 272 | 50-200 |
| 280 | 200-1000 |
| 281 | 200-1000 |
| 282 | 50-200 |
| 283 | 50-200 |
| 284 | 200-1000 |
| 287 | 200-1000 |
| 288 | 1000-2000 |
| 290 | 50-200 |
| 291 | 50-200 |
| 292 | 200-1000 |
| 293 | 50-200 |
| 294 | 50-200 |
| 295 | 50-200 |
| 296 | <50 |
| 297 | 200-1000 |
| 298 | 200-1000 |
| 299 | 50-200 |
| 300 | 50-200 |
| 301 | 50-200 |
| 302 | 50-200 |
| 303 | 50-200 |
| 304 | 50-200 |
| 305 | 50-200 |
| 306 | 200-1000 |
| 307 | 50-200 |
| 308 | 50-200 |
| 309 | 50-200 |
| 310 | 200-1000 |
| 311 | 200-1000 |
| 312 | 50-200 |
| 313 | 50-200 |
| 314 | 200-1000 |
| 315 | 200-1000 |
| 316 | 200-1000 |
| 317 | 200-1000 |
| 318 | 50-200 |
| 319 | 50-200 |
| 320 | <50 |
| 321 | 200-100 |
| 322 | 50-200 |
| 323 | 200-1000 |
| 324 | 50-200 |
| 327 | 1000-2000 |
| 328 | 200-1000 |
| 329 | 50-200 |
| 330 | 50-200 |
| 331 | 50-200 |
| 332 | 50-200 |
| 333 | 200-1000 |
| 340 | 200-1000 |
| 341 | 200-1000 |
| 342 | 200-1000 |
| 343 | 200-1000 |
| 344 | 200-1000 |
| 350 | 200-1000 |
| 351 | 200-1000 |
| 352 | 50-200 |
| 354 | 200-1000 |
| 355 | 50-200 |
| 356 | 50-200 |

What is claimed is:

1. A compound represented by the following Formula:

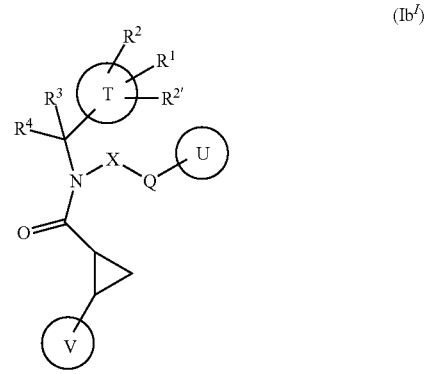

(Ib$^t$)

wherein

X is an alkylene group having 1 to 6 carbon atoms optionally substituted with 1 or 2 substituents selected from fluoro or $C_1$-$C_6$-alkyl, Q is a single bond, U is cycloalkenyl, heterocyclyl or heteroaryl, each of the above groups being optionally substituted with 1 to 3 substituents selected from Hal, $NO_2$, CN, —$SO_2$—$C_1$-$C_6$-alkyl, —S—$C_1$-$C_6$-alkyl, $NMe_2$, $C_1$-$C_6$-alkyl, —C(O)O—$C_1$-$C_6$-alkyl, O—$C_1$-$C_6$-alkyl, —(CH$_2$)$_m$—O—$C_1$-$C_6$-alkyl, —$C_1$-$C_6$-halo-alkyl, or a 5-6-membered heteroaromatic group being optionally substituted by Hal, V is an aryl group optionally substituted with 1 to 3 substituents selected from Hal, $NO_2$, CN, $SO_2$—$C_1$-$C_6$ alkyl, $NMe_2$, $C_1$-$C_6$-alkyl, O—$C_1$-$C_6$-alkyl, —(CH$_2$)$_m$—O—$C_1$-$C_6$-alkyl, —$C_1$-$C_6$-halo-alkyl, O—$C_1$-$C_6$-halo-alkyl or a 5-6-membered heteroaromatic group, T denotes phenyl, triazolyl, thiazolyl, oxazolyl, oxadiazolyl, or pyrazolyl, $R^1$ is Hal, —$C_1$-$C_6$-alkyl, O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, cyano or —$C_1$-$C_6$-halo-alkyl, $R^2$ and $R^{2'}$ are independently from one another H, Hal, —$C_1$-$C_6$-alkyl, —O—$C_1$-$C_6$-alkyl, —$(CH_2)_m$—O—$C_1$-$C_6$-alkyl, O—$C_1$-$C_6$-halo-alkyl, —$(CH_2)_m$—O—$C_1$-$C_6$-halo-alkyl, —$SO_2$—$C_1$-$C_6$-alkyl, —$(CH_2)_m$—$SO_2$—$C_1$-$C_6$-alkyl, —$SO_2$—$C_1$-$C_6$-halo-alkyl, —$(CH_2)_m$—$SO_2$—$C_1$-$C_6$-halo-alkyl, —$SO_2$-3-8-cycloalkyl, —$(CH_2)_m$—$SO_2$-3-8-cycloalkyl, —$C_1$-$C_6$-halo-alkyl, or $R^1$ and $R^2$ are linked to form with the ring T to which they are attached a 7-12-membered fused heterocyclyl or 7-12-membered fused cycloalkyl, each of which may be optionally substituted with 1 to 3 Hal, —$C_1$-$C_6$-halo-alkyl, $NO_2$, CN, $C_1$-$C_6$-alkyl, —$(CH_2)_m$—O—$C_1$-$C_6$-alkyl, or —O—$C_1$-$C_6$-alkyl, $R^3$ is $C_1$-$C_6$-alkyl, $C_1$-$C_6$-haloalkyl, —$(CH_2)_m$—O—$C_1$-$C_6$-alkyl, or —$(CH_2)_m$—O—$C_1$-$C_6$-haloalkyl; a 3-8-membered cycloalkyl group, optionally substituted with 1 to 3 substituents independently selected from Hal, —$C_1$-$C_6$-halo-alkyl, or $C_1$-$C_6$-alkyl; or a 3-8-membered heterocyclic group, optionally substituted with 1 to 3 substituents independently selected from Hal, —$C_1$-$C_6$-halo-alkyl, $NO_2$, CN, $C_1$-$C_6$-alkyl, —$(CH_2)_m$—O—$C_1$-$C_6$-alkyl, —$(CH_2)_m$—$SO_2$—$C_1$-$C_6$-alkyl, —$SO_2$—$C_1$-$C_6$-alkyl, —O—$C_1$-$C_6$-alkyl, —$(CH_2)_m$—O—$C_1$-$C_6$-halo-alkyl, —$(CH_2)_m$—$SO_2$—$C_1$-$C_6$-halo-alkyl, —$SO_2$—$C_1$-$C_6$-halo-alkyl, —O—$C_1$-$C_6$-halo-alkyl, —C(O)—$C_1$-$C_6$-alkyl, or —C(O)O—$C_1$-$C_6$-alkyl, $R^4$ denotes H, $C_1$-$C_6$-alkyl, or forms together with $R^3$ a 3-8-membered cycloalkyl ring, optionally substituted with Hal, —$C_1$-$C_6$-halo-alkyl, $NO_2$, CN, $C_1$-$C_6$-alkyl, —$(CH_2)_m$—O—$C_1$-$C_6$-alkyl, —O—$C_1$-$C_6$-alkyl, —C(O)—$C_1$-$C_6$-alkyl, or —C(O)O—$C_1$-$C_6$-alkyl, m is selected from 1, 2, 3 or 4, preferably 1 or 2, Hal is F, Cl, Br, or I, or a pharmaceutically acceptable salts thereof, or an enantiomeric mixture of 2 enantiomers in all ratios, and/or as a mixture of diastereoisomers in all ratios.

2. The compound according to claim 1 or a pharmaceutically acceptable salt thereof wherein V is a phenyl group optionally substituted with 1 to 3 substituents selected from Hal, $NO_2$, CN, $SO_2$—$C_1$-$C_6$ alkyl, $NMe_2$, $C_1$-$C_6$-alkyl, O—$C_1$-$C_6$-alkyl, —$(CH_2)_m$—O—$C_1$-$C_6$-alkyl, —$C_1$-$C_6$-halo-alkyl, O—$C_1$-$C_6$-halo-alkyl or a 5-6-membered heteroaromatic group.

3. The compound according to claim 1 or a pharmaceutically acceptable salt thereof wherein V is a phenyl group optionally substituted with 1 to 3 substituents selected from Hal, —$C_1$-$C_6$-halo-alkyl, O—$C_1$-$C_6$-halo-alkyl or $SO_2$—$C_1$-$C_6$ alkyl.

4. The compound according to claim 1 or a pharmaceutically acceptable salt thereof wherein U is a 5-12-membered heterocyclyl or a 5-6 membered heteroaryl, each of the above groups being optionally substituted with 1 to 3 substituents selected from Hal, $NO_2$, CN, $SO_2$, $NMe_2$, $C_1$-$C_6$-alkyl, O—$C_1$-$C_6$-alkyl, —$(CH_2)_m$—O—$C_1$-$C_6$-alkyl, —C(O)O-$C_1$-$C_6$-alkyl, —$SO_2$—$C_1$-$C_6$-alkyl, —S—$C_1$-$C_6$-alkyl, —$C_1$-$C_6$-halo-alkyl, or a 5-6-membered heteroaromatic group being optionally substituted by Hal.

5. The compound according to claim 1 or a pharmaceutically acceptable salt thereof wherein U is selected from pyridinyl, pyrazinyl, pyridazinyl, pyrimidinyl, imidazolyl, pyrazolyl, tetrahydropyranyl, 8-azabicyclo[3.2.1]octan-3-yl, triazolyl and piperidinyl, each of the above groups being optionally substituted with 1 to 3 substituents selected from Hal, $NO_2$, CN, $SO_2$, $NMe_2$, $C_1$-$C_6$-alkyl, O—$C_1$-$C_6$-alkyl, —$(CH_2)_m$—O—$C_1$-$C_6$-alkyl, —C(O)O—$C_1$-$C_6$-alkyl, —$SO_2$—$C_1$-$C_6$-alkyl, —S—$C_1$-$C_6$-alkyl, —$C_1$-$C_6$-halo-alkyl, or a 5-6-membered heteroaromatic group being optionally substituted by Hal.

6. The compound according to claim 1 or a pharmaceutically acceptable salt thereof wherein U is selected from pyridinyl, pyridazinyl and pyrazolyl, each of the above groups being optionally substituted with 1 to 3 substituents selected from $CF_3$, —$SO_2$—$C_1$-$C_6$-alkyl, $C_1$-$C_6$-alkyl or Hal.

7. The compound according to claim 1 or a pharmaceutically acceptable salt thereof wherein T is phenyl, triazolyl, or oxadiazolyl.

8. The compound according to claim 1 or a pharmaceutically acceptable salt thereof wherein T is phenyl.

9. The compound according to claim 1 or a pharmaceutically acceptable salt thereof wherein $R^1$ is O—$C_1$-$C_6$-alkyl, Hal, —$(CH_2)_m$—O—$C_1$-$C_6$-alkyl, —$C_1$-$C_6$-alkyl, O—$C_1$-$C_6$-halo-alkyl, —$SO_2$—$C_1$-$C_6$-alkyl, —$C_1$-$C_6$-halo-alkyl, —$SO_2$-3-8-cycloalkyl, or cyano, in which m is 1.

10. The compound according to claim 1 or a pharmaceutically acceptable salt thereof wherein $R^2$ and $R^{2'}$ are H or Hal.

11. The compound according to claim 1 or a pharmaceutically acceptable salt thereof wherein $R^2$ is H or Hal and $R^{2'}$ is H.

12. The compound according to claim 1 or a pharmaceutically acceptable salt thereof wherein $R^1$ is O—$C_1$-$C_6$-alkyl, Hal, —$(CH_2)_m$—O—$C_1$-$C_6$-alkyl, —$C_1$-$C_6$-alkyl, O—$C_1$-$C_6$-halo-alkyl, —$SO_2$—$C_1$-$C_6$-alkyl, —$C_1$-$C_6$-halo-alkyl, —$SO_2$-3-8-cycloalkyl, or cyano, in which m is 1, $R^2$ is H or Hal and $R^{2'}$ is H.

13. The compound according to claim 1 or a pharmaceutically acceptable salt thereof wherein $R^1$ and $R^2$ are linked to form with the ring T to which they are attached a dihydrobenzofuranyl, an indanyl,

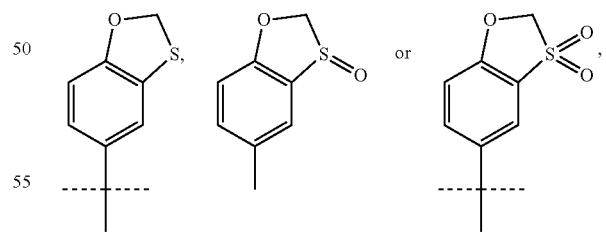

each of these groups being optionally substituted with 1 to 3 Hal, —$C_1$-$C_6$-halo-alkyl, $NO_2$, CN, $C_1$-$C_6$-alkyl, —$(CH_2)_m$—O—$C_1$-$C_6$-alkyl, or —O—$C_1$-$C_6$-alkyl.

14. The compound according to claim 1 or a pharmaceutically acceptable salt thereof wherein T is phenyl, triazolyl, oxadiazolyl or diazolyl; $R^1$ is O—$C_1$-$C_6$-alkyl, Hal, —$(CH_2)_m$—O—$C_1$-$C_6$-alkyl, —$C_1$-$C_6$-alkyl, O—$C_1$-$C_6$-halo-alkyl, —$SO_2$—$C_1$-$C_6$-alkyl, —$C_1$-$C_6$-halo-alkyl, —$SO_2$-3-8-cycloalkyl, or cyano, in which m is 1; $R^2$ is H or Hal and $R^{2'}$ is H; or $R^1$ and $R^2$ are linked to form with the ring T to which they are attached a dihydrobenzofuranyl, an indanyl,

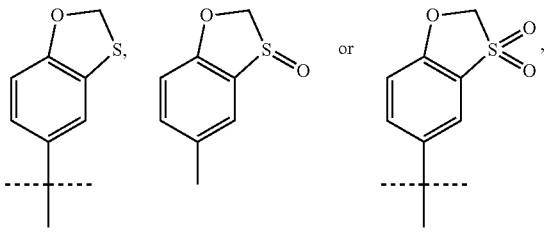

each of these groups being optionally substituted by 1 to 3 —$C_1$-$C_6$-alkyl.

15. The compound according to claim 1 or a pharmaceutically acceptable salt thereof wherein $R^4$ is H and $R^3$ is $C_1$-$C_6$ alkyl, cyclopropyl, or a 3-8-membered heterocyclic group.

16. The compound according to claim 1 or a pharmaceutically acceptable salt thereof wherein $R^4$ is H and $R^3$ is $C_1$-$C_6$ alkyl or cyclopropyl.

17. The compound according to claim 1 or a pharmaceutically acceptable salt thereof wherein $R^4$ is H and $R^3$ is cyclopropyl.

18. The compound according to claim 1 or a pharmaceutically acceptable salt thereof wherein $R^4$ is H and $R^3$ is ethyl.

19. The compound according to claim 1 or a pharmaceutically acceptable salt thereof wherein $R^3$ and $R^4$ are independently $C_1$-$C_3$-alkyl.

20. The compound according to claim 19 or a pharmaceutically acceptable salt thereof wherein $R^3$ and $R^4$ are both methyl.

21. The compound according to claim 1 wherein $R^3$ and $R^4$ are methyl and T is phenyl and $R^1$, $R^2$, and $R^{2'}$ are all H.

22. A pharmaceutical composition comprising a compound according to claim 1 together with a pharmaceutically acceptable vehicle.

23. A process of making compounds as defined in claim 1 comprising the steps of reacting a compound of Formula:

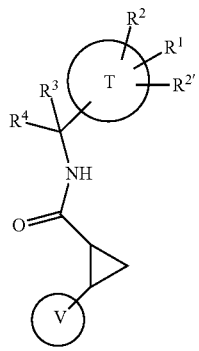

wherein $R^1$, $R^2$, $R^{2'}$, $R^3$, $R^4$, T and V are as defined in claim 1, with a compound of Formula:

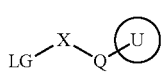

wherein X, Q and U are as defined in claim 1 and wherein LG is a suitable leaving group 1.

24. The compound according to claim 1 of the formula

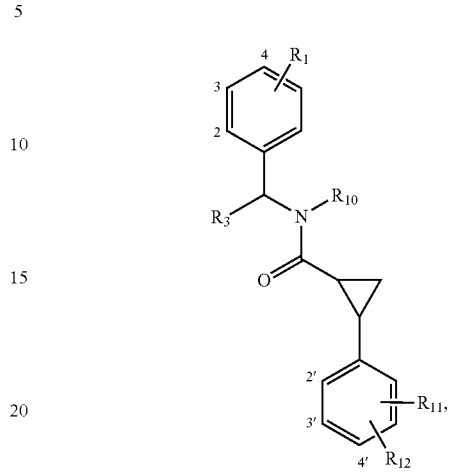

wherein

| $R_1$ | $R_3$ | $R_{10}$ | $R_{11}$ | $R_{12}$ |
|---|---|---|---|---|
| 4-OCHF$_2$ | iPr | b | 4'-F | — |
| 4-OCHF$_2$ | iPr | b | 4'-F | — |
| 4-OCHF$_2$ | iPr | ag | 4'-F | — |
| 4-OCHF$_2$ | iPr | a | 4'-F | — |
| 4-OCHF$_2$ | iPr | a | 4'-F | — |
| 4-OCHF$_2$ | iPr | b | 2'-F | 4'-F |
| 4-SO$_2$Et | Et | b | 4'-F | — |
| 4-SO$_2$Et | Et | b | 4'-F | — |
| 4-SO$_2$Et | Et | a | 4'-F | — |
| 4-SO$_2$Et | Et | d | 2'-F | 4'-F |
| 4-SO$_2$Me | Et | d | 4'-F | — |
| 4-SO$_2$Me | Et | d | 4'-F | — |
| 4-SO$_2$Me | Et | b | 4'-F | — |
| 4-SO$_2$Me | Me | a | 4'-F | — |
| 4-SO$_2$Me | Et | a | 4'-F | — |
| 4-SO$_2$Me | Et | a | 4'-F | — |
| 4-SO$_2$Me | Me | d | 4'-F | — |
| 4-SO$_2$Me | Et | d | 2'-F | 4'-F |
| 4-SO$_2$Me | Et | d | 2'-F | 4'-F |
| 4-SO$_2$Me | Et | d | 2'-F | 4'-F |
| 4-SO$_2$iPr | Et | a | 4'-F | —, | and a is

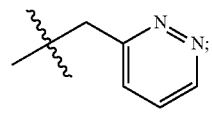 [SMILES: *Cc1cccnn1]

b is

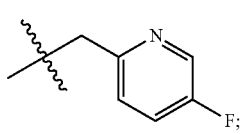

d is

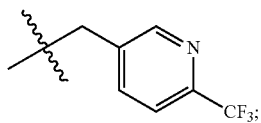 [SMILES: *Cc1ccc(C(F)(F)F)nc1]

and
ag is

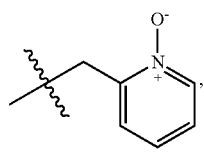

or a pharmaceutically acceptable salts thereof, or an enantiomeric mixture of 2 enantiomers in all ratios, and/or as a mixture of diastereoisomers in all ratios.

25. The compound according to claim 1 of the formula

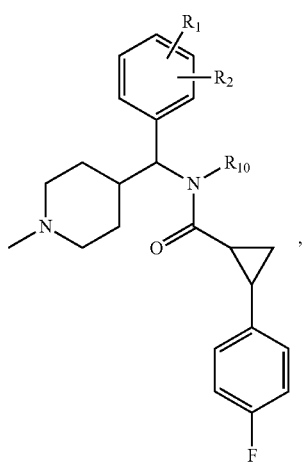

wherein

| $R_1$ | $R_2$ | $R_{10}$ |
|---|---|---|
| 4-OCHF$_2$ | — | b |
| 4-OCHF$_2$ | — | b |
| 3-SO$_2$Et | — | b |
| 4-F | — | b |
| 4-F | — | b |
| 3-CF$_3$ | — | b |
| 3-CF$_3$ | — | b |
| 3-CF$_3$ | — | b, | and
b is

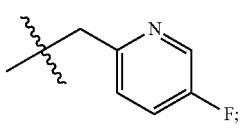

c is

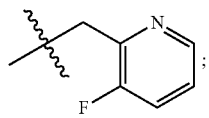 [SMILES: *Cc1ncccc1F]

and
q is

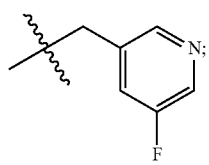 [SMILES: *Cc1cncc(F)c1]

or a pharmaceutically acceptable salts thereof, or an enantiomeric mixture of 2 enantiomers in all ratios, and/or as a mixture of diastereoisomers in all ratios.

26. The compound according to claim 1 of the formula

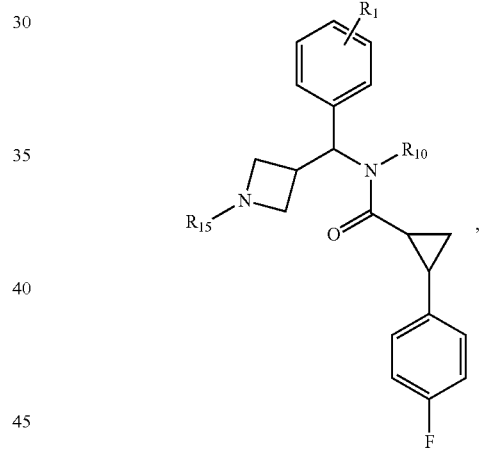

wherein

| $R_1$ | $R_{15}$ | $R_{10}$ |
|---|---|---|
| 4-OCHF$_2$ | Me | c |
| 4-OCHF$_2$ | Me | c |
| 4-OCHF$_2$ | H | b |
| 4-OCHF$_2$ | H | b |
| 4-OCHF$_2$ | Me | b |
| 4-F | Me | c |
| 4-F | Me | c |
| 4-F | H | c |
| 4-F | H | b |
| 4-OCF$_3$ | Me | b |
| 4-OCHF$_2$ | Me | af |
| 4-OCHF$_2$ | Me | af |
| 4-OCF$_3$ | Me | q |
| 4-OCF$_3$ | Me | q, | and b is

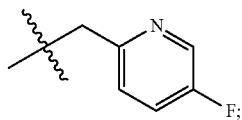

c is

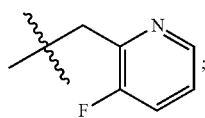 [SMILES: *Cc1ncccc1F]

q is

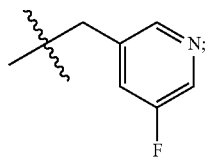 [SMILES: *Cc1cncc(F)c1]

and af is

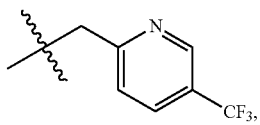 [SMILES: *Cc1ccc(C(F)(F)F)cn1]

or a pharmaceutically acceptable salts thereof, or an enantiomeric mixture of 2 enantiomers in all ratios, and/or as a mixture of diastereoisomers in all ratios.

27. The compound according to claim 1 of the formula

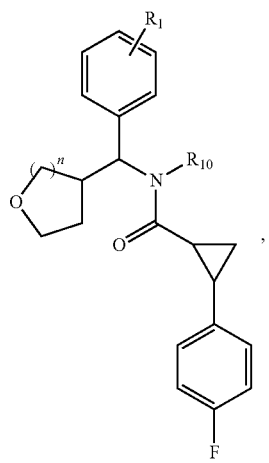

wherein

| $R_1$ | n | $R_{10}$ |
|---|---|---|
| 3-SO$_2$Et | 2 | c |
| 4-F | 1 | c |
| 4-F | 1 | c |
| 4-F | 1 | a |
| 4-F | 1 | a |
| 4-F | 1 | b |
| 4-F | 1 | b, | and a is

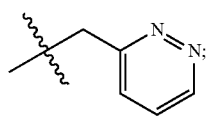 [SMILES: *Cc1cccnn1]

b is

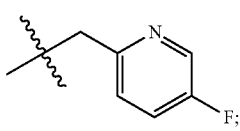 [SMILES: *Cc1ccc(F)cn1]

and c is

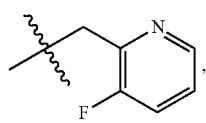

or a pharmaceutically acceptable salts thereof, or an enantiomeric mixture of 2 enantiomers in all ratios, and/or as a mixture of diastereoisomers in all ratios.

28. The compound according to claim 1 of the formula

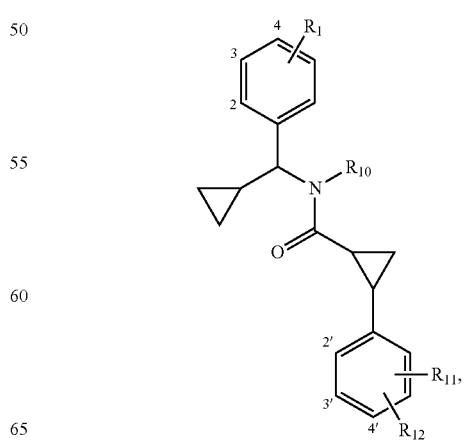

wherein

| R₁ | R₁₀ | R₁₁ | R₁₂ |
|---|---|---|---|
| 4-OCHF₂ | a | 3'-F | 4'-F |
| 4-OCHF₂ | a | 3'-F | 4'-F |
| 4-OCHF₂ | a | 2'-F | 4'-F |
| 4-OCHF₂ | k | 4'-F | — |
| 4-OCHF₂ | a | 3'-CF₃ | — |
| 4-OCHF₂ | r | 4'-F | — |
| 4-OCHF₂ | r | 4'-F | — |
| 4-OCHF₂ | y | 4'-F | — |
| 4-OCHF₂ | a | 2-OCF₃ | — |
| 4-OCHF₂ | z | 4'-F | — |
| 4-OCHF₂ | aa | 4'-F | — |
| 3-SO₂Et | m | 4'-F | — |
| 3-SO₂Et | ab | 4'-F | — |
| 3-SO₂Et | b | 2'-F | 4'-F |
| 3-SO₂Et | b | 2'-F | 4'-F |
| 3-SO₂Et | b | 2'-F | 4'-F |
| 3-SO₂Et | b | 3'-F | 4'-F |
| 3-SO₂Et | b | 3'-F | 4'-F |
| 3-SO₂Et | b | 3'-F | 4'-F |
| 3-SO₂Et | b | 3'-CF₃ | — |
| 3-SO₂Et | b | 3'-CF₃ | — |
| 3-SO₂Et | b | 3'-CF₃ | — |
| 3-SO₂Et | b | 3'-CF₃ | — |
| 3-SO₂Et | q | 4'-F | — |
| 3-SO₂Et | b | 4'-F | — |
| 3-SO₂Et | e | 3'-CF₃ | — |
| 3-SO₂Et | e | 3'-CF₃ | — |
| 3-SO₂Et | c | 4'-F | — |
| 3-SO₂Et | b | 4'-OCHF₂ | — |
| 3-SO₂Et | a | 4'-F | — |
| 3-SO₂Et | a | 4'-F | — |
| 3-SO₂Et | a | 3'-CF₃ | — |
| 3-SO₂Et | a | 3'-CF₃ | — |
| 4-SO₂Et | b | 3'-CF₃ | — |
| 4-SO₂Et | b | 3'-CF₃ | — |
| 4-SO₂Et | b | 2'-F | 4'-F |
| 4-SO₂Et | b | 2'-F | 4'-F |
| 4-SO₂Et | a | 4'-F | — |
| 4-SO₂Et | b | 4'-F | — |
| 4-SO₂Et | b | 4'-F | — |
| 4-SO₂iPr | c | 4'-F | — |
| 4-SO₂iPr | c | 4'-F | — |
| 4-SO₂iPr | a | 4'-F | — |
| 4-SO₂iPr | a | 4'-F | — |
| 4-SO₂iPr | b | 4'-F | — |
| 4-SO₂iPr | b | 4'-F | — |
| 3-SO₂iPr | a | 4'-F | — |
| 3-SO₂iPr | a | 4'-F | — |
| 3-SO₂iPr | b | 4'-F | — |
| 3-SO₂iPr | b | 4'-F | — |
| 3-SO₂iPr | q | 4'-F | — |
| 3-SO₂iPr | c | 4'-F | — |
| 3-SO₂iPr | c | 4'-F | — |
| 3-SO₂iPr | ab | 4'-F | — |
| 4-SO₂cPr | a | 4'-F | — |
| 4-SO₂cPr | a | 4'-F | — |
| 4-SO₂cPr | b | 4'-F | — |
| 3-CN | c | 4'-F | — |
| 3-CN | c | 4'-F | — |
| 4-Cl | ac | 4'-F | — |
| 4-Cl | ad | 4'-F | — |
| 4-Cl | ac | 4'-F | — |
| 4-Cl | e | 4'-F | — |
| 4-OCHF₂ | a | 4'-F | — |
| 3-SO₂Et | d | 4'-F | — |
| 4-OCHF₂ | a | 4'-F | — | and a is

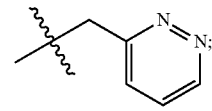 [SMILES: *Cc1cccnn1]

b is

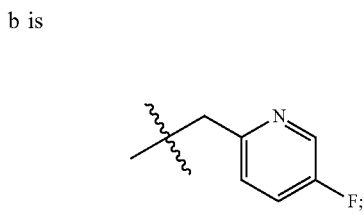

c is

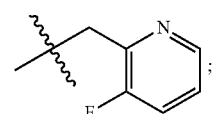

d is

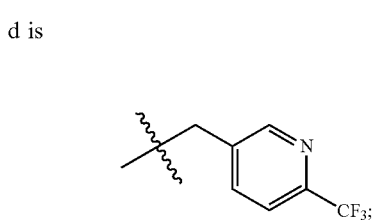

e is

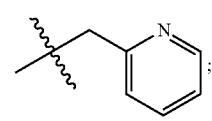 [SMILES: *Cc1ccccn1]

k is

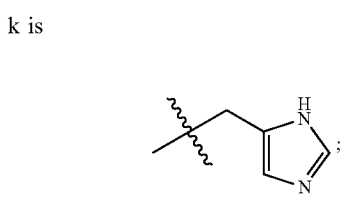

m is

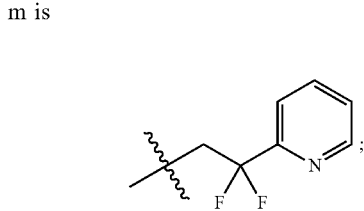

q is
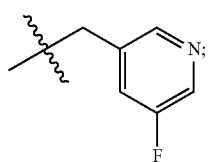 [SMILES: *Cc1cncc(F)c1]
r is
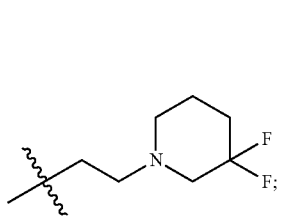 [SMILES: *CCN1CCCC(F)(F)C1]
y is
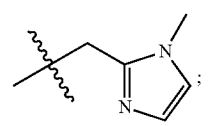 [SMILES: *Cc1nccn1C]
z is
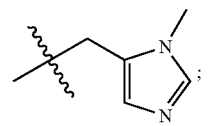 [SMILES: *Cc1cncn1C]
aa is
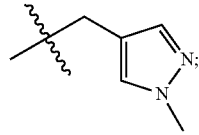 [SMILES: *Cc1cnn(C)c1]
ab is
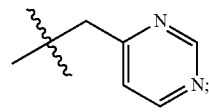 [SMILES: *Cc1ccncn1]
ac is
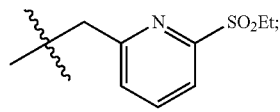
and
ad is
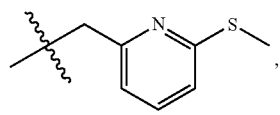 [SMILES: *Cc1cccc(SC)n1]
or a pharmaceutically acceptable salts thereof, or an enantiomeric mixture of 2 enantiomers in all ratios, and/or as a mixture of diastereoisomers in all ratios.
\* \* \* \* \*